US 9,738,907 B2

(12) United States Patent
Radcliffe et al.

(10) Patent No.: US 9,738,907 B2
(45) Date of Patent: *Aug. 22, 2017

(54) VIRAL VECTOR

(75) Inventors: Philippa Radcliffe, Oxford (GB); James E. Miskin, Oxford (GB); Fraser J. Wilkes, Oxford (GB); Kyriacos A. Mitrophanous, Oxford (GB); Susan M. Kingsman, Oxford (GB)

(73) Assignee: Oxford BioMedica (UK) Limited, Oxford (GB)

( * ) Notice: Subject to any disclaimer, the term of this patent is extended or adjusted under 35 U.S.C. 154(b) by 1043 days.

This patent is subject to a terminal disclaimer.

(21) Appl. No.: 10/841,603

(22) Filed: May 7, 2004

(65) Prior Publication Data

US 2005/0106559 A1 May 19, 2005

Related U.S. Application Data

(63) Continuation-in-part of application No. PCT/GB03/00418, filed on Feb. 3, 2003.

(30) Foreign Application Priority Data

Feb. 1, 2002 (GB) .................................. 0202403.2
May 31, 2002 (GB) .................................. 0212768.6

(51) Int. Cl.
| | |
|---|---|
| C12N 15/867 | (2006.01) |
| C12N 15/11 | (2006.01) |
| C12N 7/00 | (2006.01) |
| A61K 48/00 | (2006.01) |
| C12N 15/86 | (2006.01) |

(52) U.S. Cl.
CPC .............. *C12N 15/86* (2013.01); *A61K 48/00* (2013.01); *C12N 2740/15043* (2013.01); *C12N 2830/003* (2013.01); *C12N 2830/008* (2013.01); *C12N 2830/50* (2013.01); *C12N 2830/85* (2013.01); *C12N 2840/20* (2013.01); *C12N 2840/203* (2013.01); *C12N 2840/44* (2013.01)

(58) Field of Classification Search
None
See application file for complete search history.

(56) References Cited

U.S. PATENT DOCUMENTS

| | | | | |
|---|---|---|---|---|
| 5,917,122 | A * | 6/1999 | Byrne | 800/18 |
| 6,096,538 | A * | 8/2000 | Kingsman et al. | 435/325 |
| 6,613,569 | B1 * | 9/2003 | Dougherty et al. | 435/457 |
| 7,419,829 | B2 * | 9/2008 | Mitrophanous et al. | 435/456 |
| 2002/0034732 | A1 * | 3/2002 | Capon et al. | 435/5 |
| 2003/0026791 | A1 * | 2/2003 | Humeau et al. | 424/93.21 |
| 2003/0119770 | A1 * | 6/2003 | Lai et al. | 514/44 |
| 2003/0143205 | A1 * | 7/2003 | Slingsby et al. | 424/93.2 |
| 2007/0077597 | A1 * | 4/2007 | Gilchrist et al. | 435/7.1 |

FOREIGN PATENT DOCUMENTS

| | | |
|---|---|---|
| WO | WO 94/05785 | 3/1994 |
| WO | WO-96/37623 | 11/1996 |
| WO | WO-97/14809 | 4/1997 |
| WO | WO-98/15636 A1 | 4/1998 |
| WO | WO 99/32646 | 7/1999 |
| WO | WO 01/25466 * | 4/2001 |
| WO | 01/79518 | 10/2001 |

OTHER PUBLICATIONS

Hofmann et al, Rapid retroviral delivery of tetracycline-inducible genes in a single autoregulatory cassette, PNAS 1996;93;5185-5190.*
Clontech, Retrovirus Resource Site—Common Packaging lines, downloaded from the web May 23, 2007.*
VandenDriessche et al, Lentiviral vectors containing the human immunodeficiency virus type-1 central polypurine tract can efficiently transduce nondividing hepatocytes and antigen-presenting cells in vivo, Blood. 2002;100:(3), 813-822.*
Kotsopoulou et al, A Rev-Independent Human Immunodeficiency Virus Type 1 (HIV-1)-Based Vector That Exploits a Codon-Optimized HIV-1 gag-pol Gene, Journal of Virology, May 2000, p. 4839-4852.*
Fuller et al. Helper plasmids for production of HIV-1-derived vectors. Human Gene Therapy, 2001, 12: 2081-2093.
Clinical Gene Medicine VI Gene Therapy and Prevention 32-34 (T. Kosho, Y. Shimizu, T. Kitakawa, & K. Takebe eds., A. Fujimitsu 1995).
Mimoun Azzouz, et al., *Multicistronic Lentiviral Vector-Mediated Striatal Gene Transfer of Aromatic L-Amino Acid Decarboxylase, Tyrosine Hydroxylase, and GTP Cyclohydrolase I Induces Sustained Transgene Expression, Dopamine Production, and Functional Improvement in a Rat Model of Parkinson's Disease*, Journal of Neuroscience, Dec. 1, 2002, 22(23): 10302-10312.
Molly Bray, et al., *A Small Element from the Mason-Pfizer Monkey Virus Genome Makes Human Immunodeficiency Virus Type-1 Expression and Repliction Rev-Independent*, Biochemistry, Feb. 1994, 91: 1256-1260.
M. Fuller and D. S. Anson, *Helper Plasmids for Production of HIV-I Derived Vectors*, Human Gene Therapy, Nov. 20, 2001, 12: 2081-2093.
Yongjun Guan, et al., *Construction and In Vitro Properties of a Seris of Attenuated Simian Immunodeficiency Viruses with All Accessory Genes Deleted*, Journal of Virology, May 2001, 75(9): 4056-4067.
Steffan Indraccolo, et al., *DNA Immunization of Mice Against SIV mac239 Gag and Env Using Rev-Independent Expression Plasmids*, AIDS Research and Human Retroviruses, 1998, 14(1): 83-90.
Ekaterini Kotsopoulou, et al., *A Rev-Independent Human Immunodeficiency Virus Type 1 (HIV-1)-Based Vector That Exploits a Codon-Optimized HIV-1 gag-pol Gene*, Journal of Virology, May 2000, 74(10): 4839-4852.
Ken-Lien Nguyen, et al., *Codon Optimization of the HIV-I vpu and vif Genes Stabilizes their MRNA and Allows for Highly Efficient Rev-Independent Expression*, Virology, 2004, 319: 163-175.

(Continued)

*Primary Examiner* — Maria Marvich
(74) *Attorney, Agent, or Firm* — Grimes & Yvon LLP

(57) ABSTRACT

Provided is a multicistronic retroviral vector genome having a first nucleic acid sequence upstream of at least one internal regulatory element, such that the level of genomic RNA available for packaging in the absence of rev, or a functional equivalent thereof, is increased.

31 Claims, 50 Drawing Sheets

(56) References Cited

OTHER PUBLICATIONS

Theophile Ohlmann, et al., *An Internal Ribosome Entry Segment Promotes Translation of the Simian Immunodeficiency Virus Genomic RNA*, Journal of Biological Chemistry, Apr. 21, 2000, 275(16): 11899-11906.

Ralf Schneider, et al., *Inactivation of the Human Immunodeficiency Virus Type I Inhibitory Elements Allows Rev-Independent Expression of Gag and Gag/Protease and Particle Formation*, Journal of Virology, 71(7), 4892-4903, 1997.

Naransimhachar Srinivasakumar and Frederich Schuening, *Novel Tat-Encoding Bicistronic Human Immunodeficiency Virus Type I-Based Gene Transfer Vectors for High-Level Transgene Expression*, Journal of Virology, Jul. 2000, 74(14): 6659-6668.

Agneta von Gegerfelt and Barbara K. Felber; *Replacement of Posttransciptional Regulation in SIVmac239 Generated a Rev-Independent Infectious Virus Able to Propagate in Rhesus Peripheral Blood Mononuclear Cells*, Virology, 1997, 232: 291-299.

Susan Kingsman,"Safety features in the design, manufacture and clinical monitoring of lentivectors for the treatment of Parkinson's disease, prostate cancer and aids," FDA/BRMA, Oct. 25-26, 2001—56 pages.

Cockrell et al., The HIV-1 Rev/RRE system is required for HIV-1 5' UTR cis elements to augment encapsidation of heterologous RNA into HIV-1 viral . . . , Retrovirology 8:51 (2011).

Morgenstern et al., Advanced mammalian gene transfer: high titre retroviral vectors with multiple drug selection markers . . . , Nucl. Acids Res. 18:3587-3596 (1990).

Naldini et al., In Vivo Gene Delivery and Stable Transduction of Nondividing Cells by a Lentiviral Vector, Science 272:263-267 (Apr. 12, 1996).

Pandya et al., Development of an Rev-Independent, Minimal Simian Immunodeficiency Virus-Derived Vector System, Hum. Gene Ther. 12:847-857 (May 1, 2001).

Parolin et al., Use of cis- and trans-Acting Viral Regulatory Sequences to Improve Expression of Human Immunodeficiency Virus Vectors . . . , Virology 222:415-422 (1996).

Yu, et al., Self-inactivating retroviral vectors designed for transfer of whole genes into mammalian cells, Proc. Natl. Acad. Sci. USA, May 1986, 83:3194-3198.

* cited by examiner

Fig 7
Size (kb)
pONY8.1 G
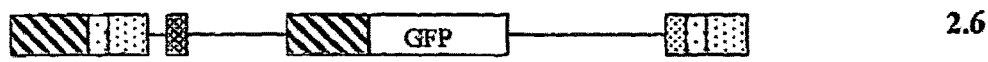
2.6
pONY8.4ZCG
6.1
pONY8.GCZ
6.1
 CMV promoter
 EIAV U3
 EIAV R region
 EIAV U5 region
 Packaging signal
 Modified packaging signal
 Hybrid U3

Figure 8A

AGATCTTGAATAATAAAATGTGTGTTTGTCCGAAATACGCGTTTTGAGATTTCTGTCGCC
GACTAAATTCATGTCGCGCGATAGTGGTGTTTATCGCCGATAGAGATGGCGATATTGGAA
AAATTGATATTTGAAAATATGGCATATTGAAAATGTCGCCGATGTGAGTTTCTGTGTAAC
TGATATCGCCATTTTTCCAAAAGTGATTTTTGGGCATACGCGATATCTGGCGATAGCGCT
TATATCGTTTACGGGGGATGGCGATAGACGACTTTGGTGACTTGGGCGATTCTGTGTGTC
GCAAATATCGCAGTTTCGATATAGGTGACAGACGATATGAGGCTATATCGCCGATAGAGG
CGACATCAAGCTGGCACATGGCCAATGCATATCGATCTATACATTGAATCAATATTGGCC
ATTAGCCATATTATTCATTGGTTATATAGCATAAATCAATATTGGCTATTGGCCATTGCA
TACGTTGTATCCATATCGTAATATGTACATTTATATTGGCTCATGTCCAACATTACCGCC
ATGTTGACATTGATTATTGACTAGTTATTAATAGTAATCAATTACGGGGTCATTAGTTCA
TAGCCCATATATGGAGTTCCGCGTTACATAACTTACGGTAAATGGCCCGCCTGGCTGACC
GCCCAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGCAGT
ACATCAAGTGTATCATATGCCAAGTCCGCCCCCTATTGACGTCAATGACGGTAAATGGCC
CGCCTGGCATTATGCCCAGTACATGACCTTACGGGACTTTCCTACTTGGCAGTACATCTA
CGTATTAGTCATCGCTATTACCATGGTGATGCGGTTTTGGCAGTACACCAATGGGCGTGG
ATAGCGGTTTGACTCACGGGGATTTCCAAGTCTCCACCCCATTGACGTCAATGGGAGTTT
GTTTTGGCACCAAAATCAACGGGACTTTCCAAAATGTCGTAACAACTGCGATCGCCCGCC
CCGTTGACGCAAATGGGCGGTAGGCGTGTACGGTGGGAGGTCTATATAAGCAGAGCTCGT
TTAGTGAACCGGGCACTCAGATTCTGCGGTCTGAGTCCCTTCTCTGCTGGGCTGAAAAGG
CCTTTGTAATAAATATAATTCTCTACTCAGTCCCTGTCTCTAGTTTGTCTGTTCGAGATC
CTACAGTTGGCGCCCGAACAGGGACCTGAGAGGGGCGCAGACCCTACCTGTTGAACCTGG
CTGATCGTAGGATCCCCGGGACAGCAGAGGAGAACTTACAGAAGTCTTCTGGAGGTGTTC
CTGGCCAGAACACAGGAGGACAGGTAAGATTGGGAGACCCTTTGACATTGGAGCAAGGC
G
CTCAAGAAGTTAGAGAAGGTGACGGTACAAGGGTCTCAGAAATTAACTACTGGTAACTGT
AATTGGGCGCTAAGTCTAGTAGACTTATTTCATGATACCAACTTTGTAAAAGAAAAGGAC
TGGCAGCTGAGGGATGTCATTCCATTGCTGGAAGATGTAACTCAGACGCTGTCAGGACAA
GAAAGAGAGGCCTTTGAAAGAACATGGTGGGCAATTTCTGCTGTAAAGATGGGCCTCCAG
ATTAATAATGTAGTAGATGGAAAGGCATCATTCCAGCTCCTAAGAGCGAAATATGAAAAG
AAGACTGCTAATAAAAAGCAGTCTGAGCCCTCTGAAGAATATCTCTAGAACTAGTGGATC
CCCCGGGCTGCAGGAGTGGGGAGGCACGATGGCCGCTTTGGTCGAGGCGGATCCGGCCAT
TAGCCATATTATTCATTGGTTATATAGCATAAATCAATATTGGCTATTGGCCATTGCATA
CGTTGTATCCATATCATAATATGTACATTTATATTGGCTCATGTCCAACATTACCGCCAT
GTTGACATTGATTATTGACTAGTTATTAATAGTAATCAATTACGGGGTCATTAGTTCATA
GCCCATATATGGAGTTCCGCGTTACATAACTTACGGTAAATGGCCCGCCTGGCTGACCGC
CCAACGACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGCAGTAC
ATCAAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTACG
TATTAGTCATCGCTATTACCATGGTGATGCGGTTTTGGCAGTACATCAATGGGCGTGGAT
AGCGGTTTGACTCACGGGGATTTCCAAGTCTCCACCCCATTGACGTCAATGGGAGTTTGT
TTTGGCACCAAAATCAACGGGACTTTCCAAAATGTCGTAACAACTCCGCCCCATTGACGC
AAATGGGCGGTAGGCATGTACGGTGGGAGGTCTATATAAGCAGAGCTCGTTTAGTGAACC
GTCAGATCGCCTGGAGACGCCATCCACGCTGTTTTGACCTCCATAGAAGACACCGGGACC
GATCCAGCCTCCGCGGCCCCAAGCTTGTTGGGATCCACCGGTCGCCACCATGGTGAGCAA
GGGCGAGGAGCTGTTCACCGGGGTGGTGCCCATCCTGGTCGAGCTGGACGGCGACGTAAA
CGGCCACAAGTTCAGCGTGTCCGGCGAGGGCGAGGGCGATGCCACCTACGGCAAGCTGAC
CCTGAAGTTCATCTGCACCACCGGCAAGCTGCCCGTGCCCTGGCCCACCCTCGTGACCAC
CCTGACCTACGGCGTGCAGTGCTTCAGCCGCTACCCCGACCACATGAAGCAGCACGACTT
CTTCAAGTCCGCCATGCCCGAAGGCTACGTCCAGGAGCGCACCATCTTCTTCAAGGACGA
CGGCAACTACAAGACCCGCGCCGAGGTGAAGTTCGAGGGCGACACCCTGGTGAACCGCAT
CGAGCTGAAGGGCATCGACTTCAAGGAGGACGGCAACATCCTGGGGCACAAGCTGGAGT
ACAACTACAACAGCCACAACGTCTATATCATGGCCGACAAGCAGAAGAACGGCATCAAG
GTGAACTTCAAGATCCGCCACAACATCGAGGACGGCAGCGTGCAGCTCGCCGACCACTAC

Figure 8B

CAGCAGAACACCCCCATCGGCGACGGCCCCGTGCTGCTGCCCGACAACCACTACCTGAGC
ACCCAGTCCGCCCTGAGCAAAGACCCCAACGAGAAGCGCGATCACATGGTCCTGCTGGAG
TTCGTGACCGCCGCCGGGATCACTCTCGGCATGGACGAGCTGTACAAGTAAAGCGGCCGC
GACTCTAGAGTCGACCTGCAGGAATTCGATATCAAGCTTATCGATACCGTCGAATTGGAA
GAGCTTTAAATCCTGGCACATCTCATGTATCAATGCCTCAGTATGTTTAGAAAAACAAGGG
GGGAACTGTGGGGTTTTTATGAGGGGTTTTATAAATGATTATAAGAGTAAAAAGAAAGTT
GCTGATGCTCTCATAACCTTGTATAACCCAAAGGACTAGCTCATGTTGCTAGGCAACTAAA
CCGCAATAACCGCATTTGTGACGCGAGTTCCCCATTGGTGACGCGTTAACTTCCTGTTTT
TACAGTATATAAGTGCTTGTATTCTGACAATTGGGCACTCAGATTCTGCGGTCTGAGTCC
CTTCTCTGCTGGGCTGAAAAGGCCTTTGTAATAAATATAATTCTCTACTCAGTCCCTGTC
TCTAGTTTGTCTGTTCGAGATCCTACAGAGCTCATGCCTTGGCGTAATCATGGTCATAGC
TGTTTCCTGTGTGAAATTGTTATCCGCTCACAATTCCACACAACATACGAGCCGGAAGCA
TAAAGTGTAAAGCCTGGGGTGCCTAATGAGTGAGCTAACTCACATTAATTGCGTTGCGCT
CACTGCCCGCTTTCCAGTCGGGAAACCTGTCGTGCCAGCTGCATTAATGAATCGGCCAAC
GCGCGGGGAGAGGCGGTTTGCGTATTGGGCGCTCTTCCGCTTCCTCGCTCACTGACTCGC
TGCGCTCGGTCGTTCGGCTGCGGCGAGCGGTATCAGCTCACTCAAAGGCGGTAATACGGT
TATCCACAGAATCAGGGGATAACGCAGGAAAGAACATGTGAGCAAAAGGCCAGCAAAAG
GCCAGGAACCGTAAAAAGGCCGCGTTGCTGGCGTTTTTCCATAGGCTCCGCCCCCCTGACG
AGCATCACAAAAATCGACGCTCAAGTCAGAGGTGGCGAAACCCGACAGGACTATAAAGA
TACCAGGCGTTTCCCCCTGGAAGCTCCCTCGTGCGCTCTCCTGTTCCGACCCTGCCGCTTA
CCGGATACCTGTCCGCCTTTCTCCCTTCGGGAAGCGTGGCGCTTTCTCATAGCTCACGCT
GTAGGTATCTCAGTTCGGTGTAGGTCGTTCGCTCCAAGCTGGGCTGTGTGCACGAACCCC
CCGTTCAGCCCGACCGCTGCGCCTTATCCGGTAACTATCGTCTTGAGTCCAACCCGGTAA
GACACGACTTATCGCCACTGGCAGCAGCCACTGGTAACAGGATTAGCAGAGCGAGGTATG
TAGGCGGTGCTACAGAGTTCTTGAAGTGGTGGCCTAACTACGGCTACACTAGAAGGACAG
TATTTGGTATCTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAGCAGCAGATTA
CGCGCAGAAAAAAAGGATCTCAAGAAGATCCTTTGATCTTTTCTACGGGGTCTGACGCTC
AGTGGAACGAAAACTCACGTTAAGGGATTTTGGTCATGAGATTATCAAAAAGGATCTTCA
CCTAGATCCTTTTAAATTAAAAATGAAGTTTTAAATCAATCTAAAGTATATATGAGTAAA
CTTGGTCTGACAGTTACCAATGCTTAATCAGTGAGGCACCTATCTCAGCGATCTGTCTAT
TTCGTTCATCCATAGTTGCCTGACTCCCCGTCGTGTAGATAACTACGATACGGGAGGGCT
TACCATCTGGCCCCAGTGCTGCAATGATACCGCGAGACCCACGCTCACCGGCTCCAGATT
TATCAGCAATAAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGTTCGCCAGTTA
ATAGTTTGCGCAACGTTGTTGCCATTGCTACAGGCATCGTGGTGTCACGCTCGTCGTTTG
GTATGGCTTCATTCAGCTCCGGTTCCCAACGATCAAGGCGAGTTACATGATCCCCCATGT
TGTGCAAAAAAGCGGTTAGCTCCTTCGGTCCTCCGATCGTTGTCAGAAGTAAGTTGGCCG
CAGTGTTATCACTCATGGTTATGGCAGCACTGCATAATTCTCTTACTGTCATGCCATCCG
TAAGATGCTTTTCTGTGACTGGTGAGTACTCAACCAAGTCATTCTGAGAATAGTGTATGC
GGCGACCGAGTTGCTCTTGCCCGGCGTCAATACGGGATAATACCGCGCCACATAGCAGAA
CTTTAAAAGTGCTCATCATTGGAAAACGTTCTTCGGGGCGAAAACTCTCAAGGATCTTAC
CGCTGTTGAGATCCAGTTCGATGTAACCCACTCGTGCACCCAACTGATCTTCAGCATCTT
TTACTTTCACCAGCGTTTCTGGGTGAGCAAAAACAGGAAGGCAAAATGCCGCAAAAAAGG
GAATAAGGGCGACACGGAAATGTTGAATACTCATACTCTTCCTTTTTCAATATTATTGAA
GCATTTATCAGGGTTATTGTCTCATGAGCGGATACATATTTGAATGTATTTAGAAAAATA
AACAAATAGGGGTTCCGCGCACATTTCCCCGAAAAGTGCCACCTAAATTGTAAGCGTTAA
TATTTTGTTAAAATTCGCGTTAAATTTTTGTTAAATCAGCTCATTTTTTAACCAATAGGC
CGAAATCGGCAAAATCCCTTATAAATCAAAAGAATAGACCGAGATAGGGTTGAGTGTTGT
TCCAGTTTGGAACAAGAGTCCACTATTAAAGAACGTGGACTCCAACGTCAAAGGGCGAAA
AACCGTCTATCAGGGCGATGGCCCACTACGTGAACCATCACCCTAATCAAGTTTTTTGGG
GTCGAGGTGCCGTAAAGCACTAAATCGGAACCCTAAAGGGAGCCCCCGATTTAGAGCTTG
ACGGGGAAAGCCAACCTGGCTTATCGAAATTAATACGACTCACTATAGGGAGACCGGC

Figure 9A

AGATCTTGAATAATAAAATGTGTGTTTGTCCGAAATACGCGTTTTGAGATTTCTGTCGCC
GACTAAATTCATGTCGCGCGATAGTGGTGTTTATCGCCGATAGAGATGGCGATATTGGAA
AAATTGATATTTGAAAATATGGCATATTGAAAATGTCGCCGATGTGAGTTTCTGTGTAAC
TGATATCGCCATTTTTCCAAAAGTGATTTTTGGGCATACGCGATATCTGGCGATAGCGCT
TATATCGTTTACGGGGGATGGCGATAGACGACTTTGGTGACTTGGGCGATTCTGTGTGTC
GCAAATATCGCAGTTTCGATATAGGTGACAGACGATATGAGGCTATATCGCCGATAGAGG
CGACATCAAGCTGGCACATGGCCAATGCATATCGATCTATACATTGAATCAATATTGGCC
ATTAGCCATATTATTCATTGGTTATATAGCATAAATCAATATTGGCTATTGGCCATTGCA
TACGTTGTATCCATATCGTAATATGTACATTTATATTGGCTCATGTCCAACATTACCGCC
ATGTTGACATTGATTATTGACTAGTTATTAATAGTAATCAATTACGGGGTCATTAGTTCA
TAGCCCATATATGGAGTTCCGCGTTACATAACTTACGGTAAATGGCCCGCCTGGCTGACC
GCCCAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGCAGT
ACATCAAGTGTATCATATGCCAAGTCCGCCCCTATTGACGTCAATGACGGTAAATGGCC
CGCCTGGCATTATGCCCAGTACATGACCTTACGGGACTTTCCTACTTGGCAGTACATCTA
CGTATTAGTCATCGCTATTACCATGGTGATGCGGTTTTGGCAGTACACCAATGGGCGTGG
ATAGCGGTTTGACTCACGGGGATTTCCAAGTCTCCACCCCATTGACGTCAATGGGAGTTT
GTTTTGGCACCAAAATCAACGGGACTTTCCAAAATGTCGTAACAACTGCGATCGCCCGCC
CCGTTGACGCAAATGGGCGGTAGGCGTGTACGGTGGGAGGTCTATATAAGCAGAGCTCGT
TTAGTGAACCGGGCACTCAGATTCTGCGGTCTGAGTCCCTTCTCTGCTGGGCTGAAAAGG
CCTTTGTAATAAATATAATTCTCTACTCAGTCCCTGTCTCTAGTTTGTCTGTTCGAGATC
CTACAGTTGGCGCCCGAACAGGGACCTGAGAGGGGCGCAGACCCTACCTGTTGAACCTGG
CTGATCGTAGGATCCCCGGGACAGCAGAGGAGAACTTACAGAAGTCTTCTGGAGGTGTTC
CTGGCCAGAACACAGGAGGACAGGTAAGATTGGGAGACCCTTTGACATTGGAGCAAGGC
G
CTCAAGAAGTTAGAGAAGGTGACGGTACAAGGGTCTCAGAAATTAACTACTGGTAACTGT
AATTGGGCGCTAAGTCTAGTAGACTTATTTCATTGATACCAACTTTGTAAAAGAAAAGGA
CTGGCAGCTGAGGGATTGTCATTCCATTGCTGGAAGATTGTAACTCAGACGCTGTCAGGA
CAAGAAAGAGAGGCCTTTGAAAGAACATTGGTGGGCAATTTCTGCTGTAAAGATTGGGCC
TCCAGATTAATAATTGTAGTAGATTGGAAAGGCATCATTCCAGCTCCTAAGAGCGAAATA
TTGAAAAGAAGACTGCTAATAAAAAGCAGTCTGAGCCCTCTGAAGAATATCTCTAGAACT
AGTGGATCCCCGGGCTGCAGGAATTCGATATCAAGCTTCAGCTGCTCGAGGATCTGCGG
ATCCGGGGAATTCCCCAGTCTCAGGATCCACCATGGGGGATCCCGTCGTTTTACAACGTC
GTGACTGGGAAAACCCTGGCGTTACCCAACTTAATCGCCTTGCAGCACATCCCCCTTTCG
CCAGCTGGCGTAATAGCGAAGAGGCCCGCACCGATCGCCCTTCCCAACAGTTGCGCAGCC
TGAATGGCGAATGGCGCTTTGCCTGGTTTCCGGCACCAGAAGCGGTGCCGGAAAGCTGGC
TGGAGTGCGATCTTCCTGAGGCCGATACTGTCGTCGTCCCCTCAAACTGGCAGATGCACG
GTTACGATGCGCCCATCTACACCAACGTAACCTATCCCATTACGGTCAATCCGCCGTTTG
TTCCCACGGAGAATCCGACGGGTTGTTACTCGCTCACATTTAATGTTGATGAAAGCTGGC
TACAGGAAGGCCAGACGCGAATTATTTTTGATGGCGTTAACTCGGCGTTTCATCTGTGGT
GCAACGGGCGCTGGGTCGGTTACGGCCAGGACAGTCGTTTGCCGTCTGAATTTGACCTGA
GCGCATTTTTACGCGCCGGAGAAAACCGCCTCGCGGTGATGGTGCTGCGTTGGAGTGACG
GCAGTTATCTGGAAGATCAGGATATGTGGCGGATGAGCGGCATTTTCCGTGACGTCTCGT
TGCTGCATAAACCGACTACACAAATCAGCGATTTCCATGTTGCCACTCGCTTTAATGATG
ATTTCAGCCGCGCTGTACTGGAGGCTGAAGTTCAGATGTGCGGCGAGTTGCGTGACTACC
TACGGGTAACAGTTTCTTTATGGCAGGGTGAAACGCAGGTCGCCAGCGGCACCGCGCCTT
TCGGCGGTGAAATTATCGATGAGCGTGGTGGTTATGCCGATCGCGTCACACTACGTCTGA
ACGTCGAAACCCGAAACTGTGGAGCGCCGAAATCCCGAATCTCTATCGTGCGGTGGTTG
AACTGCACACCGCCGACGGCACGCTGATTGAAGCAGAAGCCTGCGATGTCGGTTTCCGCG
AGGTGCGGATTGAAAATGGTCTGCTGCTGCTGAACGGCAAGCCGTTGCTGATTCGAGGCG
TTAACCGTCACGAGCATCATCCTCTGCATGGTCAGGTCATGGATGAGCAGACGATGGTGC
AGGATATCCTGCTGATGAAGCAGAACAACTTTAACGCCGTGCGCTGTTCGCATTATCCGA
ACCATCCGCTGTGGTACACGCTGTGCGACCGCTACGGCCTGTATGTGGTGGATGAAGCCA
ATATTGAAACCCACGGCATGGTGCCAATGAATCGTCTGACCGATGATCCGCGCTGGCTAC
CGGCGATGAGCGAACGCGTAACGCGAATGGTGCAGCGCGATCGTAATCACCCGAGTGTGA
TCATCTGGTCGCTGGGGAATGAATCAGGCCACGGCGCTAATCACGACGCGCTGTATCGCT

Figure 9B

```
GGATCAAATCTGTCGATCCTTCCCGCCCGGTGCAGTATGAAGGCGGCGGAGCCGACACCA
CGGCCACCGATATTATTTGCCCGATGTACGCGCGCGTGGATGAAGACCAGCCCTTCCCGG
CTGTGCCGAAATGGTCCATCAAAAAATGGCTTTCGCTACCTGGAGAGACGCGCCCGCTGA
TCCTTTGCGAATACGCCCACGCGATGGGTAACAGTCTTGGCGGTTTCGCTAAATACTGGC
AGGCGTTTCGTCAGTATCCCCGTTTACAGGGCGGCTTCGTCTGGGACTGGGTGGATCAGT
CGCTGATTAAATATGATGAAAACGGCAACCCGTGGTCGGCTTACGGCGGTGATTTTGGCG
ATACGCCGAACGATCGCCAGTTCTGTATGAACGGTCTGGTCTTTGCCGACCGCACGCCGC
ATCCAGCGCTGACGGAAGCAAAACACCAGCAGCAGTTTTCCAGTTCCGTTTATCCGGGC
AAACCATCGAAGTGACCAGCGAATACCTGTTCCGTCATAGCGATAACGAGCTCCTGCACT
GGATGGTGGCGCTGGATGGTAAGCCGCTGGCAAGCGGTGAAGTGCCTCTGGATGTCGCTC
CACAAGGTAAACAGTTGATTGAACTGCCTGAACTACCGCAGCCGGAGAGCGCCGGGCAAC
TCTGGCTCACAGTACGCGTAGTGCAACCGAACGCGACCGCATGGTCAGAAGCCGGGCACA
TCAGCGCCTGGCAGCAGTGGCGTCTGGCGGAAAACCTCAGTGTGACGCTCCCCGCCGCGT
CCCACGCCATCCCGCATCTGACCACCAGCGAAATGGATTTTTGCATCGAGCTGGGTAATA
AGCGTTGGCAATTTAACCGCCAGTCAGGCTTTCTTTCACAGATGTGGATTGGCGATAAAA
AACAACTGCTGACGCCGCTGCGCGATCAGTTCACCCGTGCACCGCTGGATAACGACATTG
GCGTAAGTGAAGCGACCCGCATTGACCCTAACGCCTGGGTCGAACGCTGGAAGGCGGCGG
GCCATTACCAGGCCGAAGCAGCGTTGTTGCAGTGCACGGCAGATACACTTGCTGATGCGG
TGCTGATTACGACCGCTCACGCGTGGCAGCATCAGGGGAAAACCTTATTTATCAGCCGGA
AAACCTACCGGATTGATGGTAGTGGTCAAATGGCGATTACCGTTGATGTTGAAGTGGCGA
GCGATACACCGCATCCGGCGCGGATTGGCCTGAACTGCCAGCTGGCGCAGGTAGCAGAGC
GGGTAAACTGGCTCGGATTAGGGCCGCAAGAAAACTATCCCGACCGCCTTACTGCCGCCT
GTTTTGACCGCTGGGATCTGCCATTGTCAGACATGTATACCCCGTACGTCTTCCCGAGCG
AAAACGGTCTGCGCTGCGGGACGCGCGAATTGAATTATGGCCCACACCAGTGGCGCGGCG
ACTTCCAGTTCAACATCAGCCGCTACAGTCAACAGCAACTGATGGAAACCAGCCATCGCC
ATCTGCTGCACGCGGAAGAAGGCACATGGCTGAATATCGACGGTTTCCATATGGGGATTG
GTGGCGACGACTCCTGGAGCCCGTCAGTATCGGCGGAATTCCAGCTGAGCGCCGGTCGCT
ACCATTACCAGTTGGTCTGGTGTCAAAAATAATAATAACCGGGCAGGGGGGATCCGCAGA
TCCGGCTGTGGAATGTGTGTCAGTTAGGGTGTGGAAAGTCCCCAGGCTCCCCAGCAGGCA
GAAGTATGCAAAGCTAGAACTAGTGGATCCCCGGGCTGCAGGAGTGGGGAGGCACGAT
G
GCCGCTTTGGTCGAGGCGGATCCGGCCATTAGCCATATTATTCATTGGTTATATAGCATA
AATCAATATTGGCTATTGGCCATTGCATACGTTGTATCCATATCATAATATGTACATTTA
TATTGGCTCATGTCCAACATTACCGCCATGTTGACATTGATTATTGACTAGTTATTAATA
GTAATCAATTACGGGGTCATTAGTTCATAGCCCATATATGGAGTTCCGCGTTACATAACT
TACGGTAAATGGCCCGCCTGGCTGACCGCCCAACGACCCCCGCCCATTGACGTCAATAAT
GACGTATGTTCCCATAGTAACGCCAATAGGGACTTTCCATTGACGTCAATGGGTGGAGTA
TTTACGGTAAACTGCCCACTTGGCAGTACATCAAGTGTATCATATGCCAAGTACGCCCCC
TATTGACGTCAATGACGGTAAATGGCCCGCCTGGCATTATGCCCAGTACATGACCTTATG
GGACTTTCCTACTTGGCAGTACATCTACGTATTAGTCATCGCTATTACCATGGTGATGCG
GTTTTGGCAGTACATCAATGGGCGTGGATAGCGGTTTGACTCACGGGGATTTCCAAGTCT
CCACCCCATTGACGTCAATGGGAGTTTGTTTTGGCACCAAAATCAACGGGACTTTCCAAA
ATGTCGTAACAACTCCGCCCCATTGACGCAAATGGGCGGTAGGCATGTACGGTGGGAGGT
CTATATAAGCAGAGCTCGTTTAGTGAACCGTCAGATCGCCTGGAGACGCCATCCACGCTG
TTTTGACCTCCATAGAAGACACCGGGACCGATCCAGCCTCCGCGGCCCCAAGCTTGTTGG
GATCCACCGGTCGCCACCATGGTGAGCAAGGGCGAGGAGCTGTTCACCGGGGTGGTGCCC
ATCCTGGTCGAGCTGGACGGCGACGTAAACGGCCACAAGTTCAGCGTGTCCGGCGAGGGC
GAGGGCGATGCCACCTACGGCAAGCTGACCCTGAAGTTCATCTGCACCACCGGCAAGCTG
CCCGTGCCCTGGCCCACCCTCGTGACCACCCTGACCTACGGCGTGCAGTGCTTCAGCCGC
TACCCCGACCACATGAAGCAGCACGACTTCTTCAAGTCCGCCATGCCCGAAGGCTACGTC
CAGGAGCGCACCATCTTCTTCAAGGACGACGGCAACTACAAGACCCGCGCCGAGGTGAAG
TTCGAGGGCGACACCCTGGTGAACCGCATCGAGCTGAAGGGCATCGACTTCAAGGAGGAC
GGCAACATCCTGGGGCACAAGCTGGAGTACAACTACAACAGCCACAACGTCTATATCATG
GCCGACAAGCAGAAGAACGGCATCAAGGTGAACTTCAAGATCCGCCACAACATCGAGGA
C
GGCAGCGTGCAGCTCGCCGACCACTACCAGCAGAACACCCCCATCGGCGACGGCCCCGTG
CTGCTGCCCGACAACCACTACCTGAGCACCCAGTCCGCCCTGAGCAAAGACCCCAACGAG
AAGCGCGATCACATGGTCCTGCTGGAGTTCGTGACCGCCGCCGGGATCACTCTCGGCATG
```

Figure 9C

GACGAGCTGTACAAGTAAAGCGGCCGCGACTCTAGCCTGCAGGAATTCGATATCAAGCTT
ATCGATACCGTCGAATTGGAAGAGCTTTAAATCCTGGCACATCTCATGTATCAATGCCTC
AGTATGTTTAGAAAAACAAGGGGGGAACTGTGGGGTTTTTATGAGGGGTTTTATAAAAAT
GAAAGACCCCACCTGTAGGTTTGGCAAGCTAGCTTAAGTAACGCCATTTTGCAAGGCATG
GAAAAATACATAACTGAGAATAGAGAAGTTCAGATCAAGGTCAGGAACAGATGGAACAG
C
TGAATATGGGCCAAACAGGATATCTGTGGTAAGCAGTTCCTGCCCCGGCTCAGGGCCAAG
AACAGATGGAACAGCTGAATATGGGCCAAACAGGATATCTGTGGTAAGCAGTTCCTGCCC
CGGCTCAGGGCCAAGAACAGATGGTCCCCAGATGCGGTCCAGCCCTCAGCAGTTTCTAGA
GAACCATCAGATGTTTCCAGGGTGCCCCAAGGACCTGAAATGACCCTGTGCCTTATTTGA
ACTAACCAATCAGTTCGCTTCTCGCTTCTGTTCGCGCGCTTCTGCTCCCCGAGCTCAATA
AAAGAGCCCACAACCCCTCACTCGGGGGGCACTCAGATTCTGCGGTCTGAGTCCCTTCTC
TGCTGGGCTGAAAAGGCCTTTGTAATAAATATAATTCTCTACTCAGTCCCTGTCTCTAGT
TTGTCTGTTCGAGATCCTACAGAGCTCATGCCTTGGCGTAATCATGGTCATAGCTGTTTC
CTGTGTGAAATTGTTATCCGCTCACAATTCCACACAACATACGAGCCGGAAGCATAAAGT
GTAAAGCCTGGGGTGCCTAATGAGTGAGCTAACTCACATTAATTGCGTTGCGCTCACTGC
CCGCTTTCCAGTCGGGAAACCTGTCGTGCCAGCTGCATTAATGAATCGGCCAACGCGCGG
GGAGAGGCGGTTTGCGTATTGGGCGCTCTTCCGCTTCCTCGCTCACTGACTCGCTGCGCT
CGGTCGTTCGGCTGCGGCGAGCGGTATCAGCTCACTCAAAGGCGGTAATACGGTTATCCA
CAGAATCAGGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTACCGGA
TACCTGTCCGCCTTTCTCCCTTCGGGAAGCGTGGCGCTTTCTCATAGCTCACGCTGTAGGT
ATCTCAGTTCGGTGTAGGTCGTTCGCTCCAAGCTGGGCTGTGTGCACGAACCCCCCGTTC
AGCCCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTAGGCG
GTGCTACAGAGTTCTTGAAGTGGTGGCCTAACTACGGCTACACTAGAAGGACAGTATTTG
GTATCTGCGCTCTGCTGAAGCCAGTTACCTTCGGAAAAAGAGTTGGTAGCTCTTGATCCG
GCAAACAAACCACCGCTGGTAGCGGTGGTTTTTTTGTTTGCAAGCAGCAGATTACGCGCA
GAAAAAAAGGATCTCAAGAAGATCCTTTGATCTTTTCTACGGGGTCTGACGCTCAGTGGA
ACGAAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTTGGT
CTGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCAT
CTGGCCCCAGTGCTGCAATGATACCGCGAGACCCACGCTCACCGGCTCCAGATTTATCAG
CAATAAACCAGCCAGCCGGAAGGGCCGAGCGCAGAAGTGGTCCTGCAACTTTATCCGCCT
CCATCCAGTCTATTAATTGTTGCCGGGAAGCTAGAGTAAGTAGTTCGCCAGTTAATAGTT
TGCGCAACGTTGTTGCCATTGCTACAGGCATCGTGGTGTCACGCTCGTCGTTTGGTATGG
CTTCATTCAGCTCCGGTTCCCAACGATCAAGGCGAGTTACATGATCCCCCATGTTGTGCA
AAAAAGCGGTTAGCTCCTTCGGTCCTCCGATCGTTGTCAGAAGTAAGTTGGCCGCAGTGT
TATCACTCATGGTTATGGCAGCACTGCATAATTCTCTTACTGTCATGCCATCCGTAAGAT
GCTTTTCTGTGACTGGTGAGTACTCAACCAAGTCATTCTGAGAATAGTGTATGCGGCGAC
CGAGTTGCTCTTGCCCGGCGTCAATACGGGATAATACCGCGCCACATAGCAGAACTTTAA
AAGTGCTCATCATTGGAAAACGTTCTTCGGGGCGAAAACTCTCAAGGATCTTACCGCTGT
TGAGATCCAGTTCGATGTAACCCACTCGTGCACCCAACTGATCTTCAGCATCTTTTACTT
TCACCAGCGTTTCTGGGTGAGCAAAAACAGGAAGGCAAAATGCCGCAAAAAAGGGAATA
AGGGCGACACGGAAATGTTGAATACTCATACTCTTCCTTTTTCAATATTATTGAAGCATTT
ATCAGGGTTATTGTCTCATGAGCGGATACATATTTGAATGTATTTAGAAAAATAAACAAA
TAGGGGTTCCGCGCACATTTCCCCGAAAAGTGCCACCTAAATTGTAAGCGTTAATATTTT
GTTAAAATTCGCGTTAAATTTTTGTTAAATCAGCTCATTTTTTAACCAATAGGCCGAAAT
CGGCAAAATCCCTTATAAATCAAAAGAATAGACCGAGATAGGGTTGAGTGTTGTTCCAGT
TTGGAACAAGAGTCCACTATTAAAGAACGTGGACTCCAACGTCAAAGGGCGAAAAACCGT
CTATCAGGGCGATGGCCCACTACGTGAACCATCACCCTAATCAAGTTTTTTGGGGTCGAG
GTGCCGTAAAGCACTAAATCGGAACCCTAAAGGGAGCCCCCGATTTAGAGCTTGACGGGG
AAAGCCAACCTGGCTTATCGAAATTAATACGACTCACTATAGGGAGACCGGC

Figure 10A

AGATCTTGAATAATAAAATGTGTGTTTGTCCGAAATACGCGTTTTGAGATTTCTGTCGCC
GACTAAATTCATGTCGCGCGATAGTGGTGTTTATCGCCGATAGAGATGGCGATATTGGAA
AAATTGATATTTGAAAATATGGCATATTGAAAATGTCGCCGATGTGAGTTTCTGTGTAAC
TGATATCGCCATTTTTCCAAAAGTGATTTTTGGGCATACGCGATATCTGGCGATAGCGCT
TATATCGTTTACGGGGGATGGCGATAGACGACTTTGGTGACTTGGGCGATTCTGTGTGTC
GCAAATATCGCAGTTTCGATATAGGTGACAGACGATATGAGGCTATATCGCCGATAGAGG
CGACATCAAGCTGGCACATGGCCAATGCATATCGATCTATACATTGAATCAATATTGGCC
ATTAGCCATATTATTCATTGGTTATATAGCATAAATCAATATTGGCTATTGGCCATTGCA
TACGTTGTATCCATATCGTAATATGTACATTTATATTGGCTCATGTCCAACATTACCGCC
ATGTTGACATTGATTATTGACTAGTTATTAATAGTAATCAATTACGGGGTCATTAGTTCA
TAGCCCATATATGGAGTTCCGCGTTACATAACTTACGGTAAATGGCCCGCCTGGCTGACC
GCCCAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGCAGT
ACATCAAGTGTATCATATGCCAAGTCCGCCCCCTATTGACGTCAATGACGGTAAATGGCC
CGCCTGGCATTATGCCCAGTACATGACCTTACGGGACTTTCCTACTTGGCAGTACATCTA
CGTATTAGTCATCGCTATTACCATGGTGATGCGGTTTTGGCAGTACACCAATGGGCGTGG
ATAGCGGTTTGACTCACGGGGATTTCCAAGTCTCCACCCCATTGACGTCAATGGGAGTTT
GTTTTGGCACCAAAATCAACGGGACTTTCCAAAATGTCGTAACAACTGCGATCGCCCGCC
CCGTTGACGCAAATGGGCGGTAGGCGTGTACGGTGGGAGGTCTATATAAGCAGAGCTCGT
TTAGTGAACCGGGCACTCAGATTCTGCGGTCTGAGTCCCTTCTCTGCTGGGCTGAAAAGG
CCTTTGTAATAAATATAATTCTCTACTCAGTCCCTGTCTCTAGTTTGTCTGTTCGAGATC
CTACAGTTGGCGCCCGAACAGGGACCTGAGAGGGGCGCAGACCCTACCTGTTGAACCTGG
CTGATCGTAGGATCCCCGGGACAGCAGAGGAGAACTTACAGAAGTCTTCTGGAGGTGTTC
CTGGCCAGAACACAGGAGGACAGGTAAGATTGGGAGACCCTTTGACATTGGAGCAAGGC
G
CTCAAGAAGTTAGAGAAGGTGACGGTACAAGGGTCTCAGAAATTAACTACTGGTAACTGT
AATTGGGCGCTAAGTCTAGTAGACTTATTTCATTGATACCAACTTTGTAAAAGAAAAGGA
CTGGCAGCTGAGGGATTGTCATTCCATTGCTGGAAGATTGTAACTCAGACGCTGTCAGGA
CAAGAAAGAGAGGCCTTTGAAAGAACATTGGTGGGCAATTTCTGCTGTAAAGATTGGGCC
TCCAGATTAATAATTGTAGTAGATTGGAAAGGCATCATTCCAGCTCCTAAGAGCGAAATA
TTGAAAAGAAGACTGCTAATAAAAAGCAGTCTGAGCCCTCTGAAGAATATCTCTAGAGTC
GACGGTACCGCGGGCCCGGGATCCACCGGTCGCCACCATGGTGAGCAAGGGCGAGGAGC
T
GTTCACCGGGGTGGTGCCCATCCTGGTCGAGCTGGACGGCGACGTAAACGGCCACAAGTT
CAGCGTGTCCGGCGAGGGCGAGGGCGATGCCACCTACGGCAAGCTGACCCTGAAGTTCAT
CTGCACCACCGGCAAGCTGCCCGTGCCCTGGCCCACCCTCGTGACCACCCTGACCTACGG
CGTGCAGTGCTTCAGCCGCTACCCCGACCACATGAAGCAGCACGACTTCTTCAAGTCCGC
CATGCCCGAAGGCTACGTCCAGGAGCGCACCATCTTCTTCAAGGACGACGGCAACTACAA
GACCCGCGCCGAGGTGAAGTTCGAGGGCGACACCCTGGTGAACCGCATCGAGCTGAAGG
G
CATCGACTTCAAGGAGGACGGCAACATCCTGGGGCACAAGCTGGAGTACAACTACAACA
G
CCACAACGTCTATATCATGGCCGACAAGCAGAAGAACGGCATCAAGGTGAACTTCAAGAT
CCGCCACAACATCGAGGACGGCAGCGTGCAGCTCGCCGACCACTACCAGCAGAACACCCC
CATCGGCGACGGCCCCGTGCTGCTGCCCGACAACCACTACCTGAGCACCCAGTCCGCCCT
GAGCAAAGACCCCAACGAGAAGCGCGATCACATGGTCCTGCTGGAGTTCGTGACCGCCGC
CGGGATCACTCTCGGCATGGACGAGCTGTACAAGTAAAGCGGCCGCTCTAGAACTAGTGG
ATCCCCCGGGCTGCAGGAGTGGGGAGGCACGATGGCCGCTTTGGTCGAGGCGGATCCGGC
CATTAGCCATATTATTCATTGGTTATATAGCATAAATCAATATTGGCTATTGGCCATTGC
ATACGTTGTATCCATATCATAATATGTACATTTATATTGGCTCATGTCCAACATTACCGC
CATGTTGACATTGATTATTGACTAGTTATTAATAGTAATCAATTACGGGGTCATTAGTTC
ATAGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCCAA
TAGGGACTTTCCATTGACGTCAATGGGTGGAGTATTTACGGTAAACTGCCCACTTGGCAG
TACATCAAGTGTATCATATGCCAAGTACGCCCCCTATTGACGTCAATGACGGTAAATGGC
CCGCCTGGCATTATGCCCAGTACATGACCTTATGGGACTTTCCTACTTGGCAGTACATCT

Figure 10 B

ACGTATTAGTCATCGCTATTACCATGGTGATGCGGTTTTGGCAGTACATCAATGGGCGTG
GATAGCGGTTTGACTCACGGGGATTTCCAAGTCTCCACCCCATTGACGTCAATGGGAGTT
TGTTTTGGCACCAAAATCAACGGGACTTTCCAAAATGTCGTAACAACTCCGCCCCATTGA
CGCAAATGGGCGGTAGGCATGTACGGTGGGAGGTCTATATAAGCAGAGCTCGTTTAGTGA
ACCGTCAGATCGCCTGGAGACGCCATCCACGCTGTTTTGACCTCCATAGAAGACACCGGG
ACCGATCCAGCCTCCGCGGCCCCAAGCTTCAGCTGCTCGAGGATCTGCGGATCCGGGGAA
TTCCCCAGTCTCAGGATCCACCATGGGGGATCCCGTCGTTTTACAACGTCGTGACTGGGA
AAACCCTGGCGTTACCCAACTTAATCGCCTTGCAGCACATCCCCCTTTCGCCAGCTGGCG
TAATAGCGAAGAGGCCCGCACCGATCGCCCTTCCCAACAGTTGCGCAGCCTGAATGGCGA
ATGGCGCTTTGCCTGGTTTCCGGCACCAGAAGCGGTGCCGGAAAGCTGGCTGGAGTGCGA
TCTTCCTGAGGCCGATACTGTCGTCGTCCCCTCAAACTGGCAGATGCACGGTTACGATGC
GCCCATCTACACCAACGTAACCTATCCCATTACGGTCAATCCGCCGTTTGTTCCCACGGA
GAATCCGACGGGTTGTTACTCGCTCACATTTAATGTTGATGAAAGCTGGCTACAGGAAGG
CCAGACGCGAATTATTTTTGATGGCGTTAACTCGGCGTTTCATCTGTGGTGCAACGGGCG
CTGGGTCGGTTACGGCCAGGACAGTCGTTTGCCGTCTGAATTTGACCTGAGCGCATTTTT
ACGCGCCGGAGAAAACCGCCTCGCGGTGATGGTGCTGCGTTGGAGTGACGGCAGTTATCT
GGAAGATCAGGATATGTGGCGGATGAGCGGCATTTTCCGTGACGTCTCGTTGCTGCATAA
ACCGACTACACAAATCAGCGATTTCCATGTTGCCACTCGCTTTAATGATGATTTCAGCCG
CGCTGTACTGGAGGCTGAAGTTCAGATGTGCGGCGAGTTGCGTGACTACCTACGGGTAAC
AGTTTCTTTATGGCAGGGTGAAACGCAGGTCGCCAGCGGCACCGCGCCTTTCGGCGGTGA
AATTATCGATGAGCGTGGTGGTTATGCCGATCGCGTCACACTACGTCTGAACGTCGAAAA
CCCGAAACTGTGGAGCGCCGAAATCCCGAATCTCTATCGTGCGGTGGTTGAACTGCACAC
CGCCGACGGCACGCTGATTGAAGCAGAAGCCTGCGATGTCGGTTTCCGCGAGGTGCGGAT
TGAAAATGGTCTGCTGCTGCTGAACGGCAAGCCGTTGCTGATTCGAGGCGTTAACCGTCA
CGAGCATCATCCTCTGCATGGTCAGGTCATGGATGAGCAGACGATGGTGCAGGATATCCT
GCTGATGAAGCAGAACAACTTTAACGCCGTGCGCTGTTCGCATTATCCGAACCATCCGCT
GTGGTACACGCTGTGCGACCGCTACGGCCTGTATGTGGTGGATGAAGCCAATATTGAAAC
CCACGGCATGGTGCCAATGAATCGTCTGACCGATGATCCGCGCTGGCTACCGGCGATGAG
CGAACGCGTAACGCGAATGGTGCAGCGCGATCGTAATCACCCGAGTGTGATCATCTGGTC
GCTGGGGAATGAATCAGGCCACGGCGCTAATCACGACGCGCTGTATCGCTGGATCAAATC
TGTCGATCCTTCCCGCCCGGTGCAGTATGAAGGCGGCGGAGCCGACACCACGGCCACCGA
TATTATTTGCCCGATGTACGCGCGCGTGGATGAAGACCAGCCCTTCCCGGCTGTGCCGAA
ATGGTCCATCAAAAAATGGCTTTCGCTACCTGGAGAGACGCGCCCGCTGATCCTTTGCGA
ATACGCCCACGCGATGGGTAACAGTCTTGGCGGTTTCGCTAAATACTGGCAGGCGTTTCG
TCAGTATCCCCGTTTACAGGGCGGCTTCGTCTGGGACTGGGTGGATCAGTCGCTGATTAA
ATATGATGAAAACGGCAACCCGTGGTCGGCTTACGGCGGTGATTTTGGCGATACGCCGAA
CGATCGCCAGTTCTGTATGAACGGTCTGGTCTTTGCCGACCGCACGCCGCATCCAGCGCT
GACGGAAGCAAAACACCAGCAGCAGTTTTTCCAGTTCCGTTTATCCGGGCAAACCATCGA
AGTGACCAGCGAATACCTGTTCCGTCATAGCGATAACGAGCTCCTGCACTGGATGGTGGC
GCTGGATGGTAAGCCGCTGGCAAGCGGTGAAGTGCCTCTGGATGTCGCTCCACAAGGTAA
ACAGTTGATTGAACTGCCTGAACTACCGCAGCCGGAGAGCGCCGGGCAACTCTGGCTCAC
AGTACGCGTAGTGCAACCGAACGCGACCGCATGGTCAGAAGCCGGGCACATCAGCGCCTG
GCAGCAGTGGCGTCTGGCGGAAAACCTCAGTGTGACGCTCCCCGCCGCGTCCCACGCCAT
CCCGCATCTGACCACCAGCGAAATGGATTTTTGCATCGAGCTGGGTAATAAGCGTTGGCA
ATTTAACCGCCAGTCAGGCTTTCTTTCACAGATGTGGATTGGCGATAAAAAACAACTGCT
GACGCCGCTGCGCGATCAGTTCACCCGTGCACCGCTGGATAACGACATTGGCGTAAGTGA
AGCGACCCGCATTGACCCTAACGCCTGGGTCGAACGCTGGAAGGCGGCGGGCCATTACCA
GGCCGAAGCAGCGTTGTTGCAGTGCACGGCAGATACACTTGCTGATGCGGTGCTGATTAC
GACCGCTCACGCGTGGCAGCATCAGGGGAAAACCTTATTTATCAGCCGGAAAACCTACCG
GATTGATGGTAGTGGTCAAATGGCGATTACCGTTGATGTTGAAGTGGCGAGCGATACACC
GCATCCGGCGCGGATTGGCCTGAACTGCCAGCTGGCCAGGTAGCAGAGCGGGTAAACTG
GCTCGGATTAGGGCCGCAAGAAAACTATCCCGACCGCCTTACTGCCGCCTGTTTTGACCG
CTGGGATCTGCCATTGTCAGACATGTATACCCCGTACGTCTTCCCGAGCGAAAACGGTCT
GCGCTGCGGGACGCGCGAATTGAATTATGGCCCACACCAGTGGCGCGGCGACTTCCAGTT
CAACATCAGCCGCTACAGTCAACAGCAACTGATGGAAACCAGCCATCGCCATCTGCTGCA
CGCGGAAGAAGGCACATGGCTGAATATCGACGGTTTCCATATGGGGATTGGTGGCGACGA
CTCCTGGAGCCCGTCAGTATCGGCGGAATTCCAGCTGAGCGCCGGTCGCTACCATTACCA
GTTGGTCTGGTGTCAAAAATAATAATAACCGGGCAGGGGGGATCCGCAGATCCGGCTGTG

Figure 10C

GAATGTGTGTCAGTTAGGGTGTGGAAAGTCCCCAGGCTCCCCAGCAGGCAGAAGTATGCA
AAGCATGCCTGCAGGAATTCGATATCAAGCTTATCGATACCGTCGAATTGGAAGAGCTTT
AAATCCTGGCACATCTCATGTATCAATGCCTCAGTATGTTTAGAAAAACAAGGGGGGAAC
TGTGGGGTTTTTATGAGGGGTTTTATAAAAATGAAAGACCCCACCTGTAGGTTTGGCAAG
CTAGCTTAAGTAACGCCATTTTGCAAGGCATGGAAAAATACATAACTGAGAATAGAGAAG
TTCAGATCAAGGTCAGGAACAGATGGAACAGCTGAATATGGGCCAAACAGGATATCTGTG
GTAAGCAGTTCCTGCCCCGGCTCAGGGCCAAGAACAGATGGAACAGCTGAATATGGGCCA
AACAGGATATCTGTGGTAAGCAGTTCCTGCCCCGGCTCAGGGCCAAGAACAGATGGTCCC
CAGATGCGGTCCAGCCCTCAGCAGTTTCTAGAGAACCATCAGATGTTTCCAGGGTGCCCC
AAGGACCTGAAATGACCCTGTGCCTTATTTGAACTAACCAATCAGTTCGCTTCTCGCTTC
TGTTCGCGCGCTTCTGCTCCCCGAGCTCAATAAAAGAGCCCACAACCCCTCACTCGGGGG
GCACTCAGATTCTGCGGTCTGAGTCCCTTCTCTGCTGGGCTGAAAAGGCCTTTGTAATAA
ATATAATTCTCTACTCAGTCCCTGTCTCTAGTTTGTCTGTTCGAGATCCTACAGAGCTCA
TGCCTTGGCGTAATCATGGTCATAGCTGTTTCCTGTGTGAAATTGTTATCCGCTCACAAT
TCCACACAACATACGAGCCGGAAGCATAAAGTGTAAAGCCTGGGGTGCCTAATGAGTGAG
CTAACTCACATTAATTGCGTTGCGCTCACTGCCCGCTTTCCAGTCGGGAAACCTGTCGTG
CCAGCTGCATTAATGAATCGGCCAACGCGCGGGGAGAGGCGGTTTGCGTATTGGGCGCTC
TTCCGCTTCCTCGCTCACTGACTCGCTGCGCTCGGTCGTTCGGCTGCGGCGAGCGGTATC
AGCTCACTCAAAGGCGGTAATACGGTTATCCACAGAATCAGGGGATAACGCAGGAAAGA
A
CATGTGAGCAAAAGGCCAGCAAAAGGCCAGGAACCGTAAAAAGGCCGCGTTGCTGGCGT
T
TTTCCATAGGCTCCGCCCCCCTGACGAGCATCACAAAAATCGACGCTCAAGTCAGAGGTG
GCGAAACCCGACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCCCTTCGGGAAG
CGTGGCGCTTTCTCATAGCTCACGCTGTAGGTATCTCAGTTCGGTGTAGGTCGTTCGCTC
CAAGCTGGGCTGTGTGCACGAACCCCCCGTTCAGCCCGACCGCTGCGCCTTATCCGGTAA
CTATCGTCTTGAGTCCAACCCGGTAAGACACGACTTATCGCCACTGGCAGCAGCCACTGG
TAACAGGATTAGCAGAGCGAGGTATGTAGGCGGTGCTACAGAGTTCTTGAAGTGGTGGCC
TAACTACGGCTACACTAGAAGGACAGTATTTGGTATCTGCGCTCTGCTGAAGCCAGTTAC
CTTCGGAAAAAGAGTTGGTAGCTCTTGATCCGGCAAACAAACCACCGCTGGTAGCGGTGG
TTTTTTTGTTTGCAAGCAGCAGATTACGCGCAGAAAAAAAGGATCTCAAGAAGATCCTTT
GATCTTTTCTACGGGGTCTGACGCTCAGTGGAACGAAAACTCACGTTAAGGGATTTTGGT
CATGAGATTATCAAAAAGGATCTTCACCTAGATCCTTTTAAATTAAAAATGAAGTTTTAA
ATCAATCTAAAGTATATATGAGTAAACTTGGTCTGACAGTTACCAATGCTTAATCAGTGA
GGCACCTATCTCAGCGATCTGTCTATTTCGTTCATCCATAGTTGCCTGACTCCCCGTCGT
GTAGATAACTACGATACGGGAGGGCTTACCATCTGGCCCCAGTGCTGCAATGATACCGCG
AGACCCACGCTCACCGGCTCCAGATTTATCAGCAATAAACCAGCCAGCCGGAAGGGCCGA
GCGCAGAAGTGGTCCTGCAACTTTATCCGCCTCCATCCAGTCTATTAATTGTTGCCGGGA
AGCTAGAGTAAGTAGTTCGCCAGTTAATAGTTTGCGCAACGTTGTTGCCATTGCTACAGG
CATCGTGGTGTCACGCTCGTCGTTTGGTATGGCTTCATTCAGCTCCGGTTCCCAACGATC
AAGGCGAGTTACATGATCCCCCATGTTGTGCAAAAAAGCGGTTAGCTCCTTCGGTCCTCC
GATCGTTGTCAGAAGTAAGTTGGCCGCAGTGTTATCACTCATGGTTATGGCAGCACTGCA
TAATTCTCTTACTGTCATGCCATCCGTAAGATGCTTTTCTGTGACTGGTGAGTACTCAAC
CAAGTCATTCTGAGAATAGTGTATGCGGCGACCGAGTTGCTCTTGCCCGGCGTCAATACG
GGATAATACCGCGCCACATAGCAGAACTTTAAAAGTGCTCATCATTGGAAAACGTTCTTC
GGGGCGAAAACTCTCAAGGATCTTACCGCTGTTGAGATCCAGTTCGATGTAACCCACTCG
TGCACCCAACTGATCTTCAGCATCTTTTACTTTCACCAGCGTTTCTGGGTGAGCAAAAAC
AGGAAGGCAAAATGCCGCAAAAAAGGGAATAAGGGCGACACGGAAATGTTGAATACTCA
TACTCTTCCTTTTTCAATATTATTGAAGCATTTATCAGGGTTATTGTCTCATGAGCGGATA
CATATTTGAATGTATTTAGAAAAATAAACAAATAGGGGTTCCGCGCACATTTCCCCGAAA
AGTGCCACCTAAATTGTAAGCGTTAATATTTTGTTAAAATTCGCGTTAAATTTTTGTTAA
ATCAGCTCATTTTTTAACCAATAGGCCGAAATCGGCAAAATCCCTTATAAATCAAAAGAA
TAGACCGAGATAGGGTTGAGTGTTGTTCCAGTTTGGAACAAGAGTCCACTATTAAAGAAC
GTGGACTCCAACGTCAAAGGGCGAAAAACCGTCTATCAGGGCGATGCCCACTACGTGAA
CCATCACCCTAATCAAGTTTTTTGGGGTCGAGGTGCCGTAAAGCACTAAATCGGAACCCT
AAAGGGAGCCCCCGATTTAGAGCTTGACGGGGAAAGCCAACCTGGCTTATCGAAATTAAT
ACGACTCACTATAGGGAGACCGGC

Figure 12

TGTGGGGTTTTTATGAGGGGTTTTATAATGAAAGACCCCACCTGTAGGTTTGGCAAGCT
AGCTTAAGTAACGCCATTTTGCAAGGCATGGAAAAATACATAACTGAGAATAGAGAAGTT
CAGATCAAGGTCAGGAACAGATGGAACAGCTGAATATGGGCCAAACAGGATATCTGTGG
T
AAGCAGTTCCTGCCCCGGCTCAGGGCCAAGAACAGATGGAACAGCTGAATATGGGCCAA
A
CAGGATATCTGTGGTAAGCAGTTCCTGCCCCGGCTCAGGGCCAAGAACAGATGGTCCCCA
GATGCGGTCCAGCCCTCAGCAGTTTCTAGAGAACCATCAGATGTTTCCAGGGTGCCCCAA
GGACCTGAAATGACCCTGTGCCTTATTTGAACTAACCAATCAGTTCGCTTCTCGCTTCTG
TTCGCGCGCTTCTGCTCCCCGAGCTCAATAAAAGAGCCCACAACCCCTCACTCGGGGGGC
ACTCAGATTCTGCGGTCTGAGTCCCTTCTCTGCTGGGCTGAAAAGGCCTTTGTAATAAAT

Figure 13A

```
AGATCTTGAATAATAAAATGTGTGTTTGTCCGAAATACGCGTTTTGAGATTTCTGTCGCCG
ACTAAATTCATGTCGCGCGATAGTGGTGTTTATCGCCGATAGAGATGGCGATATTGGAAA
AATTGATATTTGAAAATATGGCATATTGAAAATGTCGCCGATGTGAGTTTCTGTGTAACTG
ATATCGCCATTTTTCCAAAAGTGATTTTTGGGCATACGCGATATCTGGCGATAGCGCTTA
TATCGTTTACGGGGGATGGCGATAGACGACTTTGGTGACTTGGGCGATTCTGTGTGTCG
CAAATATCGCAGTTTCGATATAGGTGACAGACGATATGAGGCTATATCGCCGATAGAGG
CGACATCAAGCTGGCACATGGCCAATGCATATCGATCTATACATTGAATCAATATTGGCC
ATTAGCCATATTATTCATTGGTTATATAGCATAAATCAATATTGGCTATTGGCCATTGCATA
CGTTGTATCCATATCGTAATATGTACATTTATATTGGCTCATGTCCAACATTACCGCCATG
TTGACATTGATTATTGACTAGTTATTAATAGTAATCAATTACGGGTCATTAGTTCATAGC
CCATATATGGAGTTCCGCGTTACATAACTTACGGTAAATGGCCCGCCTGGCTGACCGCC
CAACGACCCCCGCCCATTGACGTCAATAATGACGTATGTTCCCATAGTAACGCCAATAG
GGACTTTCCATTGACGTCAATGGGTGGAGTATTTACGGTAAACTGCCCACTTGGCAGTA
CATCAAGTGTATCATATGCCAAGTCCGCCCCCTATTGACGTCAATGACGGTAAATGGCC
CGCCTGGCATTATGCCCAGTACATGACCTTACGGGACTTTCCTACTTGGCAGTACATCTA
CGTATTAGTCATCGCTATTACCATGGTGATGCGGTTTTGGCAGTACACCAATGGGCGTG
GATAGCGGTTTGACTCACGGGGATTTCCAAGTCTCCACCCCATTGACGTCAATGGGAGT
TTGTTTTGGCACCAAAATCAACGGGACTTTCCAAAATGTCGTAACAACTGCGATCGCCCG
CCCCGTTGACGCAAATGGGCGGTAGGCGTGTACGGTGGGAGGTCTATATAAGCAGAGC
TCGTTTAGTGAACCGGGCACTCAGATTCTGCGGTCTGAGTCCCTTCTCTGCTGGGCTGA
AAAGGCCTTTGTAATAAATATAATTCTCTACTCAGTCCCTGTCTCTAGTTTGTCTGTTCGA
GATCCTACAGTTGGCGCCCGAACAGGGACCTGAGAGGGGCGCAGACCCTACCTGTTGA
ACCTGGCTGATCGTAGGATCCCCGGGACAGCAGAGGAGAACTTACAGAAGTCTTCTGGA
GGTGTTCCTGGCCAGAACACAGGAGGACAGGTAAGATTGGGAGACCCTTTGACATTGGA
GCAAGGCGCTCAAGAAGTTAGAGAAGGTGACGGTACAAGGGTCTCAGAAATTAACTACT
GGTAACTGTAATTGGGCGCTAAGTCTAGTAGACTTATTTCATGATACCAACTTTGTAAAAG
AAAAGGACTGGCAGCTGAGGGATGTCATTCCATTGCTGGAAGATGTAACTCAGACGCTG
TCAGGACAAGAAAGAGAGGCCTTTGAAAGAACATGGTGGGCAATTTCTGCTGTAAAGAT
GGGCCTCCAGATTAATAATGTAGTAGATGGAAAGGCATCATTCCAGCTCCTAAGAGCGA
AATATGAAAAGAAGACTGCTAATAAAAAGCAGTCTGAGCCCTCTGAAGAATATCTCTAGA
ACTAGTGGATCCCCCGGGCTGCAGGAGTGGGGAGGCACGATGGCCGCTTTGGTCGAG
GCGGATCCGGCCATTAGCCATATTATTCATTGGTTATATAGCATAAATCAATATTGGCTAT
TGGCCATTGCATACGTTGTATCCATATCATAATATGTACATTTATATTGGCTCATGTCCAA
CATTACCGCCATGTTGACATTGATTATTGACTAGTTATTAATAGTAATCAATTACGGGGTC
ATTAGTTCATAGCCCATATATGGAGTTCCGCGTTACATAACTTACGGTAAATGGCCCGCC
TGGCTGACCGCCCAACGACCCCCGCCCATTGACGTCAATAATGACGTATGTTCCCATAG
TAACGCCAATAGGGACTTTCCATTGACGTCAATGGGTGGAGTATTTACGGTAAACTGCCC
ACTTGGCAGTACATCAAGTGTATCATATGCCAAGTACGCCCCCTATTGACGTCAATGACG
GTAAATGGCCCGCCTGGCATTATGCCCAGTACATGACCTTATGGGACTTTCCTACTTGG
CAGTACATCTACGTATTAGTCATCGCTATTACCATGGTGATGCGGTTTTGGCAGTACATC
AATGGGCGTGGATAGCGGTTTGACTCACGGGGATTTCCAAGTCTCCACCCCATTGACGT
CAATGGGAGTTTGTTTTGGCACCAAAATCAACGGGACTTTCCAAAATGTCGTAACAACTC
CGCCCCATTGACGCAAATGGGCGGTAGGCATGTACGGTGGGAGGTCTATATAAGCAGA
GCTCGTTTAGTGAACCGTCAGATCGCCTGGAGACGCCATCCACGCTGTTTTGACCTCCA
TAGAAGACACCGGGACCGATCCAGCCTCCGCGGCCCCAAGCTTCAGCTGCTCGAGGAT
CTGCGGATCCGGGGAATTCCCCAGTCTCAGGATCCACCATGGGGGATCCCGTCGTTTA
CAACGTCGTGACTGGGAAAACCCTGGCGTTACCCAACTTAATCGCCTTGCAGCACATCC
CCCTTTCGCCAGCTGGCGTAATAGCGAAGAGGCCCGCACCGATCGCCCTTCCCAACAG
TTGCGCAGCCTGAATGGCGAATGGCGCTTTGCCTGGTTTCCGGCACCAGAAGCGGTGC
CGGAAAGCTGGCTGGAGTGCGATCTTCCTGAGGCCGATACTGTCGTCGTCCCCTCAAAC
TGGCAGATGCACGGTTACGATGCGCCCATCTACACCAACGTAACCTATCCCATTACGGT
CAATCCGCCGTTTGTTCCCACGGAGAATCCGACGGGTTGTTACTCGCTCACATTTAATGT
TGATGAAAGCTGGCTACAGGAAGGCCAGACGCGAATTATTTTTGATGGCGTTAACTCGG
CGTTTCATCTGTGGTGCAACGGGCGCTGGGTCGGTTACGGCCAGGACAGTCGTTTGCC
GTCTGAATTTGACCTGAGCGCATTTTTACGCGCCGGAGAAAACCGCCTCGCGGTGATGG
TGCTGCGTTGGAGTGACGGCAGTTATCTGGAAGATCAGGATATGTGGCGGATGAGCGG
CATTTTCCGTGACGTCTCGTTGCTGCATAAACCGACTACACAAATCAGCGATTTCCATGT
```

Figure 13B

```
TGCCACTCGCTTTAATGATGATTTCAGCCGCGCTGTACTGGAGGCTGAAGTTCAGATGT
GCGGCGAGTTGCGTGACTACCTACGGGTAACAGTTTCTTTATGGCAGGGTGAAACGCAG
GTCGCCAGCGGCACCGCGCCTTTCGGCGGTGAAATTATCGATGAGCGTGGTGGTTATG
CCGATCGCGTCACACTACGTCTGAACGTCGAAAACCCGAAACTGTGGAGCGCCGAAATC
CCGAATCTCTATCGTGCGGTGGTTGAACTGCACACCGCCGACGGCACGCTGATTGAAG
CAGAAGCCTGCGATGTCGGTTTCCGCGAGGTGCGGATTGAAAATGGTCTGCTGCTGCT
GAACGGCAAGCCGTTGCTGATTCGAGGCGTTAACCGTCACGAGCATCATCCTCTGCATG
GTCAGGTCATGGATGAGCAGACGATGGTGCAGGATATCCTGCTGATGAAGCAGAACAAC
TTTAACGCCGTGCGCTGTTCGCATTATCCGAACCATCCGCTGTGGTACACGCTGTGCGA
CCGCTACGGCCTGTATGTGGTGGATGAAGCCAATATTGAAACCCACGGCATGGTGCCAA
TGAATCGTCTGACCGATGATCCGCGCTGGCTACCGGCGATGAGCGAACGCGTAACGCG
AATGGTGCAGCGCGATCGTAATCACCCGAGTGTGATCATCTGGTCGCTGGGGAATGAAT
CAGGCCACGGCGCTAATCACGACGCGCTGTATCGCTGGATCAAATCTGTCGATCCTTCC
CGCCCGGTGCAGTATGAAGGCGGCGGAGCCGACACCACGGCCACCGATATTATTTGCC
CGATGTACGCGCGCGTGGATGAAGACCAGCCCTTCCCGGCTGTGCCGAAATGGTCCAT
CAAAAAATGGCTTTCGCTACCTGGAGAGACGCGCCCGCTGATCCTTTGCGAATACGCCC
ACGCGATGGGTAACAGTCTTGGCGGTTTCGCTAAATACTGGCAGGCGTTTCGTCAGTAT
CCCCGTTTACAGGGCGGCTTCGTCTGGGACTGGGTGGATCAGTCGCTGATTAAATATGA
TGAAAACGGCAACCCGTGGTCGGCTTACGGCGGTGATTTTGGCGATACGCCGAACGAT
CGCCAGTTCTGTATGAACGGTCTGGTCTTTGCCGACCGCACGCCGCATCCAGCGCTGA
CGGAAGCAAAACACCAGCAGCAGTTTTTCCAGTTCCGTTTATCCGGGCAAACCATCGAA
GTGACCAGCGAATACCTGTTCCGTCATAGCGATAACGAGCTCCTGCACTGGATGGTGGC
GCTGGATGGTAAGCCGCTGGCAAGCGGTGAAGTGCCTCTGGATGTCGCTCCACAAGGT
AAACAGTTGATTGAACTGCCTGAACTACCGCAGCCGGAGAGCGCCGGGCAACTCTGGC
TCACAGTACGCGTAGTGCAACCGAACGCGACCGCATGGTCAGAAGCCGGGCACATCAG
CGCCTGGCAGCAGTGGCGTCTGGCGGAAAACCTCAGTGTGACGCTCCCCGCCGCGTCC
CACGCCATCCCGCATCTGACCACCAGCGAAATGGATTTTTGCATCGAGCTGGGTAATAA
GCGTTGGCAATTTAACCGCCAGTCAGGCTTTCTTTCACAGATGTGGATTGGCGATAAAAA
ACAACTGCTGACGCCGCTGCGCGATCAGTTCACCCGTGCACCGCTGGATAACGACATTG
GCGTAAGTGAAGCGACCCGCATTGACCCTAACGCCTGGGTCGAACGCTGGAAGGCGGC
GGGCCATTACCAGGCCGAAGCAGCGTTGTTGCAGTGCACGGCAGATACACTTGCTGAT
GCGGTGCTGATTACGACCGCTCACGCGTGGCAGCATCAGGGGAAAACCTTATTTATCAG
CCGGAAAACCTACCGGATTGATGGTAGTGGTCAAATGGCGATTACCGTTGATGTTGAAG
TGGCGAGCGATACACCGCATCCGGCGCGGATTGGCCTGAACTGCCAGCTGGCGCAGGT
AGCAGAGCGGGTAAACTGGCTCGGATTAGGGCCGCAAGAAAACTATCCCGACCGCCTT
ACTGCCGCCTGTTTTGACCGCTGGGATCTGCCATTGTCAGACATGTATACCCCGTACGT
CTTCCCGAGCGAAAACGGTCTGCGCTGCGGGACGCGCGAATTGAATTATGGCCCACAC
CAGTGGCGCGGCGACTTCCAGTTCAACATCAGCCGCTACAGTCAACAGCAACTGATGGA
AACCAGCCATCGCCATCTGCTGCACGCGGAAGAAGGCACATGGCTGAATATCGACGGTT
TCCATATGGGGATTGGTGGCGACGACTCCTGGAGCCCGTCAGTATCGGCGGAATTCCA
GCTGAGCGCCGGTCGCTACCATTACCAGTTGGTCTGGTGTCAAAAATAATAATAACCGG
GCAGGGGGGATCCGCAGATCCGGCTGTGGAATGTGTGTCAGTTAGGGTGTGGAAAGTC
CCCAGGCTCCCCAGCAGGCAGAAGTATGCAAAGCATGCCTGCAGGAATTCGATATCAAG
CTTATCGATACCGTCGAATTGGAAGAGCTTTAAATCCTGGCACATCTCATGTATCAATGC
CTCAGTATGTTTAGAAAAACAAGGGGGGAACTGTGGGGTTTTTATGAGGGGTTTTATAAT
GAAAGACCCCACCTGTAGGTTTGGCAAGCTAGCTTAAGTAACGCCATTTTGCAAGGCAT
GGAAAAATACATAACTGAGAATAGAGAAGTTCAGATCAAGGTCAGGAACAGATGGAACA
GCTGAATATGGGCCAAACAGGATATCTGTGGTAAGCAGTTCCTGCCCCGGCTCAGGGC
CAAGAACAGATGGAACAGCTGAATATGGGCCAAACAGGATATCTGTGGTAAGCAGTTCC
TGCCCCGGCTCAGGGCCAAGAACAGATGGTCCCCAGATGCGGTCCAGCCCTCAGCAGT
TTCTAGAGAACCATCAGATGTTTCCAGGGTGCCCCAAGGACCTGAAATGACCCTGTGCC
TTATTTGAACTAACCAATCAGTTCGCTTCTCGCTTCTGTTCGCGCGCTTCTGCTCCCCGA
GCTCAATAAAAGAGCCCACAACCCCTCACTCGGGGGGCACTCAGATTCTGCGGTCTGAG
TCCCTTCTCTGCTGGGCTGAAAAGGCCTTTGTAATAAATATAATTCTCTACTCAGTCCCTG
TCTCTAGTTTGTCTGTTCGAGATCCTACAGAGCTCATGCCTTGGCGTAATCATGGTCATA
GCTGTTTCCTGTGTGAAATTGTTATCCGCTCACAATTCCACACAACATACGAGCCGGAAG
CATAAAGTGTAAAGCCTGGGGTGCCTAATGAGTGAGCTAACTCACATTAATTGCGTTGCG
CTCACTGCCCGCTTTCCAGTCGGGAAACCTGTCGTGCCAGCTGCATTAATGAATCGGCC
```

Figure 13C

```
AACGCGCGGGGAGAGGCGGTTTGCGTATTGGGCGCTCTTCCGCTTCCTCGCTCACTGA
CTCGCTGCGCTCGGTCGTTCGGCTGCGGCGAGCGGTATCAGCTCACTCAAAGGCGGTA
ATACGGTTATCCACAGAATCAGGGGATAACGCAGGAAAGAACATGTGAGCAAAAGGCCA
GCAAAAGGCCAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAAACCCGACAG
GACTATAAAGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTGGCGCTTTC
TCATAGCTCACGCTGTAGGTATCTCAGTTCGGTGTAGGTCGTTCGCTCCAAGCTGGGCT
GTGTGCACGAACCCCCGTTCAGCCCGACCGCTGCGCCTTATCCGGTAACTATCGTCTT
GAGTCCAACCCGGTAAGACACGACTTATCGCCACTGGCAGCAGCCACTGGTAACAGGAT
TAGCAGAGCGAGGTATGTAGGCGGTGCTACAGAGTTCTTGAAGTGGTGGCCTAACTACG
GCTACACTAGAAGGACAGTATTTGGTATCTGCGCTCTGCTGAAGCCAGTTACCTTCGGA
AAAAGAGTTGGTAGCTCTTGATCCGGCAAACAAACCACCGCTGGTAGCGGTGGTTTTTTT
GTTTGCAAGCAGCAGATTACGCGCAGAAAAAAAGGATCTCAAGAAGATCCTTTGATCTTT
TCTACGGGGTCTGACGCTCAGTGGAACGAAAACTCACGTTAAGGGATTTTGGTCATGAG
ATTATCAAAAAGGATCTTCACCTAGATCCTTTTAAATTAAAAATGAAGTTTTAAATCAATCT
AAAGTATATATGAGTAAACTTGGTCTGACAGTTACCAATGCTTAATCAGTGAGGCACCTA
TCTCAGCGATCTGTCTATTTCGTTCATCCATAGTTGCCTGACTCCCCGTCGTGTAGATAA
CTACGATACGGGAGGGCTTACCATCTGGCCCCAGTGCTGCAATGATACCGCGAGACCC
ACGCTCACCGGCTCCAGATTTATCAGCAATAAACCAGCCAGCCGGAAGGGCCGAGCGC
AGAAGTGGTCCTGCAACTTTATCCGCCTCCATCCAGTCTATTAATTGTTGCCGGGAAGCT
AGAGTAAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATCAAG
GCGAGTTACATGATCCCCCATGTTGTGCAAAAAAGCGGTTAGCTCCTTCGGTCCTCCGA
TCGTTGTCAGAAGTAAGTTGGCCGCAGTGTTATCACTCATGGTTATGGCAGCACTGCATA
ATTCTCTTACTGTCATGCCATCCGTAAGATGCTTTTCTGTGACTGGTGAGTACTCAACCA
AGTCATTCTGAGAATAGTGTATGCGGCGACCGAGTTGCTCTTGCCCGGCGTCAATACGG
GATAATACCGCGCCACATAGCAGAACTTTAAAAGTGCTCATCATTGGAAAACGTTCTTCG
GGGCGAAAACTCTCAAGGATCTTACCGCTGTTGAGATCCAGTTCGATGTAACCCACTCG
TGCACCCAACTGATCTTCAGCATCTTTTACTTTCACCAGCGTTTCTGGGTGAGCAAAAAC
AGGAAGGCAAAATGCCGCAAAAAAGGGAATAAGGGCGACACGGAAATGTTGAATACTCA
TACTCTTCCTTTTTCAATATTATTGAAGCATTTATCAGGGTTATTGTCTCATGAGCGGATA
CATATTTGAATGTATTTAGAAAAATAAACAAATAGGGGTTCCGCGCACATTTCCCCGAAAA
GTGCCACCTAAATTGTAAGCGTTAATATTTTGTTAAAATTCGCGTTAAATTTTTGTTAAATC
AGCTCATTTTTTAACCAATAGGCCGAAATCGGCAAAATCCCTTATAAATCAAAAGAATAGA
CCGAGATAGGGTTGAGTGTTGTTCCAGTTTGGAACAAGAGTCCACTATTAAAGAACGTG
GACTCCAACGTCAAAGGGCGAAAAACCGTCTATCAGGGCGATGGCCCACTACGTGAAC
CATCACCCTAATCAAGTTTTTTGGGGTCGAGGTGCCGTAAAGCACTAAATCGGAACCCTA
AAGGGAGCCCCCGATTTAGAGCTTGACGGGGAAAGCCAACCTGGCTTATCGAAATTAAT
ACGACTCACTATAGGGAGACCGGC
```

Figure 17A pONY8.4TCOG

AGATCTTGAATAATAAAATGTGTGTTTGTCCGAAATACGCGTTTTGAGATTTCTGTCGCC
GACTAAATTCATGTCGCGCGATAGTGGTGTTTATCGCCGATAGAGATGGCGATATTGGAA
AAATTGATATTTGAAAATATGGCATATTGAAAATGTCGCCGATGTGAGTTTCTGTGTAAC
TGATATCGCCATTTTTCCAAAAGTGATTTTTGGGCATACGCGATATCTGGCGATAGCGCT
TATATCGTTTACGGGGGATGGCGATAGACGACTTTGGTGACTTGGGCGATTCTGTGTGTC
GCAAATATCGCAGTTTCGATATAGGTGACAGACGATATGAGGCTATATCGCCGATAGAGG
CGACATCAAGCTGGCACATGGCCAATGCATATCGATCTATACATTGAATCAATATTGGCC
ATTAGCCATATTATTCATTGGTTATATAGCATAAATCAATATTGGCTATTGGCCATTGCA
TACGTTGTATCCATATCGTAATATGTACATTTATATTGGCTCATGTCCAACATTACCGCC
ATGTTGACATTGATTATTGACTAGTTATTAATAGTAATCAATTACGGGTCATTAGTTCA
TAGCCCATATATGGAGTTCCGCGTTACATAACTTACGGTAAATGGCCCGCCTGGCTGACC
GCCCAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGCAGT
ACATCAAGTGTATCATATGCCAAGTCCGCCCCCTATTGACGTCAATGACGGTAAATGGCC
CGCCTGGCATTATGCCCAGTACATGACCTTACGGGACTTTCCTACTTGGCAGTACATCTA
CGTATTAGTCATCGCTATTACCATGGTGATGCGGTTTTGGCAGTACACCAATGGGCGTGG
ATAGCGGTTTGACTCACGGGGATTTCCAAGTCTCCACCCCATTGACGTCAATGGGAGTTT
GTTTTGGCACCAAAATCAACGGGACTTTCCAAAATGTCGTAACAACTGCGATCGCCCGCC
CCGTTGACGCAAATGGGCGGTAGGCGTGTACGGTGGGAGGTCTATATAAGCAGAGCTCGT
TTAGTGAACCGGGCACTCAGATTCTGCGGTCTGAGTCCCTTCTCTGCTGGGCTGAAAAGG
CCTTTGTAATAAATATAATTCTCTACTCAGTCCCTGTCTCTAGTTTGTCTGTTCGAGATC
CTACAGTTGGCGCCCGAACAGGGACCTGAGAGGGGCGCAGACCCTACCTGTTGAACCTGG
CTGATCGTAGGATCCCCGGGACAGCAGAGGAGAACTTACAGAAGTCTTCTGGAGGTGTTC
CTGGCCAGAACACAGGAGGACAGGTAAGATTGGGAGACCCTTTGACATTGGAGCAAGGCG
CTCAAGAAGTTAGAGAAGGTGACGGTACAAGGGTCTCAGAAATTAACTACTGGTAACTGT
AATTGGGCGCTAAGTCTAGTAGACTTATTTCATTGATACCAACTTTGTAAAAGAAAAGGA
CTGGCAGCTGAGGGATTGTCATTCCATTGCTGGAAGATTGTAACTCAGACGCTGTCAGGA
CAAGAAAGAGAGGCCTTTGAAAGAACATTGGTGGGCAATTTCTGCTGTAAAGATTGGGCC
TCCAGATTAATAATTGTAGTAGATTGGAAAGGCATCATTCCAGCTCCTAAGAGCGAAATA
TTGAAAAGAAGACTGCTAATAAAAAGCAGTCTGAGCCCTCTGAAGAATATCTCTAGCGTC
GACCAATTGATGTCTAGATTAGATAAAAGTAAAGTGATTAACAGCGCATTAGAGCTGCTT
AATGAGGTCGGAATCGAAGGTTTAACAACCCGTAAACTCGCCCAGAAGCTAGGTGTAGAG
CAGCCTACATTGTATTGGCATGTAAAAAATAAGCGGGCTTTGCTCGACGCCTTAGCCATT
GAGATGTTAGATAGGCACCATACTCACTTTTGCCCTTTAGAAGGGGAAAGCTGGCAAGAT
TTTTTACGTAATAACGCTAAAAGTTTTAGATGTGCTTTACTAAGTCATCGCGATGGAGCA
AAAGTACATTTAGGTACACGGCCTACAGAAAAACAGTATGAAACTCTCGAAAATCAATTA
GCCTTTTTATGCCAACAAGGTTTTTCACTAGAGAATGCATTATATGCACTCAGCGCTGTG
GGGCATTTTACTTTAGGTTGCGTATTGGAAGATCAAGAGCATCAAGTCGCTAAAGAAGAA
AGGGAAACACCTACTACTGATAGTATGCCGCCATTATTACGACAAGCTATCGAATTATTT
GATCACCAAGGTGCAGAGCCAGCCTTCTTATTCGGCCTTGAATTGATCATATGCGGATTA
GAAAAACAACTTAAATGTGAAAGTGGGTCCGCGTACAGCGGATCCCGGGAATTCAGATCT
TATTAAGGTACCTAACGGACCGCGGTTAACCAGCTGAGCACTGGCCGGCCTAGGTGGCCG
GTTCGAATTAGGTACCGATGTACGGGCCAGATATACGCGTTGACATTGATTATTGACTAG
TTATTAATAGTAATCAATTACGGGGTCATTAGTTCATAGCCCATATATGGAGTTCCGCGT
TACATAACTTACGGTAAATGGCCCGCCTGGCTGACCGCCCAACGACCCCCGCCCATTGAC
GTCAATAATGACGTATGTTCCCATAGTAACGCCAATAGGGACTTTCCATTGACGTCAATG
GGTGGAGTATTTACGGTAAACTGCCCACTTGGCAGTACATCAAGTGTATCATATGCCAAG
TACGCCCCCTATTGACGTCAATGACGGTAAATGGCCCGCCTGGCATTATGCCCAGTACAT
GACCTTATGGGACTTTCCTACTTGGCAGTACATCTACGTATTAGTCATCGCTATTACCAT
GGTGATGCGGTTTTGGCAGTACATCAATGGGCGTGGATAGCGGTTTGACTCACGGGGATT
TCCAAGTCTCCACCCCATTGACGTCAATGGGAGTTTGTTTTGGAACCAAAATCAACGGGA
CTTTCCAAAATGTCGTAACAACTCCGCCCCATTGACGCAAATGGGCGGTAGGCGTGTACG
GTGGGAGGTCTATATAAGCAGAGCTCTCCCTATCAGTGATAGAGATCTCCCTATCAGTGA
TAGAGATCGTCGACGAGCTCGTTTAGTGAACCGTCAGATCGCCTGGAGACGCCATCCACG
CTGTTTTGACCTCCATAGAAGACACCGGGACCGATCCAGCCTCCGGACTCTAGCGTTTAA

Figure 17B

```
ACTTAAGCTTGTTGGGATCCACCGGTCGCCACCATGGTGAGCAAGGGCGAGGAGCTGTTC
ACCGGGGTGGTGCCCATCCTGGTCGAGCTGGACGGCGACGTAAACGGCCACAAGTTCAGC
GTGTCCGGCGAGGGCGAGGGCGATGCCACCTACGGCAAGCTGACCCTGAAGTTCATCTGC
ACCACCGGCAAGCTGCCCGTGCCCTGGCCCACCCTCGTGACCACCCTGACCTACGGCGTG
CAGTGCTTCAGCCGCTACCCCGACCACATGAAGCAGCACGACTTCTTCAAGTCCGCCATG
CCCGAAGGCTACGTCCAGGAGCGCACCATCTTCTTCAAGGACGACGGCAACTACAAGACC
CGCGCCGAGGTGAAGTTCGAGGGCGACACCCTGGTGAACCGCATCGAGCTGAAGGGCATC
GACTTCAAGGAGGACGGCAACATCCTGGGGCACAAGCTGGAGTACAACTACAACAGCCAC
AACGTCTATATCATGGCCGACAAGCAGAAGAACGGCATCAAGGTGAACTTCAAGATCCGC
CACAACATCGAGGACGGCAGCGTGCAGCTCGCCGACCACTACCAGCAGAACACCCCCATC
GGCGACGGCCCCGTGCTGCTGCCCGACAACCACTACCTGAGCACCCAGTCCGCCCTGAGC
AAAGACCCCAACGAGAAGCGCGATCACATGGTCCTGCTGGAGTTCGTGACCGCCGCCGGG
ATCACTCTCGGCATGGACGAGCTGTACAAGTAAAGCGGCCGCGACTCTAGCCTGCAGGAA
TTCGATATCAAGCTTATCGATACCGTCGAATTGGAAGAGCTTTAAATCCTGGCACATCTC
ATGTATCAATGCCTCAGTATGTTTAGAAAAACAAGGGGGGAACTGTGGGTTTTTATGAG
GGGTTTTATAAAAATGAAAGACCCCACCTGTAGGTTTGGCAAGCTAGCTTAAGTAACGCC
ATTTTGCAAGGCATGGAAAAATACATAACTGAGAATAGAGAAGTTCAGATCAAGGTCAGG
AACAGATGGAACAGCTGAATATGGGCCAAACAGGATATCTGTGGTAAGCAGTTCCTGCCC
CGGCTCAGGGCCAAGAACAGATGGAACAGCTGAATATGGGCCAAACAGGATATCTGTGGT
AAGCAGTTCCTGCCCCGGCTCAGGGCCAAGAACAGATGGTCCCCAGATGCGGTCCAGCCC
TCAGCAGTTTCTAGAGAACCATCAGATGTTTCCAGGGTGCCCCAAGGACCTGAAATGACC
CTGTGCCTTATTTGAACTAACCAATCAGTTCGCTTCTCGCTTCTGTTCGCGCGCTTCTGC
TCCCCGAGCTCAATAAAAGAGCCCACAACCCCTCACTCGGGGGGCACTCAGATTCTGCGG
TCTGAGTCCCTTCTCTGCTGGGCTGAAAAGGCCTTTGTAATAAATATAATTCTCTACTCA
GTCCCTGTCTCTAGTTTGTCTGTTCGAGATCCTACAGAGCTCATGCCTTGGCGTAATCAT
GGTCATAGCTGTTTCCTGTGTGAAATTGTTATCCGCTCACAATTCCACACAACATACGAG
CCGGAAGCATAAAGTGTAAAGCCTGGGGTGCCTAATGAGTGAGCTAACTCACATTAATTG
CGTTGCGCTCACTGCCCGCTTTCCAGTCGGGAAACCTGTCGTGCCAGCTGCATTAATGAA
TCGGCCAACGCGCGGGGAGAGGCGGTTTGCGTATTGGGCGCTCTTCCGCTTCCTCGCTCA
CTGACTCGCTGCGCTCGGTCGTTCGGCTGCGGCGAGCGGTATCAGCTCACTCAAAGGCGG
TAATACGGTTATCCACAGAATCAGGGGATAACGCAGGAAAGAACATGTGAGCAAAAGGCC
AGCAAAAGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCGCTTTCTCATA
GCTCACGCTGTAGGTATCTCAGTTCGGTGTAGGTCGTTCGCTCCAAGCTGGGCTGTGTGC
ACGAACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGCAGAG
CGAGGTATGTAGGCGGTGCTACAGAGTTCTTGAAGTGGTGGCCTAACTACGGCTACACTA
GAAGGACAGTATTTGGTATCTGCGCTCTGCTGAAGCCAGTTACCTTCGGAAAAAGAGTTG
GTAGCTCTTGATCCGGCAAACAAACCACCGCTGGTAGCGGTGGTTTTTTTGTTTGCAAGC
AGCAGATTACGCGCAGAAAAAAAGGATCTCAAGAAGATCCTTTGATCTTTTCTACGGGGT
CTGACGCTCAGTGGAACGAAAACTCACGTTAAGGGATTTTGGTCATGAGATTATCAAAAA
GGATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAGCGA
TCTGTCTATTTCGTTCATCCATAGTTGCCTGACTCCCCGTCGTGTAGATAACTACGATAC
GGGAGGGCTTACCATCTGGCCCCAGTGCTGCAATGATACCGCGAGACCCACGCTCACCGG
CTCCAGATTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAAGTAGTT
CGCCAGTTAATAGTTTGCGCAACGTTGTTGCCATTGCTACAGGCATCGTGGTGTCACGCT
CGTCGTTTGGTATGGCTTCATTCAGCTCCGGTTCCCAACGATCAAGGCGAGTTACATGAT
CCCCCATGTTGTGCAAAAAAGCGGTTAGCTCCTTCGGTCCTCCGATCGTTGTCAGAAGTA
AGTTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAGAAT
AGTGTATGCGGCGACCGAGTTGCTCTTGCCCGGCGTCAATACGGGATAATACCGCGCCAC
ATAGCAGAACTTTAAAAGTGCTCATCATTGGAAAACGTTCTTCGGGGCGAAAACTCTCAA
GGATCTTACCGCTGTTGAGATCCAGTTCGATGTAACCCACTCGTGCACCCAACTGATCTT
```

Figure 17C

CAGCATCTTTTACTTTCACCAGCGTTTCTGGGTGAGCAAAAACAGGAAGGCAAAATGCCG
CAAAAAAGGGAATAAGGGCGACACGGAAATGTTGAATACTCATACTCTTCCTTTTTCAAT
ATTATTGAAGCATTTATCAGGGTTATTGTCTCATGAGCGGATACATATTTGAATGTATTT
AGAAAAATAAACAAATAGGGGTTCCGCGCACATTTCCCCGAAAAGTGCCACCTAAATTGT
AAGCGTTAATATTTTGTTAAAATTCGCGTTAAATTTTTGTTAAATCAGCTCATTTTTTAA
CCAATAGGCCGAAATCGGCAAAATCCCTTATAAATCAAAAGAATAGACCGAGATAGGGTT
GAGTGTTGTTCCAGTTTGGAACAAGAGTCCACTATTAAAGAACGTGGACTCCAACGTCAA
AGGGCGAAAAACCGTCTATCAGGGCGATGGCCCACTACGTGAACCATCACCCTAATCAAG
TTTTTTGGGGTCGAGGTGCCGTAAAGCACTAAATCGGAACCCTAAAGGGAGCCCCCGATT
TAGAGCTTGACGGGGAAAGCCAACCTGGCTTATCGAAATTAATACGACTCACTATAGGGA
GACCGGC

Figure 18A pONY8.4TsynCOG/ pONY8.4TsynCOG1

AGATCTTGAATAATAAAATGTGTGTTTGTCCGAAATACGCGTTTTGAGATTTCTGTCGCC
GACTAAATTCATGTCGCGCGATAGTGGTGTTTATCGCCGATAGAGATGGCGATATTGGAA
AAATTGATATTTGAAAATATGGCATATTGAAAATGTCGCCGATGTGAGTTTCTGTGTAAC
TGATATCGCCATTTTTCCAAAAGTGATTTTTGGGCATACGCGATATCTGGCGATAGCGCT
TATATCGTTTACGGGGGATGGCGATAGACGACTTTGGTGACTTGGGCGATTCTGTGTGTC
GCAAATATCGCAGTTTCGATATAGGTGACAGACGATATGAGGCTATATCGCCGATAGAGG
CGACATCAAGCTGGCACATGGCCAATGCATATCGATCTATACATTGAATCAATATTGGCC
ATTAGCCATATTATTCATTGGTTATATAGCATAAATCAATATTGGCTATTGGCCATTGCA
TACGTTGTATCCATATCGTAATATGTACATTTATATTGGCTCATGTCCAACATTACCGCC
ATGTTGACATTGATTATTGACTAGTTATTAATAGTAATCAATTACGGGGTCATTAGTTCA
TAGCCCATATATGGAGTTCCGCGTTACATAACTTACGGTAAATGGCCCGCCTGGCTGACC
GCCCAACGACCCCCGCCCATTGACGTCAATAATGACGTATGTTCCCATAGTAACGCCAAT
AGGGACTTTCCATTGACGTCAATGGGTGGAGTATTTACGGTAAACTGCCCACTTGGCAGT
ACATCAAGTGTATCATATGCCAAGTCCGCCCCCTATTGACGTCAATGACGGTAAATGGCC
CGCCTGGCATTATGCCCAGTACATGACCTTACGGGACTTTCCTACTTGGCAGTACATCTA
CGTATTAGTCATCGCTATTACCATGGTGATGCGGTTTTGGCAGTACACCAATGGGCGTGG
ATAGCGGTTTGACTCACGGGGATTTCCAAGTCTCCACCCCATTGACGTCAATGGGAGTTT
GTTTTGGCACCAAAATCAACGGGACTTTCCAAAATGTCGTAACAACTGCGATCGCCCGCC
CCGTTGACGCAAATGGGCGGTAGGCGTGTACGGTGGGAGGTCTATATAAGCAGAGCTCGT
TTAGTGAACCGGGCACTCAGATTCTGCGGTCTGAGTCCCTTCTCTGCTGGGCTGAAAAGG
CCTTTGTAATAAATATAATTCTCTACTCAGTCCCTGTCTCTAGTTTGTCTGTTCGAGATC
CTACAGTTGGCGCCCGAACAGGGACCTGAGAGGGGCGCAGACCCTACCTGTTGAACCTGG
CTGATCGTAGGATCCCCGGGACAGCAGAGGAGAACTTACAGAAGTCTTCTGGAGGTGTTC
CTGGCCAGAACACAGGAGGACAGGTAAGATTGGGAGACCCTTTGACATTGGAGCAAGGCG
CTCAAGAAGTTAGAGAAGGTGACGGTACAAGGGTCTCAGAAATTAACTACTGGTAACTGT
AATTGGGCGCTAAGTCTAGTAGACTTATTTCATTGATACCAACTTTGTAAAAGAAAAGGA
CTGGCAGCTGAGGGATTGTCATTCCATTGCTGGAAGATTGTAACTCAGACGCTGTCAGGA
CAAGAAAGAGAGGCCTTTGAAAGAACATTGGTGGGCAATTTCTGCTGTAAAGATTGGGCC
TCCAGATTAATAATTGTAGTAGATTGGAAAGGCATCATTCCAGCTCCTAAGAGCGAAATA
TTGAAAAGAAGACTGCTAATAAAAAGCAGTCTGAGCCCTCTGAAGAATATCTCTAGCGTC
GACCAATTGCCGCCACCATGAGCCGCCTGGACAAGAGCAAAGTGATCAACTCCGCCCTGG
AGCTGCTGAATGAGGTCGGCATCGAGGGACTGACCACGCGCAAGCTGGCCCAAAAGCTGG
GCGTCGAGCAGCCGACCCTGTATTGGCATGTGAAGAACAAGAGGGCCCTCCTGGACGCGC
TCGCCATCGAAATGCTGGATCGGCACCACACCCACTTCTGTCCCCTCGAAGGCGAGAGCT
GGCAGGACTTTCTGAGAAACAACGCCAAGTCCTTCCGCTGCGCCCTCCTGAGCCATCGCG
ATGGGGCCAAGGTGCACCTGGGGACGCGGCCCACTGAGAAACAGTACGAAACCCTGGAGA
ATCAGCTGGCGTTCCTCTGCCAGCAGGGGTTCTCCCTGGAGAACGCCCTCTACGCACTCT
CCGCCGTGGGCCACTTTACACTCGGTTGCGTGCTGGAGGACCAGGAGCACCAAGTCGCTA
AGGAGGAGCGGGAGACCCCCACCACCGACTCCATGCCCCCACTGCTGAGGCAGGCGATTG
AGCTGTTCGACCACCAGGGAGCAGAGCCTGCGTTCCTCTTCGGGCTGGAACTCATCATCT
GCGGCCTGGAGAAGCAGCTGAAGTGCGAGAGCGGCTCCGCCTACAGCGGCAGCAGGGAGT
TCCGCTCTTACTAACGGACCGCGGTTAACCAGCTGAGCACTGGCCGGCCTAGGTGGCCGG
TTCGAATTAGGTACCGATGTACGGGCCAGATATACGCGTTGACATTGATTATTGACTAGT
TATTAATAGTAATCAATTACGGGGTCATTAGTTCATAGCCCATATATGGAGTTCCGCGTT
ACATAACTTACGGTAAATGGCCCGCCTGGCTGACCGCCCAACGACCCCGCCCATTGACG
TCAATAATGACGTATGTTCCCATAGTAACGCCAATAGGGACTTTCCATTGACGTCAATGG
GTGGAGTATTTACGGTAAACTGCCCACTTGGCAGTACATCAAGTGTATCATATGCCAAGT
ACGCCCCTATTGACGTCAATGACGGTAAATGGCCCGCCTGGCATTATGCCCAGTACATG
ACCTTATGGGACTTTCCTACTTGGCAGTACATCTACGTATTAGTCATCGCTATTACCATG
GTGATGCGGTTTTGGCAGTACATCAATGGGCGTGGATAGCGGTTTGACTCACGGGGATTT
CCAAGTCTCCACCCCATTGACGTCAATGGGAGTTTGTTTTGGAACCAAAATCAACGGGAC
TTTCCAAAATGTCGTAACAACTCCGCCCCATTGACGCAAATGGGCGGTAGGCGTGTACGG
TGGGAGGTCTATATAAGCAGAGCTCTCCCTATCAGTGATAGAGATCTCCCTATCAGTGAT

Figure 18B

AGAGATCGTCGACGAGCTCGTTTAGTGAACCGTCAGATCGCCTGGAGACGCCATCCACGC
TGTTTTGACCTCCATAGAAGACACCGGGACCGATCCAGCCTCCGGACTCTAGCGTTTAAA
CTTAAGCTTGTTGGGATCCACCGGTCGCCACCATGGTGAGCAAGGGCGAGGAGCTGTTCA
CCGGGGTGGTGCCCATCCTGGTCGAGCTGGACGGCGACGTAAACGGCCACAAGTTCAGCG
TGTCCGGCGAGGGCGAGGGCGATGCCACCTACGGCAAGCTGACCCTGAAGTTCATCTGCA
CCACCGGCAAGCTGCCCGTGCCCTGGCCCACCCTCGTGACCACCCTGACCTACGGCGTGC
AGTGCTTCAGCCGCTACCCCGACCACATGAAGCAGCACGACTTCTTCAAGTCCGCCATGC
CCGAAGGCTACGTCCAGGAGCGCACCATCTTCTTCAAGGACGACGGCAACTACAAGACCC
GCGCCGAGGTGAAGTTCGAGGGCGACACCCTGGTGAACCGCATCGAGCTGAAGGGCATCG
ACTTCAAGGAGGACGGCAACATCCTGGGGCACAAGCTGGAGTACAACTACAACAGCCACA
ACGTCTATATCATGGCCGACAAGCAGAAGAACGGCATCAAGGTGAACTTCAAGATCCGCC
ACAACATCGAGGACGGCAGCGTGCAGCTCGCCGACCACTACCAGCAGAACACCCCCATCG
GCGACGGCCCCGTGCTGCTGCCCGACAACCACTACCTGAGCACCCAGTCCGCCCTGAGCA
AAGACCCCAACGAGAAGCGCGATCACATGGTCCTGCTGGAGTTCGTGACCGCCGCCGGGA
TCACTCTCGGCATGGACGAGCTGTACAAGTAAAGCGGCCGCGACTCTAGCCTGCAGGAAT
TCGATATCAAGCTTATCGATACCGTCGAATTGGAAGAGCTTTAAATCCTGGCACATCTCA
TGTATCAATGCCTCAGTATGTTTAGAAAAACAAGGGGGGAACTGTGGGGTTTTTATGAGG
GGTTTTATAAAAATGAAAGACCCCACCTGTAGGTTTGGCAAGCTAGCTTAAGTAACGCCA
TTTTGCAAGGCATGGAAAAATACATAACTGAGAATAGAGAAGTTCAGATCAAGGTCAGGA
ACAGATGGAACAGCTGAATATGGGCCAAACAGGATATCTGTGGTAAGCAGTTCCTGCCCC
GGCTCAGGGCCAAGAACAGATGGAACAGCTGAATATGGGCCAAACAGGATATCTGTGGTA
AGCAGTTCCTGCCCCGGCTCAGGGCCAAGAACAGATGGTCCCCAGATGCGGTCCAGCCCT
CAGCAGTTTCTAGAGAACCATCAGATGTTTCCAGGGTGCCCCAAGGACCTGAAATGACCC
TGTGCCTTATTTGAACTAACCAATCAGTTCGCTTCTCGCTTCTGTTCGCGCGCTTCTGCT
CCCCGAGCTCAATAAAAGAGCCCACAACCCCTCACTCGGGGGGCACTCAGATTCTGCGGT
CTGAGTCCCTTCTCTGCTGGGCTGAAAAGGCCTTTGTAATAAATATAATTCTCTACTCAG
TCCCTGTCTCTAGTTTGTCTGTTCGAGATCCTACAGAGCTCATGCCTTGGCGTAATCATG
GTCATAGCTGTTTCCTGTGTGAAATTGTTATCCGCTCACAATTCCACACAACATACGAGC
CGGAAGCATAAAGTGTAAAGCCTGGGGTGCCTAATGAGTGAGCTAACTCACATTAATTGC
GTTGCGCTCACTGCCCGCTTTCCAGTCGGGAAACCTGTCGTGCCAGCTGCATTAATGAAT
CGGCCAACGCGCGGGAGAGGCGGTTTGCGTATTGGGCGCTCTTCCGCTTCCTCGCTCAC
TGACTCGCTGCGCTCGGTCGTTCGGCTGCGGCGAGCGGTATCAGCTCACTCAAAGGCGGT
AATACGGTTATCCACAGAATCAGGGGATAACGCAGGAAAGAACATGTGAGCAAAAGGCCA
GCAAAAGGCCAGGAACCGTAAAAAGGCCGCGTTGCTGGCGTTTTTCCATAGGCTCCGCCC
CCCTGACGAGCATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGCTTTCTCATAG
CTCACGCTGTAGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTCTTGAGTCCAA
CCCGGTAAGACACGACTTATCGCCACTGGCAGCAGCCACTGGTAACAGGATTAGCAGAGC
GAGGTATGTAGGCGGTGCTACAGAGTTCTTGAAGTGGTGGCCTAACTACGGCTACACTAG
AAGGACAGTATTTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTTGTTTGCAAGCA
GCAGATTACGCGCAGAAAAAAAGGATCTCAAGAAGATCCTTTGATCTTTTCTACGGGGTC
TGACGCTCAGTGGAACGAAAACTCACGTTAAGGGATTTTGGTCATGAGATTATCAAAAAG
GATCTTCACCTAGATCCTTTTAAATTAAAAATGAAGTTTTAAATCAATCTAAAGTATATA
TGAGTAAACTTGGTCTGACAGTTACCAATGCTTAATCAGTGAGGCACCTATCTCAGCGAT
CTGTCTATTTCGTTCATCCATAGTTGCCTGACTCCCCGTCGTGTAGATAACTACGATACG
GGAGGGCTTACCATCTGGCCCCAGTGCTGCAATGATACCGCGAGACCCACGCTCACCGGC
TCCAGATTTATCAGCAATAAACCAGCCAGCCGGAAGGGCCGAGCGCAGAAGTGGTCCTGC
AACTTTATCCGCCTCCATCCAGTCTATTAATTGTTGCCGGGAAGCTAGAGTAAGTAGTTC
GCCAGTTAATAGTTTGCGCAACGTTGTTGCCATTGCTACAGGCATCGTGGTGTCACGCTC
GTCGTTTGGTATGGCTTCATTCAGCTCCGGTTCCCAACGATCAAGGCGAGTTACATGATC
CCCCATGTTGTGCAAAAAAGCGGTTAGCTCCTTCGGTCCTCCGATCGTTGTCAGAAGTAA
GTTGGCCGCAGTGTTATCACTCATGGTTATGGCAGCACTGCATAATTCTCTTACTGTCAT
GCCATCCGTAAGATGCTTTTCTGTGACTGGTGAGTACTCAACCAAGTCATTCTGAGAATA
GTGTATGCGGCGACCGAGTTGCTCTTGCCCGGCGTCAATACGGGATAATACCGCGCCACA

Figure 18C

TAGCAGAACTTTAAAAGTGCTCATCATTGGAAAACGTTCTTCGGGGCGAAAACTCTCAAG
GATCTTACCGCTGTTGAGATCCAGTTCGATGTAACCCACTCGTGCACCCAACTGATCTTC
AGCATCTTTTACTTTCACCAGCGTTTCTGGGTGAGCAAAAACAGGAAGGCAAAATGCCGC
AAAAAAGGGAATAAGGGCGACACGGAAATGTTGAATACTCATACTCTTCCTTTTTCAATA
TTATTGAAGCATTTATCAGGGTTATTGTCTCATGAGCGGATACATATTTGAATGTATTTA
GAAAAATAAACAAATAGGGGTTCCGCGCACATTTCCCCGAAAAGTGCCACCTAAATTGTA
AGCGTTAATATTTTGTTAAAATTCGCGTTAAATTTTTGTTAAATCAGCTCATTTTTTAAC
CAATAGGCCGAAATCGGCAAAATCCCTTATAAATCAAAAGAATAGACCGAGATAGGGTTG
AGTGTTGTTCCAGTTTGGAACAAGAGTCCACTATTAAAGAACGTGGACTCCAACGTCAAA
GGGCGAAAAACCGTCTATCAGGGCGATGGCCCACTACGTGAACCATCACCCTAATCAAGT
TTTTTGGGGTCGAGGTGCCGTAAAGCACTAAATCGGAACCCTAAAGGGAGCCCCCGATTT
AGAGCTTGACGGGGAAAGCCAACCTGGCTTATCGAAATTAATACGACTCACTATAGGGAG
ACCGGC

|  | MH | WT | CO |
|---|---|---|---|
| Ala C | 53 | 29 | 59 |
| U | 17 | 35 | 6 |
| GC A | 13 | 29 | 12 |
| G | 17 | 6 | 24 |
| Arg C | 37 | 8 | 42 |
| CG U | 7 | 17 | 0 |
| A | 6 | 8 | 0 |
| G | 21 | 25 | 25 |
| AG A | 10 | 25 | 8 |
| G | 18 | 17 | 25 |
| Asn C | 78 | 29 | 71 |
| AA T | 22 | 71 | 29 |
| Ile C | 77 | 50 | 83 |
| AT T | 18 | 33 | 17 |
| A | 5 | 17 | 0 |

|  | MH | WT | CO |
|---|---|---|---|
| Cys C | 68 | 67 | 83 |
| TG U | 32 | 33 | 17 |
| Gln A | 12 | 75 | 17 |
| CA G | 88 | 25 | 83 |
| Glu A | 25 | 68 | 18 |
| GA G | 75 | 32 | 81 |
| Gly C | 50 | 7 | 50 |
| GG T | 12 | 43 | 7 |
| A | 14 | 29 | 14 |
| G | 24 | 21 | 29 |
| His C | 79 | 33 | 78 |
| CA T | 21 | 67 | 22 |
| Asp C | 75 | 13 | 75 |
| GA T | 25 | 88 | 25 |

|  | MH | WT | CO |
|---|---|---|---|
| Leu C | 26 | 12 | 30 |
| CT U | 5 | 9 | 0 |
| A | 3 | 9 | 0 |
| G | 58 | 3 | 70 |
| UU A | 2 | 55 | 0 |
| G | 6 | 12 | 0 |
| Lys A | 18 | 83 | 17 |
| AA G | 82 | 17 | 83 |
| Pro C | 48 | 0 | 57 |
| CC T | 19 | 57 | 14 |
| A | 16 | 29 | 14 |
| G | 17 | 14 | 14 |
| Phe C | 80 | 30 | 80 |
| TT T | 20 | 70 | 20 |

|  | MH | WT | CO |
|---|---|---|---|
| Ser C | 28 | 14 | 43 |
| TC U | 13 | 14 | 7 |
| A | 5 | 7 | 0 |
| G | 9 | 0 | 0 |
| AG C | 34 | 29 | 50 |
| U | 10 | 36 | 0 |
| Thr C | 57 | 9 | 64 |
| AC T | 14 | 45 | 9 |
| A | 14 | 45 | 9 |
| G | 15 | 0 | 18 |
| Tyr C | 74 | 20 | 80 |
| TA T | 26 | 80 | 20 |
| Val C | 25 | 25 | 38 |
| GT T | 7 | 0 | 0 |
| A | 5 | 50 | 0 |

```
             10        20        30
      ----------+---------+---------+-
  1  ATGAGCCGCCTGGACAAGAGCAAAGTGATC CO
  1  ATGTCTAGATTAGATAAAAGTAAAGTGATT WT 40        50        60
      ----------+---------+---------+-
 31  AACTCCGCCCTGGAGCTGCTGAATGAGGTC CO
 31  AACAGCGCATTAGAGCTGCTTAATGAGGTC WT 70        80        90
      ----------+---------+---------+-
 61  GGCATCGAGGGACTGACCACGCGCAAGCTG CO
 61  GGAATCGAAGGTTTAACAACCCGTAAACTC WT 100       110       120
      ----------+---------+---------+-
 91  GCCCAAAAGCTGGGCGTCGAGCAGCCGACC CO
 91  GCCCAGAAGCTAGGTGTAGAGCAGCCTACA WT 130       140       150
      ----------+---------+---------+-
121  CTGTATTGGCATGTGAAGAACAAGAGGGCC CO
121  TTGTATTGGCATGTAAAAAATAAGCGGGCT WT 160       170       180
      ----------+---------+---------+-
151  CTCCTGGACGCGCTCGCCATCGAAATGCTG CO
151  TTGCTCGACGCCTTAGCCATTGAGATGTTA WT 190       200       210
      ----------+---------+---------+-
181  GATCGGCACCACCACCCACTTCTGTCGCCTC CO
181  GATAGGCACCATAGTCACTTTTGCCCTTTA WT 220       230       240
      ----------+---------+---------+-
211  GAAGGCGAGAGCTGGCAGGACTTTCTGAGA CO
211  GAAGGGGAAAGCTGGCAAGATTTTTTACGT WT 250       260       270
      ----------+---------+---------+-
241  AACAACGCCAAGTCCTTCCGCTGCGCCCTC CO
241  AATAACGCTAAAAGTTTTAGATGTGCTTTA WT 280       290       300
      ----------+---------+---------+-
271  CTGAGCCATCGCGATGGGGCCAAGGTGCAC CO
271  CTAAGTCATCGCGATGGAGCAAAAGTACAT WT
```

```
       580        590        600
   ----------+----------+----------+-
571 GAA C T C ATCAT C T GCGG CC T G GA G AA G CA G   CO
571 GAA T T G ATCAT A T GCGG AT T A GA A AA A CA A   WT 610        620        630
   ----------+----------+----------+-
601 C T G AA G T G C GA G AG C GG C TCCG C T ACAGC   CO
601 C T T AA A T G T GA A AG T GG G TCCG G T ACAGC   WT 640        650
   ----------+----------+----------
631 GG C AG C A GGGA G TTC CGC TCTTA C T AA    CO
631 GG A TC C C GGGA A TTC AGA TCTTA T T AA    WT
```

| Virus | TITRE |
|---|---|
| 1 8.1T+pONY3.1+Rev | 1.29E+06 |
| 2 8.1T+pESYNGP+pClNeo | 6.55E+03 |
| 3 8.1T+pESYNGP+Rev | 3.42E+05 |
| 4 8.4NCZ+pESYNGP+Rev | 4.15E+05 |
| 5 8.4NCZ+pESYNGP+pClNeo | 2.59E+05 |
| 6 8.4NCT+pESYNGP+Rev | 4.19E+05 |
| 7 8.4NCT+pESYNGP+pClNeo | 1.92E+05 |
| 8 8.7NCT+pESYNGP+Rev | 3.59E+05 |
| 9 8.7NCT+pESYNGP+pClNeo | 4.41E+05 |
| 10 8.4NCT+pESYNGP+Rev | 3.94E+05 |
| 11 8.4NCT+pESYNGP+pClNeo | 2.44E+05 |
| 10 8.7NCZ+pESYNGP+pClNeo | 1.15E+06 |
| 11 8.7NCZ+pESYNGP+pESYNRev | 1.67E+06 |

CODON OPTIMISED HUMAN GDNF

ATGAAGCTGTGGGACGTGGTGGCCGTGTGCCTGGTGCTGCTGCACACCGCCTCCGCCTTC
CCCCTGCCCGCCGGCAAGCGCCCCCCTGAGGCCCCCGCCGAGGACCGCTCCCTGGGCCGC
CGCAGGGCCCCCTTCGCCCTGAGCAGCGACAGCAACATGCCCGAGGACTACCCCGACCAG
TTCGACGACGTGATGGACTTCATCCAGGCCACCATCAAGCGCCTGAAGCGCAGCCCCGAC
AAGCAGATGGCCGTGCTGCCCCGCCGCGAGCGCAACCGCCAGGCCGCCGCTGCCAACCCC
GAGAACTCCCGCGGCAAGGGCCGCCGCGGCCAGCGCGGCAAGAACCGCGGCTGCGTGCTG
ACCGCCATCCACCTGAACGTGACCGACCTGGGCCTGGGCTACGAGACCAAGGAGGAGCTG
ATCTTCCGCTACTGCAGCGGCAGCTGCGACGCCGCCGAGACCACCTACGACAAGATCCTG
AAGAACCTGTCCCGCAACCGCCGCCTGGTGAGCGACAAAGTGGGCCAGGCCTGCTGCCGC
CCCATCGCCTTCGACGACGACCTGAGCTTCCTGGACGACAACCTGGTGTACCACATCCTG
CGCAAGCACTCCGCCAAGCGCTGCGGCTGCATCTGA

FIGURE 29

VIRAL VECTOR

CROSS-REFERENCE TO RELATED APPLICATIONS

This application is a continuation-in-part of International application No. PCT/GB03/00418, filed on Feb. 3, 2003, which claims priority to British application Nos. GB 0202403.2, filed on Feb. 1, 2002, and GB 0212768.6, filed on May 31, 2002.

All of the foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates to a viral vector genome, a production system and viral particle comprising it, and particularly but not exclusively to its use in therapy. The present invention also relates to a method for identifying a target moiety and/or an associated modulating moiety. The present invention further relates to vector capable of being used in the identifying method of the present invention.

BACKGROUND OF THE INVENTION

Retroviral vector systems, such as lentiviral vector systems, have been proposed as a delivery system for inter alia the transfer of a nucleotide of interest to one or more sites of interest. Indeed, the concept of using viral vectors for gene therapy is well known (Verma and Somia (1997) Nature 389:239-242). Retrovirus genomes contain accessory genes, such as a rev gene, a tat gene, a vif gene, a nef gene, a vpr gene or an S2 gene. The deletion of such accessory genes, particularly when using retroviral vector systems in gene therapy is highly advantageous. Firstly it permits vectors to be produced without genes normally associated with disease in retroviral (e.g. HIV) infections. Secondly, the deletion of accessory genes permits the vector to package more heterologous DNA. Thirdly, genes whose function is unknown such as dUTPase and S2, may be omitted, thus reducing the risk of causing undesirable effects. We have previously taught, e.g. in our WO98/17815, how to remove many of the accessory genes. Further in our WO99/45126 we describe codon optimisation of the gag-pol sequence as a means of seeking to overcome the Rev/RRE requirement for export and to enhance RNA stability. However, the need remains to provide strategies for the provision of useful and safe viral vectors, and efficient means for their production.

For many gene transfer applications involving viral vectors, transduction of more than one gene is needed, and inconsistent results are sometimes obtained when coexpressing two transgenes linked by an internal ribosomal entry site (IRES) in a single bicistronic lentiviral vector (LV) transcript. Yu and coworkers described bicistronic LVs containing a gene of interest followed by an IRES and the GFP reporter gene that failed to emit detectable GFP fluorescence, possibly due to promoter interference (Yu, et al. (2003) Mol. Ther. 7: 827-38). Using a single LV containing two constitutive promoters, strong and sustained expression of both transgenes in transduced engrafting CD34(+) HSCs and their progeny was achieved, as well as in other human cell types. Thus, such dual-promoter LVs were found to coexpress multiple transgenes efficiently in a single target cell. However, it was heretofore unknown whether the presence of three promoters would be able to consistently and efficiently co-express multiple transgenes.

The present invention addresses these problems and particularly advantageously aims to provide a safer system in which viral accessory genes, such as rev, are not required in either the viral vector particle, which is used in treatment, or in their production. Further, the present invention addresses a need in the art for viral vectors that advantageously comprise three promoters that do not exhibit promoter interference and efficiently co-express multiple transgenes.

SUMMARY OF THE INVENTION

Thus in one aspect of the present invention there is provided a multicistronic retroviral vector genome comprising a first nucleic acid sequence upstream of an internal regulatory element, such as a promoter or an Internal Ribosome Entry Site (IRES), such that the level of genomic RNA available for packaging in the absence of rev, or a functional equivalent thereof, is increased.

Thus, we have also now found it possible to provide a viral vector which is independent of rev without detrimental effect on viral titre.

According to the present invention there is also provided a retroviral, such as a lentiviral vector wherein the vector is multicistronic and wherein the vector genome contains a nucleotide sequence operably linked to the viral LTR and wherein said nucleotide sequence is upstream of an internal regulatory element. The nucleotide sequence preferably encodes a polypeptide or fragment thereof.

According to the present invention there is also provided a retroviral, such as a lentiviral vector wherein the vector is multicistronic and wherein the vector genome contains a nucleotide sequence operably linked to the viral LTR and wherein said nucleotide sequence is upstream of an internal promoter or IRES and is capable of increasing the level of genomic RNA available for packaging in the absence of Rev. The nucleotide sequence preferably encodes a polypeptide or fragment thereof.

Preferably the vector genome is bi-, tricistronic, or quadcistronic.

Preferably the vector is in the form of a lentiviral vector genome.

Preferably the first nucleic acid sequence is an open reading frame (ORF) or a part thereof.

In one embodiment the first nucleic acid sequence is a reporter moiety or selectable marker.

Preferably the ORF is downstream of a viral LTR.

Preferably the ORF is operably linked to the LTR.

Preferably a nucleic acid sequence encoding the auxiliary gene rev, or a functional equivalent thereof, is disrupted such that said auxiliary gene is incapable of encoding the functional auxiliary proteins, or removed from the vector genome, or is not supplied in trans from another source.

In another embodiment the first nucleic acid sequence encodes a modulator gene.

Preferably the modulator gene is selected from tetracycline repressors, such as TetR, and tetracycline-controlled transactivators, such as tTA and rtTA.

Preferably the tetracycline repressor is codon optimised for expression in a mammalian cell.

Preferably the tetracycline repressor is linked to a nuclear localised signal.

In a preferred embodiment the vector further comprises one or more NOIs downstream of the internal promoter or IRES, and optionally operably linked thereto.

Preferably the NOI gives rise to a therapeutic effect.

In one embodiment one or more of the NOIs are operably linked to a tetracycline operator.

In another embodiment the vector comprises a further tetracycline repressor downstream of the internal promoter or IRES.

Preferably the vector is derived from HIV-1, HIV-2, SIV, FIV, BLV, EIAV, CEV or visna lentivirus.

Preferably the vector is derived from a non-primate lentivirus.

Preferably the vector genome comprises a cPPT sequence.

Preferably the vector genome comprises a post-transcriptional regulatory element or a translational element.

Preferably the ATG motifs of the gag packaging signal of the wild type lentiviral vector genome are ATTG motifs.

Preferably the distance between the R regions of the vector genome is substantially the same as that in the wild type lentiviral vector.

Preferably the 3' U3 region of the vector genome includes sequence from a viral and/or a eukaryotic promoter.

Preferably the 3' U3 region of the vector genome includes a wild type viral and/or a eukaryotic promoter.

Preferably the viral promoter is an EIAV or MLV U3 region.

Preferably the promoter is a self-inactivating LTR.

Thus according to the present invention there is provided a lentiviral vector wherein the vector has the following: the ATG motifs of the gag packaging signal of the wild type lentiviral vector are ATTG motifs; the distance between the R regions of the lentiviral vector is substantially the same as that in the wild type lentiviral vector; and the 3' U3 region of the lentiviral vector includes sequence from a viral and/or eukaryotic promoter. Preferably, the 3' U3 region may include sequence from either EIAV or MLV U3 region, or other viral or eukaryotic promoters. In one embodiment, the 3' U3 region may include wild type viral or eukaryotic promoters.

According to another aspect of the present invention there is provided a retroviral vector production system for producing a retrovirus-derived vector particle, which system comprises a set of nucleic acid sequences encoding the components of the vector including the vector genome of any one of claims, gag and pol proteins, env protein or a functional substitute therefor, wherein the genome of the vector is multicistronic and comprises a first nucleic acid sequence upstream of an internal regulatory element such as a promoter or an Internal Ribosome Entry Site (IRES), such that the level of genomic RNA available for packaging in the absence of rev, or analogous auxiliary gene from the lentivirus from which said particles are derived, is increased.

Preferably in the system a nucleic acid sequence encoding the auxiliary gene rev, or analogous auxiliary gene from the retrovirus from which said particles are derived, is disrupted such that said auxiliary gene is incapable of encoding the functional auxiliary proteins, or removed from the system, and is not supplied in trans from another source.

Preferably in the system the nucleic acid sequences encoding at least one of the auxiliary genes vpr, vif, tat and nef, or analogous auxiliary genes, from the retrovirus from which said particles are derived, are also disrupted such that said auxiliary genes are incapable of encoding the functional auxiliary proteins, or removed from the system.

Preferably the vector is derived from a lentivirus.

Preferably the vector is derived from HIV-1, HIV-2, SIV, FIV, BLV, EIAV, CEV or visna lentivirus.

Preferably the vector is derived from a non-primate lentivirus.

Preferably the set of nucleic acid sequences encoding the components of the vector includes three DNA constructs which encode the RNA genome of the vector, Gag and Pol proteins, and Env protein, or functional substitutes therefor.

According to another aspect of the present invention there is provided a DNA construct for use in the system of the present invention, said DNA construct encoding a packagable RNA vector genome according to the invention.

According to another aspect of the present invention there is provided a set of DNA constructs for use in the system of the invention comprising the DNA construct according to the invention, and a DNA construct encoding Gag and Pol proteins or functional substitute thereof.

Preferably the set further comprises a DNA construct encoding Env protein or a functional substitute thereof.

According to another aspect of the present invention there is provided a process for preparing a retroviral vector particle comprising introducing a set of nucleic acid sequences or DNA constructs of the invention into a host cell, obtaining the retroviral vector particle, and a retroviral vector particle produced by the system or process according to the invention.

According to another aspect of the present invention there is provided a retrovirus-derived vector particle comprising an RNA genome of the vector, Gag and Pol proteins, and Env protein, or functional substitutes therefor, wherein the genome of the vector is as defined according to the invention.

In another aspect there is provided a cell transduced with the retroviral vector particle of claim or DNA construct of the invention.

In another aspect of the invention there is provided a pharmaceutical composition comprising the vector, the system, a particle or a cell in accordance with the invention, together with a pharmaceutically acceptable carrier or diluent.

In another aspect of the invention there is provided use of a retroviral vector particle or DNA construct or cell of the invention for the preparation of a medicament to deliver an NOI to a target site in need of same.

In another aspect of the invention there is provided a delivery system in the form of a retroviral vector particle or DNA construct or cell of the invention for use in medicine.

In complex organisms, each gene product is part of a network or pathway that, in many cases, may represent only a single step in a series of complex intracellular or extracellular interactions and the function of a gene product appears to depend on its cellular context. Thus, by understanding the function of a gene product within a cell and tying it to a biological process, a candidate for pharmacological manipulation, that is a therapeutic target, can be identified. It is clear that establishing the value of any potential gene target entails the discovery and validation of its role in a disease process. Ideally, the unique role of the target candidate gene is elucidated in a disease-associated regulatory pathway. However, the genetic regulatory mechanisms at the cellular level are highly complex and reflect the intricate nature of the signalling pathways. The elucidation of the role of a potential target gene is also further complicated by issues of cell type specificity. That is, functions of a potential gene target in one cell type, or even in one species, may differ in another cell type.

Another problem is the elucidation of the relationship between a target gene, its clinical applicability and the resulting gene product. If there is a unique "cause and effect" relationship, in the biological regulatory system, then the function of a potential target gene may be relatively easy to elucidate. By way of example, some highly successful biopharmaceutical products, including insulin, erythropoietin (EPO), and granulocyte colony stimulating factor (GCSF), operate through their ability to modulate such relationships. However, unique "cause and effect" relationships are the exception and not the rule. In addition, developing receptor ligands as therapeutics is complicated by ligand redundancies and cell type specificities. By way of example, ligands such as vascular endothelial growth factors (VEGFs), fibroblast growth factors (FGFs), interleukins (IL-10, IL-12, IL-18 and so on), transforming growth factor beta (TGF-b) and tumour necrosis factors (TNFs) may display redundancies, cell type specificities and non linear dose dependencies may result in the failure of these potential therapeutics in clinical trials.

Previous attempts to address the challenges posed by cellular regulatory complexities have focused on developing techniques to help in unravelling and understanding the complex biological networks. These techniques have included but are not limited to methods for identifying individual pathway components including proteomics, multi hybrid systems, expression cloning and DNA chips. These methods work by inferring function from direct and indirect association between individual signalling components or by hypothesising function from correlation of events. However, such methods are laborious, time consuming and often deliver ambiguous results.

By way of example, novel assays for measuring the interaction of G proteins with G protein coupled receptors (GPCRs) have been developed that employ the "chip" concept to immobilize receptors on a solid surface to enable easy detection of their activity (see Bieri et al Nat Biotechnol (1999) 17: 1105-1108). The key feature of this system is that the receptor—G protein complex is immobilised on the sensor chip in a functional form. That is, the patterned immobilisation of GPCRs on a chip surface and the direct detection of a functional response. Possible applications of this approach include screening for small molecules or peptides that can activate either known or orphan receptors. However, this screening system suffers from the disadvantage that antagonists would not be recognised because the receptor must be active to cause G protein release. Moreover, technical problems associated with chip based screens include determining whether the GPCR will remain functional and accessible during high throughput screens.

Other approaches for addressing signalling pathway complexities have used engineered cell based assays to screen drug candidates for efficacy directly against specific disease related genetic sites using high throughput techniques, such as high throughput screens (HTS). Such screens are based on the activity of reporter genes introduced into cells that directly indicate the activity of a gene at any regulated site within the genome. By way of example, cell based assays are useful in identifying target GPCRs because if the target GPCR is cell based, then it must perform most aspects of the functions it would carry out in its native context including assembly into the plasma membrane in a proper ligand binding configuration and transduction of the ligand binding signal to the cell interior.

Some cell based screening methods have also been developed using retroviral vectors. By way of example, Li et al Nucleic Acids Research (2000) 28(13):2605-2612 discloses a functional genomics approach using a hairpin ribozyme gene library with randomized target recognition sequences constructed in a retroviral vector. By way of further example, Beger et al PNAS (2001) 98(1) 130-135 teaches that retroviral vectors can be used to produce a ribozyme library vector to identify cellular genes regulating BRCA1 expression. However, retroviral vector screens suffer from a disadvantage because retroviral vectors are unable to transduce non-dividing cells such as primary, differentiated non-dividing cells.

Consequently, although some target moieties have been identified to date using standard screening techniques, these screening techniques have not permitted the selection of a candidate moiety that is particular for a target host cell. In particular, these screening techniques have not permitted the development of a screening technique which is tailored for a particular target cell. More in particular, these screening techniques have not permitted the selection of a candidate moiety that is particular for a target host cell that has stopped differentiating and which is in a non-dividing state.

Thus the purpose of this aspect of the present invention is to provide a cell based screen to identify unknown components of cellular response pathways which may be useful as potential drug targets for therapeutic intervention.

This aspect of the present invention also seeks to identify components capable of interacting with these targets which may be useful as potential therapeutics.

The screens also facilitate the detection of altered cellular response to those which normally occur in a given environmental conditions or disease states.

This aspect of the present invention is advantageous because it provides a means for:
(i) Tailoring a screen to suit specific cells or disease states;
(ii) Identifying both new target moieties and/or associated modulating moieties, through combinations using a screen which can be performed using non-dividing or slowly dividing cell types such as a primary terminally differentiated non-dividing cell;
(iii) Identification of possible target and therapeutic sequences using a dual purpose screen;
(iv) Screening using pathways which are particularly relevant to the in vivo situation.

Other advantages are discussed and made apparent in the following commentary.

This aspect of the present invention seeks to provide an improved screening method for a candidate target moiety and/or an associated modulating moiety using a screening system that permits the selection of a candidate moieties and that is appropriate for a non-dividing or slowly dividing cell.

Thus, the present invention seeks to provide an improved screening method for a candidate target moiety using a screening system that permits the selection of a candidate target moiety and/or associated modulating moiety using a vector that is appropriate for a non-dividing or slowly dividing cell.

According to this aspect of the present invention there is provided a method for identifying a cellular response moiety and/or an associated modulating moiety wherein the method comprises:

(i) providing a target non-dividing or slowly dividing cell comprising a collection of NOIs encoding more than one modulating moiety;
(ii) optionally exposing the cell to a biological response modifier;
(iii) detecting a phenotypic difference between the target non-dividing or slowly dividing cell encoding or expressing at least one modulating moiety and a control cell lacking the modulating moiety, wherein the phenotypic difference is a consequence of the association of the modulating moiety with the cellular response moiety; and
(iv) recovering the cellular response moiety and/or the associated modulating moiety.

Examples of important target cells that do not divide include neurones, certain cells of the immune system, certain epithelial cells, liver cells and pancreatic islets. In addition, there are many cells, e.g. in a human body, that do divide but do so very slowly. These slowly dividing cells are also poor recipients of genes delivered by e.g. MLV-based vectors and they include cells within solid tumours and some non-neuronal cells in the brain. For example, most cells at any one time within a tumour are not dividing or are dividing slowly. In addition, cells which normally do not divide in the body may slowly divide when in culture, e.g. primary and neuronal cells in culture. Thus, the present invention is applicable to slowly dividing, as well as non-dividing, cells.

In a particularly preferred embodiment, the collection of NOIs is constructed in a viral vector. In particular, the viral vector may be selected from the group consisting of a lentiviral vector, an adenoviral vector, an adeno-associated vector, a herpes vector, a pox viral vector, a parvovirus vector and a baculoviral vector The use of a lentiviral vector is particularly preferred.

Preferably the viral vector of the present invention has a minimal viral genome.

As used herein, the term "minimal viral genome" means that the viral vector has been manipulated so as to remove the non-essential elements and to retain the essential elements in order to provide the required functionality to infect, transduce and deliver a nucleotide sequence of interest to a target host cell.

Preferably the viral vector with the minimal viral genome is a lentiviral vector.

In a further embodiment of the present invention, the library of candidate modulating moieties is introduced into an adeno-associated viral (AAV) vector.

In a further embodiment of the present invention, the library of candidate modulating moieties is introduced into an pox viral vector.

In a further embodiment of the present invention, the library of candidate modulating moieties is introduced into a herpes-virus vectors.

In a further embodiment of the present invention, the library of candidate modulating moieties is introduced into a baculoviral vector.

In a further embodiment of the present invention, the library of candidate modulating moieties is introduced into a parvovirus vectors (see Kestler et al 1999 Human Gene Ther 10(10):1619-32).

According to a second aspect of the present invention there is provided a method for identifying a target moiety and/or an associated modulating moiety wherein the method comprises:
optionally exposing the cell to a biological response modifier;
providing a target cell comprising a collection of NOIs constructed in a lentiviral vector and encoding more than one modulating moiety;
detecting a phenotypic difference between the target cell encoding or expressing at least one modulating moiety and a control cell lacking the modulating moiety, wherein the phenotypic difference is a consequence of the association of the modulating moiety with the target moiety; and
recovering the target moiety and/or the associated modulating moiety.

Lentiviral vectors of the invention will include primate lentiviral vectors such as HIV vectors (for example, HIV-1 and HIV-2 vectors) and SIV vectors, and non-primate lentiviral vectors. Primate lentiviral vectors have a number of disadvantages which may limit their therapeutic application to certain diseases. For example, HIV-1 has the disadvantage of being a human pathogen carrying potentially oncogenic proteins and sequences. There is the risk that introduction of vector particles produced in packaging cells which express HIV gag-pol will introduce these proteins into an individual leading to seroconversion. Therefore, in a particularly preferred embodiment, the lentiviral vector will be a non-primate lentiviral vector, such as EIAV, FIV, BIV, CAEV or MVV, with EIAV being especially preferred. Non-primate lentiviral-based vectors do not introduce HIV proteins into individuals.

In one embodiment the method further comprises isolating and/or sequencing the cellular response moiety and/or the associated modulating moiety.

In one preferred embodiment the phenotypic difference is a difference in transcription or expression of a reporter gene. Preferably, the reporter gene is operably linked to a regulatory moiety.

In another preferred embodiment, the phenotypic difference is a modulation in association of at least one polypeptide with another polypeptide.

Preferably, the phenotype difference is the appearance or loss of a detectable phenotype.

Preferably, the collection of NOIs is selected from the group consisting of a ribozyme library, an antisense library and a cDNA library. Alternatively, the NOI may be a polynucleotide sequence encoding a polypeptide selected from, or using, an antibody library. The antibody library will preferably be an intracellular antibody (or "intrabody") library.

In a preferred embodiment, the NOI is constitutively expressed. In another embodiment expression of the NOI is under the control of a regulatable promoter.

In a preferred embodiment, the optional biological response modifier mimics a disease state.

Preferably the lentivirus vector is an EIAV vector.

In a preferred embodiment the target cell comprises a reporter moiety operably linked to a regulatable moiety. In one embodiment the regulatory moiety is a regulatory element.

Regulatory elements include ischaemic like responsive elements (ILRE) such as the hypoxia responsive element (HRE). In another embodiment the regulatory element is a promoter.

According to another aspect of the present invention there is provided a target moiety and/or an associated modulating moiety identified by the method according to any one of the preceding claims.

According to a third aspect of the present invention there is provided a composition comprising the identified target moiety and/or the associated modulating moiety according to the present invention for use in medicine.

According to a fourth aspect of the present invention there is provided a method of treating a disease in a subject wherein the method comprises administering to the subject the identified target moiety and/or the associated modulating moiety according to the present invention.

According to a fifth aspect of the present invention there is provided use of the identified target moiety and/or the associated modulating moiety according to the present invention in the preparation of a medicament for the treatment of a disease associated with the cellular response moiety and/or the associated modulating moiety.

In a further aspect of the invention, use may be made of a library vector comprising:
(i) an optional first nucleotide sequence encoding a selectable marker;
(ii) one or more optional second nucleotide sequences each independently encoding a marker or modulating gene; and
(iii) a third nucleotide sequence, operably linked to a promoter, encoding a gene product capable of binding to and effecting the cleavage, directly or indirectly, of a nucleotide sequence;
wherein (i), (ii), and (iii) are operably linked to a regulatory sequence capable of directing transcription of (i), (ii), and (iii) as a continuous RNA molecule in a host.

In another embodiment use may be made of the target vector comprising:
(a) a first nucleotide sequence encoding a modulator gene;
(b) a second nucleotide sequence encoding a detectable marker gene which is operably linked to a nucleotide sequence upon which said first nucleotide sequence modulates, and a promoter; and
(c) a nucleotide sequence of interest;
wherein (a), (b) and (c) are operably linked to a regulatory sequence capable of directing transcription of (a), (b) and (c) as a continuous RNA molecule in a host.

The screening methods of the present invention may be used in a variety of applications. For example, cDNA libraries may be screened for proteins that interact with a protein of interest (functional genomics) to assist in dissecting protein interaction pathways.

Libraries of randomised sequences, especially partially randomised sequences may be used in directed evolution screens to "evolve" proteins or nucleotides with improved binding affinities or catalytic activity as compared to wild type proteins/nucleotides. For example, randomised libraries may be used to select DNA binding proteins with particular specificity for a given sequence. Another application of this approach is the affinity maturation of antibodies.

Other applications include screening libraries encoding peptides to identify peptide inhibitors or activators of proteins such as enzymes.

BRIEF DESCRIPTION OF THE DRAWINGS

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings in which:

FIG. 7 is a schematic representation of EIAV genomes;

FIGS. 8A and 8B give the total plasmid sequence of pONY8.1G (SEQ ID NO: 1);

FIGS. 9A-9C give the total plasmid sequence of pONY8.4ZCG (SEQ ID NO: 2);

FIGS. 10A-10C give the total plasmid sequence of pONY8.4GCZ (SEQ ID NO: 3);

FIG. 12 gives the sequence of the hybrid LTR (SEQ ID NO: 23);

FIGS. 13A-13C give the sequence of pONY8.1Zhyb (SEQ ID NO: 4);

FIGS. 17A-17C show the full sequence of pONY8.4TCOG (SEQ ID NO: 5);

FIGS. 18A-18C show the full sequence of pONY8.4TsynCOG/pONY8.4TsynCOG1 (SEQ ID NO: 6;

FIG. 21 shows the analysis of codon usage of the TetR gene. MH=Mammalian highly expressed genes, WT=wild type TetR gene, CO=codon optimised TetR gene. The codon use has been altered such that it more closely resembles that of highly expressed mammalian genes;

Figure 22B:
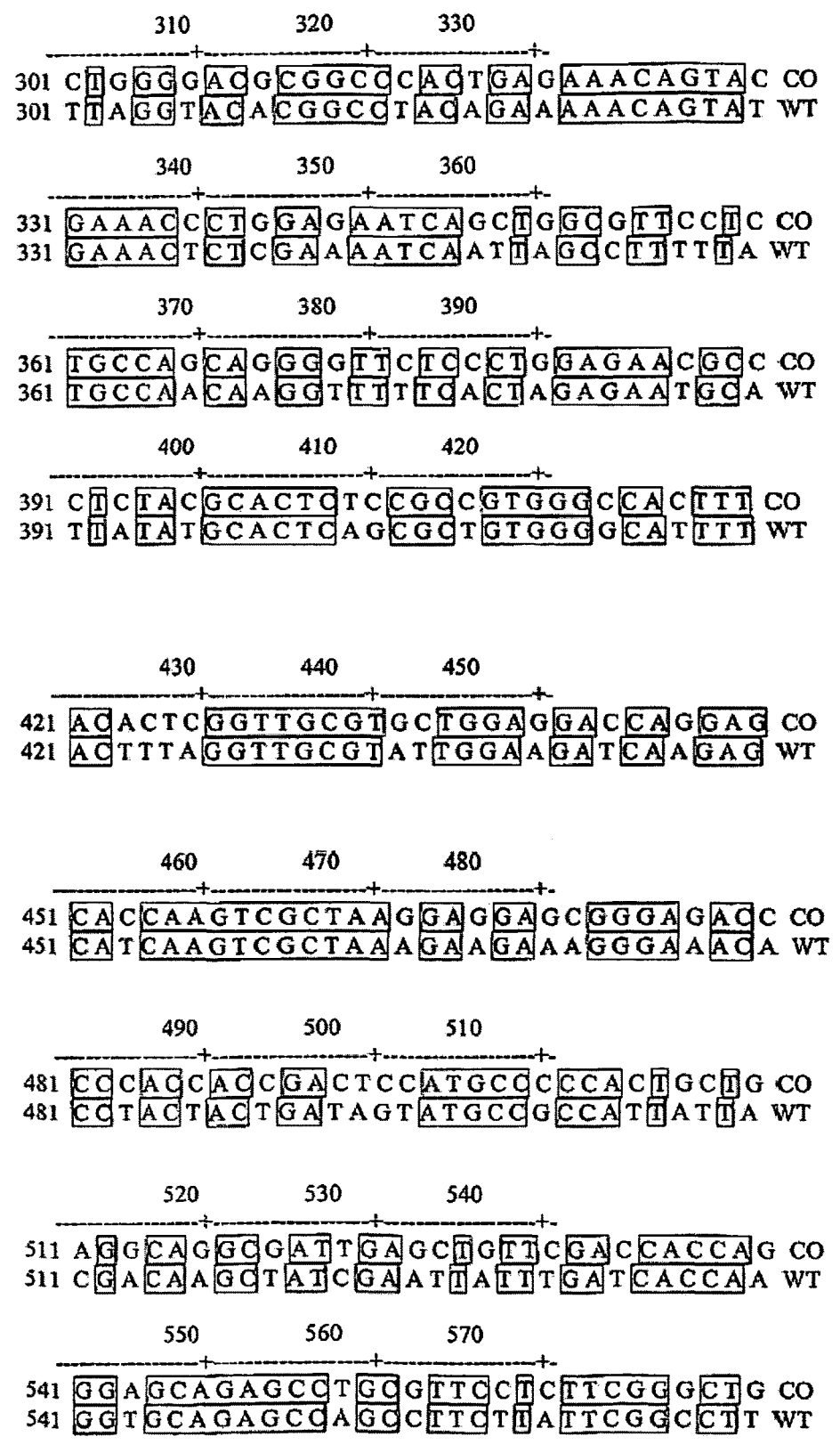

FIGS. 22A-22C show alignment of wild type (SEQ ID NO: 7) and codon-optimised Tet Repressor (SEQ ID NO: 8) gene sequences. The sequences are 71% identical at the nucleotide level (longest run of homology 13 bp);

FIG. 29 shows the codon-optimized sequence of GDNF (SEQ ID NO: 9).

DETAILED DESCRIPTION OF THE INVENTION

Figure 1:
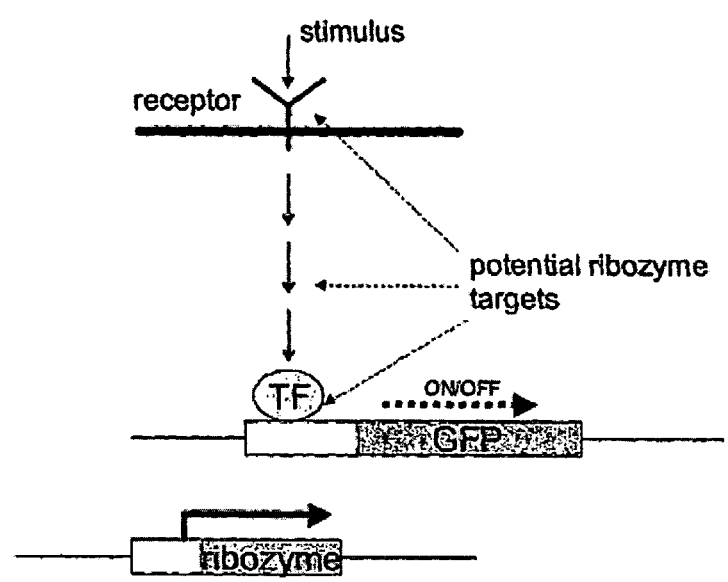
FIG. 1 is a schematic representation of the method of the present invention.

Various preferred features and embodiments of the present invention will now be described by way of non-limiting example. Although in general the techniques mentioned herein are well known in the art, reference may be made in particular to Sambrook et al., Molecular Cloning, A Laboratory Manual (1989) and Ausubel et al., Short Protocols in Molecular Biology (1999) $4^{th}$ Ed, John Wiley & Sons, Inc (as well as the complete version Current Protocols in Molecular Biology).

Retroviruses and Lentiviruses

As previously mentioned, the concept of using viral vectors for gene therapy is well known (Verma and Somia (1997) Nature 389:239-242).

There are many retroviruses. For the present application, the term "retrovirus" includes: murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses.

A detailed list of retroviruses may be found in Coffin et al ("Retroviruses" 1997 Cold Spring Harbour Laboratory Press Eds: J M Coffin, S M Hughes, H E Varmus pp 758-763).

Lentiviruses also belong to the retrovirus family, but they can infect both dividing and non-dividing cells (Lewis et al (1992) EMBO J. 3053-3058).

The lentivirus group can be split into "primate" and "non-primate". Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

Details on the genomic structure of some lentiviruses may be found in the art. By way of example, details on HIV and EIAV may be found from the NCBI Genbank database (i.e. Genome Accession Nos. AF033819 and AF033820 respectively). Examples of HIV-1 variants may be found in the HIV databases maintained by Los Alamos National Laboratory. Details of EIAV clones may be found at the NCBI database maintained by the National Institutes of Health.

During the process of infection, a retrovirus initially attaches to a specific cell surface receptor. On entry into the susceptible host cell, the retroviral RNA genome is then copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular genes. The provirus encodes the proteins and other factors required to make more virus, which can leave the cell by a process sometimes called "budding".

Each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5'end of the RNA. The sizes of the three elements can vary considerably among different retroviruses.

For the viral genome, the site of transcription initiation is at the boundary between U3 and R in the left hand side LTR and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins. Some retroviruses have any one or more of the following genes that code for proteins that are involved in the regulation of gene expression: tat, rev, tax and rex.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome. The env gene encodes the surface (SU) glycoprotein and the transmembrane (TM) protein of the virion, which form a complex that interacts specifically with cellular receptor proteins. This interaction leads ultimately to infection by fusion of the viral membrane with the cell membrane.

Retroviruses may also contain "additional" genes which code for proteins other than gag, pol and env. Examples of additional genes include in HIV, one or more of vif, vpr, vpx, vpu, tat, rev and nef EIAV has (amongst others) the additional gene S2.

Proteins encoded by additional genes serve various functions, some of which may be duplicative of a function provided by a cellular protein. In EIAV, for example, tat acts as a transcriptional activator of the viral LTR. It binds to a stable, stem-loop RNA secondary structure referred to as TAR. Rev regulates and co-ordinates the expression of viral genes through rev-response elements (RRE). The mechanisms of action of these two proteins are thought to be broadly similar to the analogous mechanisms in the primate viruses. The function of S2 is unknown. In addition, an EIAV protein, Ttm, has been identified that is encoded by the first exon of tat spliced to the env coding sequence at the start of the transmembrane protein.

In one embodiment of the present invention, the lentiviral vector of the present invention is a recombinant lentiviral vector.

As used herein, the term "recombinant lentiviral vector" (RLV) refers to a vector with sufficient genetic information to allow packaging of an RNA genome, in the presence of packaging components, into a viral particle capable of infecting and transducing a target cell. Infection and transduction of a target cell includes reverse transcription and integration into the target cell genome. The RLV carries non-viral coding sequences which are to be delivered by the vector to the target cell. An RLV is incapable of independent replication to produce infectious retroviral particles within the final target cell. Usually the RLV lacks a functional gag-pol and/or env gene and/or other genes essential for replication. The vector of the present invention may be configured as a split-intron vector. An example of a split intron vector is described WO 99/15683.

Preferably the recombinant lentiviral vector (RLV) of the present invention has a minimal viral genome.

As used herein, the term "minimal viral genome" means that the viral vector has been manipulated so as to remove the non-essential elements and to retain the essential elements in order to provide the required functionality to infect, transduce and deliver a nucleotide sequence of interest to a target host cell. Further details on this strategy can be found in our WO98/17815.

A minimal lentiviral genome for use in the present invention will therefore comprise (5') R—U5—one or more first nucleotide sequences—(regulatory element-NOI)$_n$-U3-R (3'). However, the plasmid vector used to produce the lentiviral genome within a host cell/packaging cell will also include transcriptional regulatory control sequences operably linked to the lentiviral genome to direct transcription of the genome in a host cell/packaging cell. These regulatory sequences may be the natural sequences associated with the transcribed retroviral sequence, i.e. the 5' U3 region, or they may be a heterologous promoter such as another viral promoter, for example the CMV promoter. Some lentiviral genomes require additional sequences for efficient virus production. For example, in the case of HIV, rev and RRE sequence are preferably included. However the requirement for rev and RRE may be reduced or eliminated by using the present invention. Further details of this strategy can be found in our WO01/79518. In addition, the requirement for rev can be further reduced or eliminated by the use of a vector which has at least one of the following: the ATG motifs of the gag packaging signal of the wild type viral vector are ATTG motifs; the distance between the R regions of the viral vector is substantially the same as that in the wild type viral vector; the 3' U3 region of the viral vector includes sequence from an MLV U3 region; and a nucleotide sequence operably linked to the viral LTR and wherein said nucleotide sequence is upstream of an internal promoter and wherein said nucleotide sequence preferably encodes a polypeptide or fragment thereof.

Alternative sequences which perform the same function as the rev/RRE system are also known. For example, a functional analogue of the rev/RRE system is found in the Mason Pfizer monkey virus. This is known as CTE and comprises an RRE-type sequence in the genome which is believed to interact with a factor in the infected cell. The cellular factor can be thought of as a rev analogue. Thus, CTE may be used as an alternative to the rev/RRE system. Any other functional equivalents which are known or become available may be relevant to the invention. For example, it is also known that the Rex protein of HTLV-I can functionally replace the Rev protein of HIV-1. It is also known that Rev and Rex have similar effects to IRE-BP.

In a preferred embodiment, the viral genome of the first aspect of the invention lacks the Rev response element (RRE).

In a preferred embodiment, the system used in the present invention is based on a so-called "minimal" system in which some or all of the additional genes have been removed.

In one embodiment of the present invention, the lentiviral vector is a self-inactivating vector. In other words the viral promoter is a self-inactivating LTR.

By way of example, self-inactivating retroviral vectors have been constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus (Yu et al 1986 Proc Natl Acad Sci 83: 3194-3198; Dougherty and Temin 1987 Proc Natl Acad Sci 84: 1197-1201; Hawley et al 1987 Proc Natl Acad Sci 84: 2406-2410; Yee et al 1987 Proc Natl Acad Sci 91: 9564-9568). However, any promoter(s) internal to the LTRs in such vectors will still be transcriptionally active. This strategy has been employed to eliminate effects of the enhancers and promoters in the viral LTRs on transcription from internally placed genes. Such effects include increased transcription (Jolly et al 1983 Nucleic Acids Res 11: 1855-1872) or suppression of transcription (Emerman and Temin 1984 Cell 39: 449-467). This strategy can also be used to eliminate downstream transcription from the 3' LTR into genomic DNA (Herman and Coffin 1987 Science 236: 845-848). This is of particular concern in human gene therapy where it is of critical importance to prevent the adventitious activation of an endogenous oncogene.

In one embodiment of the present invention the lentiviral vector is derived from a non-primate lentivirus. The non-primate lentivirus may be any member of the family of lentiviridae which does not naturally infect a primate and may include a feline immunodeficiency virus (FIV), a bovine immunodeficiency virus (BIV), a caprine arthritis encephalitis virus (CAEV), a Maedi visna virus (MVV) or an equine infectious anaemia virus (EIAV). Preferably the lentivirus is an EIAV. Equine infectious anaemia virus infects all equidae resulting in plasma viremia and thrombocytopenia (Clabough, et al. 1991. J. Virol. 65:6242-51). Virus replication is thought to be controlled by the process of maturation of monocytes into macrophages.

EIAV has the simplest genomic structure of the lentiviruses and is particularly preferred for use in the present invention. In addition to the gag, pol and env genes EIAV encodes three other genes: tat, rev, and S2. Tat acts as a transcriptional activator of the viral LTR (Derse and Newbold 1993 Virology. 194:530-6; Maury, et al 1994 Virology. 200:632-42) and Rev regulates and coordinates the expression of viral genes through rev-response elements (RRE) (Martarano et al 1994 J. Virol. 68:3102-11). The mechanisms of action of these two proteins are thought to be broadly similar to the analogous mechanisms in the primate viruses (Martarano et al ibid). The function of S2 is unknown. In addition, an EIAV protein, Ttm, has been identified that is encoded by the first exon of tat spliced to the env coding sequence at the start of the transmembrane protein.

In our WO99/32646 we give details of features which may advantageously be applied to the present invention. In particular, it will be appreciated that the non-primate lentivirus genome (1) preferably comprises a deleted gag gene wherein the deletion in gag removes one or more nucleotides downstream of about nucleotide 350 or 354 of the gag coding sequence; (2) preferably has one or more accessory genes absent from the non-primate lentivirus genome; (3) preferably lacks the tat gene but includes the leader sequence between the end of the 5' LTR and the ATG of gag; and (4) combinations of (1), (2) and (3). In a particularly preferred embodiment the lentiviral vector comprises all of features (1) and (2) and (3).

Use may also be made of a lentiviral, e.g., non-primate, vector wherein the vector has at least one of the following: the ATG motifs of the gag packaging signal of the wild type lentiviral vector are ATTG motifs; the distance between the R regions of the lentiviral vector is substantially the same as that in the wild type lentiviral vector; the 3' U3 region of the lentiviral vector includes sequence from an MLV U3 region; and a nucleotide sequence operably linked to the viral LTR and wherein said nucleotide sequence is upstream of an internal promoter and wherein said nucleotide sequence preferably encodes a polypeptide or fragment thereof. As indicated above such a vector is independent of rev without detrimental effect on titre. It may also be used to deliver a nucleotide of interest (NOI) to a target cell. In a further preferred embodiment of the first aspect of the invention, one or more nucleotides of interest (NOI) is introduced into the vector at the cloning site. Preferably the NOI is a therapeutic gene, and such therapeutic genes may be expressed from a promoter placed in the retroviral LTR or may be expressed from an internal promoter introduced at the cloning site. In a preferred embodiment, the NOI is introduced downstream of an internal regulatory element.

It will be appreciated that the present invention may be used to deliver a nucleotide of interest (NOI) to a target cell. In a further preferred embodiment of the first aspect of the invention, one or more nucleotides of interest (NOI) is introduced into the vector at the cloning site. Preferably the NOI is a therapeutic gene, and such therapeutic genes may be expressed from a promoter placed in the retroviral LTR or may be expressed from an internal promoter introduced at the cloning site. In a preferred embodiment the NOI is introduced downstream of an internal regulatory element.

Delivery Systems

Retroviral vector systems have been proposed as a delivery system for inter alia the transfer of a NOI to one or more sites of interest. The transfer can occur in vitro, ex vivo, in vivo, or combinations thereof. Retroviral vector systems have even been exploited to study various aspects of the retrovirus life cycle, including receptor usage, reverse transcription and RNA packaging (reviewed by Miller, 1992 Curr Top Microbiol Immunol 158:1-24).

A recombinant retroviral vector particle is capable of transducing a recipient cell with an NOI. Once within the cell the RNA genome from the vector particle is reverse transcribed into DNA and integrated into the DNA of the recipient cell.

As used herein, the term "vector genome" refers to both to the RNA construct present in the retroviral vector particle and the integrated DNA construct. The term also embraces a separate or isolated DNA construct capable of encoding such an RNA genome. A retroviral or lentiviral genome should comprise at least one component part derivable from a retrovirus or a lentivirus. The term "derivable" is used in its normal sense as meaning a nucleotide sequence or a part thereof which need not necessarily be obtained from a virus such as a lentivirus but instead could be derived therefrom. By way of example, the sequence may be prepared synthetically or by use of recombinant DNA techniques. Preferably the genome comprises a psi region (or an analogous component which is capable of causing encapsidation).

The viral vector genome is preferably "replication defective" by which we mean that the genome does not comprise sufficient genetic information alone to enable independent replication to produce infectious viral particles within the recipient cell. In a preferred embodiment, the genome lacks a functional env, gag or pol gene. In a highly preferred embodiment the genome lacks env, gag and pol genes.

The viral vector genome may comprise some or all of the long terminal repeats (LTRs). Preferably the genome comprises at least part of the LTRs or an analogous sequence which is capable of mediating proviral integration, and transcription. The sequence may also comprise or act as an enhancer-promoter sequence.

The viral vector genome of the first aspect of the invention may be provided as a kit of parts. For example, the kit may comprise (i) a plasmid or plasmids containing the NOIs and IRES sequence(s); and (ii) a retroviral genome construct with suitable restriction enzyme recognition sites for cloning the NOIs and IRES(s) into the viral genome.

It is known that the separate expression of the components required to produce a retroviral vector particle on separate DNA sequences cointroduced into the same cell will yield retroviral particles carrying defective retroviral genomes that carry therapeutic genes (e.g. Reviewed by Miller 1992). This cell is referred to as the producer cell (see below).

There are two common procedures for generating producer cells. In one, the sequences encoding retroviral Gag, Pol and Env proteins are introduced into the cell and stably integrated into the cell genome; a stable cell line is produced which is referred to as the packaging cell line. The packaging cell line produces the proteins required for packaging retroviral RNA but it cannot bring about encapsidation due to the lack of a psi region. However, when a vector genome according to the first aspect of the invention (having a psi region) is introduced into the packaging cell line, the helper proteins can package the psi-positive recombinant vector RNA to produce the recombinant virus stock. This can be used to transduce the NOI into recipient cells. The recombinant virus whose genome lacks all genes required to make viral proteins can infect only once and cannot propagate. Hence, the NOI is introduced into the host cell genome without the generation of potentially harmful retrovirus. A summary of the available packaging lines is presented in "Retroviruses" (1997 Cold Spring Harbour Laboratory Press Eds: J M Coffin, S M Hughes, H E Varmus pp 449).

The present invention also provides a packaging cell line comprising a viral vector genome of the first aspect of the invention. For example, the packaging cell line may be transduced with a viral vector system comprising the genome or transfected with a plasmid carrying a DNA construct capable of encoding the RNA genome. The present invention also provides a retroviral (or lentiviral) vector particle produced by such a cell.

The second approach is to introduce the three different DNA sequences that are required to produce a retroviral vector particle i.e. the env coding sequences, the gag-pol coding sequence and the defective retroviral genome containing one or more NOIs into the cell at the same time by transient transfection and the procedure is referred to as transient triple transfection (Landau & Littman 1992; Pear et al 1993). The triple transfection procedure has been optimised (Soneoka et al 1995; Finer et al 1994). WO 94/29438 describes the production of producer cells in vitro using this multiple DNA transient transfection method.

The components of the viral system which are required to complement the vector genome may be present on one or more "producer plasmids" for transfecting into cells.

The present invention also provides a vector system, comprising
(i) a viral genome according to the first aspect of the invention;
(ii) a nucleotide sequence coding for lentiviral gag and pol proteins;
(iii) nucleotide sequences encoding other essential viral packaging components not encoded by the nucleotide sequence of ii). In a preferred embodiment, the nucleotide sequence of (iii) is capable of encoding an env protein. The present invention also provides a cell transfected with such a vector system and a retroviral vector particle produced by such a cell. Preferably the gag-pol sequence is codon optimised for use in the particular producer cell (see below).

The env protein encoded by the nucleotide sequence of iii) may be a homologous retroviral or lentiviral env protein. Alternatively, it may be a heterologous env, or an env from a non-retro or lentivirus (see below under "pseudotyping").

The term "viral vector system" is used generally to mean a kit of parts which can be used when combined with other necessary components for viral particle production to produce viral particles in host cells. For example, the retroviral vector genome may lack one or more of the genes needed for viral replication. This may be combined in a kit with a further complementary nucleotide sequence or sequences, for example on one or more producer plasmids. By cotransfection of the genome together with the producer plasmid(s), the necessary components should be provided for the production of infectious viral particles.

Alternatively, the complementary nucleotide sequence(s) may be stably present within a packaging cell line that is included in the kit.

The present invention also relates to a lentiviral vector system which is capable of delivering an RNA genome to a recipient cell, wherein the genome is longer than the wild type genome of the lentivirus. The vector system may, for example, be an EIAV vector system.

Preferably the RNA genome of the vector system has up to 5%, more preferably up to 10% more bases than the wild-type genome. Preferably the RNA genome is about 10% longer than the wild-type genome. For example, wild type EIAV comprises an RNA genome of approximately 8 kb. An EIAV vector system of the present invention may have an RNA genome of up to (preferably about) 8.8 kb.

Preferably the retroviral vector system of the present invention is a self-inactivating (SIN) vector system.

By way of example, self-inactivating retroviral vector systems have been constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus. However, any promoter(s) internal to the LTRs in such vectors will still be transcriptionally active. This strategy has been employed to eliminate effects of the enhancers and promoters in the viral LTRs on transcription from internally placed genes. Such effects include increased transcription or suppression of transcription. This strategy can also be used to eliminate downstream transcription from the 3' LTR into genomic DNA. This is of particular concern in human gene therapy where it may be important to prevent the adventitious activation of an endogenous oncogene.

Preferably a recombinase assisted mechanism is used which facilitates the production of high titre regulated lentiviral vectors from the producer cells of the present invention.

As used herein, the term "recombinase assisted system" includes but is not limited to a system using the Cre recombinase/loxP recognition sites of bacteriophage P1 or the site-specific FLP recombinase of *S. cerevisiae* which catalyses recombination events between 34 bp FLP recognition targets (FRTs).

The site-specific FLP recombinase of *S. cerevisiae* which catalyses recombination events between 34 bp FLP recognition targets (FRTs) has been configured into DNA constructs in order to generate high level producer cell lines using recombinase-assisted recombination events (Karreman et al (1996) NAR 24:1616-1624). A similar system has been developed using the Cre recombinase/loxP recognition sites of bacteriophage P1 (Vanin et al (1997) J. Virol 71:7820-7826). This was configured into a lentiviral genome such that high titre lentiviral producer cell lines were generated.

By using producer/packaging cell lines, it is possible to propagate and isolate quantities of retroviral vector particles (e.g. to prepare suitable titres of the retroviral vector particles) for subsequent transduction of, for example, a site of interest (such as adult brain tissue). Producer cell lines are usually better for large scale production or vector particles.

Transient transfection has numerous advantages over the packaging cell method. In this regard, transient transfection avoids the longer time required to generate stable vector-producing cell lines and is used if the vector genome or retroviral packaging components are toxic to cells. If the vector genome encodes toxic genes or genes that interfere with the replication of the host cell, such as inhibitors of the cell cycle or genes that induce apoptosis, it may be difficult to generate stable vector-producing cell lines, but transient transfection can be used to produce the vector before the cells die. Also, cell lines have been developed using transient infection that produce vector titre levels that are comparable to the levels obtained from stable vector-producing cell lines (Pear et al 1993, PNAS 90:8392-8396).

Producer cells/packaging cells can be of any suitable cell type. Producer cells are generally mammalian cells but can be, for example, insect cells.

As used herein, the term "producer cell" or "vector producing cell" refers to a cell which contains all the elements necessary for production of retroviral vector particles.

Preferably, the producer cell is obtainable from a stable producer cell line.

Preferably, the producer cell is obtainable from a derived stable producer cell line.

Preferably, the producer cell is obtainable from a derived producer cell line.

As used herein, the term "derived producer cell line" is a transduced producer cell line which has been screened and selected for high expression of a marker gene. Such cell lines support high level expression from the retroviral genome. The term "derived producer cell line" is used interchangeably with the term "derived stable producer cell line" and the term "stable producer cell line.

Preferably the derived producer cell line includes but is not limited to a retroviral and/or a lentiviral producer cell.

Preferably the derived producer cell line is an HIV or EIAV producer cell line, more preferably an EIAV producer cell line.

Preferably the envelope protein sequences, and nucleocapsid sequences are all stably integrated in the producer and/or packaging cell. However, one or more of these sequences could also exist in episomal form and gene expression could occur from the episome.

As used herein, the term "packaging cell" refers to a cell which contains those elements necessary for production of infectious recombinant virus which are lacking in the RNA genome. Typically, such packaging cells contain one or more producer plasmids which are capable of expressing viral structural proteins (such as codon optimised gag-pol and env) but they do not contain a packaging signal.

The term "packaging signal" which is referred to interchangeably as "packaging sequence" or "psi" is used in reference to the non-coding, cis-acting sequence required for encapsidation of retroviral RNA strands during viral particle formation. In HIV-1, this sequence has been mapped to loci extending from upstream of the major splice donor site (SD) to at least the gag start codon.

Packaging cell lines suitable for use with the above-described vector constructs may be readily prepared (see also WO 92/05266), and utilised to create producer cell lines for the production of retroviral vector particles. As already mentioned, a summary of the available packaging lines is presented in "Retroviruses" (as above).

Also as discussed above, simple packaging cell lines, comprising a provirus in which the packaging signal has been deleted, have been found to lead to the rapid production of undesirable replication competent viruses through recombination. In order to improve safety, second generation cell lines have been produced wherein the 3'LTR of the provirus is deleted. In such cells, two recombinations would be necessary to produce a wild type virus. A further improvement involves the introduction of the gag-pol genes and the env gene on separate constructs so-called third generation packaging cell lines. These constructs are introduced sequentially to prevent recombination during transfection.

Preferably, the packaging cell lines are second generation packaging cell lines.

Preferably, the packaging cell lines are third generation packaging cell lines.

In these split-construct, third generation cell lines, a further reduction in recombination may be achieved by changing the codons. This technique, based on the redundancy of the genetic code, aims to reduce homology between the separate constructs, for example between the regions of overlap in the gag-pol and env open reading frames.

The packaging cell lines are useful for providing the gene products necessary to encapsidate and provide a membrane protein for a high titre vector particle production. The packaging cell may be a cell cultured in vitro such as a tissue culture cell line. Suitable cell lines include but are not limited to mammalian cells such as murine fibroblast derived cell lines or human cell lines. Preferably the packaging cell line is a human cell line, such as for example: HEK293, 293-T, TE671, HT1080.

Alternatively, the packaging cell may be a cell derived from the individual to be treated such as a monocyte, macrophage, blood cell or fibroblast. The cell may be isolated from an individual and the packaging and vector components administered ex vivo followed by re-administration of the autologous packaging cells.

In more detail, the packaging cell may be an in vivo packaging cell in the body of an individual to be treated or it may be a cell cultured in vitro such as a tissue culture cell line. Suitable cell lines include mammalian cell such as murine fibroblast derived cell lines or human cell lines. Preferably the packaging cell line is a human cell line, such as 293 cell line, HEK293, 293-T, TE671 or HT1080.

Alternatively, the packaging cell may be a cell derived from the individual to be treated, such as a monocyte, macrophage, stem cell, blood cell or fibroblast. The cell may be isolated from an individual and the packaging and vector components administered ex vivo, followed by re-administration of the autologous packaging cells. Alternatively, the packaging and vector components may be administered to the packaging cell in vivo. Methods for introducing lentiviral packaging and vector components into cells of an individual are known in the art. For example, one approach is to introduce the different DNA sequences that are required to produce a lentiviral vector particle e.g. the env coding sequence, the gag-pol coding sequence and the defective lentiviral genome into the cell simultaneously by transient triple transfection (Landau and Littman 1992 J. Virol. 66, 5110; Soneoka et al. 1995 Nucleic Acids Res 23:628-633).

In one embodiment, the vector configuration of the present invention uses, as a production system, three transcription units expressing a genome, the gag-pol components and an envelope. The envelope expression cassette may include one of a number of envelopes such as VSV-G or various murine retrovirus envelopes such as 4070A.

Conventionally, these three cassettes would be expressed form three plasmids transiently transfected into an appropriate cell line such as 293T or from integrated copies in a stable producer cell line. An alternative approach is to use another virus as an expression system for the three cassettes, for example baculovirus or adenovirus. These are both nuclear expression systems. To date, the use of a poxvirus to express all of the components of a lentiviral vector system has not been described. In particular, given the unusual codon usage of lentiviruses and their requirement for RNA handling systems such as the rev/RRE system it has not been clear whether incorporation of all three cassettes and their subsequent expression in a vector that expresses in the cytoplasm rather than the nucleus is feasible. Until now, the possibility remained that key nuclear factors and nuclear RNA handling pathways would be required for expression of the vector components and their function in the gene delivery vehicle. Here we describe such a system and show that lentiviral components can be made in the cytoplasm and that they assemble into functional gene delivery systems. The advantage of this system Is the ease with which poxviruses can be handled, the high expression levels and the ability to retain the introns in the vector genomes.

The lentiviral vector particle according to the invention will also be capable of transducing cells which are slowly-dividing, and which non-lentiviruses such as MLV would not be able to efficiently transduce. Slowly-dividing cells divide once in about every three to four days including certain tumour cells. Although tumours contain rapidly dividing cells, some tumour cells, especially those in the center of the tumour, divide infrequently. Alternatively, the target cell may be a growth-arrested cell capable of undergoing cell division, such as a cell in a central portion of a tumour mass or a stem cell such as a haematopoietic stem cell or a CD34-positive cell. As a further alternative, the target cell may be a precursor of a differentiated cell, such as a monocyte precursor, a CD33-positive cell, or a myeloid precursor. As a further alternative, the target cell may be a differentiated cell, such as a neuron, astrocyte, glial cell, microglial cell, macrophage, monocyte, epithelial cell, endothelial cell or hepatocyte. Target cells may be transduced either in vitro after isolation from a human individual or may be transduced directly in vivo.

It is highly desirable to use high-titre virus preparations in both experimental and practical applications. Techniques for increasing viral titre include using a psi plus packaging signal as discussed above and concentration of viral stocks.

As used herein, the term "high titre" means an effective amount of a retroviral vector or particle which is capable of transducing a target site such as a cell.

As used herein, the term "effective amount" means an amount of a regulated retroviral or lentiviral vector or vector particle which is sufficient to induce expression of the NOIs at a target site.

A high-titre viral preparation for a producer/packaging cell is usually of the order of $10^5$ to $10^7$ retrovirus particles per ml. For transduction in tissues such as the brain, it is necessary to use very small volumes, so the viral preparation is concentrated by ultracentrifugation. The resulting preparation should have at least $10^8$ t.u./ml, preferably from $10^8$ to $10^9$ t.u./ml, more preferably at least $10^9$ t.u./ml. (The titer is expressed in transducing units per ml (t.u./ml) as titred on a standard D17 cell line.)

The NOIs may be operatively linked to one or more promoter/enhancer elements. Transcription of one or more NOI may be under the control of viral LTRs or alternatively promoter-enhancer elements can be engineered in with the transgene. Preferably the promoter is a strong promoter such as CMV, described in U.S. Pat. Nos. 4,963,481 and 5,168,062, the contents of which are incorporated herein by reference. The CMV promoter may also be truncated, as disclosed in U.S. Pat. Nos. 6,156,567 and 6,090,393, incorporated herein by reference. The promoter may be a regulated promoter. The promoter may be tissue-specific.

The presence of a sequence termed the central polypurine tract (cPPT) may improve the efficiency of gene delivery to non-dividing cells. This cis-acting element is located, for example, in the EIAV polymerase coding region element. Preferably the genome of the present invention comprises a cPPT sequence.

Preferably the viral genome comprises a post-translational regulatory element. For example, the genome may comprise an element such as the woodchuck hepatitis virus posttranscriptional regulatory element (WPRE).

In addition, or in the alternative, the viral genome may comprise a translational enhancer.

Pseudotyping

In the design of retroviral vector systems it is desirable to engineer particles with different target cell specificities to the native virus, to enable the delivery of genetic material to an expanded or altered range of cell types. One manner in which to achieve this is by engineering the virus envelope protein to alter its specificity. Another approach is to introduce a heterologous envelope protein into the vector particle to replace or add to the native envelope protein of the virus.

The term pseudotyping means incorporating in at least a part of, or substituting a part of, or replacing all of, an env gene of a viral genome with a heterologous env gene, for example an env gene from another virus. Pseudotyping is not a new phenomenon and examples may be found in WO 99/61639, WO-A-98/05759, WO-A-98/05754, WO-A-97/17457, WO-A-96/09400, WO-A-91/00047 and Mebatsion et al 1997 Cell 90, 841-847. In a preferred embodiment of the present invention the vector system is pseudotyped with a gene encoding at least part of the rabies G protein. In a further preferred embodiment of the present invention the vector system is pseudotyped with a gene encoding at least part of the VSV-G protein.

In more detail, the term "lentiviral particle" refers to the packaged retroviral vector that is preferably capable of binding to and entering target cells. The components of the particle, as already discussed for the vector, may be modified with respect to the wild type retrovirus. For example, the Env proteins in the proteinaceous coat of the particle may be genetically modified in order to alter their targeting specificity or achieve some other desired function.

Preferably, the viral vector preferentially transduces a certain cell type or cell types.

More preferably, the viral vector is a targeted vector, that is it has a tissue tropism which is altered compared to the native virus, so that the vector is targeted to particular cells. For lentiviral vectors, this may be achieved by modifying the Env protein. The Env protein of the retroviral secondary vector needs to be a non-toxic envelope or an envelope which may be produced in non-toxic amounts within the primary target cells, such as for example a MMLV amphotropic envelope or a modified amphotropic envelope. The safety feature in such a case is preferably the deletion of regions or sequence homology between lentiviral components.

Preferably the envelope is one which allows transduction of human cells. Examples of suitable env genes include, but are not limited to, VSV-G, a MLV amphotropic env such as the 4070A env, the RD114 feline leukaemia virus env or haemagglutinin (HA) from an influenza virus. The Env protein may be one which is capable of binding to a receptor on a limited number of human cell types and may be an engineered envelope containing targeting moieties. The env and gag-pol coding sequences are transcribed from a promoter and optionally an enhancer active in the chosen packaging cell line and the transcription unit is terminated by a polyadenylation signal. For example, if the packaging cell is a human cell, a suitable promoter-enhancer combination is that from the human cytomegalovirus major immediate early (hCMBV-MIE) gene and a polyadenylation signal from SV40 virus may be used. Other suitable promoters and polyadenylation signals are known in the art.

It has been demonstrated that a primate lentivirus minimal system can be constructed which requires none of the HIV/SIV additional genes vif, vpr, vpx, vpu, tat, rev and nef for either vector production or for transduction of dividing and non-dividing cells. It has also been demonstrated that an EIAV minimal vector system can be constructed which does not require S2 for either vector production or for transduction of dividing and non-dividing cells. The deletion of additional genes is highly advantageous. Firstly, it permits vectors to be produced without the genes associated with disease in lentiviral (e.g. HIV) infections. In particular, tat is associated with disease. Secondly, the deletion of additional genes permits the vector to package more heterologous DNA. Thirdly, genes whose function is unknown, such as S2, may be omitted, thus reducing the risk of causing undesired effects. Examples of minimal lentiviral vectors are disclosed in WO-A-99/32646 and in WO-A-98/17815.

Thus, preferably, the delivery system used in the invention is devoid of at least tat and S2 (if it is an EIAV vector system), and possibly also vif vpr, vpx, vpu and nef More preferably, the systems of the present invention are also devoid of rev. Rev was previously thought to be essential in some retroviral genomes for efficient virus production. For example, in the case of HIV, it was thought that rev and RRE sequence should be included. However, it has been found that the requirement for rev and RRE can be reduced or eliminated by codon optimisation (see below) or by replacement with other functional equivalent systems such as the MPMV system. As expression of the codon optimised gag-pol is REV independent, RRE can be removed from the gag-pol expression cassette, thus removing any potential for recombination with any RRE contained on the vector genome.

In a preferred embodiment the viral genome of the first aspect of the invention lacks the Rev response element (RRE).

In a preferred embodiment, the system used in the present invention is based on a so-called "minimal" system in which some or all of the additional genes have be removed.

Open Reading Frame (ORF)

The first nucleic acid sequence is a sequence which is capable of increasing the levels of genomic RNA which is available for packaging in the absence of Rev for example compared with the situation in which the first nucleic acid sequence is not present. Preferably the first nucleic acid sequence is an open reading frame (ORF), or a fragment thereof which increases the level of genomic RNA available for packaging in the absence of Rev. By ORF we include a series of codon triplets that include a 5' initiation codon (which may be a Kozac sequence) running through to a termination codon, and representing a putative or known gene. However any nucleic acid sequence which increases the level of genomic RNA for packaging may be used.

Thus the present invention relates to a multi-cistronic vector genome which has an ORF or partial ORF downstream and preferably operably linked to the viral LTR, and upstream of a regulatory element such as an internal promoter or IRES. The ORF can be neomycin or hypoxanthine-guanine phosphoribosyltransferase (HPRT).

When the vector genome is used with packaging components in which Rev is absent, such as through use of a codon optimised gag-pol gene it is possible to produce a totally minimal vector without any accessory viral genes, either in the producer or target cell.

Whilst not wishing to be bound by any theory we believe that in the system of the invention the transcript of the first nucleic acid sequence is recognised by a cell as being a "true" mRNA and therefore worthy of export from the nucleus. In the absence of such a sequence the mRNA appears to be degraded in the nucleus, through for example "nonsense mediated decay", before it is transported to the cytoplasm and subsequently packaged. The accessory protein Rev appears to allow bypass of this surveillance system and thus maintains viral titres where the vector genome would otherwise be degraded. The present invention provides an alternative and safer way of maintaining viral titres.

It should be noted that a genome in which a portion of the ORF was reversed resulted in differing Rev-dependencies of the parental and derivative genomes. Whilst not wishing to be bound by any theory we believe this is due to the presence of an ORF in the parental (Rev independent) genome which was destroyed in the derivative (Rev-dependent) genome. Thus, the ORF should be in the correct, and not reverse, orientation.

Usefully the ORF may be between about 0.6 to 4 kbp, for example about 0.65 or 0.7 to 3.1 or 3.0 kbp.

In one embodiment the first nucleic acid sequence is operably linked to a viral LTR, but the sequence may equally well be operably linked to another regulatory element.

Preferably the first nucleic acid sequence may be a selection gene also referred to as selectable marker. Typical selection genes encode proteins that confer resistance to antibiotics and other toxins, e.g. ampicillin, neomycin, methotrexate or tetracycline, complement auxotrophic deficiencies, or supply critical nutrients not available from complex media. Further details on suitable first nucleic acid sequences is given below in the sections on reporter genes.

It is also possible for the first nucleic acid sequence to be the nucleotide of interest (NOI) and further details on NOIs are given below; although it is generally preferable for the NOI to be operably linked to the internal promoter or IRES to obtain good levels of expression. However, the NOI may be operably linked to the LTR if a lower level of expression is desired, for example, if the NOI is cytotoxic. In this embodiment, a nucleic acid sequence such as a marker gene may be placed downstream of an internal regulatory element.

Tetracycline-Regulated Expression Systems

In another preferred embodiment the first nucleic acid sequence is a Tet repressor gene, optionally linked to a nuclear localised signal (NLS). Whilst not wishing to be bound by any theory we believe that the addition of an NLS to the carboxy terminus increases the concentration of TetR in the nucleus since the amino terminus of TetR is important for binding of the tetracycline operator (tetO). Thus in this embodiment at least one of the downstream NOIs will be the tetO. In one preferred embodiment at least a second copy of the Tet repressor gene is present downstream of an IRES or internal promoter.

In a further preferred embodiment the Tet repressor gene is codon optimised for expressed in a mammalian system. Further details on codon optimisation are given below.

Thus the present invention relates to an improved TetR gene sequence for tetracycline-regulated expression in mammalian cells obtained by codon optimisation. Thus, tetracycline-regulated expression systems have wide-ranging utility in many applications where inducible gene expression is advantageous or essential. The improvement in gene expression which may arise from codon optimising the effector protein may significantly enhance the efficiency of the system by facilitating more rapid TetR-mediated expression.

The present invention also relates to altering the 5' sequence of the TetR gene such that the first AUG is in a more favourable context for expression, thereby improving the fidelity of initiation by eukaryotic ribosomes. In one embodiment the 5' sequence is 5' gccGCCACCAUGG 3' (SEQ ID NO: 10). The G is position +4 would change the codon from serine or require insertion of an additional amino acid residue.

The present invention further relates to incorporation of an NLS increasing local concentration of TetR in the nucleus.

Codon Optimisation

Codon optimisation has previously been described in WO99/41397. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Codon optimisation has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. Codon optimisation also overcomes the Rev/RRE requirement for export, rendering optimised sequences Rev independent. Codon optimisation also reduces homologous recombination between different constructs within the vector system (for example between the regions of overlap in the gag-pol and env open reading frames). The overall effect of codon optimisation is therefore a notable increase in viral titre and improved safety.

In one embodiment only codons relating to INS are codon optimised. However, in a much more preferred and practical embodiment, the sequences are codon optimised in their entirety, with the exception of the sequence encompassing the frameshift site.

The gag-pol gene comprises two overlapping reading frames encoding gag and pol proteins respectively. The expression of both proteins depends on a frameshift during translation. This frameshift occurs as a result of ribosome "slippage" during translation. This slippage is thought to be caused at least in part by ribosome-stalling RNA secondary structures. Such secondary structures exist downstream of the frameshift site in the gag-pol gene. For HIV, the region of overlap extends from nucleotide 1222 downstream of the beginning of gag (wherein nucleotide 1 is the A of the gag ATG) to the end of gag (nt 1503). Consequently, a 281 bp fragment spanning the frameshift site and the overlapping region of the two reading frames is preferably not codon optimised. Retaining this fragment will enable more efficient expression of the gag-pol proteins.

For EIAV the beginning of the overlap has been taken to be nt 1262 (where nucleotide 1 is the A of the gag ATG). The end of the overlap is at 1461 bp. In order to ensure that the frameshift site and the gag-pol overlap are preserved, the wild type sequence has been retained from nt 1156 to 1465.

Derivations from optimal codon usage may be made, for example, in order to accommodate convenient restriction sites, and conservative amino acid changes may be introduced into the gag-pol proteins.

In a highly preferred embodiment, codon optimisation was based on lightly expressed mammalian genes. The third and sometimes the second and third base may be changed.

Due to the degenerate nature of the Genetic Code, it will be appreciated that numerous gag-pol sequences can be achieved by a skilled worker. Also there are many retroviral variants described which can be used as a starting point for generating a codon optimised gag-pol sequence. Lentiviral genomes can be quite variable. For example there are many quasi-species of HIV-1 which are still functional. This is also the case for EIAV. These variants may be used to enhance particular parts of the transduction process. Examples of HIV-1 variants may be found in the HIV databases maintained by Los Alamos National Laboratory. Details of EIAV clones may be found at the NCBI database maintained by the National Institutes of Health.

The strategy for codon optimised gag-pol and TetR sequences can be used in relation to any retrovirus. This would apply to all lentiviruses, including EIAV, FIV, BIV, CAEV, VMR, SIV, HIV-1 and HIV-2. In addition this method could be used to increase expression of genes from HTLV-1, HTLV-2, HFV, HSRV and human endogenous retroviruses (HERV), MLV and other retroviruses.

Codon optimisation can render gag-pol expression Rev independent. In order to enable the use of anti-rev or RRE factors in the retroviral vector, however, it would be necessary to render the viral vector generation system totally Rev/RRE independent. Thus, the genome also needs to be modified. This is achieved by optimising vector genome components. Advantageously, these modifications also lead to the production of a safer system absent of all additional proteins both in the producer and in the transduced cell.

As described above, the packaging components for a retroviral vector include expression products of gag, pol and env genes. In addition, efficient packaging depends on a short sequence of 4 stem loops followed by a partial sequence from gag and env (the "packaging signal"). Thus, inclusion of a deleted gag sequence in the retroviral vector genome (in addition to the full gag sequence on the packaging construct) will optimise vector titre. To date efficient packaging has been reported to require from 255 to 360 nucleotides of gag in vectors that still retain env sequences, or about 40 nucleotides of gag in a particular combination of splice donor mutation, gag and env deletions. It has surprisingly been found that a deletion of all but the N-terminal 360 or so nucleotides in gag leads to an increase in vector titre. Thus, preferably, the retroviral vector genome includes a gag sequence which comprises one or more deletions, more preferably the gag sequence comprises about 360 nucleotides derivable from the N-terminus.

The TetR sequence may be usefully codon optimised using the codons shown in FIG. 21.

NOIs

In the present invention, the term NOI (nucleotide sequence of interest) includes any suitable nucleotide sequence, which need not necessarily be a complete naturally occurring DNA or RNA sequence. Thus, the NOI can be, for example, a synthetic RNA/DNA sequence, a recombinant RNA/DNA sequence (i.e. prepared by use of recombinant DNA techniques), a cDNA sequence or a partial genomic DNA sequence, including combinations thereof. The sequence need not be a coding region. If it is a coding region, it need not be an entire coding region. In addition, the RNA/DNA sequence can be in a sense orientation or in an anti-sense orientation. Preferably, it is in a sense orientation. Preferably, the sequence is, comprises, or is transcribed from cDNA.

The NOI(s), also referred to as "heterologous sequence(s)", "heterologous gene(s)" or "transgene(s)", may be any one or more of, for example, a selection gene(s), marker gene(s) and therapeutic gene(s).

The NOI may be a candidate gene which is of potential significance in a disease process. Thus the vector system of the present invention may, for example, be used for target validation purposes.

The NOI may have a therapeutic or diagnostic application. Suitable NOIs include, but are not limited to: sequences encoding enzymes, cytokines, chemokines, hormones, antibodies, anti-oxidant molecules, engineered immunoglobulin-like molecules, a single chain antibody, fusion proteins, immune co-stimulatory molecules, immunomodulatory molecules, anti-sense RNA, small interfering RNA (siRNA), a transdominant negative mutant of a target protein, a toxin, a conditional toxin, an antigen, a tumour suppresser protein and growth factors, membrane proteins, pro-angiogenic proteins and peptides, vasoactive proteins and peptides, antiviral proteins and ribozymes, and derivatives thereof (such as with an associated reporter group). The NOIs may also encode pro-drug activating enzymes.

The NOI coding sequence may encode a segment of a coding sequence.

The lentiviral vector of the present invention may be used to deliver a NOI such as a pro-drug activating enzyme to a tumour site for the treatment of a cancer. In each case, a suitable pro-drug is used in the treatment of the individual (such as a patient) in combination with the appropriate pro-drug activating enzyme. An appropriate pro-drug is administered in conjunction with the vector. Examples of pro-drugs include: etoposide phosphate (with alkaline phosphatase, Senter et al 1988 Proc Natl Acad Sci 85: 4842-4846); 5-fluorocytosine (with cytosine deaminase, Mullen et al 1994 Cancer Res 54: 1503-1506); Doxorubicin-N-p-hydroxyphenoxyacetamide (with Penicillin-V-Amidase, Kerr et al 1990 Cancer Immunol Immunother 31: 202-206); Para-N-bis(2-chloroethyl) aminobenzoyl glutamate (with carboxypeptidase G2); Cephalosporin nitrogen mustard carbamates (with β-lactamase); SR4233 (with P450 Reductase); Ganciclovir (with HSV thymidine kinase, Borrelli et al 1988 Proc Natl Acad Sci 85: 7572-7576); mustard pro-drugs with nitroreductase (Friedlos et al 1997 J Med Chem 40: 1270-1275) and Cyclophosphamide (with P450 Chen et al 1996 Cancer Res 56: 1331-1340).

Preferably the NOI is useful in the treatment of a neurodegenerative disorder.

More preferably the NOI is useful in the treatment of Parkinson's disease.

The NOI may encode an enzyme involved in dopamine synthesis. For example, the enzyme may be one of the following: Tyrosine Hydroxylase, GTP-cyclohydrolase I and/or Aromatic Amino Acid Dopa Decarboxylase. The sequences of all three genes are available: Accession Nos. X05290, U19523 and M76180 respectively.

Alternatively the NOI may encode the vesicular monoamine transporter 2 (VMAT2). In a preferred embodiment the viral genome comprises an NOI encoding Aromatic Amino Acid Dopa Decarboxylase and an NOI encoding VMAT 2. Such a genome may be used in the treatment of Parkinson's disease, in particular in conjunction with peripheral administration of L-DOPA.

Alternatively the NOI may encode a factor capable of blocking or inhibiting degeneration in the nigrostriatal system. An example of such a factor is a neurotrophic factor. For example the NOI may encode glial cell-line derived neurotrophic factor (GDNF) or brain-derived neurotrophic factor (BDNF).

Lentiviral delivery of GDNF (lenti-GDNF) was tested for its trophic effects upon degenerating nigrostriatal neurons in nonhuman primate models of Parkinson's disease (PD) (see U.S. patent application Ser. No. 10/008,610, incorporated herein by reference). Lentiviral-GDNF vectors were injected into the striatum and substantia nigra of nonlesioned aged rhesus monkeys or young adult rhesus monkeys treated 1 week prior with 1-methyl-4-phenyl-1,2,3,6-tetrahydropyridine (MPTP). Extensive GDNF expression with anterograde and retrograde transport was seen in all animals. In aged monkeys, lentiviral-GDNF vectors augmented dopaminergic function. In MPTP-treated monkeys, lentiviral-GDNF vectors reversed functional deficits and completely prevented nigrostriatal degeneration. Additionally, lentiviral-GDNF vectors injections to intact rhesus monkeys revealed long-term gene expression (at least 8 months). In MPTP-treated monkeys, lentiviral-GDNF vector treatment reversed motor deficits in a hand-reach task. These data indicate that GDNF delivery using a lentiviral vector system can prevent nigrostriatal degeneration and induce regeneration in PD and are thus a viable therapeutic strategy for PD patients and patients with neurodegenerative conditions.

Alternatively the NOI may encode a neuroprotective factor. In particular, the NOI(s) may encode molecules which prevent TH-positive neurons from dying or which stimulate regeneration and functional recovery in the damaged nigrostriatal system.

The NOI may encode anti-angiogenic factors for treating some symptoms of Type I diabetes, growth hormone deficiencies, diabetic retinopathies, age-related macular degeneration (AMD), cancer, and anemia.

Hypothalamic diabetes insipidus (DI) is a disorder caused by a lack of arginine vasopressin (AVP), normally produced by magnocellular neurons of the supraoptic nuclei (SON) of the hypothalamus. AVP is secreted from the pituitary gland into the bloodstream and acts on the kidney, causing water reabsorption. In the AVP-deficient Brattleboro rat, AVP is not produced, causing copious water intake and secretion of dilute urine. Self-inactivating (SIN) minimal EIAV vector genomes with enhanced transduction efficiency (SMART vectors) can be used to express rat AVP in this rat model of DI. The EIAV-AVP treated animals showed a reduction of daily water intake and urine volume output compared to control animals (injected with EIAV-GFP), reaching levels similar to wild type rats. AVP was also detected in the urine of EIAV-AVP treated animals, indicating that the hormone is now produced in the SON and released in the bloodstream where it is corrects water balance. A tetracycline regulatable lentiviral system can also be used to increase AVP expression, following addition of doxycycline.

The NOI may encode all or part of the protein of interest ("POI"), or a mutant, homologue or variant thereof. For example, the NOI may encode a fragment of the POI which is capable of functioning in vivo in an analogous manner to the wild-type protein.

In a highly preferred embodiment, one of the NOIs comprises a truncated form of the TH gene, lacking the regulatory domain. Such an NOI avoids feed-back inhibition by dopamine which may limit expression of the full-length enzyme.

The term "mutant" includes POIs which include one or more amino acid variations from the wild-type sequence. For example, a mutant may comprise one or more amino acid additions, deletions or substitutions. A mutant may arise naturally, or may be created artificially (for example by site-directed mutagenesis).

Internal Ribosome Entry Site (IRES)

The viral genome of the first aspect of the invention comprises one or more NOIs. In order for more than one of the NOIs to be expressed, there may be two or more transcription units within the vector genome, one for each NOI. However, it is clear from the literature that retroviral vectors achieve the highest titres and most potent gene expression properties if they are kept genetically simple (PCT/GB96/01230; Bowtell et al., 1988 J. Virol. 62, 2464; Correll et al., 1994 Blood 84, 1812; Emerman and Temin 1984 Cell 39, 459; Ghattas et al., 1991 Mol. Cell. Biol. 11, 5848; Hantzopoulos et al., 1989 PNAS 86, 3519; Hatzoglou et al., 1991 J. Biol. Chem 266, 8416; Hatzoglou et al., 1988 J. Biol. Chem 263, 17798; L1 et al., 1992 Hum. Gen. Ther. 3, 381; McLachlin et al., 1993 Virol. 195, 1; Overell et al., 1988 Mol. Cell Biol. 8, 1803; Scharfinan et al., 1991 PNAS 88, 4626; Vile et al., 1994 Gene Ther 1, 307; Xu et al., 1989 Virol. 171, 331; Yee et al., 1987 PNAS 84, 5197) and so it is preferable to use an internal ribosome entry site (IRES) to initiate translation of the second (and subsequent) coding sequence(s) in a poly-cistronic message (Adam et al 1991 J. Virol. 65, 4985).

Insertion of IRES elements into retroviral vectors is compatible with the retroviral replication cycle and allows expression of multiple coding regions from a single promoter (Adam et al (as above); Koo et al (1992) Virology 186:669-675; Chen et al 1993 J. Virol 67:2142-2148). IRES elements were first found in the non-translated 5' ends of picornaviruses where they promote cap-independent translation of viral proteins (Jang et al (1990) Enzyme 44: 292-309). When located between open reading frames in an RNA, IRES elements allow efficient translation of the downstream open reading frame by promoting entry of the ribosome at the IRES element followed by downstream initiation of translation.

A review on IRES is presented by Mountford and Smith (TIG May 1995 vol 11, No 5:179-184). A number of different IRES sequences are known including those from encephalomyocarditis virus (EMCV) (Ghattas, I. R., et al., Mol. Cell. Biol., 11:5848-5859 (1991); BiP protein [Macejak and Sarnow, Nature 353:91 (1991)]; the Antennapedia gene of drosphilia (exons d and e) [Oh, et al., Genes & Development, 6:1643-1653 (1992)] as well as those in polio virus (PV) [Pelletier and Sonenberg, Nature 334: 320-325 (1988); see also Mountford and Smith, TIG 11, 179-184 (1985)].

According to WO-A-97/14809, IRES sequences are typically found in the 5' non-coding region of genes. In addition to those in the literature they can be found empirically by looking for genetic sequences that affect expression and then determining whether that sequence affects the DNA (i.e. acts as a promoter or enhancer) or only the RNA (acts as an IRES sequence).

IRES elements from PV, EMCV and swine vesicular disease virus have previously been used in retroviral vectors (Coffin et al, as above).

The term "IRES" includes any sequence or combination of sequences which work as or improve the function of an IRES.

The IRES(s) may be of viral origin (such as EMCV IRES or PV IRES) or cellular origin.

In order for the IRES to be capable of initiating translation of each NOI, it should be located between NOIs in the vector genome. In other words there will always be one fewer IRES sequences than NOIs. For example, for a multicistronic sequence containing n NOIs, the genome may be as follows: $[(NOI_{1-n-1})-(IRES_{1-n-1})]-NOI_n$ For bi and tricistronic sequences, the order may be as follows:
$NOI_1-IRES_1-NOI_2$
$NOI_1-IRES_1—NOI_2-IRES_2-NOI_3$ The one or more NOIs may also be operably linked to an internal promoter. A discussion on promoters is given below. It is also possible to use a combination of promoters and IRESs.

Transduced Cells

The present invention also relates to a cell which has been transduced with a vector system comprising a viral genome according to the first aspect of the invention.

Transduction with the vector system of the present invention may confer or increase the ability of the cell to produce catecholamines. It may, for example, confer or increase the ability of the cell to convert tyrosine to L-dopa and/or L-dopa to dopamine. Release of catecholamines can be measured by techniques known in the art, for example by using an electrochemical detector connected to an analytical cell. In addition of the catecholamines themselves, biproducts associated with catecholamine release (such as DOPAC, a specific degradation product of dopamine) may also be detected.

The cell may be transduced in vivo, in vitro or ex vivo. For example, if the cell is a cell from a mammalian subject, the cell may be removed from the subject and transduced ready for reimplantation into the subject (ex vivo transduction). Alternatively the cell may be transduced by direct gene transfer in vivo, using the vector system of the present invention in accordance with standard techniques (such as via injection of vector stocks expressing the NOIs). If the cell is part of a cell line which is stable in culture (i.e. which can survive numerous passages and can multiple in vitro) then it may be transduced in vitro by standard techniques, for example by exposure of the cell to viral supernatants comprising vectors expressing the NOIs.

The cell may be any cell which is susceptible to transduction. If the vector system is capable of transducing non-dividing cells (for example if it is a lentiviral system) then the cell may be a non-dividing cell such as a neuron.

In a preferred embodiment the transduced cell forms part of a genetically modified neuronal cell line. Such a cell line may, for example, be transplanted into the brain for the treatment of Parkinson's disease.

In a further embodiment the cell is a neuronal stem cell. Such a cell line may, for example, be transplanted into the brain for the treatment of Parkinson's disease.

In a further embodiment the cell is a cell in the striatum of a subject, such as a neuron or glial cell. Direct gene transfer in vivo to such a cell may, for example, convert it into a dopamine-producer cell.

Cassettes

The present invention also provides multicistronic cassettes comprising an ORF and two or more NOIs operably linked by a regulatory element such as an IRES or internal promoter. These cassettes may be used in a method for producing the vector genome in a producer cell.

The present invention also provides an expression vector comprising such a cassette. Transfection of a suitable cell with such an expression vector should result is a cell which expresses each POI encoded by the NOI in the cassette. The present invention also provides such a transfected cell.

Cloning of the cassette into an expression vector and transfection of cells with the vector (to give expression of the cassette) can be carried out by techniques well known in the art (such as those described in Sambrook et al. (Molecular Cloning: A Laboratory Manual, 2nd Edition, Cold Spring Harbor Laboratory press (1989)), and other laboratory textbooks).

Preferably the cassette comprises a promoter. In a highly preferred embodiment the cassette is bicistronic or tricistronic and comprises the following elements:
LTR-ORF-Promoter/IRES-($NOI_1$)-($IRES_1$)-($NOI_2$)
LTR-ORF-Promoter/IRES-($NOI_1$)-($IRES_1$)-($NOI_2$)-($IRES_2$)-($NOI_3$)

In a particularly preferred embodiment the cassette is bicistronic and comprises an NOI encoding tyrosine hydroxylase (or a mutant, variant or homologue thereof) and an NOI encoding GTP-cyclohydrolase I (or a mutant, variant or homologue thereof).

In another particularly preferred embodiment the cassette is tricistronic and comprises an NOI encoding tyrosine hydroxylase (or a mutant, variant or homologue thereof), an NOI encoding GTP-cyclohydrolase I (or a mutant, variant or homologue thereof) and an NOI encoding Aromatic Amino Acid Dopa Decarboxylase (or a mutant, variant or homologue thereof).

Target Moiety and Signalling Pathways

Aspects of the present invention allows the identification of unidentified components of a signalling pathway. Such a component is referred to herein as a "target moiety". The identified component of the signalling pathway or target moiety may be useful as a drug target. The expression "signalling pathway" refers to any one or more of the events that result in, or from, (and including) activation of a pathway. Preferably, by "signalling pathway" we refer to a signal transduction pathway comprising elements which interact, genetically and/or molecularly. The signalling pathway includes signalling events taking place extracellularly or at the cell membrane, as well as signalling events taking place intracellularly, for example within the cell cytoplasm or within the cell nucleus.

There is no particular restriction on the signalling pathways to which the present invention could be applied; although it should be one for which a phenotypic difference can be measured.

Examples of pathways to which the invention could usefully be applied include the Neu-Ras pathway which is associated with breast cancer, and the apoptosis pathway. A number of other pathways are implicated in breast and other cancers, for example: ErbB receptor family, oestrogen receptor, insulin-like growth factor (IGF), integrin receptor system. In prostate cancer the androgen receptor (AR) signalling pathway is thought to play a crucial role in early development as well as later progression of the disease.

A non-limiting list of disease states for which the present invention has application is later. For example, the present invention may be useful in relation to Parkinson's disease and other neuronal diseases.

In the case of patients with sickle cell disease, for example, it would be advantageous to induce expression of foetal haemoglobin. Using the promoter of this gene to drive reporter expression, peptides of cDNAs may be identified which induce expression of foetal haemoglobin. However, if expression of the gene is repressed in the adult, the use of an antisense or ribozyme library would be more appropriate. Similarly, in the case of Duchenne muscular dystrophy (DMD), caused by the loss through mutation of the protein dystrophin, research is focused on the up-regulation of the utrophin gene.

Modulating Moiety

The modulating moiety is capable of affecting the signalling pathway by associating with the target moiety, i.e. it is a compound which is capable of up-regulating or down-regulating the signalling pathway.

The term "modulate" as used herein refers to a change in the biological activity of the signalling pathway. Thus, modulation of a pathway includes inhibition or down-regulation of signalling, e.g. by compounds which block, at least to some extent, the normal biological activity of the signalling pathway. Alternatively, the term "modulation" may refer to the activation or up-regulation of signalling, e.g. by compounds which stimulate or upregulate, at least to some extent, the normal biological activity of the signalling pathway.

By modulating signalling transduction we include:
(a) activation of the signalling pathway by (i) dominant negative or inhibitors of repressors and (ii) activators; and
(b) blockade of the signalling pathway by (i) dominant negative or inhibitors of activators and (ii) inhibitors.

The modulating moiety will preferably be selected from polypeptides and fragments thereof, linear peptides, cyclic peptides, and nucleic acids which encode therefor, synthetic and natural compounds including low molecular weight organic or inorganic compounds, ribozymes, antisense molecules and antibodies.

It will be appreciated that non-functional homologues of a polypeptide of the invention may also be tested for modulation of any given signalling pathway (e.g. for inhibition of cell cycle progression) since they may compete with the wild type protein for binding to other components of the signalling pathway whilst being incapable of the normal functions of the protein. Alternatively, they may block the function of the protein when bound to a component of the signalling pathway. Such non-functional homologues may include naturally occurring mutants and modified sequences or fragments thereof.

Alternatively, instead of preventing the association of the components directly, the substance may suppress the biologically available amount of a polypeptide of the invention. This may be by inhibiting expression of the component, for example at the level of transcription, transcript stability, translation or post-translational stability. An example of such a substance would be antisense RNA or double-stranded interfering RNA sequences which suppresses the amount of mRNA biosynthesis.

Suitable candidate substances include peptides, especially of from about 5 to 30 or 10 to 25 amino acids in size, based on the sequence of the polypeptides described in the Examples, or variants of such peptides in which one or more residues have been substituted. Peptides from panels of peptides comprising random sequences or sequences which have been varied consistently to provide a maximally diverse panel of peptides may be used.

Suitable candidate substances also include antibody products (for example, monoclonal and polyclonal antibodies, single chain antibodies, chimeric antibodies and CDR-grafted antibodies) which are specific for a polypeptide of the invention. Furthermore, combinatorial libraries, peptide and peptide mimetics, defined chemical entities, oligonucleotides, and natural product libraries may be screened for activity as inhibitors of binding of a polypeptide of the invention to other components of signalling pathway machinery, for example cell division cycle machinery such as mitotic/meiotic apparatus (such as microtubules). The candidate substances may be used in an initial screen in batches of, for example, 10 substances per reaction, and the substances of those batches which show inhibition tested individually.

Candidate substances are typically added to a final concentration of from 1 to 1000 nmol/ml, more preferably from 1 to 100 nmol/ml. In the case of antibodies, the final concentration used is typically from 100 to 500 µg/ml, more preferably from 200 to 300 µg/ml.

Candidate substances may be identified by in vitro assays before being tested on whole cells. Alternatively the whole cell assay, preferably in the form of a rapid throughput screen, may be used as a preliminary screen and then the in vitro assay used to confirm that the effect. Suitable in vitro assays which may be used include binding assays in which a polypeptide is immobilised on a solid support, with a non-immobilised candidate substance determining whether and/or to what extent the polypeptide and candidate substance bind to each other. Alternatively, the candidate substance may be immobilised and the polypeptide non-immobilised.

In one embodiment, a library of candidate modulating moieties is created or used.

Library

As used herein, the term "library" includes but is not limited to a collection of nucleic acid fragments encoding candidate modulating moieties (herein called a library of candidate modulating moieties).

The library of the present invention may be generated by methods which include but are not limited to in vitro mutagenesis and/or recombination methods, such as chemical treatment, oligonucleotide mediated mutagenesis, PCR mutagenesis, DNA shuffling, random priming recombination (RPR), restriction enzyme fragment induced template switching (REFITS), and the staggered extension process (StEP), among others. Libraries of sequence variants may be random, semi-random or known sequences.

Nucleotide sequences to be screened according to the present invention typically encode polypeptides having an activity of interest or RNA molecules having catalytic activity, such as ribozymes. However nucleotide sequence that may have activity as untranscribed molecules, such as sequence motifs bound by DNA binding proteins may also be screened.

Polypeptides having an activity of interest include antibodies, antigens, enzymes, ligands such as growth factors, receptors such as cell surface receptors, other components of cellular signal transduction pathways, DNA binding proteins such as DNA repair enzymes, polymerases, recombinases and transcription factors, and structural proteins. Polypeptides also include fragments of the above.

Polypeptides used in the screening methods of the present invention may include families of polypeptides with known or suspected nucleic acid binding motifs. These may include for example zinc finger proteins (see below). Molecules according to the invention may also include helix-turn-helix proteins, homeodomains, leucine zipper proteins, helix-loop-helix proteins or β-sheet motifs which are well known to a person skilled in the art.

By way of example, DNA binding proteins may comprise, among other things, DNA binding part(s) of protein(s) such as zinc finger transcription factors, Zif268, ATF family transcription factors, ATF1, ATF2, bZIP proteins, CHOP, NF-κB, TATA binding protein (TBP), MDM, c-jun, elk, serum response factor (SRF), ternary complex factor (TCF); KRÜPPEL, Odd Skipped, even skipped and other D. melanogaster transcription factors; yeast transcription factors such as GCN4, the GAL family of galactose-inducible transcription factors; bacterial transcription factors or repressors such as lacI$^q$, or fragments or derivatives thereof. Derivatives would be considered by a person skilled in the art to be functionally and/or structurally related to the molecule(s) from which they are derived, for example through sequence homology of at least 40%.

The polypeptides may be non-randomised polypeptides, for example 'wild-type' or allelic variants of naturally occurring polypeptides, or may be specific mutant(s), or may be wholly or partially randomised polypeptides, for example randomised libraries of the DNA binding proteins as described herein where in particular, the DNA binding motifs have been randomised.

Preferably, the amino acid residues known to be important for polypeptide function, such as amino acid residues known to be important for catalytic activity or ligand binding such as nucleic acid binding or antigen binding are randomised. Detailed guidance as to which residues may be randomised, for example, zinc finger proteins and a number of other transcription factors, are given in WO 98/53057, WO 98/53060, WO 98/53058, WO 98/53059.

Randomisation is accomplished at the nucleotide level by any suitable means of mutagenesis. Mutagenesis may be performed, for example, by synthesising novel genes encoding mutant polypeptides and expressing these to obtain a variety of different proteins. Alternatively, existing genes can themselves be mutated, such as by site-directed or random mutagenesis, to obtain the desired mutant genes.

Mutations may be performed by any method known to those of skill in the art. Preferred, however, is site-directed mutagenesis of a nucleic acid sequence encoding the protein of interest. A number of methods for site-directed mutagenesis are known in the art, from methods employing single-stranded phage such as M13 to PCR-based techniques (see "PCR Protocols: A guide to methods and applications", M. A. Innis, D. H. Gelfand, J. J. Sninsky, T. J. White (eds.). Academic Press, New York, 1990). Preferably, the commercially available Altered Site II Mutagenesis System (Promega) may be employed, according to the manufacturer's instructions. Other techniques are described below.

Pluralities of nucleotide sequences encoding polypeptides of interest may be cloned from genomic DNA or cDNA; for example libraries made by PCR amplification of repertoires of antibody genes from immunised or unimmunised donors have proved very effective sources of functional antibody fragments (Winter et al., 1994 Annu Rev Immunol, 12, 433-55; Hoogenboom, 1997 Trends Biotechnol., 15, 62-70). Libraries of genes can also be made which encode all (see for example Parmley and Smith, 1988 Gene, 73, 305-18) or part of genes (see for example Lowman et al., 1991, Biochemistry, 30, 10832-8) or pools of genes (see for example Nissim et al., 1994 Embo J, 13, 692-8).

Pluralities of nucleotide sequences can also be made by introducing mutations into a nucleotide sequence or pool of nucleotide sequences 'randomly' by a variety of techniques in vivo, including; using 'mutator strains', of bacteria such as E. coli mutD5 (Low et al., 1996); and using the antibody hypermutation system of B-lymphocytes (Yelamos et al., 1995 Nature, 376, 225-9). Random mutations can also be introduced both in vivo and in vitro by chemical mutagens, and ionising or UV irradiation (see Friedberg et al., 1995 DNA repair and mutagenesis. ASM Press, Washington D.C.), or incorporation of mutagenic base analogues (Zaccolo et al., 1996 J Mol Biol, 255, 589-603). 'Random' mutations can also be introduced into genes in vitro during polymerisation for example by using error-prone polymerases (Leung et al., 1989 Technique, 1, 11-15).

Further diversification can be introduced by using homologous recombination either in vivo (see Kowalczykowski et al., 1994 Microbiol Rev, 58, 401-65) or in vitro (Stemmer, 1994a Nature, 370, 389-91; Stemmer, 1994b Proc Natl Acad Sci USA, 91, 10747-51).

A particularly preferred library of nucleotide sequences for use in the present invention is a PCR-assembled combinatorial library.

Theoretical studies indicate that the larger the number of genetic element variants created the more likely it is that a molecule will be created with the properties desired. Recently it has also been confirmed practically that larger phage-antibody repertoires do indeed give rise to more antibodies with better binding affinities than smaller repertoires. Thus, to ensure that rare variants are generated and thus are capable of being selected, a large library size is desirable. Consequently, a library of nucleotide sequences for use in the present invention typically comprises at least 100, 500, 1000 or 10000 different nucleotide sequences, preferably at least $10^5$, $10^6$ or $10^7$ different nucleotide sequences.

A plurality of nucleotide sequences for use in the screening methods of the invention may comprise RNA or DNA, but typically comprises DNA. Where the nucleotide sequences encode an RNA sequence, such as an mRNA or a catalytic ribozyme, the nucleotide sequences are typically provided as part of a nucleic acid vector comprising, in addition to a coding sequence, transcriptional regulatory sequences that are suitable for directing expression of the coding sequence in vitro. For example, vectors that comprise T7 or T3 promoters upstream of the coding sequence may be used. The nucleotide sequences may be provided as linear DNA or circular DNA. Where the coding sequence encodes a polypeptide, the coding sequence typically also comprises, in addition to sequences that encode the mature protein, sequences that direct translation of the coding sequence in an in vitro system.

Preferably the library candidate modulating moieties comprises a collection of ribozymes or antisense molecules.

Ribozymes are RNA molecules that can function to catalyse specific chemical reactions within cells without the obligatory participation of proteins. For example, group I ribozymes take the form of introns which can mediate their own excision from self-splicing precursor RNA. Other ribozymes are derived from self-cleaving RNA structures which are essential for the replication of viral RNA molecules. Like protein enzymes, ribozymes can fold into secondary and tertiary structures that provide specific binding sites for substrates as well as cofactors, such as metal ions. Examples of such structures include hammerhead, hairpin or stem-loop, pseudoknot and hepatitis delta antigenomic ribozymes have been described.

Each individual ribozyme has a motif which recognises and binds to a recognition site in a target RNA. This motif takes the form of one or more "binding arms" but generally two binding arms. The binding arms in hammerhead ribozymes are the flanking sequences Helix I and Helix III which flank Helix II. These can be of variable length, usually between 6 to 10 nucleotides each, but can be shorter or longer. The length of the flanking sequences can affect the rate of cleavage. For example, it has been found that reducing the total number of nucleotides in the flanking sequences from 20 to 12 can increase the turnover rate of the ribozyme cleaving a HIV sequence, by 10-fold (Goodchild, J V K, 1991 Arch Biochem Biophys 284: 386-391). A catalytic motif in the ribozyme Helix II in hammerhead ribozymes cleaves the target RNA at a site which is referred to as the cleavage site. Whether or not a ribozyme will cleave any given RNA is determined by the presence or absence of a recognition site for the ribozyme containing an appropriate cleavage site.

Each type of ribozyme recognizes its own cleavage site. The hammerhead ribozyme cleavage site has the nucleotide base triplet GUX directly upstream where G is guanine, U is uracil and X is any nucleotide base. Hairpin ribozymes have a cleavage site of BCUGNYR, where B is any nucleotide base other than adenine, N is any nucleotide, Y is cytosine or thymine and R is guanine or adenine. Cleavage by hairpin ribozymes takes places between the G and the N in the cleavage site.

More details on ribozymes may be found in "Molecular Biology and Biotechnology" (Ed. R A Meyers 1995 VCH Publishers Inc p831-8320 and in "Retroviruses" (Ed. J M Coffin et al 1997 Cold Spring Harbour Laboratory Press pp 683), and in our WO99/41397 and WO00/75370.

Alternatively, instead of preventing the association of the components directly, the substance may suppress the biologically available amount of a polypeptide of the invention. This may be by inhibiting expression of the component, for example at the level of transcription, transcript stability, translation or post-translational stability. An example of such a substance would be antisense RNA or double-stranded interfering RNA sequences which suppresses the amount of mRNA biosynthesis.

Protocols for the generation of cDNA libraries through reverse transcription of mRNA sequences are well known in the art and kits for doing so are commercially available (from Gibco BRL, for instance). By way of example, cells are chosen to prepare a library of complementary DNA (that is, "cDNA"). These cells include but are not limited to normal cells or cells from a subject afflicted with a pathological condition which are exemplary of the pathological condition. By way of example, if the subject has melanoma, the cells are melanoma cells. If the subject is suffering from a neural disorder, then the cells are preferably a sample of the afflicted cells. This approach is chosen because the afflicted cells are most probably the best source of cDNA. That is, such molecules which are specifically associated with the pathological condition of interest.

The preparation of the expression library is based upon the established fact that if proteins are expressed by the cells, then messenger RNA (mRNA) must be present. These mRNA molecules are not long lived, and are unstable, so they are not practical to work with. Accordingly, the cells chosen are then used to prepare a library of complementary DNA (i.e., "cDNA"). cDNA is first prepared from messenger RNA isolated from the cell by reverse transcription. Protocols for the generation of cDNA libraries through reverse transcription of mRNA sequences are well known in the art and kits for doing so are commercially available (from Gibco BRL, for instance). Once the cDNA is made, it is used to construct a vector library. In short, carrier vectors are treated, such as by cutting and splicing, to receive molecules of cDNA. The choice of vector may vary, as the skilled person is well familiar with many such examples. One commercially available vector for library generation is the GATEWAY™ vector system (Invitrogen).

In Vivo Selection Strategy

The selection of inhibitory RNA molecules, such as ribozymes, is conventionally designed theoretically. However, ribozymes which have been tested in this way often do not perform well in the cellular environment. We now provide an in vivo selection method and which is an alternative to the method described in our WO00/75370.

In more detail there is provided a vector suitable for use in vivo, comprising:
    (i) an optional first nucleotide sequence encoding a selectable marker;
    (ii) one or more optional second nucleotide sequences, each independently encoding a marker or modulator gene; and
    (iii) a third nucleotide sequence, operably linked to a promoter, encoding a gene product capable of binding to and effecting the cleavage, directly or indirectly, of a nucleotide sequence;
wherein (i), (ii) and (iii) are operably linked to a regulatory sequence capable of directing transcription of (i), (ii) and (iii) as a continuous RNA molecule in a host.

For ease of reference this is the so-called "library vector", i.e. the vector may be used to generate a library of NOIs. For the purpose of the present invention, the library vector will be used to generate a library of ribozymes.

In one embodiment, (ii) is out of frame with the regulatory sequence capable of directing its transcription.

In a preferred embodiment, the vector comprises a single second nucleotide sequence. In an even more preferred embodiment, the vector comprises two second nucleotide sequences. In a further embodiment, the vector comprises 3-5 second nucleotide sequences.

The first nucleotide preferably encodes a selectable marker gene such as an antibiotic resistance gene. The selectable marker is used to select cells having been transduced with a vector of the invention.

The third nucleotide of the selection system of the present invention may be a plurality of nucleotide sequences which encode inhibitory RNA molecules. An inhibitory RNA molecule is defined as a ribonucleic acid which is capable of inhibiting transcription and/or translation of a nucleic acid sequence by binding to the sequence. Generally, an inhibitory RNA molecule is capable of binding to and effecting the cleavage, directly or indirectly, of a nucleotide sequence, or its transcription product. Examples include ribozymes (cleave directly), external guide sequences (EGSs) and antisense, sense RNA, or siRNA (cause cleavage by other factors).

There is also provided a vector suitable for use in vivo, the system comprising:
  (a) a first nucleotide sequence encoding a modulator gene;
  (b) a second nucleotide sequence encoding a detectable marker gene which is operably linked to a nucleotide sequence upon which said first nucleotide sequence modulates, and a promoter; and
  (c) a nucleotide sequence of interest;
wherein (a), (b) and (c) are operably linked to a regulatory sequence capable of directing transcription of (a), (b) and (c) as a continuous RNA molecule in a host.

For ease of reference this is the so-called "target vector".

Sequence (c) of the target vector will preferably comprise a gene, or a fragment thereof, capable of encoding a polypeptide, or a fragment thereof, such as Parkin or Tat. The sequence will be located between (a) and (b) in the vector construct and out-of-frame with the transcriptional unit driving the expression of (a).

The vector is preferably a viral vector, such as a lentiviral vector.

The modulator acts as an activator or a repressor. For example, the modulator may be selected from tetracycline repressors, such as TetR, and tetracycline-controlled transactivators, such as tTA and rtTA, and the detectable marker gene may be operably linked to a tertracycline operator.

A detectable marker may be any gene product which expression can be detected, for example, NFAT-dependent reporter genes such as GFP or LNGFR.

In a preferred embodiment, at least one of the one or more marker genes used in the library vector is the same as the detectable marker gene used in the target vector; and/or at least one of the one or more modulator genes used in the library vector is the same as the modulator gene used in the target vector; and/or the promoter which is operably linked to the third nucleotide sequence of the library vector is the same as the promoter used in the target vector, part (b).

We also provide a method for selecting from a plurality of inhibitory molecules by
  (i) introducing the target vector and library vector into a host cell; and
  (ii) selecting the host cell if a detectable marker gene is expressed in the host cell; and optionally,
  (iii) isolating said third nucleotide sequence and determining its nucleotide sequence.

Administration of Modulating Agent

The candidate substance, i.e. the modulating moiety, may be administered to the non-dividing or slowly dividing cell in any vector that is capable of transducing a target non-dividing or slowly dividing cell. For example, it may be injected into the cell. Alternatively, in the case of polypeptide candidate substances, the cell may be transfected with a nucleic acid construct which directs expression of the polypeptide in the cell. Preferably, the expression of the polypeptide is under the control of a regulatable promoter. In one embodiment the modulating moiety is delivered in a lentiviral vector.

Vector

As it is well known in the art, a vector is a tool that allows or facilitates the transfer of an entity from one environment to another. In accordance with the present invention, and by way of example, some vectors used in recombinant DNA techniques allow entities, such as a segment of DNA (such as a heterologous DNA segment, such as a heterologous cDNA segment), to be transferred into a host cell for the purpose of replicating the vectors comprising a segment of DNA. Examples of vectors used in recombinant DNA techniques include but are not limited to plasmids, chromosomes, artificial chromosomes or viruses.

The term "vector" includes expression vectors and/or transformation vectors.

The term "expression vector" means a construct capable of in vivo or in vitro/ex vivo expression.

The term "transformation vector" means a construct capable of being transferred from one species to another.

Preferably the vector is a virus based vector.

Preferably the vector capable of transducing a target non-dividing or slowly dividing cell is a recombinant viral vectors.

In a typical vector for use in the method of the present invention, at least part of one or more protein coding regions essential for replication may be removed from the virus. This makes the retroviral vector replication-defective. Portions of the retroviral genome may also be replaced by a library encoding candidate modulating moieties operably linked to a regulatory control region and a reporter moiety in the vector genome in order to generate a vector comprising candidate modulating moieties which is capable of transducing a target non-dividing or slowly dividing host cell and/or integrating its genome into a host genome.

When vector has transduced the target cell and/or integrated in the host cell genome, the transduced cells may be screened for a candidate modulating moiety. Thus, the transfer of a library into a site of interest in a vector genome is typically achieved by (i) integrating a library encoding candidate modulating moieties into a recombinant viral vector; (2) packaging the modified viral vector into a virion coat; and (3) allowing transduction of a site of interest—such as a targeted non-dividing or slowly dividing cell or a targeted non-dividing or slowly dividing cell population.

Lentiviral Vector

Preferably the viral vector capable of transducing a target non-dividing or slowly dividing cell is a lentiviral vector.

Lentivirus vectors are part of a larger group of retroviral vectors, and such vectors useful in this aspect of the present invention are described in detail above.

The vector of the present invention may be delivered to a target site by a viral or a non-viral vector.

Non-viral delivery systems include but are not limited to DNA transfection methods. Here, transfection includes a process using a non-viral vector to deliver a gene to a target mammalian cell.

Typical transfection methods include electroporation, DNA biolistics, lipid-mediated transfection, compacted DNA-mediated transfection, liposomes, immunoliposomes, lipofectin, cationic agent-mediated, cationic facial amphiphiles (CFAS) (Nature Biotechnology 1996 14; 556), and combinations thereof.

Viral delivery systems include but are not limited to adenovirus vector, an adeno-associated viral (AAV) vector, a herpes viral vector, retroviral vector, lentiviral vector, baculoviral vector. Other examples of vectors include ex vivo delivery systems, which include but are not limited to DNA transfection methods such as electroporation, DNA biolistics, lipid-mediated transfection, compacted DNA-mediated transfection.

The delivery of one or more therapeutic genes by a vector system according to the present invention may be used alone or in combination with other treatments or components of the treatment.

Adenovirus Vectors

In another embodiment of the present invention, the library of candidate modulating moieties is introduced into an adenoviral vector.

The adenovirus is a double-stranded, linear DNA virus that does not go through an RNA intermediate. There are over 50 different human serotypes of adenovirus divided into 6 subgroups based on the genetic sequence homology. The natural target of adenovirus is the respiratory and gastrointestinal epithelia, generally giving rise to only mild symptoms. Serotypes 2 and 5 (with 95% sequence homology) are most commonly used in adenoviral vector systems and are normally associated with upper respiratory tract infections in the young.

Adenoviruses are nonenveloped, regular icosohedrons. A typical adenovirus comprises a 140 nm encapsidated DNA virus. The icosahedral symmetry of the virus is composed of 152 capsomeres: 240 hexons and 12 pentons. The core of the particle contains the 36 kb linear duplex DNA which is covalently associated at the 5' ends with the Terminal Protein (TP) which acts as a primer for DNA replication. The DNA has inverted terminal repeats (ITR) and the length of these varies with the serotype.

Entry of adenovirus into cells involves a series of distinct events. Attachment of the virus to the cell occurs via an interaction between the viral fibre (37 nm) and the fibre receptors on the cell. This receptor has recently been identified for Ad2/5 serotypes and designated as CAR (Coxsackie and Adeno Receptor, Tomko et al (1997 Proc Natl Acad Sci 94: 3352-2258). Internalisation of the virus into the endosome via the cellular $\alpha v\beta 3$ and $\alpha v\beta 5$ integrins is mediated by and viral RGD sequence in the penton-base capsid protein (Wickham et al., 1993 Cell 73: 309-319). Following internalisation, the endosome is disrupted by a process known as endosomolysis, an event which is believed to be preferentially promoted by the cellular $\alpha v\beta 5$ integrin (Wickham et al., 1994 J Cell Biol 127: 257-264). In addition, there is recent evidence that the Ad5 fibre knob binds with high affinity to the MHC class 1 $\alpha 2$ domain at the surface of certain cell types including human epithelial and B lymphoblast cells (Hong et al., 1997 EMBO 16: 2294-2306).

Subsequently the virus is translocated to the nucleus where activation of the early regions occurs and is shortly followed by DNA replication and activation of the late regions. Transcription, replication and packaging of the adenoviral DNA requires both host and viral functional protein machinery.

Viral gene expression can be divided into early (E) and late (L) phases. The late phase is defined by the onset of viral DNA replication. Adenovirus structural proteins are generally synthesised during the late phase. Following adenovirus infection, host cellular mRNA and protein synthesis is inhibited in cells infected with most serotypes. The adenovirus lytic cycle with adenovirus 2 and adenovirus 5 is very efficient and results in approximately 10,000 virions per infected cell along with the synthesis of excess viral protein and DNA that is not incorporated into the virion. Early adenovirus transcription is a complicated sequence of interrelated biochemical events but it entails essentially the synthesis of viral RNAs prior to the onset of DNA replication.

The Schematic diagram below is of the adenovirus genome showing the relative direction and position of early and late gene transcription:

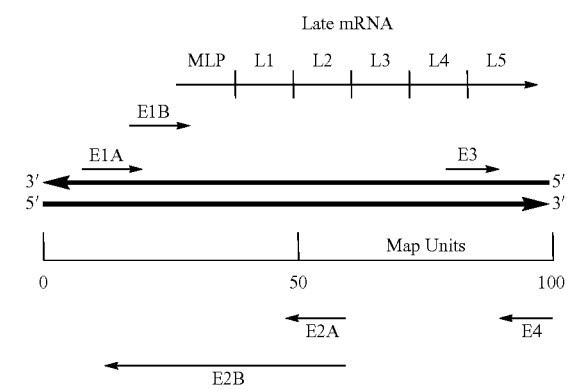

The organisation of the adenovirus genome is similar in all of the adenovirus groups and specific functions are generally positioned at identical locations for each serotype studied. Early cytoplasmic messenger RNAs are complementary to four defined, noncontiguous regions on the viral DNA. These regions are designated E1-E4. The early transcripts have been classified into an array of intermediate early (E1a), delayed early (E1b, E2a, E2b, E3 and E4), and intermediate regions.

The early genes are expressed about 6-8 hours after infection and are driven from 7 promoters in gene blocks E1-4.

The E1a region is involved in transcriptional transactivation of viral and cellular genes as well as transcriptional repression of other sequences. The E1a gene exerts an important control function on all of the other early adenovirus messenger RNAs. In normal tissues, in order to transcribe regions E1b, E2a, E2b, E3 or E4 efficiently, active E1a product is required. However, the E1a function may be bypassed. Cells may be manipulated to provide E1a-like functions or may naturally contain such functions. The virus may also be manipulated to bypass the E1a function. The viral packaging signal overlaps with the E1a enhancer (194-358 nt).

The E1b region influences viral and cellular metabolism and host protein shut-off. It also includes the gene encoding the pIX protein (3525-4088 nt) which is required for packaging of the full length viral DNA and is important for the thermostability of the virus. The E1b region is required for the normal progression of viral events late in infection. The E1b product acts in the host nucleus. Mutants generated within the E1b sequences exhibit diminished late viral mRNA accumulation as well as impairment in the inhibition of host cellular transport normally observed late in adenovirus infection. E1b is required for altering functions of the host cell such that processing and transport are shifted in favour of viral late gene products. These products then result in viral packaging and release of virions. E1b produces a 19 kD protein that prevents apoptosis. E1b also produces a 55 kD protein that binds to p53. For a review on adenoviruses and their replication, see WO 96/17053.

The E2 region is essential as it encodes the 72 kDa DNA binding protein, DNA polymerase and the 80 kDa precursor of the 55 kDa Terminal Protein (TP) needed for protein priming to initiate DNA synthesis.

A 19 kDa protein (gp19K) is encoded within the E3 region and has been implicated in modulating the host immune response to the virus. Expression of this protein is upregulated in response to TNF alpha during the first phase of the infection and this then binds and prevents migration of the MHC class I antigens to the epithelial surface, thereby dampening the recognition of the adenoviral infected cells by the cytotoxic T lymphocytes. The E3 region is dispensible in in vitro studies and can be removed by deletion of a 1.9 kb XbaI fragment.

The E4 region is concerned with decreasing the host protein synthesis and increasing the DNA replication of the virus.

There are 5 families of late genes and all are initiated from the major late promoter. The expression of the late genes includes a very complex post-transcriptional control mechanism involving RNA splicing. The fibre protein is encoded within the L5 region. The adenoviral genome is flanked by the inverted terminal repeat which in Ad5 is 103 bp and is essential for DNA replication. 30-40 hours post infection viral production is complete.

Adenoviruses may be converted for use as vectors for gene transfer by deleting the E1 gene, which is important for the induction of the E2, E3 and E4 promoters. The E1-replication defective virus may be propagated in a cell line that provides the E1 polypeptides in trans, such as the human embryonic kidney cell line 293. A therapeutic gene or genes can be inserted by recombination in place of the E1 gene. Expression of the gene is driven from either the E1 promoter or a heterologous promoter.

Even more attenuated adenoviral vectors have been developed by deleting some or all of the E4 open reading frames (ORFs). However, certain second generation vectors appear not to give longer-term gene expression, even though the DNA seems to be maintained. Thus, it appears that the function of one or more of the E4 ORFs may be to enhance gene expression from at least certain viral promoters carried by the virus.

An alternative approach to making a more defective virus has been to "gut" the virus completely maintaining only the terminal repeats required for viral replication. The "gutted" or "gutless" viruses can be grown to high titres with a first generation helper virus in the 293 cell line but it has been difficult to separate the "gutted" vector from the helper virus.

The adenovirus provides advantages as a vector for identifying candidate modulating moieties over other gene therapy vector systems for the following reasons:

It is a double stranded DNA nonenveloped virus that is capable of in vivo and in vitro transduction of a broad range of cell types of human and non-human origin. These cells include respiratory airway epithelial cells, hepatocytes, muscle cells, cardiac myocytes, synoviocytes, primary mammary epithelial cells and post-mitotically terminally differentiated cells such as neurons.

Adenoviral vectors are also capable of transducing non dividing cells. This is very important for diseases, such as cystic fibrosis, in which the affected cells in the lung epithelium, have a slow turnover rate. In fact, several trials are underway utilising adenovirus-mediated transfer of cystic fibrosis transporter (CFTR) into the lungs of afflicted adult cystic fibrosis patients.

Adenoviruses have been used as vectors for gene therapy and for expression of heterologous genes. The large (36 kilobase) genome can accommodate up to 8 kb of foreign insert DNA and is able to replicate efficiently in complementing cell lines to produce very high titres of up to $10^{12}$. Adenovirus is thus one of the best systems to study the expression of genes in primary non-replicative cells.

The expression of viral or foreign genes from the adenovirus genome does not require a replicating cell. Adenoviral vectors enter cells by receptor mediated endocytosis. Once inside the cell, adenovirus vectors rarely integrate into the host chromosome. Instead, it functions episomally (independently from the host genome) as a linear genome in the host nucleus. Hence the use of recombinant adenovirus alleviates the problems associated with random integration into the host genome.

Pox Viral Vectors

In another embodiment of the present invention, the library of candidate modulating moieties is introduced into a pox viral vector.

Pox viral vectors may be used in accordance with the present invention, as large fragments of DNA are easily cloned into its genome and recombinant attenuated vaccinia variants have been described (Meyer, et al., 1991, J. Gen. Virol. 72: 1031-1038, Smith and Moss 1983 Gene, 25:21-28).

Examples of pox viral vectors include but are not limited to leporipoxvirus: Upton, et al J. Virology 60:920 (1986) (shope fibroma virus); capripoxvirus: Gershon, et al J. Gen. Virol. 70:525 (1989) (Kenya sheep-1); orthopoxvirus: Weir, et al J. Virol 46:530 (1983) (vaccinia); Esposito, et al Virology 135:561 (1984) (monkeypox and variola virus); Hruby, et al PNAS, 80:3411 (1983) (vaccinia); Kilpatrick, et al Virology 143:399 (1985) (Yaba monkey tumour virus); avipoxvirus: Binns, et al J. Gen. Virol 69:1275 (1988) (fowlpox); Boyle, et al Virology 156:355 (1987) (fowlpox); Schnitzlein, et al J. Virological Method, 20:341 (1988) (fowlpox, quailpox); entomopox (Lytvyn, et al J. Gen. Virol 73:3235-3240 (1992)].

Poxvirus vectors are used extensively as expression vehicles for genes of interest in eukaryotic cells. Their ease of cloning and propagation in a variety of host cells has led, in particular, to the widespread use of poxvirus vectors for expression of foreign protein and as delivery vehicles for vaccine antigens (Moss, B. 1991, Science 252: 1662-7).

Preferred vectors for use in accordance with the present invention are recombinant pox viral vectors such as fowl pox virus (FPV), entomopox virus, vaccinia virus such as NYVAC, canarypox virus, MVA or other non-replicating viral vector systems such as those described for example in WO 95/30018. Pox virus vectors have also been described where at least one immune evasion gene has been deleted (see WO 00/29428).

In one preferred embodiment, the pox virus vector is an entomopox virus vector.

Vaccinia Viral Vectors

Preferably the pox viral vector is a vaccinia viral vector.

Preferably, the vector is a vaccinia virus vector such as MVA or NYVAC. Most preferred is the vaccinia strain modified virus ankara (MVA) or a strain derived therefrom. Alternatives to vaccinia vectors include avipox vectors such as fowlpox or canarypox known as ALVAC and strains derived therefrom which can infect and express recombinant proteins in human cells but are unable to replicate.

Construction of a Pox Viral Vector Library

Typically, a nucleic acid fragment or collection of nucleic acid fragments encoding a candidate modulating moiety is introduced into the poxvirus genome by homologous recombination. The nucleic acid fragment or collection of nucleic acid fragments encoding a candidate modulating moiety are cloned behind a vaccinia promoter flanked by sequences homologous to a non-essential region in the poxvirus and the plasmid intermediate is recombined into the viral genome by homologous recombination. This methodology works efficiently for relatively small inserts tolerated by prokaryotic hosts.

The method is less viable in cases requiring large inserts as the frequency of homologous recombination is low and decreases with increasing insert size; in cases requiring construction of labor intensive plasmid intermediates such as in library production of nucleic acid fragments; and, in cases where the propagation of DNA is not tolerated in bacteria.

Alternative methods using direct ligation vectors have been developed to efficiently construct chimeric genomes in situations not readily amenable for homologous recombination (Merchlinsky, M. et al., 1992, Virology 190: 522-526; Scheiflinger, F. et al., 1992, Proc. Natl. Acad. Sci. USA. 89: 9977-9981). These direct ligation protocols have obviated the need for homologous recombination to generate poxvirus chimeric genomes. In such protocols, the DNA from the genome is digested, ligated to insert DNA in vitro, and transfected into cells infected with a helper virus (Merchlinsky, M. et al., 1992, Virology 190: 522-526, Scheiflinger, F. et al., 1992, Proc. Natl. Acad. Sci. USA 89: 9977-9981). In one protocol, the genome is digested at the unique NotI site and a DNA insert containing elements for selection or detection of the chimeric genomes is ligated to the genomic arms (Scheiflinger, F. et al., 1992, Proc. Natl. Acad. Sci. USA. 89: 9977-9981). This direct ligation method is described for the insertion of foreign DNA into the vaccinia virus genome (Pfleiderer et al., 1995, J. General Virology 76: 2957-2962). Alternatively, the vaccinia WR genome is modified by removing the NotI site in the HindIII F fragment and reintroducing a NotI site proximal to the thymidine kinase gene such that insertion of a sequence at this locus disrupts the thymidine kinase gene, allowing isolation of chimeric genomes via use of drug selection (Merchlinsky, M. et al., 1992, Virology 190: 522-526).

The direct ligation vector, vNotI/tk, allows one to efficiently clone and propagate DNA inserts at least 26 kilobase pairs in length (Merchlinsky, M. et al., 1992, Virology, 190: 522-526). Although, large DNA fragments are efficiently cloned into the genome, proteins encoded by the DNA insert will only be expressed at the low level corresponding to the thymidine kinase gene, a relatively weakly expressed early class gene in vaccinia. In addition, the DNA is inserted in both orientations at the NotI site.

Improved and modified vaccinia virus vectors for efficient construction of such DNA libraries can be prepared using a "trimolecular recombination" approach to improve screening efficiency.

In one embodiment of the invention, a representative library of nucleic acid fragments encoding candidate modulating moieties is constructed in vaccinia virus. Preferably, a tri-molecular recombination method employing modified vaccinia virus vectors and related transfer plasmids is used to construct the representative library in vaccinia virus. This method generates close to 100% recombinant vaccinia virus (see WO 00/28016).

Tri-Molecular Recombination

The above-described tri-molecular recombination strategy yields close to 100% viral recombinants. This is a highly significant improvement over current methods for generating viral recombinants by transfection of a plasmid transfer vector into vaccinia virus infected cells. This latter procedure yields viral recombinants at a frequency of the order of only 0.1%. The high yield of viral recombinants in tri-molecular recombination makes it possible to efficiently construct libraries in a vaccinia virus derived vector. A titer of 6×10 recombinant virus can be obtained following transfection with a mix of 20 micrograms of Not I and Apa I digested vaccinia vector arms together with an equimolar concentration of tumor cell cDNA. This technological advance creates the possibility of new and efficient screening and selection strategies for isolation of specific genomic and clones comprising candidate modulating moieties.

The tri-molecular recombination method as herein disclosed may be used with other viruses such as mammalian viruses including vaccinia and herpes viruses. Typically, two viral arms which have no homology are produced. The only way that the viral arms can be linked is by bridging through homologous sequences that flank the insert in a transfer vector such as a plasmid. When the two viral arms and the transfer vector are present in the same cell the only infectious virus produced is recombinant for a DNA insert in the transfer vector.

Libraries constructed in vaccinia and other mammalian viruses by the tri-molecular recombination method of the present invention may be used in identifying candidate modulating moieties in the screening system of the present invention.

Target Cells

The term "target cell" includes any cell derivable from a suitable organism which a vector is capable of transfecting or transducing. Preferably the cell is a non-dividing or slowly dividing cell.

Cells useful in the method of the invention may be from any source, for example from primary cultures, from established cell lines, in organ culture or in vivo. Cell lines useful in the invention include fibroblast cell lines, carcinoma cell lines such as neuroblastoma cell lines and cell lines of haematopoietic origin. Other examples of host cells include but are not limited to respiratory airway epithelial cells, hepatocytes, muscle cells, cardiac myocytes, synoviocytes, primary mammary epithelial cells and post-mitotically terminally differentiated non-replicating cells such as macrophages and/or neurons. Suitable cell lines may be obtained from the American Type Culture Collection.

Immortalisation of Cell Line

One advantage associated with the use of an immortalised cell lines derived from non-dividing or slowly dividing cells is that they are more likely to mirror the in vivo situation than the use of general cell lines. In one embodiment of the present invention the target cell is a non-dividing or slowly dividing cell, but immediately after, or at the same time as, transduction with the NOI, the target cell is immortalised. Immortalisation may be carried out through, e.g. the addition of telomerase or fusion with a neoplastic cell to form a hybridoma, or the addition of the SV40 large T antigen either by protein or gene delivery.

The invention also encompasses the performance of the assay in transgenic animals, preparable for example by pronuclear microinjection or by the preparation of ES cell chimeras, according to established techniques.

Post Translational Modification

A host cell strain may be chosen which modulates the expression of the candidate moiety or modifies and processes the expressed candidate modulating moiety in the specific fashion desired. Such modifications (e.g., glycosylation) and processing (e.g. cleavage) of protein products may be important for the function of the protein. Different host cells have characteristic and specific mechanisms for the post-translational processing and modification of proteins and gene products. Appropriate cell lines or host systems can be chosen to ensure the correct modification of the foreign protein expressed. To this end, eucaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, HT 1080 and WI38 cell lines.

In a preferred embodiment, the host cell is a mammalian cell. In a highly preferred embodiment, the host cell is a human cell.

The present invention also provides a method comprising culturing a transduced host cell—which cell has been transduced with a vector according to the present invention under conditions suitable for the expression and/or detection of the candidate moiety of the present invention.

Biological Response Modifiers (BRMS)

The pathway of interest does not have to be responsive to a stimulus per se. By way of example, the screening method of the present invention can be applied in the case of constitutively expressed genes of interest. In another embodiment a BRM may be employed to modulate the signalling pathway under investigation.

Environmental stressors may include but are not limited to one or more of the following: oxygen depletion; radiation; heat shock; pH change; hypothermia; or glucose starvation.

A vast array of molecules such as immunomodulators, cytokines, growth factors, cell surface receptors, hormones, mitogens, circulatory molecule, inflammatory cytokines, and pathogenic agents such a viruses, bacteria, parasites or yeast may be used as BRMs. Examples of these biological response modifiers include but are not limited to ApoE, Apo-SAA, BDNF, Cardiotrophin-1, EGF, ENA-78, Eotaxin, Eotaxin-2, Exodus-2, FGF-acidic, FGF-basic, fibroblast growth factor-10 (Marshall 1998 Nature Biotechnology 16: 129), FLT3 ligand (Kimura et al. (1997), Fractalkine (CX3C), GDNF, G-CSF, GM-CSF, GF-β1, insulin, IFN-γ, IGF-I, IGF-II, IL-1α, IL-1β, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein (Marshall 1998 ibid), M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNIL-1, TPO, VEGF, GCP-2, GRO/MGSA, GRO-β and GRO-γ.

Stress factors, such as hypoxia, heat shock, ischaemia, osmolarity change, also induce cellular responses via signalling pathways and such factors may be used as BRMs.

Environmental stresses may also be used as BRMs and include oxygen depletion, anoxia, radiation, heat shock, pH change, hypothermia and glucose starvation.

In addition to modulating pathways via environmental stimuli or extracellular molecules it is also envisaged that the over-expression of proteins which are known components of specific signalling machinery could be used as BRMs.

Stimuli (BRM) Particular to Disease States

The neuronal apoptotic response can be induced in vitro by stimuli that can be used to mimic such disease states. Among the possible stimuli are hypoxia, ischaemia, hypoxia/ischaemia, glutamate, kainate, 6-hydroxy dopamine, staurosporine, nitric oxide, or wortmanin.

Ischaemia

Ischaemia can be an insufficient supply of blood to a specific organ or tissue. A consequence of decreased blood supply is an inadequate supply of oxygen to the organ or tissue (hypoxia). Prolonged hypoxia may result in injury to the affected organ or tissue.

By way of example, conditions that are like ischaemia or are caused by ischaemia include hypoxia and/or low glucose concentration(s).

Hypoxia

As used herein, the term "hypoxia" refers to the presence of less than normal amounts of dioxygen in a vertebrate or in its blood. Inflamed tissues and solid tumours, particularly necrotic regions, are likely to have a low or oxygen tensions (<1% oxygen) or an inadequate supply of oxygen. These tissues with low oxygen tensions are termed hypoxic tissues. Thus, the term "hypoxia" includes both hypoxic and inflammatory sites.

Hypoxia is a powerful regulator of gene expression in a wide range of different cell types (Wang and Sememnza 1993 Proc Natl Acad Sci USA 90:4304) and acts by the induction of the activity of hypoxia-inducible transcription factors such as hypoxia inducible factor-1 (HIF-1) (Wang and Sememnza 1993 ibid), which bind to cognate DNA recognition sites, the hypoxia-response elements (HREs) on various gene promoters such as GAPDH and VEGF thus upregulating the expression of that gene. By way of example, Dachs et al (1997 ibid) used a multimeric form of the HRE from the mouse phosphoglycerate kinase-1 (PGK-1) gene (Firth et al 1994 Proc Natl Acad Sci USA 91: 6496) to control expression of both marker and therapeutic genes by human fibrosarcoma cells in response to hypoxia in vitro and within solid tumours in vivo (Dachs et al 1997 ibid).

Nuclear accumulation of HIF-1 is slow compared with other transcription factors (Kallio, et al *Embo J* 1998. 17: 6573-86) and upregulation of HIF/HRE-dependent genes may take several hours (Semenza, G et al *J Biol Chem* 1994. 269: 23757-63), Nuclear factor κB and nuclear factor IL-6 have also been implicated in the hypoxic response of several cell types (Royds et al *Mol Pathol* 1998. 51: 55-61, Matsui et al *Cardiovasc Res* 1999. 42: 104-12, Yan, et al *J Biol Chem* 1997. 272: 4287-94) and induction of several members of the bZIP (basic/leucine zipper domain) transcription factor class is seen in fibroblasts during anoxia (Estes et al *Exp Cell Res* 1995.220: 47-54).

Alternatively, the fact that marked glucose deprivation is also present in ischaemic areas of tumours, means that low glucose levels can be used to activate heterologous gene expression specifically in tumours. A truncated 632 base pair sequence of the grp78 gene promoter, known to be activated specifically by glucose deprivation, has also been shown to be capable of driving high level expression of a reporter gene in murine tumours in vivo (Gazit et al 1995 Cancer Res. 55: 1660).

Phenotype Changes

The present invention involves detecting phenotypic differences between the target cell and a control cell. The control cell may be the target cell before commencement of the method of the present invention, i.e. in this embodiment there is no separate control cell, rather a phenotypic characteristic of the target cell is observed before and after the target cell is challenged with the modulating moiety.

We use the term "phenotype" in its normal sense, i.e. the observable functional and structural characteristics of an organism as determined by the interaction of its genetic constitution and the environment.

The invention is not limited to any particular functional or structural characteristic. The following are given by way of example only.

Suitable general and directed phenotypic screens include the use of fundus photography, blood pressure, behaviour analysis, X-ray fluoroscopy, dual-energy X-ray absorptiometry (DEXA), CAT scans, complete blood counts (CBC), urinalysis, blood chemistry, insulin levels, glucose tolerance, fluorescence-activated cell sorting (FACS), magnetic cell sorting technology (MACS), FRET, histopathology, expression data, developmental biology.

The phenotypic difference may be cell death. Cytotoxicity assays may be used to study necrosis and apoptosis. Cytotoxicity assays are principally of two types. Radioactive and non-radioactive assays that measure increases in plasma membrane permeability, since dying cells become leaky. Colorimetric assays that measure reduction in the metabolic activity of mitochondria as mitochondria in dead cells cannot metabolize dyes. Assays for apoptosis include those which can measure one of the following apoptotic parameters: fragmentation of DNA in populations or in individual cells; alterations in membrane symmetry (phoshatidylserine translocates from the cytoplasmic to the extracellular side of the cell membrane); activation of apoptotic caspases (this family of proteins sets off a cascade of events that disable a multitude of cell functions); release of cytochrome C and AIF into cytoplasm by mitochondria.

Methods for studying apoptosis in cell populations have particularly concentrated on two kep apoptopic events in the cell: 1) apoptosis and cell mediated cytotoxicity are characterised by cleavage of the genomic DNA into discrete fragments. The DNA fragments may be assayed: as "ladders" (with the 180 bp multiples as "rungs" of the ladder) derived from populations of the cells, e.g. with the Apoptotic DNA Ladder Kit; or by quantification of histone complexed DNA fragments with an ELISA. 2) Caspase activity can be analysed in different ways including: by an in vitro assay. Activity of a specific caspase, for instance caspase 3, can be determined in cellular lysates by capturing of the caspase and measuring proteolytic cleavage of a suitable substrate; and detection of cleavage of an in vivo caspase substrate. For example caspase 3 is activated during early stages. Its substrate PARP (Poly-ADP-Ribose-polymerase) and the cleaved fragments can be detected with an anti PARP antibody.

Methods for studying apoptosis in individual cells focus on: 1) DNA fragmentation. The methods used to assess DNA strand brakes are based on labelling/staining the cellular DNA. The labelled/stained DNA is subsequently analyzed by flow cytometry, fluorescence microscopy or light microscopy. In general two different labelling methods by be used to identify DNA in apoptotic cells: Enzyme labelling in which cellular DNA is labelled with modified muceltoides (e.g. biotin-dUTP, DIG-dUTP, fluorescein-dUTP) using exogenous enzymes (e.g. terminal transferase, DNA polymerase). This labelling detects extensive DNA strand breaks. Enzyme labelling techniques include the so-called TUNEL (TdT-mediated X-dUTP nick end labelling) enzymatic labelling assay and ISNT (In Situ Nick Translation) techniques. 2) In addition, individual cell death may be studied by assays that measure alterations in plasma membranes (alterations in the asymmetry or permeability of individual cell membranes, which occur as the membrane shrinks and becomes increasingly convoluted). For example, during apoptosis, phosphatidylserine translocates from the cytoplasmic side of the membrane to the extracellular side and can be detected with Annexin V.

Assays for measuring cytotoxicity are generally based on alterations of plasma membrane permeability and the consequent release (leakage) of components into the supernatant or the uptake of dyes, normally excluded by viable cells. Alternatively dead cells are unable to metabolize various tetrazolium slats. This allows the use of colorimetric assays, such as MTT, XTT or WST-1, to measure cell survival.

The viability as well as proliferation of individual cells can be assessed by standard microscopic methods. For example, cells may be treated with a vital strain or exclusion dye and counted directly in a hemocytometer. The same cell parameters may be determined by flow cytometry if the cells are differentially stained with fluorescent dyes that bind DNA (DNA fluorochromes). Assays that look at proliferation include assays that measure DNA synthesis, i.e. is labelled DNA precursors are added to cell culture, cells that are about to divide incorporate this precursor into their DNA; and assays that monitor expression of cell cycle-associated antigens: Molecules that regulate the cell cycle are measured either by their activity (e.g. CDK kinase assays) or by quantifying their amounts (e.g. Western blots, ELISA or immunohistochemistry).

The phenotypic difference may be a change in morphology as evidence by, e.g. size, shape, colour, odour, texture, degree of adherence to a medium, seriological characteristics of the target cell.

Agar based assays provide convenience and high throughput and in particular give qualitative assessment of the potency and efficacy of test compounds. Thus, the phenotypic difference may be the ability of a cell to grow on soft agar.

Phenotypic difference may be the ability of a cell to differentiate. The ability of a cell to differentiate may be determined by the adherence of the cell to a surface in culture.

The phenotypic difference may be resistance to a drug e.g. a drug selected from the group consisting of cisplatin, doxirubicin, taxol, camptothecin, daunorubicin, and methotrexate.

Phenotypic difference may be a difference in transcription or expression of a reporter gene or cDNA. In one preferred embodiment, the phenotypic difference may be a change in the expression level of a reporter gene linked to a gene whose regulation it is desired to alter.

Screening may be carried out at an appropriate stage in the cell cycle.

It is also possible to employ secondary screening within the present invention, for example, Yeast Two-hybrid vectors.

Reporter Based Construct

Here the principle is based on the hypothesis that expression of a gene is controlled by its transcriptional promoter. The levels of reporter gene expression (such as EGFP) may be correlated with the levels of endogeneous levels of the RNA of that particular gene. Cells can be functionally selected for altered levels of expression of that particular gene. For example, levels of the reporter gene can be compared in ribozyme library transduced cells and in non transduced cells. Cells can be selected which result in selected ribozymes conferring an increase in selected gene promoter mediated gene expression resulting in elevated levels of the reporter gene.

The sequence of a particular ribozyme can be used to identify the putative target gene. Thus, a ribozyme based selection system can be used to target and identify modulators of a particular promoter driven reporter system. This approach allows the functional selection of ribozymes that target key cellular factors involved in a particular phenotype. In addition, this approach allows the identification of genes that directly regulate not only a particular promoter but also any biologically relevant upstream regulators.

Reporter Gene Construction

Reporter genes may be constructed according to standard techniques known in the art. In general, the reporter may be either a coding sequence which is heterologous to the selected regulatory sequence (see below); or a modification of the coding sequence normally associated with the selected regulatory sequence, such that expression thereof is detectable; or, in some cases, the natural coding sequence normally associated with the selected regulatory sequence may be usable as a reporter gene, if expression of that sequence is or gives rise to a detectable event.

The reporter gene may be directly or indirectly induced by events related to LTP induction. That is, the expression of immediate early genes which is associated with LTP may be used as a second signal to induce expression of a reporter gene. This is facilitated by the fact that several immediate early gene products are transcription factors, such as zif-268, or are otherwise involved in the regulation of gene transcription. In this instance, the reporter gene is operatively linked to sequences which are responsive to the expression of immediate early gene products. For example, the reporter gene may be under the control of a zif-268-responsive enhancer, or may comprise a CRE.

In a preferred aspect of the invention, the reporter gene may be incorporated into a vector designed for replication of DNA, and/or transient or permanent transformation of cells and expression of the reporter gene.

As used herein, vector (or plasmid) refers to discrete elements that are used to introduce heterologous DNA into cells for either expression or replication thereof. Selection and use of such vehicles are well within the skill of the artisan. Many vectors are available, and selection of appropriate vector will depend on the intended use of the vector, i.e. whether it is to be used for DNA amplification or for DNA expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequences that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2µ plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in *E. coli* and then the same vector is transfected into yeast or mammalian cells even though it is not capable of replicating independently of the host cell chromosome. DNA can alternatively be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in *E. coli*, an *E. coli* genetic marker and an *E. coli* origin of replication are advantageously included. These can be obtained from *E. coli* plasmids, such as pBR322, Bluescript© vector or a pUC plasmid, e.g. pUC18 or pUC19, which contain both *E. coli* replication origin and *E. coli* genetic marker conferring resistance to antibiotics, such as ampicillin.

Suitable selectable markers for mammalian cells are those that enable the identification of cells which have taken up the vector, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes the reporter gene. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression and cloning vectors usually contain a promoter that is recognised by the host organism and is operably linked to the reporter construct. Such a promoter may be inducible or constitutive, but will in any case be subject to regulation by a regulatory sequence as defined herein. The promoters may be operably linked to DNA encoding the reporter gene by removing the promoter from the source DNA and inserting the isolated promoter sequence into the vector. Both the native promoter sequence normally associated with the reporter and many heterologous promoters may be used to direct expression of the reporter gene. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Preferably, the promoter is itself responsive to modulation by events associated with LTP. Thus, it may be a promoter derived from a gene whose expression is modulated in association with LTP, or it may be a promoter which is modulated by the gene product of a gene which is whose expression is modulated in association with LTP.

Transcription of a reporter gene by higher eukaryotes may be modulated by inserting an enhancer sequence into the vector. This permits a promoter which is not normally responsive to events associated with LTP induction to be rendered so responsive. Enhancers are relatively orientation and position independent. Many enhancer sequences are known from immediate early genes which are subject to LTP-associated modulation and can be selected by a person skilled in the art according to need.

Eukaryotic expression vectors may also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding the reporter gene.

An expression vector includes any vector capable of expressing a reporter gene as described herein. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding a reporter gene may be inserted into a vector suitable for expression of cDNAs in mammalian cells, e.g. a CMV enhancer-based vector such as pEVRF (Matthias, et al., (1989) NAR 17, 6418).

Useful for practising the present invention are expression vectors that provide for the transient expression of DNA encoding reporter genes in mammalian cells. Transient expression usually involves the use of an expression vector that is able to replicate efficiently in a host cell, such that the host cell accumulates many copies of the expression vector, and, in turn, synthesises high levels of the reporter gene when stimulated to do so.

Construction of vectors according to the invention employs conventional ligation techniques. Isolated plasmids or DNA fragments are cleaved, tailored, and re-ligated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing reporter gene expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

Amplification

According to a further aspect of the present invention the method comprises the further step of amplifying the genetic elements. Selective amplification may be used as a means to enrich for genetic elements encoding the desired gene product.

In all the above configurations, genetic material comprised in the genetic elements may be amplified and the process repeated in iterative steps. Amplification may be by the polymerase chain reaction (Saiki et al., 1988) or by using one of a variety of other gene amplification techniques including; Qβ replicase amplification (Cahill, Foster and Mahan, 1991; Chetverin and Spirin, 1995; Katanaev, Kumasov and Spirin, 1995); the ligase chain reaction (LCR) (Landegren et al., 1988; Barany, 1991); the self-sustained sequence replication system (Fahy, Kwoh and Gingeras, 1991) and strand displacement amplification (Walker et al., 1992).

Transformation of Cells

Cells suitable for performing an assay according to the invention are preferably higher eukaryote cells derived from a multicellular organism, and advantageously are mammalian cells. The preferred cell types are neural cells, which may be primary cultures of cells of a neural lineage, or immortalised cell lines of a neural lineage.

Cells may be transformed by any suitable technique available in the art. A number of techniques, such as calcium phosphate precipitation and electroporation are described in Sambrook et al., (1989) Molecular Biology: A Laboratory Manual, Cold Spring Harbor, which is incorporated herein by reference. The preferred number of cells is from about 1 to about $5\times10^5$ cells, or about $2\times10^2$ to about $5\times10^4$ cells. In these methods the predetermined amount or concentration of the molecule to be tested is typically based upon the volume of the sample, or be from about 1.0 pM to about 20 µM, or from about 10 nM to about 500 µM.

The invention also encompasses the performance of the assay in transgenic animals, preparable for example by pronuclear microinjection or by the preparation of ES cell chimeras, according to established techniques.

Exposure of Cells to Test Compounds

Typically the contacting is effected from about 1 to about 24 hours, preferably from about 2 to about 12 hours. Also the contacting is typically effected with more than one predetermined amount of the molecule to be tested. The molecule to be tested in these methods can be a purified molecule, a mixture of molecules or a homogenous sample.

Cells or tissues to be assayed are preferably incubated with the test compound or mixture in an isotonic salt solution, such as Hank's balanced salt solution (HBSS), or artificial cerebrospinal fluid (ACSF) for the period of the exposure. The test compound may be added to the cells by simple addition, or, preferably, by substitution with a "potentiation medium" which includes the compound(s) to be tested. The medium is then advantageously changed, to a medium which supports growth of the cell type in question. In the case of neural cells, a neural growth medium such as NeuroBasal (Gibco BRL) may be used. The cells are then assayed for reporter gene expression as described below.

Compounds or mixtures of compounds are advantageously brought into contact with cells in the context of a high-throughput screening assay. Thus, a number of test systems may be contacted with different compounds or mixtures of compounds, or different amounts of compounds or mixtures, at the same time. The effects of the addition of the compounds are measured by following the detectable signal selected for the test system in use, according to the present invention.

LTP may be induced by chemical or other means, and the activity of the test compound(s) in modulating LTP monitored by means of the assay of the invention. For example, LTP may be induced chemically, as described below, or by field electrical stimulation in cultured cells. The cells may be arranged in a multiwell plate and stimulated using a grid to supply a suitable electrical field, with LTP induction measured by optical screening as described.

Generation of a Detectable Signal

A detectable signal may be generated in any one of a number of ways, depending on the nature of the reporter gene employed in the method of the invention. For example, the detectable signal may be a luminescent, such as a fluorescent signal, e.g. GFP. GFP is a fluorescent polypeptide which produces a fluorescent signal without the need for a substrate or cofactors. GFP expression and detection techniques are well known in the art, and kits are available commercially, for example from Clontech. GFP expression may be assayed in intact cells without the need to lyse them or to add further reagents. Alternatively, the detectable signal may be a signal generated as a result of enzymatic activity or the recognition of a cell surface marker, e.g. LNGFR, or detected following antibiotic selection or through the activation of suicide genes, e.g. addition of GCV to cells expressing TK.

Luciferase may also be used as a basis for an assay. Luciferase expression is known in the art, and luciferase expression and detection kits are available commercially from Clontech (Palo Alto, Calif.). The presence of luciferase is advantageously assessed by cell lysis and addition of luciferin substrate to the cells, before monitoring for a luminescent signal by scintillation counting.

Enzyme-based assays are conducted in a manner similar to a luciferase-based assay, except that the detection is not necessarily via luminescence. The detection technique will depend on the enzyme, and may therefore be optical (such as in the case of β-galactosidase).

Possible Regulatory Components in Pathways

As used herein, the term "transcriptional regulatory control element" includes but is not limited to an element which binds a transcription factor (s) which bind and alters the activity of a gene promoter either positively (induction) or negatively (repression). By way of example, a stress responsive element" or "stress-responsive regulatory element" is a regulatory element which binds transcription factors activated by the cell in response to environmental stress.

Possible Promoters

Other examples of regulatory control elements include but are not limited to a tissue specific promoter, an inducible promoter, a physiologically regulated promoter or any other kind of optimised promoter. These promoter elements may be naturally derivable promoter elements or synthetic promoter elements. The synthetic promoter elements may be prepared by the new synthetic promoter construction method (SPCM) as outlined in Edelman et al (2000) ibid.

The control sequences of the present invention may be modified, for example by the addition of further transcriptional regulatory elements to make the level of transcription directed by the control sequences more responsive to transcriptional modulators.

The nucleotide sequence encoding a promoter of interest is operably linked to a nucleotide sequence encoding a reporter of interest.

Operably Linked

The term "operably linked" means that the components described are in a relationship permitting them to function in their intended manner. A library comprising a regulatory sequence "operably linked" to a reporter sequence is ligated in such a way that expression of the nucleic acid reporter sequence is achieved under conditions compatible with the control sequences.

Promoters

The term promoter is well-known in the art and is used in the normal sense of the art, e.g. as an RNA polymerase binding site. The term encompasses nucleic acid regions ranging in size and complexity from minimal promoters to promoters including upstream elements and enhancers.

The promoter is typically selected from promoters which are functional in mammalian, cells, although promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of α-actin, β-actin, tubulin) or, alternatively, a tissue-specific manner (such as promoters of the genes for pyruvate kinase).

Preferably the promoter is a modified H5 or sE/L promoter (see Carroll, M W, G W Wilkinson & K Lunstrom 2001 Mammalian expression systems and vaccination Genetically Engineered Viruses Ed C J Ring & E D Blair pp 107-157 BIOS Scientific Oxford UK).

Preferably the promoter is an early late promoter used for maximum protein production and which allows optimal sensitivity during antibody identification process.

One preferred promoter-enhancer combination is a human cytomegalovirus (hCMV) major immediate early (MIE) promoter/enhancer combination.

Preferably the promoter is designed using data in Davison & Moss (J. Mol. Biol. 1989 210:749-769).

The level of expression of a nucleotide sequence(s) under the control of a particular promoter may be modulated by manipulating the promoter region. For example, different domains within a promoter region may possess different gene regulatory activities. The roles of these different regions are typically assessed using vector constructs having different variants of the promoter with specific regions deleted (that is, deletion analysis).

Preferably the promoter is a hypoxia regulated promoter.

Preferably the hypoxia regulated promoter is a cell-specific hypoxia regulated promoter.

Preferably the hypoxia regulated promoter is derived from a combination of known DNA-binding moieties optimal for a particular cell type.

The enhancer and/or promoter may be preferentially active in a hypoxic or ischaemic or low glucose environment, when the host cell is cultivated under certain conditions such as ischaemic conditions. The enhancer element or other elements conferring regulated expression may be present in multiple copies. The enhancer and/or promoter may be preferentially active in a hypoxic or ischaemic or low glucose environment, when the host cell is cultivated under certain conditions such as ischaemic conditions. The enhancer element or other elements conferring regulated expression may be present in multiple copies.

Likewise, or in addition, the enhancer and/or promoter may be preferentially active in one or more specific host cell types—such as any one or more of macrophages, endothelial cells or combinations thereof.

Preferably the tissue specific promoters are cardiomyocyte promoters.

Preferably the tissue specific promoters are macrophage promoters.

Examples of suitable tissue restricted promoters/enhancers include but are not limited to those which are highly active in tumour cells such as a promoter/enhancer from a MUC1 gene, a CEA gene or a 5T4 antigen gene. Examples of temporally restricted promoters/enhancers are those which are responsive to ischaemia and/or hypoxia, such as hypoxia response elements or the promoter/enhancer of a grp78 or a grp94 gene. The alpha fetoprotein (AFP) promoter is also a tumour-specific promoter.

Preferably the promoters of the present invention are tissue specific.

The term "tissue specific" means a promoter which is not restricted in activity to a single tissue type but which nevertheless shows selectivity in that they may be active in one group of tissues and less active or silent in another group. A desirable characteristic of the promoters of the present invention is that they possess a relatively low activity in the absence of activated hypoxia-regulated enhancer elements. One means of achieving this is to use "silencer" elements which suppress the activity of a selected promoter in the absence of hypoxia.

The level of expression of one or more nucleotide sequence(s) of interest under the control of a particular promoter may be modulated by manipulating the promoter region. For example, different domains within a promoter region may possess different gene regulatory activities. The roles of these different regions are typically assessed using vector constructs having different variants of the promoter with specific regions deleted (that is, deletion analysis). This approach may be used to identify, for example, the smallest region capable of conferring tissue specificity or the smallest region conferring hypoxia sensitivity.

A number of tissue specific promoters, described above, may be particularly advantageous in practising the present invention. In most instances, these promoters may be isolated as convenient restriction digestion fragments suitable for cloning in a selected vector. Alternatively, promoter fragments may be isolated using the polymerase chain reaction. Cloning of the amplified fragments may be facilitated by incorporating restriction sites at the 5' end of the primers.

Preferably the ischaemic responsive promoter is a tissue restricted ischaemic responsive promoter.

Preferably the tissue restricted ischaemic responsive promoter is a macrophage specific promoter restricted by repression.

Preferably the tissue restricted ischaemic responsive promoter is an endothelium specific promoter.

Preferably the tissue restricted ischaemic responsive promoter of the present invention is an ILRE responsive promoter.

For example, the glucose-regulated proteins (grp's) such as grp78 and grp94 are highly conserved proteins known to be induced by glucose deprivation (Attenello and Lee 1984 Science 226 187-190). The grp 78 gene is expressed at low levels in most normal healthy tissues under the influence of basal level promoter elements but has at least two critical "stress inducible regulatory elements" upstream of the TATA element (Attenello 1984 ibid; Gazit et al 1995 Cancer Res 55: 1660-1663). Attachment to a truncated 632 base pair sequence of the 5'end of the grp78 promoter confers high inducibility to glucose deprivation on reporter genes in vitro (Gazit et al 1995 ibid). Furthermore, this promoter sequence in retroviral vectors was capable of driving a high level expression of a reporter gene in tumour cells in murine fibrosarcomas, particularly in central relatively ischaemic/fibrotic sites (Gazit et al 1995 ibid).

Preferably the selected physiologically regulated promoter elements are heat shock promoter elements.

Preferably the selected physiologically regulated promoter elements are radiation elements.

Preferably the selected physiologically regulated promoter elements are ischaemia elements.

Enhancer

In addition, any of these promoters of the present invention may be modified by the addition of further regulatory sequences, for example enhancer sequences. Chimeric promoters may also be used comprising sequence elements from two or more different promoters described above.

The term "enhancer" includes a DNA sequence which binds to other protein components of the transcription initiation complex and thus facilitates the initiation of transcription directed by its associated promoter.

Other examples of suitable tissue restricted promoters/enhancers are those which are highly active in tumour cells such as a promoter/enhancer from a MUC1 gene, a CEA gene or a 5T4 antigen gene. The alpha fetoprotein (AFP) promoter is also a tumour-specific promoter. One preferred promoter-enhancer combination is a human cytomegalovirus (hCMV) major immediate early (MIE) promoter/enhancer combination.

A preferred enhancer is an is an hypoxia response element (HRE).

HRE

As mentioned above, hypoxia is a powerful regulator of gene expression in a wide range of different cell types and acts by the induction of the activity of hypoxia-inducible transcription factors such as hypoxia inducible factor-1 (HIF-1; Wang & Semenza 1993 Proc Natl Acad Sci 90:430), which bind to cognate DNA recognition sites, the hypoxia-responsive elements (HREs) on various gene promoters. Dachs et al (1997 Nature Med 5: 515) have used a multimeric form of the HRE from the mouse phosphoglycerate kinase-1 (PGK-1) gene (Firth et al 1994 Proc Natl Acad Sci 91:6496-6500) to control expression of both marker and therapeutic genes by human fibrosarcoma cells in response to hypoxia in vitro and within solid tumours in vivo (Dachs et al ibid).

Hypoxia response enhancer elements (HREEs) have also been found in association with a number of genes including the erythropoietin (EPO) gene (Madan et al 1993 Proc Natl Acad Sci 90: 3928; Semenza and Wang 1992 Mol Cell Biol 1992 12: 5447-5454). Other HREEs have been isolated from regulatory regions of both the muscle glycolytic enzyme pyrivate kinase (PKM) gene (Takenaka et al 1989 J Biol Chem 264: 2363-2367), the human muscle-specific β-enolase gene (ENO3; Peshavaria and Day 1991 Biochem J 275: 427-433) and the endothelin-1 (ET-1) gene (Inoue et al 1989 J Biol Chem 264: 14954-14959).

Preferably the HRE of the present invention is selected from, for example, the erythropoietin HRE element (HREE1), muscle pyruvate kinase (PKM), HRE element, phosphoglycerate kinase (PGK) HRE, β-enolase (enolase 3; ENO3) HRE element, endothelin-1 (ET-1) HRE element and metallothionein II (MTII) HRE element.

Agent

The expression and/or detection of a candidate target moiety and/or modulating moiety of the present invention may be carried out using an agent capable directly or indirectly of recognising the candidate moiety. The agent may include but is not limited to a sample which may include but is not limited to a sample obtained from a subject or a sample obtained from an animal or a sample of tissue or a sample of body fluid.

The term "tissue" is used herein to refer to any biological matter made up of one cell, multiple cells, an agglomeration of cells, or an entire organ. The term tissue also encompasses a cell or cells which can be either normal or abnormal (i.e. a tumor). A "body fluid" may be any liquid substance extracted, excreted, or secreted from an organism or a tissue of an organism. The body fluid need not necessarily contain cells. Body fluids of relevance to the present invention include, but are not limited to, whole blood, serum, plasma, urine, cerebral spinal fluid, tears, and amniotic fluid.

Binding Partner (BP)

Detection of expression of the candidate target and/or modulating moiety of the present invention may be achieved, for instance, by the application of a binding partner capable of specifically reacting with the reporter moiety of the present invention.

Preferably, the binding partner (BP) comprises one or more binding domains capable of detecting a reporter moiety and/or binding to one or more host cells expressing a reporter moiety. Thus the BP is directed to a particular cell by its affinity for a reporter moiety.

The one or more binding domains of the BP may consist of, for example, a natural ligand for a reporter moiety, which natural ligand may be an adhesion molecule or a growth-factor receptor ligand (eg epidermal growth factor), or a fragment of a natural ligand which retains binding affinity for the reporter moiety.

Alternatively, the binding domains may be derived from heavy and light chain sequences from an immunoglobulin (Ig) variable region. Such a variable region may be derived from a natural human antibody or an antibody from another species such as a rodent antibody. Alternatively the variable region may be derived from an engineered antibody such as a humanised antibody or from a phage display library from an immunised or a non-immunised animal or a mutagenised phage-display library. As a second alternative, the variable region may be derived from a single-chain variable fragment (scFv). The BP may contain other sequences to achieve multimerisation or to act as spacers between the binding domains or which result from the insertion of restriction sites in the genes encoding the BP, including Ig hinge sequences or novel spacers and engineered linker sequences.

The BP may comprise, in addition to one or more immunoglobulin variable regions, all or part of an Ig heavy chain constant region and so may comprise a natural whole Ig, an engineered Ig, an engineered Ig-like molecule, a single-chain Ig or a single-chain Ig-like molecule. Alternatively, or in addition, the BP may contain one or more domains from another protein such as a toxin.

Antibody

Preferably the binding partner is an antibody.

As used herein, an "antibody" refers to a protein consisting of one or more polypeptides substantially encoded by immunoglobulin genes or fragments of immunoglobulin genes. Antibodies may exist as intact immunoglobulins or as a number of fragments, including those well-characterized fragments produced by digestion with various peptidases. While various antibody fragments are defined in terms of the digestion of an intact antibody, one of skill will appreciate that antibody fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibody fragments encompassed by the use of the term "antibodies" include, but are not limited to, Fab, Fab', F (ab') 2, scFv, Fv, dsFv diabody, and Fd fragments.

Antibodies specifically immunoreactive with the reporter moiety of the present invention represent still another embodiment of the invention. These antibodies may be monoclonal or polyclonal. The antibodies may optionally be recombinant or purely synthetic. The antibody may be an intact antibody or fragment. The preparation of antibodies specific to the candidate moiety of the present invention would be routine for those skilled in the art.

An antibody array may be used in the present invention. The antibodies on the array may be monoclonal or polyclonal. They may be intact antibodies or fragments of antibodies that are capable of specifically binding the reporter moiety of the present invention. Preferably the antibody array comprises at least four different antibodies, and preferably more than about 10 different antibodies. For instance, methods of detecting and/or assaying for expression of a reporter moiety comprises first contacting a sample of body fluid or tissue obtained from the animal or an antibody array with a clone from a library of the candidate modulating moieties of the present invention. The reporter moiety may be contacted with tissue or fluid samples from an animal or directly with an antibody array, and binding of the reporter moiety to the antibody on the array detected. Alternatively, the tissue or fluid sample may be purified to isolate the antibody or mRNA transcripts prior to contact with the clone.

Preferably the antibody is a monoclonal antibody or a polyclonal antibody.

Preferably the antibody is of high affinity and titre. If the antibody is of low affinity and/or titre, then preferably the reporter moiety is expressed at high levels.

Screens for the Target Candidate Modulating Moiety

The direct or indirect detection of expression of the reporter moiety of the present invention may be achieved, for instance, by the application of labeled antibodies specifically immunoreactive with the reporter moiety expression product. The antibodies may be derived from tissue or from body fluid samples removed from a human or an animal. Various forms of typical immunoassays known to those skilled in the art would be applicable here. These assays include both competitive and non-competitive assays. For instance, in one type of assay sometimes referred to as a "sandwich assay", immobilized antibodies that specifically react with the reporter moiety are contacted with the biological tissue or fluid sample. The presence of the immobilized reporter moiety antibody complex could then be achieved by application of a second, labeled antibody immunoreactive with either the reporter moiety or the reporter moiety-antibody complex. A Western blot type of assay could also be used in an alternative embodiment of the present invention.

Use of the Identified Target and/or Modulating Moiety

The identified target and/or modulating moiety of the present invention may be used in a vector operably linked to a regulatory control region and/or a nucleotide sequence of interest (NOI). In one embodiment, the identified target and/or modulating moiety of the present invention may operably linked to a regulatory control region and/or a nucleotide sequence in a vector for vector delivery to, for example, a target cell or target tissue.

Pharmaceutical Compositions

In one aspect, the present invention provides a pharmaceutical composition, which comprises a vector comprising an identified modulating moiety operably linked to a regulatory control region and/or a NOI and a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the pharmaceutical composition is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose or chalk, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Administration

Typically, a physician will determine the actual dosage which will be most suitable for an individual subject and it will vary with the age, weight and response of the particular patient and severity of the condition. The dosages below are exemplary of the average case. There can, of course, be individual instances where higher or lower dosage ranges are merited.

The compositions (or component parts thereof) of the present invention may be administered orally. In addition or in the alternative the compositions (or component parts thereof) of the present invention may be administered by direct injection. In addition or in the alternative the compositions (or component parts thereof) of the present invention may be administered topically. In addition or in the alternative the compositions (or component parts thereof) of the present invention may be administered by inhalation. In addition or in the alternative the compositions (or component parts thereof) of the present invention may also be administered by one or more of: parenteral, mucosal, intramuscular, intravenous, subcutaneous, intraocular or transdermal administration means, and are formulated for such administration.

By way of further example, the pharmaceutical composition of the present invention may be administered in accordance with a regimen of 1 to 10 times per day, such as once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The term "administered" also includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Hence, the pharmaceutical composition of the present invention may be administered by one or more of the following routes: oral administration, injection (such as direct injection), topical, inhalation, parenteral administration, mucosal administration, intramuscular administration, intravenous administration, subcutaneous administration, intraocular administration or transdermal administration.

Diseases

Pharmaceutical compositions comprising an effective amount of vector comprising an identified modulating moiety operably linked to an NOI may be used in the treatment of disorders such as those listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; diseases associated with viruses and/or other intracellular pathogens; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimoorchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue. Specific cancer related disorders include but not limited to: solid tumours; blood born tumours such as leukemias; tumor metastasis; benign tumours, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; wound granulation; corornay collaterals; cerebral collaterals; arteriovenous malformations; ischeniic limb angiogenesis; neovascular glaucoma; retrolental fibroplasia; diabetic neovascularization; heliobacter related diseases, fractures, vasculogenesis, hematopoiesis, ovulation, menstruation and placentation.

The present invention will now be further described by way of the following non-limiting examples, provided for illustrative purposes only.

EXAMPLES

Example 1. Steps in Identifying a Cellular Response Moiety and a Modulating Moiety Identify a target gene (use expression profiling)
Identifying a target cell
Introduce a construct comprising a promoter (and enhancer) operably linked to a reporter gene (eg GFP, LNGFR) into the target cell
Culture the cells and identify suitably transduced cells
Transduce the cells with a library of interest
Screen cells under conditions which activate a cellular response pathway and result in a detectable phenotype (eg reporter expression/increase in transcription etc, cell death etc)
Collect cells showing a change in phenotype
Isolate and library insert and amplify
This allows you to identify the cellular response moiety and the modulating moiety
Optionally re-test the modulating moieties
FIG. 1 is a schematic representation of the method of the present invention.
Step 1=Identification of a Target NOI
The present invention provides a screening method for isolating unidentified components of signalling pathways which are tailored for the cellular response pathway of interest.

In this example, the approach requires the prior identification of an NOI whose expression is specifically up or down-regulated in response to a stimulus (or its withdrawal) which activates the pathway.

If a suitable target NOI is not already known, the target NOI may be identified candidates by expression profiling.
Step 2=Prepare a Construct A construct comprising the promoter of the NOI operably linked to a reporter gene is prepared. By way of example, the promoter of the NOI is then used to drive expression of a reporter gene, such as GFP or LNGFR.
Step 3=Identification of a Target Cell of Interest A target cell is identified and the construct may be introduced into the target cell by transfection with a construct consisting of the reporter cDNA flanked with sufficient sequence to allow homologous recombination to the site of interest (Hanson & Sedivy 1995 Mol cell Biol 15(1):45-51). This approach has the advantage that the full length promoter, including any enhancers, will be driving reporter expression.

Alternatively, expression cassette may be cloned into a viral vector and used to transduce a target cells of interest (to give a stably expressing target cell).

Step 4=Identification of Suitably Transfected or Transduced Target Cell

The transfected/transduced cells are maintained under appropriate cell culture conditions allow the identification of transfected/transduced cells.

Step 5=Introduction of a Library of Interest into the Transduced Cell

Figure 2:
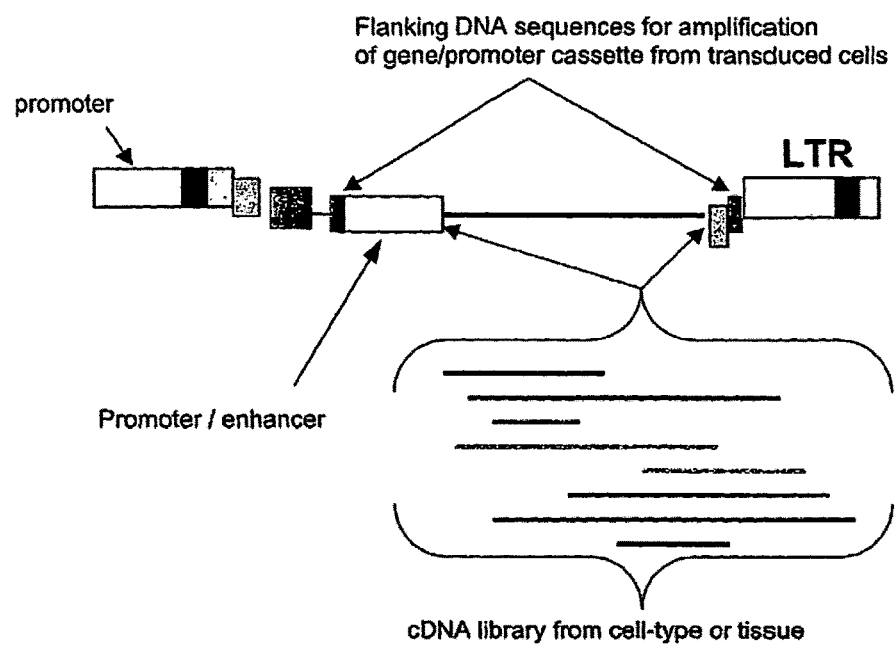
FIG. 2 is a schematic representation of a library construct suitable for introducing an NOI into a target cell.

Once stably transfected/transduced cells have been cloned, or cells expressing similar GFP levels pooled, a library of modulating moieties such as a ribozyme library or an antisense library may be introduced into the target cells by either transfection or transduction. A schematic representation of a library vector is given in FIG. 2.

The vector genomes may be designed with a view to studying a specific condition.

Constitutive Expression of the Encoded cDNA

The vector genome may be designed such that expression of the encoded cDNA will be either constitutive (the technology for this is as described in our WO98/17816, WO99/32646 and WO98/17815); or limited to transduced cells only (the technology for this is as described in our WO99/15683).

Limiting expression of genes to transduced cells only allows the construction of libraries within bacterial hosts, and their subsequent production as lentiviral vectors in eukaryotic cells whilst maintaining a representative sample of all the genes expressed within a given cell or tissue. This avoids the problems associated with obtaining libraries representative for toxic genes, as unregulated expression will not arise during the construction of the library or production of the lentiviral vector.

The vector genome may incorporate GATEWAY™ cloning technology (Gibco BRL) to allow the rapid cloning of commercially available GATEWAY™ libraries of interest into the vector.

Briefly, the libraries may be constructed in a GATEWAY™ entry clone chosen with the required outcome in mind. The lentiviral genome(s) may be adapted for GATEWAY™ technology by incorporation of the conversion cassette as described by the manufacturer.

The use of GATEWAY™ technology facilitates the subsequent validation of genes of interest; for instance the use of other GATEWAY™ compatible vectors may provide a rapid means of secondary screening and validation (for example, Yeast Two-hybrid vectors) to determine the mechanism of action of a given gene.

The vector genomes may incorporate a promoter cassette that will facilitate rapid alterations in the promoter and/or enhancer regions responsible for gene expression. This allows the promoter within the vector genome to be chosen with the target cell/tissue type in mind. For example, in order to study the effect of library genes on tissues during the hypoxic response, a hypoxia response element (HRE) could be incorporated into the enhancer region of the vector promoter, thus enhancing expression of the gene(s) of interest under such experimental conditions.

Once a cell/tissue type/library combination has been selected the library of interest may be cloned into the GATEWAY™-compatible lentiviral genome containing the required promoter/enhancer cassette; this will be carried out using the LR Reaction as outlined in the GATEWAY™ Cloning Technology user manual (Gibco BRL).

Another important consideration for the design of suitable vector genomes is to ensure that the retrieval of genes of interest from transduced cells may be carried out rapidly. In order to do this, vector-specific regions of DNA will be designed to flank the integrated gene/promoter cassette; this will allow the retrieval of genes from cell DNA extracts by PCR using oligonucleotide primers specific for the flanking regions.

The further validation of interesting gene(s) will be facilitated by the simple and rapid transfer of such gene(s) into other GATEWAY™ vectors. This is carried out by alternate LR and BP reactions as described in the GATEWAY™ manual.

Once the lentiviral library virus has been produced, it will be used to transduce cells. These can be cells exposed to a specific environmental condition, or tissues in a specific diseased state. Analysis of the transduced cells/tissues will be aimed at detecting an altered cellular response to that which normally occurs in the given environmental conditions or disease state.

A similar approach as to that described above for lentiviral vector libraries can be designed for other vector systems. Possible examples of other vector systems are: Retrovirus (eg. MoMLV)-based system; Adenovirus-based system, or Adeno Associated Virus-2 (AAV-2)-based system.

Step 6=Screening of Transfected/Transduced Cells

The transfected/transduced cells is subsequently screened, under conditions for activating a cellular response pathway and hence reporter expression. By way of example, in the case of a promoter which is down-regulated by activation of the pathway transduced cells are screened for GFP switch-on.

Step 7=Isolation of Cells Expression a Phenotype of Interest

Identified cells expressing a phenotype of interest (eg upregulation or down regulation of GFP expression) are collected by FACS and the library insert is amplified by PCR using primers to the flanking regions. Candidates are further tested by re-transduction of target cells.

Example 2. Immortalisation

A target cell, which may be terminally differentiated or a primary cell of limited proliferative potential (which may also be described as non-dividing or slowly dividing/senescent/quiescent), is transduced with a lentiviral vector encoding an NOI(s) which is able to induce/maintain cell division (immortalisation). The NOI(s) may be one or more 'immortalising genes', for example ectopic expression of a combination of human telomerase (hTERT) and a temperature-sensitive mutant of simian virus large-tumour antigen has been shown to conditionally immortalise freshly isolated mammary fibroblasts and endothelial cells (O'Hare, M. J. et al Proc Natl Acad Sci USA (16 Jan. 2001) 98(2):646-51). In the case of an inhibitory protein(s) preventing cell division the NOI(s) may include a ribozyme(s).

The purpose of this being to reproduce, as closely as possible, the cellular environment in the in vivo situation, whilst facilitating screening of manipulated cells.

The choice of target cell and method is ultimately a balance between these two factors, with the following cells cultured in vitro listed in descending order of 'desirability' with regard to resembling cells in vivo and ascending order with regard to ease of handling:

1. primary cells in vitro
2. primary cells 'immortalised' by delivery of appropriate NOI by lentiviral vector
3. established immortalised cell line

The present invention allows all of these cell types to be screened, whereas current technology limits the target cell to being a dividing cell.

Example 3. Identification of Drug Targets and Modulating Moieties Implicated in a Cancer Response Pathway, Such as Breast Cancer Neu-Ras Pathway Breast cancer is the most common malignancy among women. Most of these cancers over-express cyclin D1 (Gillett et al 1994 Cancer Res 54(7):1812-7). In mammary epithelial cells the Neu-Ras pathway is connected to the cell cycle machinery by cyclin D1 (Yu et al 2001 Nature 411 (6841):1017-21), which is an absolute requirement for malignant transformation in this tissue. Anti-cyclin D1 therapies are thought to have great potential in treating human breast cancers with activated Neu-Ras pathways. The method of the present invention may be used to identify targets other than cyclin D1 which mediate the Neu-Ras signal causing inappropriate up-regulation of the cyclin D1 promoter.

Prepare a Construct for Introduction into the Target Cell

Prepare a construct comprising the cyclin D1 promoter operably linked to a reporter gene.

Cells other than mammary epithelial cells may be used for the selection procedure because mammary epithelial cells will not proliferate in the absence of cyclin D1. Possible target cells include but are not limited to Ras and Neu-driven fibroblast tumours which express high levels of cyclin D2 and cyclin D3 in addition to cyclin D1 thus ablation of cyclin D1 would not prevent cell proliferation. The choice of these cells has the advantage of directing selection towards cyclin D1-specific targets which leaves cyclin D2 and/or D3 expression unaffected. Cells such as HT1080, an immortalised human fibroblast cell line, may also be suitable.

Maintenance of the Cells Under Conditions Which Activate the Response Pathway

Activation of the pathway could be achieved by over-expression of Ras or of Neu (which is upstream of Ras). Reporter expression may be dependent on the stage of the cell cycle. Accordingly, the screening method may be tailored so that the screens are carried out at a stage in the cell cycle (eg G1) where cyclin D1 expression is normally highly. Alternatively, it may be possible to synchronise the target cells by block and release or elutriation prior to screening. Another option would be to perform successive screens such that the probability of all cells being screened at the appropriate time in their cell cycle is unity.

Figure 3:
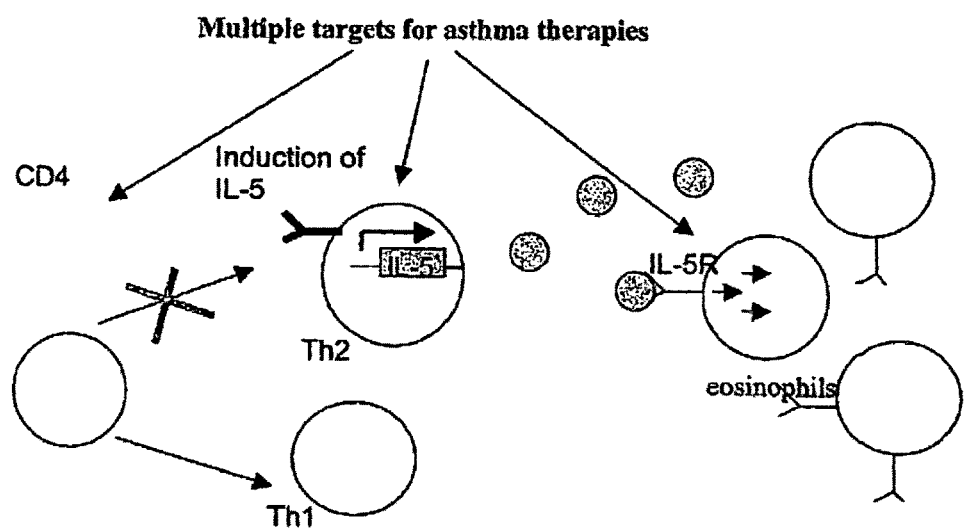
FIG. 3 is a schematic representation of a lentiviral strategy for identifying drug targets for inflammatory disease.

Example 4. Identification of Drug Targets and Modulating Moieties Implicated in an Inflammatory Disease Response Pathway, Such as Asthma A schematic of lentiviral strategy for identifying drug targets for inflammatory disease is shown in FIG. 3.

Inflammatory Diseases

Many inflammatory disease states are attributed to the imbalance of T helper cell populations (Stirling & Chung 2000 Eur Respir J 16(6):1158-74). The identification of targets in signalling pathways leading to Th2 rather than Th1 differentiation of CD4 progenitors could prove valuable in a range of inflammatory disease types.

Asthma

The asthmatic response is a multifactorial response pathway characterised by an upregulation in eosinophil levels. The IL-5 receptor is expressed on cells of the eosinophil lineage and acts to induce eosinophil differentiation and prolong their survival. The asthmatic response may also be attributed to an imbalance in T helper cell populations. Thus, intervention at one of following stages may help to alleviate eosinophilia:

These possible intervention strategies include but are not limited to:
Inhibiting/blocking the IL-5 pathway in eosinophils
Inhibition of Th-2-derived cytokine expression eg. IL-5
Reducing the number of circulating Th2 cells by inhibition of Th2 differentiation.

Glucocorticoids are also known to act to repress transcription of the IL-5 promoter in Th2 cells but to have undesirable side effects (Weltman & Karim 2000 Expert Opin Investig Drugs 9(3):491-6). Thus, the identification of proteins which lead to IL-5 transcription in T-cells may also provide alternative drug targets to prevent IL-5 secretion by T-cells.

IL-5 Signalling Pathway

The IL-5 receptor is expressed on cells of the eosinophil lineage and acts to induce eosinophil differentiation and prolong their survival. Eosinophilia is a characteristic of asthma and inhibition of the IL-5 signalling pathway should relieve symptoms of the disease.

Preparation of a Construct Using the IL-S Promoter

The promoter of an NOI up-regulated by IL-5 is used to drive reporter gene expression in a suitable cell type.

Identification of a Suitable Target Cell

A suitable IL-5 dependent target cell is chosen, such as a TF-1.8 cell line. Alternatively, use of target T cells, such as Th1 and Th2 cells may allow the identification of targets in signalling pathways leading to Th2 rather than Th1 differentiation of CD4 progenitors could prove valuable in a range of inflammatory disease types.

Example 5. Identification of Drug Targets and Modulating Moieties Implicated in a Neurodegenerative Response Disease Pathway Such as Alzheimer's Disease Alzheimer's disease is characterised by deposition of Aβ-amyloid and neurofibrillary tangles in many brain regions. Two β-secretases, BACE1 and BACE2, are involved in generation of toxic Alzheimer's disease Aβ peptides. These are generated by endoproteolytic cleavage of β-amyloid precursor protein (APP) by β- and γ-secretase. It has been reported that secretion of Aβ peptides is abolished in cultures of BACE-1 deficient cortical neurons (Cai, H. et al Nat Neurosci. (March 2001) 4(3):233-4.). In brain, BACE1 mRNA is high. BACE1 is synthesised as a pro-enzyme which is cleaved by furin to produce the mature enzyme. There are no apparent adverse effects associated with BACE1 deficiency in mice and therefore it has been suggested that inhibition of BACE1 in humans may not have mechanism-based toxicity (Luo et al 2001).

Preparation of a Construct

The BACE1 promoter is chosen to drives reporter expression.

Target Cell

The target cell is a neuron.

Maintenance of the Target Cell

In this case expression of the reporter will be constitutive.

Introduction of a Library of Interest

Following transduction with a library (antisense, cDNA or ribozyme), cells are screened for reporter switch-off.

Identification of Cells Expressing a Phenotype of Interest

Molecules which ablate expression of reporter, and hence BACE1, are potential therapies/drug targets for the treatment of Alzheimers.

A similar strategy may be followed for γ-secretase.

Example 6

Genes of Interest:
Genes that prevent an apoptotic response.
Disease State:
Parkinson's disease.
Hypoxia-induced apoptosis in neuronal cells.
Target/Host Cells:
Rat neuronal cells.
Rationale:
Apoptosis of neuronal cells is an important factor in the pathogenesis of a number of neuronal diseases, including Parkinson's disease.
Stimuli In Vitro:
The neuronal apoptotic response can be induced in vitro by stimuli that can be used to mimic such disease states. Among the possible stimuli are hypoxia, ischaemia, hypoxia/ischaemia, glutamate, kainate, 6-hydroxy dopamine, staurosporine, nitric oxide, or wortmanin.

Apoptosis can be rapidly evaluated by histology and immunohistochemistry, combined with molecular assays such as the activation of Caspase-3, DNA laddering or permeation of cell membranes cells surviving hypoxia-induced apoptosis are indicative of non-apoptotic cells.

For example, in order to identify genes with the capacity to prevent hypoxia-induced apoptosis in neuronal cells, a cDNA library will be constructed in a lentiviral vector (for example a representative rat neuronal [or other rat cell type/tissue] cDNA library).
Vector Design:
Genes will be expressed under the control of a minimal CMV promoter and HRE.
Target Host Cell:
Rat neuronal cells will be transduced with this lentiviral vector library.
Identify Gene of Interest:
Cells surviving hypoxia-induced apoptosis would be analysed by a PCR based assay, designed to amplify the cDNA expressed by the transducing vector.
Secondary Screens Using a Vector Genome+Gene:
Once gene(s) have been isolated, sequenced and identified, the vector genome will be reconstructed and secondary screens designed to test the ability of the gene to inhibit both hypoxia-induced apoptosis and apoptosis induced by alternative stimuli.
Further Characterisation Studies
Further studies will be carried out to characterise the mode of action of gene(s) of interest and to identify possible uses of the gene in a therapeutic or other field.

Example 7. Use of Lentiviral Vectors to Identify Genes that Allow Human Eosinophils to Survive In Vitro in the Absence of IL-5

Eosinophils, and eosinophilic cell lines such as TF-1, are dependent upon exogenous IL-5 for their survival in vitro. Removal of IL-5 from these cells results in rapid cell death.
CDNA Library:
A library that expresses cDNAs isolated from the eosinophilic cell line AML14.3D10; this cell line is not dependent upon exogenous IL-5 for its survival.

Vector Design:
A lentiviral cDNA library vector will be constructed (for example a library that expresses cDNAs isolated from the eosinophilic cell line AML14.3D10; this cell line is not dependent upon exogenous IL-5 for its survival);
Target Host Cells:
IL-5 dependent eosinophils or TF-1 cells will be transduced with this library and the exogenous IL-5 will be removed.
Screens:
Cells that are able to survive in the absence of IL-5 will be isolated.
Isolation of cDNA of Interest:
The cDNA expressed by the transducing vector will be amplified by PCR, cloned and sequenced. Secondary screens will be designed to test the ability of the gene to inhibit the cell death associated with IL-5 removal from eosinophils and TF-1 cells. Further studies will be carried out to characterise the mode of action of gene(s) of interest and to identify possible uses of the gene in a therapeutic (eg asthma) or other field.

Example 8

This approach may prove useful for the identification of directed immunosuppressive cDNAs or ribozymes for use in organ transplantation or other therapeutic areas. The identified nucleotides may be useful as a replacement for drugs that have to be taken for life following organ transplantation.

This approach can be adapted to study a positive or negative regulatory effect upon any cellular transcription factor (another example is the Nuclear Factor Kappa B (NF-κB) family of transcription factors).

Use of lentiviral vector libraries to identify genes that affect the activation of a transcription factor-dependent reporter gene. An example of this could be to look for genes that prevent the activation of the Nuclear Factor of Activated T-cells (NFAT) transcription factor.

Briefly, NFAT can be activated in vitro by stimulation of cells containing NFAT (such as human T-cell lines) with calcium ionophore (e.g., ionomycin) and phorbal ester (e.g., Phorbal Myristyl Acetate, PMA). This treatment activates calcineurin phosphatase ($Ca^{2+}$-dependent Ser/Thr protein phosphatase), which in-turn dephosphorylates NFAT. Dephosphorylation of NFAT leads to its nuclear localisation where, together with the transcriptional co-activator AP-1 (activated by PMA treatment), it initiates transcription of NFAT-dependent genes.

In order to detect cDNAs that affect transcription of genes dependent on the transcription factor of interest, it is necessary to obtain a cell line that expresses a reporter gene dependent on that factor. This can then be exploited using lentiviral libraries for genes with a positive or negative regulatory effect.
CDNA Library:
Prepare a cDNA library expressing cDNAs from a variety of human immune cell types, under the control of a constitutively active promoter.
Target Host Cells (Comprising a Reporter Gene):
Human T-cell lines will be stably transfected with an NFAT-dependent reporter gene, such as GFP (or LNGFR).
Vector Genome Design:
These cells will be transduced with a lentiviral vector cDNA library expressing cDNAs from a variety of human immune cell types, under the control of a constitutively active promoter.

Stimulation of Host Cells:

Transduced cells will be exposed to stimuli that would normally result in the activation of the GFP reporter gene.

Cell Screens:

Cells will be FACS sorted to remove cells expressing high levels of GFP.

These cells will be grown under continuous stimulation and subjected to further rounds of FACS enrichment of low level GFP-expressing cells.

Single cells will be isolated and the cDNA(s) expressed by the transduced virus cloned, sequenced and identified. These genes will be evaluated alongside a known inhibitor of the relevant transcription factor (eg. Cyclosporin A is a potent inhibitor of NFAT-dependent gene expression).

This approach may prove useful for the identification of directed immunosuppressive cDNAs for use in organ transplantation or other therapeutic areas. This approach can be adapted to study a positive or negative regulatory effect upon any cellular transcription factor (another example is the Nuclear Factor Kappa B (NF-κB) family of transcription factors). In order to detect cDNAs that affect transcription of genes dependent on the transcription factor of interest, it is necessary to obtain a cell line that expresses a reporter gene dependent on that factor. This can then be exploited using lentiviral libraries for genes with a positive or negative regulatory effect.

A second possibility is to use a lentiviral ribozyme library. This is used to isolate artificial negative regulators of the transcriptional factor.

Example 9. Chronic Myeloid Leukaemia (CML): Ablation of the Bcr-Abl Tyrosine Kinase CML is a haematopoietic malignancy of stem cell origin. It is associated with a specific cytogenetic lesion, the Philadelphia chromosomal translocation. Genomic sequences within the BCR gene on chromosome 22 are juxtaposed with those of the ABL tyrosine kinase gene on chromosome 9. This results in replacement of sequences encoded by the first exon of ABL with BCR derived sequence and expression of a 210 Kd chimeric fusion protein Bcr-Abl with deregulated kinase activity. In a subset of acute lymphoblastic leukaemia (ALL) a chimeric protein product of 185 kDa is formed reflecting an alternative site of BCR rearrangement.

Expression of this protein leads to cytoskeletal and adhesive abnormalities and generates proliferative and antiapoptotic signals via the activation of RAS, PI 3' kinase, STAT, ERK and JNK MAP kinase pathways. It is retained exclusively in the cytoplasm of transformed cells and when trapped inside of the nucleus is reported to induce apoptosis (Vigneri & Wang 2001 Nat Med. 2001 February; 7(2):228-34.).

The drug STI-571 (Gleevec), a tyrosine kinase inhibitor has proved very successful in treating the early, chronic phase of CML by binding and switching off p210. However in the later acute phase, 'blast crisis' caused by further genomic instability, patients initially respond well to the drug but most relapse. This is as a result of blast-crisis cells becoming resistant to STI-571, through a single mutation in p210 or an increase in BCR-ABL gene number (Gorre et al 2001 Science. 2001 Aug. 3; 293(5531):876-80.). Because of this it is thought that a cocktail of drugs will be vital in treating this stage of CML (McCormick 2001 Nature. 2001 Jul. 19; 412(6844):281-2.). The fact that Bcr-Abl remains active in STI-571 resistant cells suggests that the chimeric onco-protein remains a rational drug target and a number of therapies in which BCR-ABL oncogene expression is inhibited at the level of translation have been proposed (Jahagirdar et al 2001 Exp Hematol. 2001 May; 29(5):543-56.).

Experimental Strategy:

One approach would be to identify genes whose transcription is upregulated by Bcr-Abl and utilise their promoters to drive reporter expression in order to identify downstream effectors of the fusion protein. However, the drawback with this strategy is that the tyrosine kinase is likely to have many substrates, for example it directly phosphorylates STAT5 (Sillaber et al 2000 Blood. 2000 Mar. 15; 95(6):2118-25), and targeting all pathways activated by Bcr-Abl would be difficult. Also it is likely that these signal transduction pathways may be critical to the function of normal cells.

A better strategy would be to inhibit expression of the BCR-ABL oncogene itself.

Transcriptional control is under the BCR promoter whose function is reported to remain intact in spite of genomic rearrangement. This would also have the effect of inhibiting the expression of the Bcr protein encoded by the normal allele, a serine/threonine kinase whose function is not known (Liu et al 1996 Mol Cell Biol. 1996 March; 16(3):998-1005), but which is reported to antagonise the oncogenic effects of Bcr-Abl (Arlinghaus 1998 Crit Rev Oncog. 1998; 9(1):1-18). The BCR promoter has been functionally localised to a region 1 kb 5' of BCR exon I coding sequences (Shah et al 1991 Mol Cell Biol. 1991 April; 11(4):1854-60; Zhu et al 1990 Nucleic Acids Res 1990 Dec. 11; 18(23):7119-7125), however, low steady state levels of BCR mRNA were reported. Therefore to improve the detection of reporter gene product the use of LNGFR, rather than GFP, would be advantageous.

Bcr has been reported to be evolutionarily conserved and expressed in many different types of human cells (Collins et al, 1987 Mol Cell Biol 1987 August; 7(8):2870-2876) therefore the possibility that ablation of BCR expression may be toxic to normal cells should be considered. Nevertheless, treatment over a short time period with an inhibitor of BCR expression combined with STI-571 may be sufficient to provide an effective therapy. Importantly, BCR is not an essential gene (Voncken et al 1998 Int J Mol Med 1998 November; 2(5):577-583) and bcr null mutant mice show normal development and fertility, although reported to exhibit increased neutrophil respiratory burst and defects in hormonal and behavioral stress responses (Voncken et al 1995 Cell 1995 Mar. 10; 80(5):719-728; 1998 Oncogene 1998 Apr. 16; 16(15):2029-2032). It has been reported that, from analysis of fresh CML and normal haematopoietic bone marrow cells, p210 and the normal Bcr and Abl proteins, are expressed primarily in the early stages of myeloid maturation, and that levels of expression are reduced significantly as the cells mature to polymorphonuclear leukocytes (Wetzler et al, 1993 J Clin Invest 1993 October; 92(4):1925-1939).

The approach is validated by data which demonstrate that a treatment strategy which combines an agent that lowers Bcr-Abl levels, e.g. arsenic trioxide (As2O3), with an agent that inhibits Bcr-Abl TK activity, e.g. STI-571, can potently induce apoptosis and differentiation of BCR-ABL-positive human leukaemic cells. (Perkins et al, 2000 Blood. 2000 Feb. 1; 95(3):1014-22; Porosnicu et al, 2001 Leukemia 2001 May; 15(5):772-778). Indeed in the prechemotherapy era arsenic derivatives were used for treatment of chronic myelogenous leukaemia (Kwong & Todd, 1997 Blood. 1997 May 1; 89(9):3487-8. Puccetti et al 2000 Cancer Res 2000 Jul. 1; 60(13):3409-3413).

A study of the level of expression of the BCR-ABL transcript in chronic and blast phase cells showed occasionally increased steady state levels occur in blast phase cells in the absence of genomic amplification. This was attributed to changes in BCR promoter activity (Andrews & Collins, 1987 Leukemia. 1987 October; 1(10):718-24.), pointing to the importance of identifying elements that control BCR expression.

Experimental Outline:
1. Construction of a lentiviral vector containing an LNGFR reporter gene cassette under control of the BCR promoter.
2. Testing of the construct in Philadelphia chromosome positive and negative cell lines.
3. Establish stable cell line or pool containing the reporter construct.
4. Transduction of reporter cells with lentiviral ribozyme library (containing antibiotic resistance marker).
5. Isolation of transduced cells by antibiotic selection.
6. Use MACs beads to remove LNGFR expressing cells.
7. Isolate library constructs from remaining cells for re-testing.
8. Further downstream testing and validation.

An alternative approach to identify elements which up-regulate expression would involve screening a cDNA library (A Ph+ CML library in a Gateway™ compatible vector is available).

Example 11. Polycystic Kidney Disease

The PKD1 gene accounts for 85% of autosomal dominant polycystic kidney disease (ADPKD), the most common human genetic disorder with a frequency ranging from 1:400 to 1:1000 (Dalgaard 1957 Acta Med Scand 1957; 328:1-255.), which is responsible for nearly 10% of cases of end-stage renal failure in adults. The disease is usually of late onset (between third to seventh decade), primarily characterized by the formation of fluid-filled cysts in the kidneys.

Renal cysts most probably arise after a second somatic event, which inactivates the inherited healthy allele of the same or a counterpart gene. The 2.5-kilobase pair poly (purine.pyrimidine) (poly(R.Y)) tract present in intron 21 of the polycystic kidney disease 1 (PKD1) gene has been proposed to contribute to the high mutation frequency of the gene by stimulating repair and/or recombination functions (Bacolla et al 2001 J. Biol. Chem. 2001 May 25; 276(21): 18597-604.). Although it has also been suggested that the intrinsically high frequency of somatic second hits in epithelia appears to be sufficient to explain the frequent occurrence of somatic second hits in the disease-causing genes (Amaout 2001 Annu Rev Med. 2001; 52:93-123. Review.).

About one-half of people with the major type of PKD progress to kidney failure, i.e., end-stage renal disease (ESRD), when the patient requires dialysis or kidney transplantation.

Figure 4:
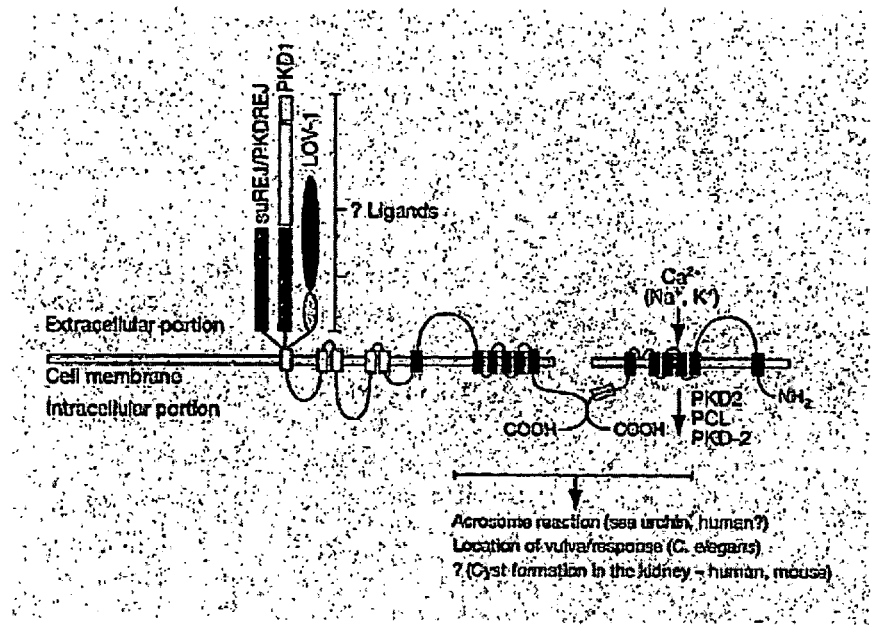
FIG. 4 shows two components of the proposed polycystin signalling pathway.

The identical clinical phenotype in human patients and targeted Pkd1 and Pkd2 mutant mouse models provides evidence that both gene products act in the same pathogenic pathway. Whilst the predicted protein domain structure of polycystin-1 suggests it is involved in cell-cell or cell-matrix interactions, the similarity of polycystin-2 and polycystin-L to the pore-forming domains of some cation channels suggests that they all form subunits of a large plasma membrane ion channel. The PKD proteins can initiate signal transduction, leading to the activation of a number of downstream effectors, including heterotrimeric G-proteins, protein kinase C, mitogen-activated protein kinases, beta-catenin, and the AP-1 transcription factor. In addition, polycystin-2 may function in mediating calcium flux. FIG. 4 shows two components of the proposed polycystin signalling pathway.

The pathogenesis of cyst formation is currently thought to involve increased cell proliferation, fluid accumulation, and basement membrane remodeling. It now appears that cyclic adenosine monophosphate (cAMP) metabolism is a central component of cyst formation, stimulating apical chloride secretion through CFTR channels and driving the accumulation of cyst fluid. In contrast to normal kidney cells whose cell proliferation is inhibited by cyclic AMP, ADPKD cells are stimulated to proliferate. Thus, it is likely that an alteration in polycystin function transforms the normal cellular phenotype to one that responds to elevated cyclic AMP by an increased rate of cell proliferation and that the enlarging cyst expands by an increased rate of cyclic AMP-driven fluid secretion. Cyclic AMP and growth factors, including epidermal growth factor, have complementary effects to accelerate the enlargement of ADPKD cysts, and thereby to contribute to the progression of the disease. This knowledge should facilitate the discovery of inhibitors of signal transduction cascades that can be used in the treatment of ADPKD (Calvet & Grantham 2001 Semin Nephrol. 2001 March; 21(2):107-23. Review.).

Increased cell proliferation and apoptosis have been implicated in the pathogenesis of cystic diseases. Boletta et al (2000 Mol Cell. 2000 November; 6(5):1267-73.) suggest that PKD1 may function to regulate both pathways, allowing cells to enter a differentiation pathway that results in tubule formation. In a recent review Grantham (2001 Curr Opin Nephrol Hypertens. 2001 July; 10(4):533-42.) predicts the converging of the disciplines of physiology and molecular biology on a signal transduction pathway that controls epithelial morphogenesis and maturation and whose breakdown lies at the heart of the cyst problem. Amould et al (1999 Mol Cell Biol. 1999 May; 19(5):3423-34.) found that PKD2 upregulated AP-1-dependent transcription in human embryonic kidney 293T cells. The PKD2-mediated AP-1 activity was dependent upon activation of the mitogen-activated protein kinases p38 and JNK1 and protein kinase C (PKC) epsilon, a calcium-independent PKC isozyme.

Coexpression of PKD2 with the interacting C terminus of PKD1 dramatically augmented PKD2-mediated AP-1 activation. AP-1 is a transcription factor that regulates different cellular programs such as proliferation, differentiation, and apoptosis. Activation of these signaling cascades may promote the full maturation of developing tubular epithelial cells, while inactivation of these signaling cascades may impair terminal differentiation and facilitate the development of renal tubular cysts.

At the cellular level, PKD mutations result in abnormal distribution of epidermal growth factor receptor (EGFR) in tubule epithelia. This receptor is normally restricted to the basolateral domain of tubule epithelia but in cyst epithelia it appears at the apical (luminal) surface. Because cyst fluid contains epidermal growth factor, and EGFR transduces mitogenic signals upon binding its ligand, the mislocalization of EGFR might be a crucial mechanism driving cyst growth. Cyst formation can be prevented in organ culture by blocking EGFR activity using anti-EGFR antibodies or tyrphostins, which inhibit the tyrosine kinase activity of the receptor (Pugh et al 1995 Kidney Int. 1995 March; 47(3): 774-81.).

In the Tg737 deficient mouse (a model of polycystic kidney disease), introducing inactive EGFR (which blocks the activity of the mislocalized EGFR) into cyst epithelium substantially reduces cyst formation (Richard et al 1998 J Clin Invest. 1998 Mar. 1; 101(5):935-9.). Future therapies for polycystic kidney diseases may be directed towards inhibiting the activity of mislocalized EGFR using gene therapy or tyrphostins, or neutralizing epidermal growth factor in urine with antibodies or other neutralizing agents.
Experimental Strategy:
1. Confirm expression of PKD1 expression in A431 cells (Northern)
2. Delete by homologous recombination (2 rounds)
3. Array profiling of knock-out gene expression v. control
4. Short-list genes whose expression/repression requires PKD1
5. Select candidate promoter for driving reporter gene expression
6. Construct stable cell line with promoter/reporter cassette
7. Transduce with lentiviral library
8. Screen for reporter shut-off/switch-on PKD1 is highly expressed in foetal kidney (Ibraghimov-Beskrovnaya et al 1997 Proc Natl Acad Sci USA. 1997 Jun. 10; 94(12):6397-402.) and mice homozygous for mutant PKD1 allele are embryonic lethal (Kim 2000 Proc Natl Acad Sci USA. 2000 Feb. 15; 97(4):1731-6.). Polycystin 1 is detected in epithelia, astrocytes, endothelial and vascular smooth muscle cells. The use of an additional alternative cell type would be useful in investigating whether pathways induced by PKD1 signalling are common or specialised in the tissue types known to require PKD1 for proper function.

The selection of candidates for driving reporter gene expression should also take into consideration that only a single branch of the signalling pathway(s) activated by PKD1 may be targeted. Therefore the selection of additional candidates and conducting parallel screens with alternative reporter constructs where practical would be advantageous.

Mice and rat models for PKD and in vitro models for cyst formation exist (Pey et al 1999 In Vitro Cell Dev Biol Anim. 1999 November-December; 35(10):571-9.) facilitating further downstream testing.

Example 12. Use of Lentiviral Vector Libraries to Identify Genes that Affect the Activation of the NFAT Family of Transcription Factors Nuclear Factor of Activated T-cells (NFAT) is a family of transcription factors first identified in human T-cells. The NFAT family is composed of (to-date) 5 members, the 4 best characterised of which (NFAT1-4) are regulated by the ubiquitously expressed $Ca^{2+}$-dependent Ser-Thr protein phosphatase, calcineurin (CaN). NFAT can be activated in vitro by stimulation with calcium ionophore (eg. ionomycin) and phorbal ester (PMA which non-specifically activates PKC). CaN is the main target for the immunosppressive drug, Cyclosporin A (CsA); CsA acts by first binding to the immunophilin ligand Cyclophilin A (CypA) and then this drug-immunophilin complex binds to, and inactivates, CaN phosphatase activity. By inhibition of CaN, CsA prevents the CaN-mediated activation of NFAT, and thus NFAT-dependent gene transcription. Inactive NFAT resides in a phosphorylated state in the cytoplasm of resting T-cells; upon CaN activation by release of intracellular $Ca^{2+}$, NFAT is dephosphorylated by CaN. This leads to exposure of a Nuclear Localisation Signal (NLS) and NFAT is transported to the nucleus. Once in the nucleus, NFAT acts together with the transcriptional coactivator, AP-1 (activated by the PKC pathway) to initiate transcription of genes containing NFAT elements in their promoter-enhancer regulatory domains.

CsA is the current drug of choice in the multi-billion dollar organ transplant market. Another immunosuppressive drug (FK506) acts in an analogous way, through binding to an immunophilin, FKBP12 and inactivation of CaN phosphatase activity. Rapamycin is an alternative drug that also inhibits NFAT, albeit by an alternative mechanism. NFAT regulation and function is reviewed in Rao et al *Annu. Rev. Immunol.* 15, 707-747.

There is a need for more specific means of immunosuppression; CsA has a wide range of serious side effects including kidney failure and various cancers. The nature of organ transplantation requires patients to take CsA continually for the remainder of their life, thus increasing the chance occurrence of side effects in such patients. One approach to develop new more specific mechanisms of immunosuppression has been through the utilisation of peptides containing the IXIT CaN-binding motif (SPRIEIT) (SEQ ID NO: 11) present in CaN-regulated NFAT proteins (Patent International Publication Number WO 99/40930). As yet there have been no human genes shown to regulate CaN-mediated activation of NFAT by virtue of this CaN-binding motif. However, there is one protein which has been shown to take advantage of this motif, and inhibits CaN phosphatase activity through binding CaN at the same site as NFAT. This is the A238L protein from African Swine Fever Virus (Miskin et al 1998 & 2000 Science, 281, 562-565; J. Virol., 74, 9412-9420.). A238L has also been shown to inhibit NF-κB-dependent gene transcription (Powell et al J. Virol., 70, 8527-33; Tait et al J. Biol. Chem., 275, 34656-64).
Strategy:

Human T-cell lines are engineered to contain an NFAT-dependent reporter gene, such as GFP (or LNGFR); this is achieved by transducing T-cells (either Alo-T-cells or a cell line such as Jurkats). This reporter could take a number of different forms; one possibility is to control reporter gene expression using an artificial NFAT promoter-enhancer region containing 3 tandem copies of the NFAT enhancer element upstream of a minimal CMV promoter. A second possibility is to clone a promoter from a known NFAT-dependent gene (such as IL-2 in CD4+ T-cells). However this will almost certainly produce more confusing results as a number of other transcription factors are known to contribute to IL-2 transcriptional control. A further possibility is a promoter that is silenced by NFAT-NFATc2 and may possess silencer activity of the Interleukin-12 (IL-12) receptor beta 2 proximal promoter in human T helper cells. The reporter is validated using known inhibitors of NFAT-dependent gene transcription (eg. Cyclosporin A is a potent inhibitor of NFAT-dependent gene expression), or A238L from ASFV.

These cells are transduced with a lentiviral vector cDNA library expressing cDNAs from a variety of human immune cell types (such as T-cells), under the control of a regulated or constitutively active promoter. Transduced cells are exposed to stimuli that would normally result in the activation of the GFP reporter gene (eg. PMA and ionomycin). Cells are FACS sorted to remove cells expressing high levels of GFP (reversed if silencing promoter was used). These cells are grown under continuous stimulation and subjected to further rounds of FACS enrichment of low level GFP-expressing cells. Single cells are isolated and the cDNA(s) expressed by the transduced virus cloned, sequenced and identified. These genes are evaluated alongside a known inhibitor of the relevant transcription factor. This approach may prove useful for the identification of directed immunosuppressive cDNAs for use in organ transplantation or other therapeutic areas (eg. CsA is used in RA).

A second possibility is to use a lentiviral ribozyme library. This is used to isolate active ribozymes that inhibit NFAT activation or expression.

Example 13. Ribozyme Selection Strategy

The selection of ribozymes is carried out in vivo (tissue culture). Ribozymes constructed 'theoretically' and tested in vitro often do not perform well in the cellular environment. In one embodiment the present invention employs a multi-cistronic, preferably bi-cistronic, approach.

Figure 5A:
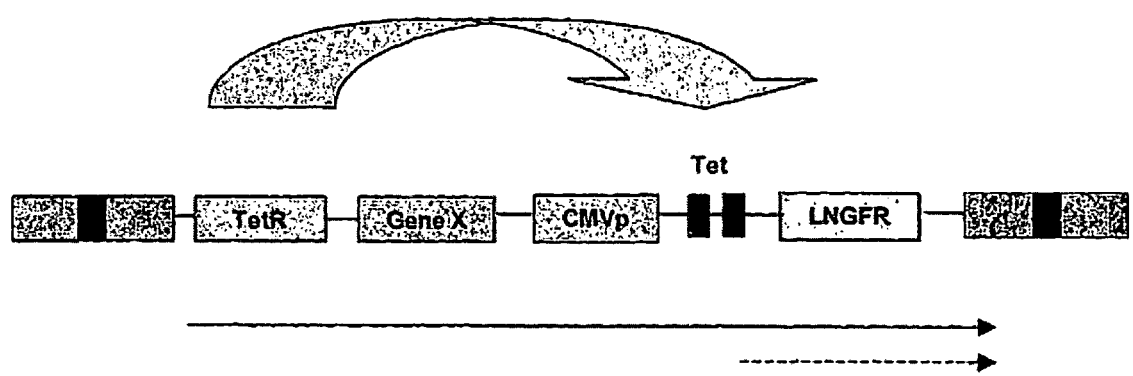
FIG. 5a is a schematic representation of a bi-cistronic target vector.

In this embodiment the target vector, which may be pONY8.4 based, is bi-cistronic: expression of the tetracycline repressor is driven by the LTR. The target gene, or sequence, is cloned downstream of the tetracycline repressor, preferably there will be no IRES so expression of protein from the noi of interest will not occur. Transduced reporter cells can be selected for by adding Dox. Dox binds the tetracycline repressor, therefore the Tet operator will be de-repressed and LNGFR expressed. The cells can then be selected by FACS, MACS or other suitable method. After selection the Dox is removed and LNGFR will no longer be expressed. A schematic representation of the target vector is shown in FIG. 5a.

Figure 5B:
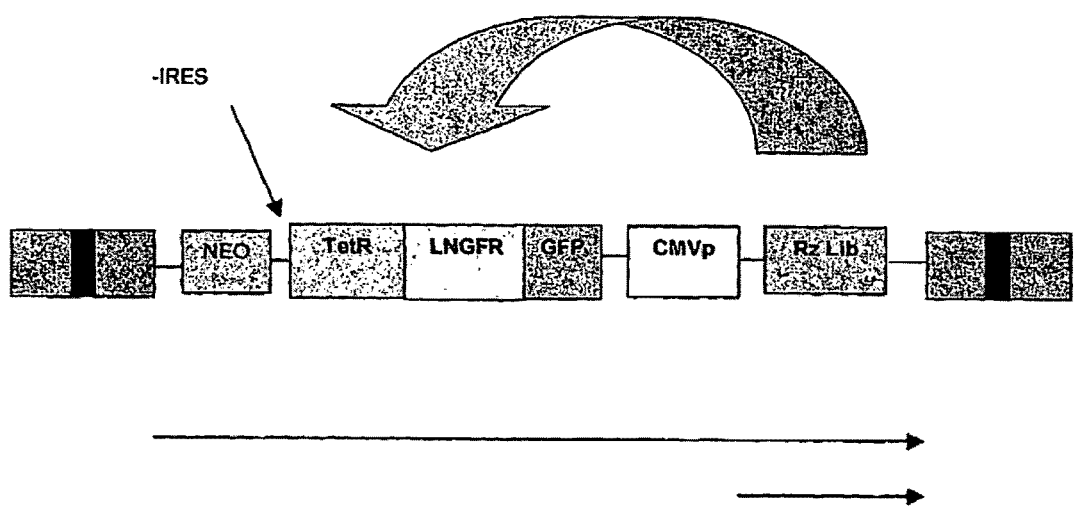
FIG. 5b is a schematic representation of a bi-cistronic library vector.
Figure 6:
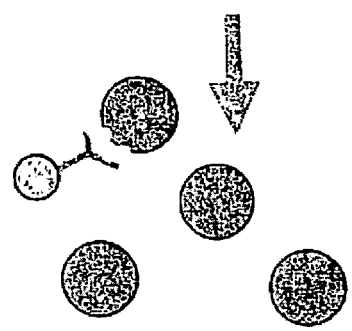
FIG. 6 illustrates the isolation of cells.

The library vector (also pONY8.4-based) is also bicistronic. Expression of neo is driven by the LTR allowing selection if required. Downstream of this, out of frame and/or with no IRES, are a number of genes of which cleavage by ribozymes would be undesirable. These include the tetracycline repressor, LNGFR and GFP. If a ribozyme in the library cleaves any of these gene sequences there will be no genome to package and the ribozyme should not be represented in the vector library used for transducing reporter cells. Also, if the ribozyme cleaves an essential molecule (eg, RNA polymerase), the producer cell will die. Expression of ribozymes is under control of the CMV promoter. A schematic representation of this library vector is shown in FIG. 5b.

Outline of Strategy:

Transduce reporter cells (containing target vector) with ribozyme library.

Cleavage of Gene X will result in degradation of the mRNA encoding TetR.

The Tet operator is de-repressed and LNGFR will be expressed.

Isolation of Cells:

Cells are labelled with α-LNGFR, incubated with appropriately conjugated MACS beads & and passed through a MACS column. This approach is illustrated in FIG. 7.

LNGFR expressing cells are retained. These can be passaged to bulk up cell numbers (neo selection can be applied to ensure only cells containing a library vector are present). FACS analysis can be performed to measure LNGFR expression levels. The ribozyme can be amplified and sequenced by PCR.

Example 14. pONY 8.4 pONY 8.4 series of vectors has a number of modifications which enable it to function as part of a transient or stable vector system totally independent of accessory proteins, with no detrimental effect on titre. Conventionally lentiviral vector genomes have required the presence of the viral protein rev in producer cells (transient or stable) in order to obtain adequate titres. This includes current HIV vector systems as well as earlier EIAV vectors.

There are 4 modifications when compared with the pONY 8.1 series of vector genomes, these are:

a) All the ATG motifs which are derived from gag and form part of the packaging signal have been modified to read ATTG. This allows the insertion of an open reading frame which can be driven by a promoter in the LTR.

b) The length of the genome i.e. distance between the R regions is closer to that seen in the wt virus (7.9 kb).

c) The 3' U3 region has been modified to include sequences from the moloney leukemia virus (MLV) U3 region, so upon transduction it can drive second open reading frame (ORF) in addition to the internal cassette, In this example we have MLV but this could be any promoter.

d) The vector contains a nucleotide sequence operably linked to the viral LTR and wherein said nucleotide sequence is upstream of an internal promoter and wherein said nucleotide sequence encodes a polypeptide or fragment thereof.

Together these modifications allow production of viral delivery system without the need for accessory proteins and only 10% of the original viral sequence is integrated into the target cell. These factors are important for future safety considerations in terms of an immune response and probability of the generation of replication competent viruses. Further details on modifying LTRs can be found in our WO96/37623 and WO98/17816.

Figure 11:
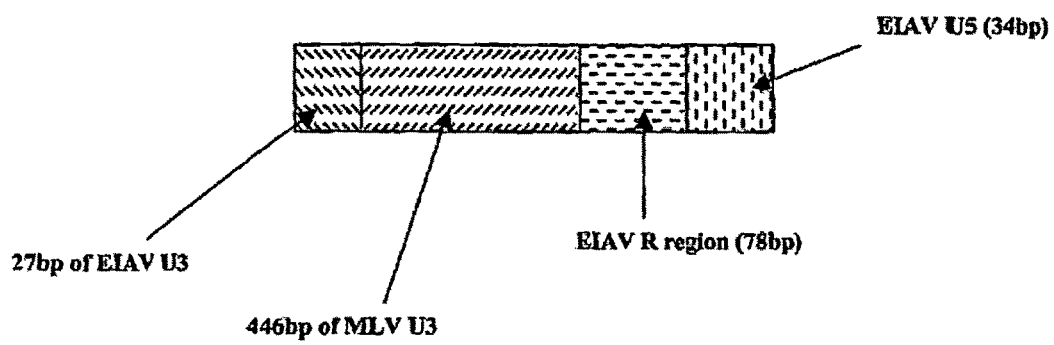
FIG. 11 is a schematic representation of the hybrid U3 region.

FIG. 7 is a schematic representation of EIAV genomes. These may be used for transfection in accordance with the method of the present invention. Upon transfection the 3' LTR will be copied to the 5' LTR. FIG. 8 gives the total plasmid sequence of pONY8.1G. FIG. 9 gives the total plasmid sequence of pONY8.4ZCG. FIG. 10 gives the total plasmid sequence of pONY8.4GCZ. FIG. 11 is a schematic representation of the hybrid U3 region. FIG. 12 gives the sequence of the hybrid LTR.

Example 15. The Construction of EIAV/MLV Hybrid LTR Vectors

PCR was carried out as follows:

Product A=primers KM001+KM003, with the pONY8.1Z as target.

Product B=primers KM004+KM005, with the pHIT111 as target.

Product C=primers KM006+KM002, with the pONY8.1Z as target.

Figure 14:
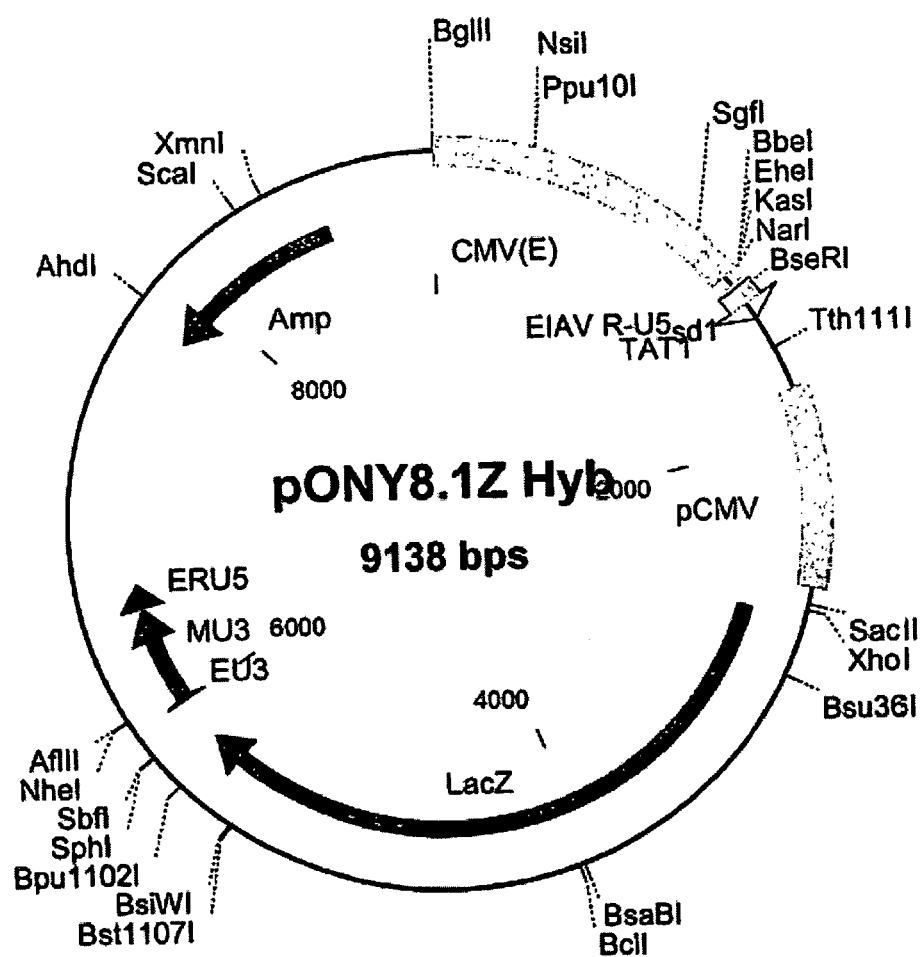
FIG. 14 is a schematic representation of pONY8.1Zhyb.

The PCR products (A, B and C) were gel purified. A PCR reaction was set up using Product A and B (with primers KM001 and KM005) to give Product D. A PCR reaction was set up using Product B and C (with primers KM004 and KM002) to give Product E. Product D and E were gel purified and used in a PCR reaction, as targets with primers KM001 and KM002 to give Product F. The PCR Product F was gel purified (approximately 1 kb). This was then cut with Sap I and subcloned into pONY8.1Z cut with Sap I. This gave the vector pONY8.1Zhyb shown in FIGS. 13 and 14. The 3' LTR of EIAV has now been replaced with an EIAV/MLV hybrid LTR. The EIAV U3 has been almost replaced with the MLV U3 region. The EIAV 5' U3 sequences of the 3'LTR have been retained as these comprise the att site, that is the sequences needed for integration.

The primer sequences are shown below:

```
EIAV/MLV hybrid U3
KM001
CAAAGCATGCCTGCAGGAATTCG (SEQ ID NO: 12)

KM002
GAGCGCAGCGAGTCAGTGAGCGAG (SEQ ID NO: 13)

KM003
GCCAAACCTACAGGTGGGGTCTTTCATTATAAAACCCCTCATAAAAACCC
(SEQ ID NO: 14)

CACAG

KM004
CTGTGGGGTTTTTATGAGGGGTTTTATAATGAAAGACCCCACCTGTAGGT

TTGGC (SEQ ID NO: 15)

KM005
GAAGGGACTCAGACCGCAGAATCTGAGTGCCCCCCGAGTGAGGGGTTGTG

GGCTCT (SEQ ID NO: 16)

KM006
AGAGCCCACAACCCCTCACTCGGGGGGCACTCAGATTCTGCGGTCTGAGT

CCCTTC (SEQ ID NO: 17)
```

Sequence of final PCR product.

```
EIAV PPT/U3
CAAAGCATGCCTGCAGGAATTCGATATCAAGCTTATCGATACCGTCGAAT

TGGAAGAGCTTTAAATCCTGGCACATCTCATGTATCAATGCCTCAGTATG

TTTAGAAAAACAAGGGGGGAACTGTGGGGTTTTTATGAGGGGTTTTATAA
(SEQ ID NO: 18)

MLV U3
TGAAAGACCCCACCTGTAGGTTTGGCAAGCTAGCTTAAGTAACGCCATTT

TGCAAGGCATGGAAAAATACATAACTGAGAATAGAGAAGTTCAGATCAAG

GTCAGGAACAGATGGAACAGCTGAATATGGGCCAAACAGGATATCTGTGG

TAAGCAGTTCCTGCCCCGGCTCAGGGCCAAGAACAGATGGAACAGCTGAA

TATGGGCCAAACAGGATATCTGTGGTAAGCAGTTCCTGCCCCGGCTCAGG

GCCAAGAACAGATGGTCCCCAGATGCGGTCCAGCCCTCAGCAGTTTCTAG

AGAACCATCAGATGTTTCCAGGGTGCCCCAAGGACCTGAAATGACCCTGT

GCCTTATTTGAACTAACCAATCAGTTCGCTTCTCGCTTCTGTTCGCGCGC

TTCTGCTCCCCGAGCTCAATAAAAGAGCCCACAACCCCTCACTCGGG
(SEQ ID NO: 19)

MLV U3/EIAV R/U5
GGGCACTCAGATTCTGCGGTCTGAGTCCCTTCTCTGCTGGGCTGAAAAGG

CCTTTGTAATAAATATAATTCTCTACTCAGTCCCTGTCTCTAGTTTGTCT

GTTCGAGATCCTACAGAGCTCATGCCTTGGCGTAATCATGGTCATAGCTG

TTTCCTGTGTGAAATTGTTATCCGCTCACAATTCCACACAACATACGAGC

CGGAAGCATAAAGTGTAAAGCCTGGGGTGCCTAATGAGTGAGCTAACTCA

CATTAATTGCGTTGCGCTCACTGCCCGCTTTCCAGTCGGGAAACCTGTCG

TGCCAGCTGCATTAATGAATCGGCCAACGCGCGGGGAGAGGCGGTTTGCG

TATTGGGCGCTCTTCCGCTTCCTCGCTCACTGACTCGCTGCGCTC
(SEQ ID NO: 20)
```

Example 16. Parkinson's Disease—Identification of Regulators of Tyrosine Hydroxylase Tyrosine hydroxylase (TH) is an enzyme which is required for dopamine synthesis. Nerve growth factor is known to induce TH in rat sympathetic ganglia, adrenal medulla, sympathetic neurons and chromaffin cells.

A development in molecular biology with therapeutic potential for treating Parkinson's disease is the cloning of genes encoding neurotrophins and growth factors. For example, glial-derived neurotrophic factor (GDNF) has been reported to halt the progression of degeneration in the substantia nigra induced by the neurotoxin MPTP (1-methyl-4-phenyl-1,2,3,6-tetrahydropyridine) and GDNF infusion has been reported to reduce symptoms in primate parkinsonian models. The signalling molecule Sonic hedgehog, known to have important roles in a number developmental contexts, is able to induce neurons of the developing midbrain to differentiate with a dopaminergic phenotype in vitro. These results suggest new therapeutic strategies could be to identify molecules that promote the differentiation or survival of dopaminergic neurons.

An alternative hypothesis is that dopaminergic neurons simply cease expression of genes involved in dopamine production. In response to GDNF the dopaminergic cells may in fact be activating expression of these genes. If this is the case then the identification of molecules that activate expression of these genes would be of considerable therapeutic function. Thus these molecules would lead to the therapeutic effect seen with GDNF without the side effects of cellular proliferation.

One approach to identify molecules which regulate the expression of tyrosine hydroxylase is:

Strategy
1. The tyrosine hydroxylase promoter is cloned such that its activity is monitored by a suitable reporter gene such as green fluorescent protein (GFP), low affinity growth factor receptor (LNGFR) or thymidine kinase (TK).
2. The promoter-reporter cassette is introduced into a dopaminergic cell line such as IRB3AN27 or primary neurons which may or may not normally express tyrosine hydroxylase.
3. The reporter cells are transduced with a suitable library (such as cDNA or ribozyme) in an EIAV vector.
4. Optionally the cells are grown in the presence of GDNF or other growth factor.
5. Cells in which reporter gene expression is altered are isolated, and the modulating moiety isolated from the library vector by sequencing.
6. Identify the target moiety from the sequence of the library insert.

Example 17

Figure 15:
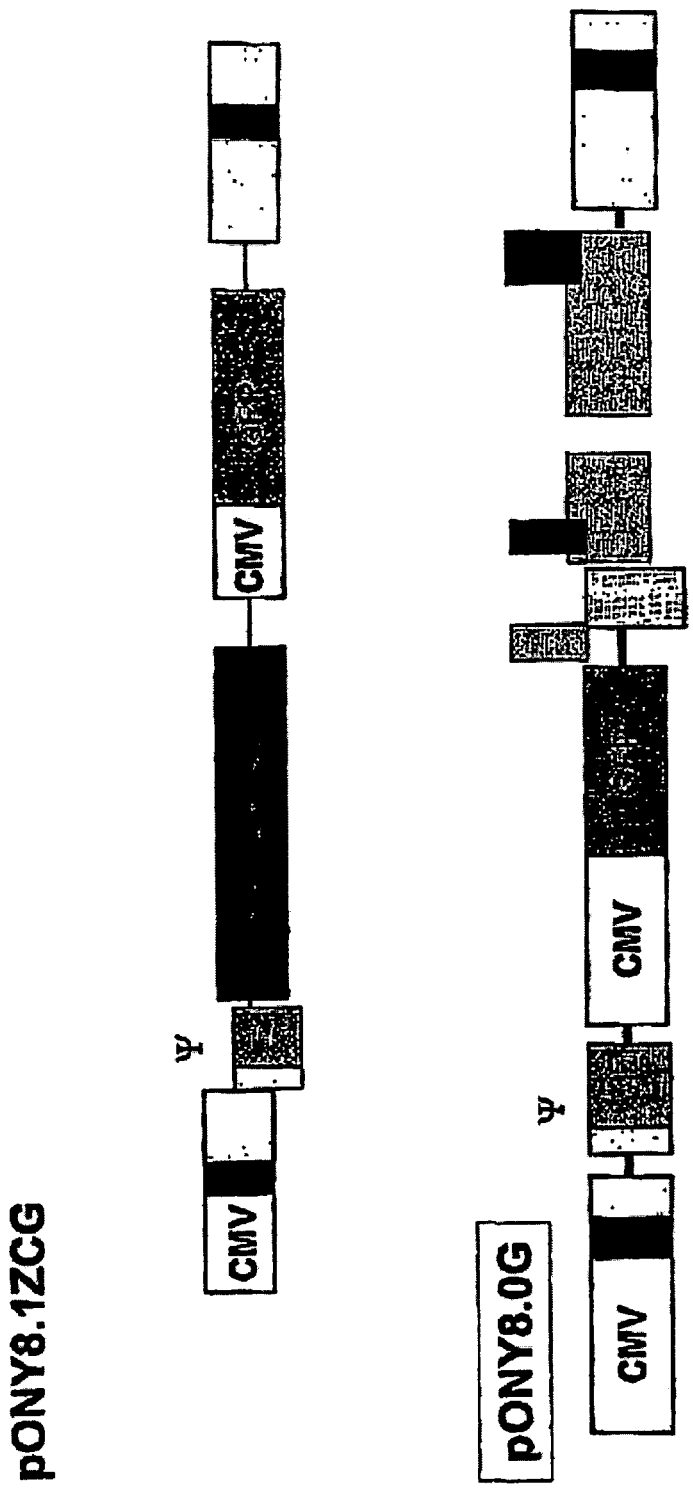
FIG. 15 is a schematic representation of pONY8.1ZCG and pONY8.0G.
Figure 16:
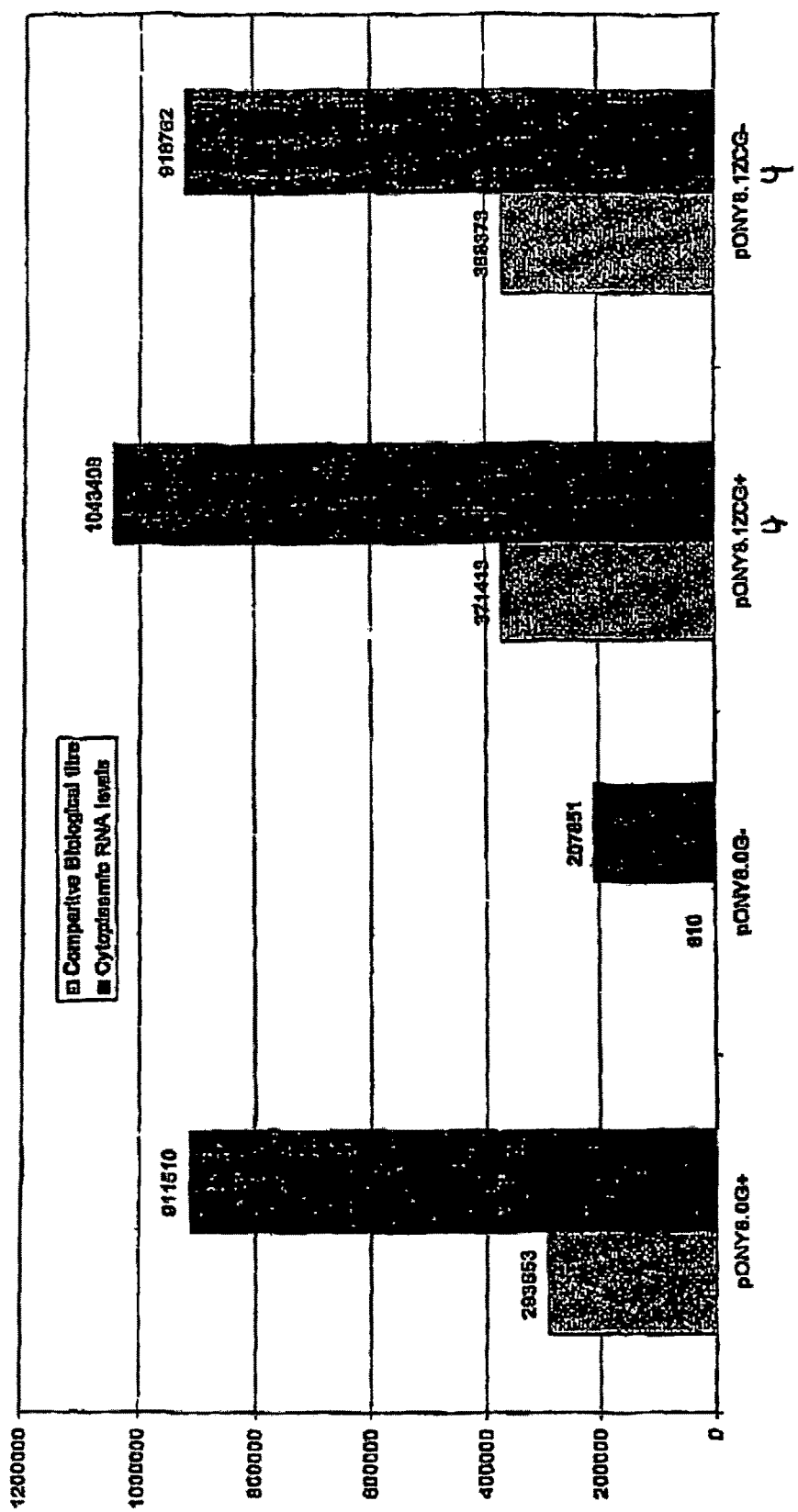
FIG. 16 is graphical representation showing the relative transduction efficiency of pONY8.1ZCG and pONY8.0G in the presence and absence of Rev.

The relative REV dependencies of pONY8.1ZCG and pONY8.0G were determined by evaluating transduction efficiencies in the presence and absence of REV (see FIG. 16). This was achieved using the pESYNREV vector. pESYNREV and pONY8.0Z are described in WO 0179518. pONY8.0G is derived form pONY8.0Z with GFP replacing lacZ. pONY8.1ZCG is derived from pONY8.4ZCG but does not have the hybrid LTR or complete ATTG sequence. A schematic of pONY8.1ZCG and pONY8.0G is shown in FIG. 15. Transduction efficiencies of pONY8.1ZCG and pONY8.0G were evaluated using standard cell lines in the presence and absence of REV.

Cytoplasmic RNA levels in the producer cells were measured using quantitative PCR and were normalised to a 100 copies of cellular β-actin. The measurements were taken at the time of viral harvesting and show that the levels of RNA with the EIAV packaging signal are reduced in the pONY8.0G producer cells in the absence of REV. This difference is not seen in the pONY8.1ZCG producer cells. The data shows the pONY8.0G (+/−pESYNREV) construct to be REV dependent, whilst pONY8.1ZCG transduction efficiency is independent of REV.

Example 18

Figure 19:
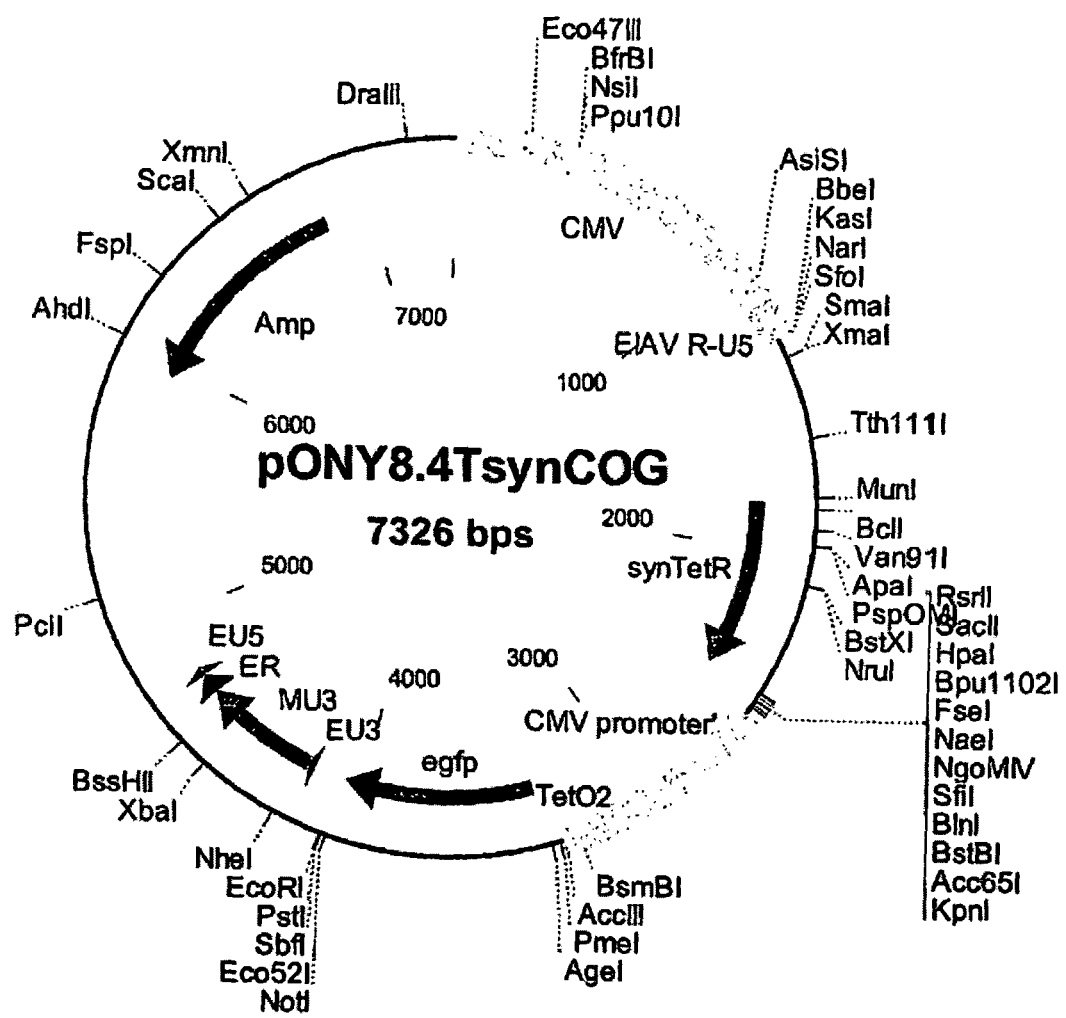
FIG. 19 is a schematic representation of pONY8.4TsynCOG/pONY8.4TsynCOG1.
Figure 20:
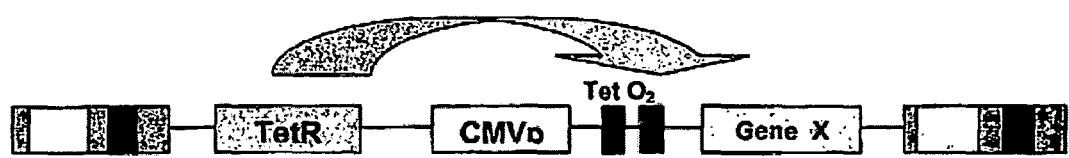
FIG. 20 is schematic representation of an example of a bicistronic tetracycline-regulated vector.
Figure 23:
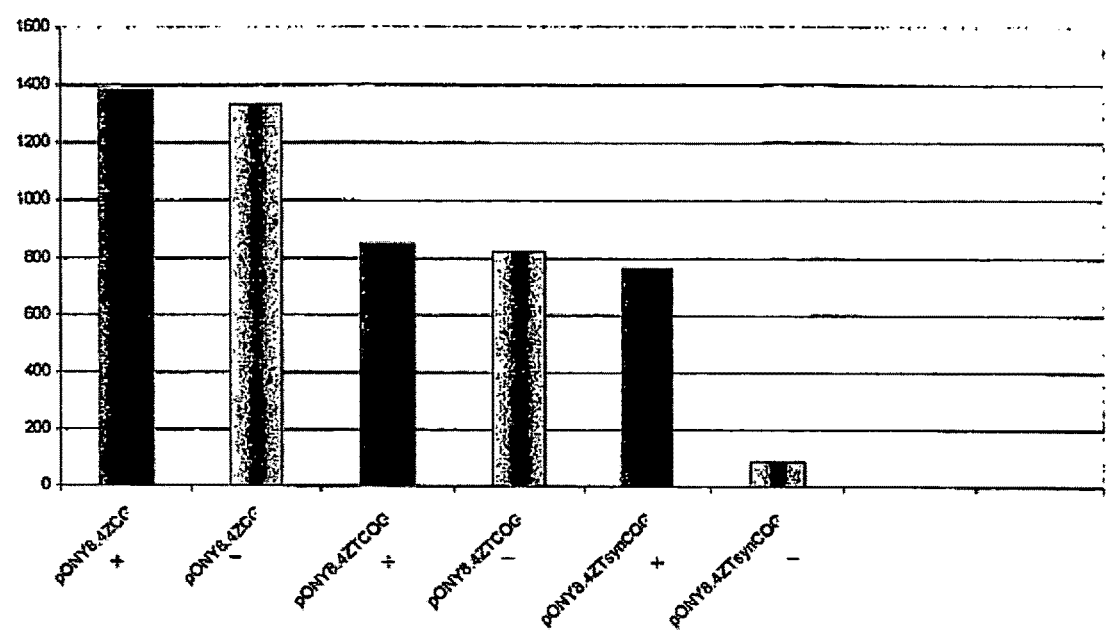
FIG. 23 shows that with codon optimised TetR allows GFP expression in the in the absence of dox 10 times lower than in the presence of dox. This difference is significantly larger than when using other vectors, suggesting that pONY8.4ZTsynCOG allow better control of repression.

Tetracycline regulated vectors were created using pONY8.4 EIAV vector and incorporating the T-Rex tetracycline regulation system to make PONY8.4ZTsynCoG (FIGS. 19 and 20). The Tet $O_2$ promoter was codon optimised for expression on mammalian cells (FIG. 21). GFP was used as a reporter gene to measure expression. The expression levels of pONY8.4ZTsynCO G1 (FIG. 23) was shown to be 10 times higher in the presence of Doxycyline (dox), which binds TetR and relieves the repression of $TetO_2$, than in the absence of it. Comparison of GFP expression with the parent plasmids pONY8.4ZCG and pONY8.4ZTCOG1 shows that the level of repression in the absence of dox is significantly better in pONY8.4ZTsynCOG1.

Example 19

Figure 24:
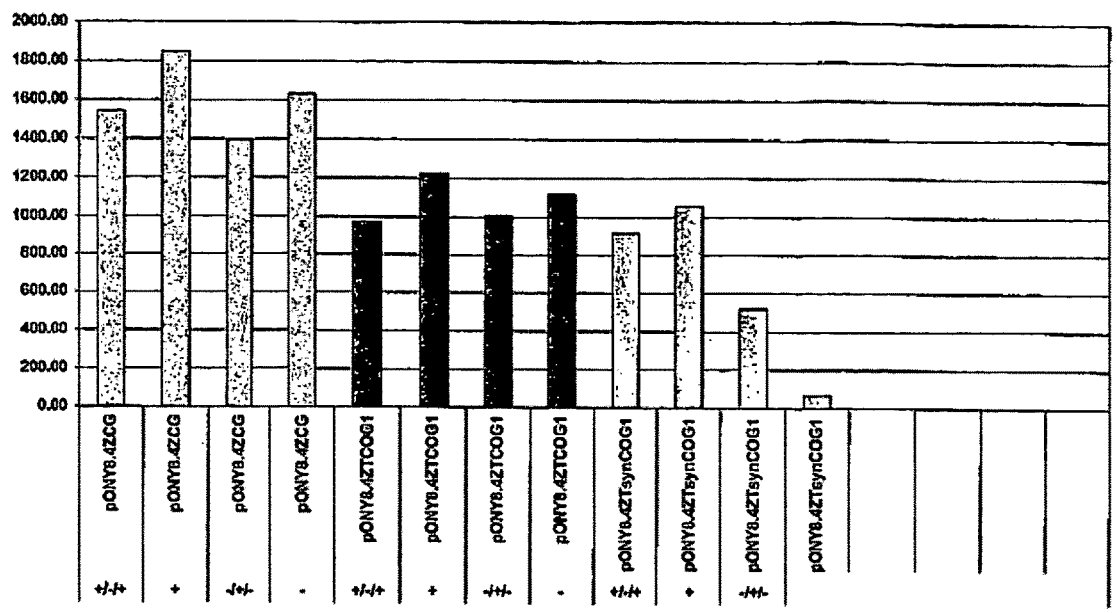
FIG. 24 shows the reversibility of Tet-regulated gene expression from vectors containing codon optimised TetR.

Cells transduced with pONY8.4ZCG derived vectors were cultured in media with or without dox, then switched to induce or repress expression as appropriate, then switched back again. The 'reversibility' of the Tet-regulated gene expression from the vectors containing codon optimised TetR was confirmed. The GFP expression seen in the switched cells as shown in FIG. 24 has yet to reach maximal/minimal levels observed in cells which have been continually grown either + or − dox.

Example 20

The pONY8.4TsynnlsCOG1 was made in which TetR contained a Nuclear Localisation signal (NLS):

```
5' GAC CCC AAG AAG AAG CGC AAG GTG TAA
(SEQ ID NO: 21)
    D   P   K   K   K   R   K   V  stop
(SEQ ID NO: 22)
``` at its C terminus. The NLS is reported to improve the rate of transcriptional repression threefold (Ogueta et al) by increasing the concentration of TetR in the nucleus. The NLS was attached to the C terminal end so that it did not interfere with the N-terminus of TetR, which is important for binding $TetO_2$.

A time course was carried out to determine how quickly the expression occurs following the addition of dox (decrease in expression following removal of dox as measured by GFP is influenced by protein turnover). FIG. 24 shows that the expression is near maximal within 24 hr of the addition of the dox and that the NLS-tagged codon optimised TetR did not have a lower basal expression level than the untagged version.

Example 21

Figure 25:
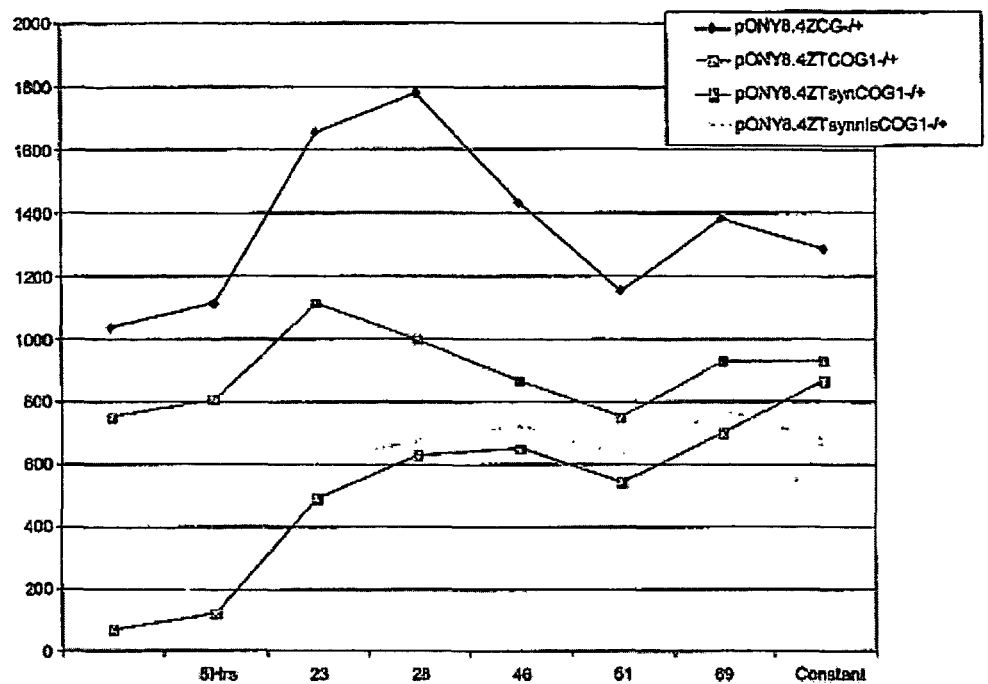
FIG. 25 shows a time course for the expression of GFP after the addition of doxycycline.

FIG. 25 shows the expression of GFP from the alternative LTRs PGK and RSV in pONY8.3 vectors, proving that alternative hybrid LTRs can also be used in the pONY8.4 configured vectors.

Example 22

Figure 26:
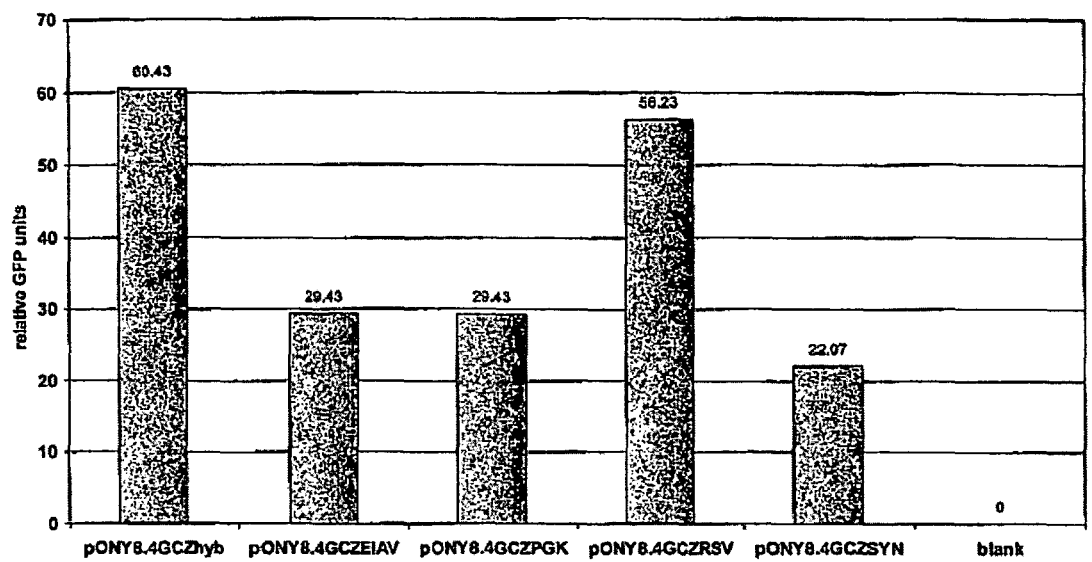
FIG. 26 shows expression from alternative LTRs.
Figure 27:
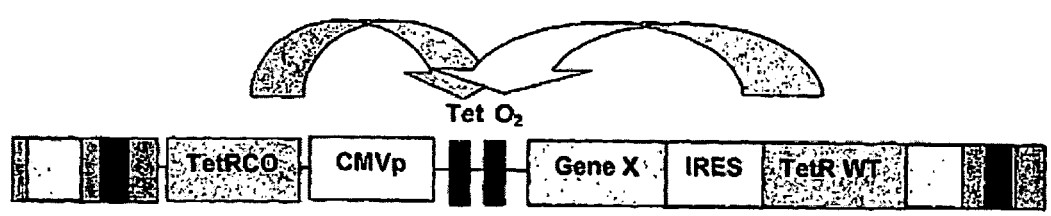
FIG. 27 is a schematic of the modification of the bicistronic Tet-regulated vector incorporating a second copy of the Tet repressor gene.
Figure 28:
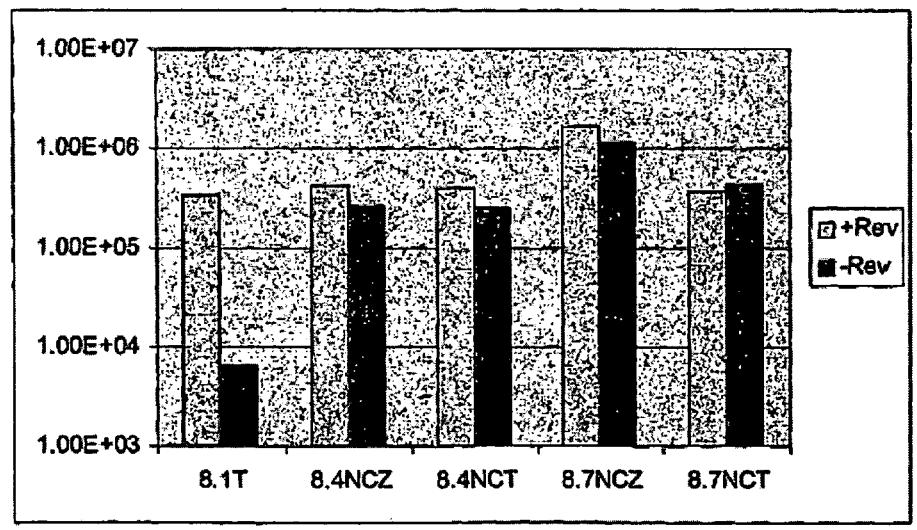
FIG. 28 shows the viral titres of pONY8.4 and pONY8.7 vectors with and without Rev present. Expression of pONY8.4 and pONY8.7 is Rev independent.

The bicistronic Tet-regulated vector may be modified to incorporate a second copy of the Tet repressor gene (FIG. 26). The second copy is downstream of an IRES. This will be actively expressed when a cell is first transduced and initially contains no TetR protein: as protein levels build up, transcription of gene X and the TetR located downstream of the IRES is shut down (no tetracycline or doxycycline present). This repression will be more rapid in the modified construct shown here.

In the absence of the LTR driven TetR there would be a feedback loop resulting in cycling of transcription of gene X depending on the threshold levels of TetR. The presence of a constitutively transcribed copy of TetR avoids this by maintaining a constant level of TetR in the cell. In this example the TetR gene downstream of the IRES is the wild type version minimising the possibility of undesirable recombination occurring, however, any combination of gene sequences coding for the TetR protein can be envisaged (the NOI can also be located downstream of the IRES).

Example 23

The expression from the pONY8.4 and pONY 8.7 vectors was checked in the presence and absence of Rev by assaying viral titres from infected cells. The virus data shown is unconcentrated and from a single plate. pONY8.7NCZ was tested on a different week to the other vectors, hence slightly higher titres. The absence of Rev did not lead to a significant difference in the titre pONY8.4 and pONY8.7 based vectors, showing that they are rev independent.

Example 24

The expression of GDNF from pONY8.95 and pONY 8.7 vectors was measured in mouse cortical neurons and in 293T cells by enzyme-linked immunosorbent assay (ELISA). The codon-optimized sequence of GDNF is shown in FIG. 29. The following viruses were used at the indicated amounts to infect cells: pONY 8.95 TREX-GDNF at $3.15 \times 10^7$ TU/mL ($2.96 \times 10^5$ int copies/mL); pONY8.95 TREX-G (ref ML003) at $8.54 \times 10^7$ TU/mL ($2.11 \times 10^4$ int copies/mL); pONY8.7 NCG (ref ML004) at $1.57 \times 10^8$ TU/mL ($4.64 \times 10^4$ int copies/mL); pONY8.7NC-GDNFnoNLS (ref ML005) at $3.04 \times 10^7$ TU/mL ($1.42 \times 10^2$ int copies/mL).

Figure 30:
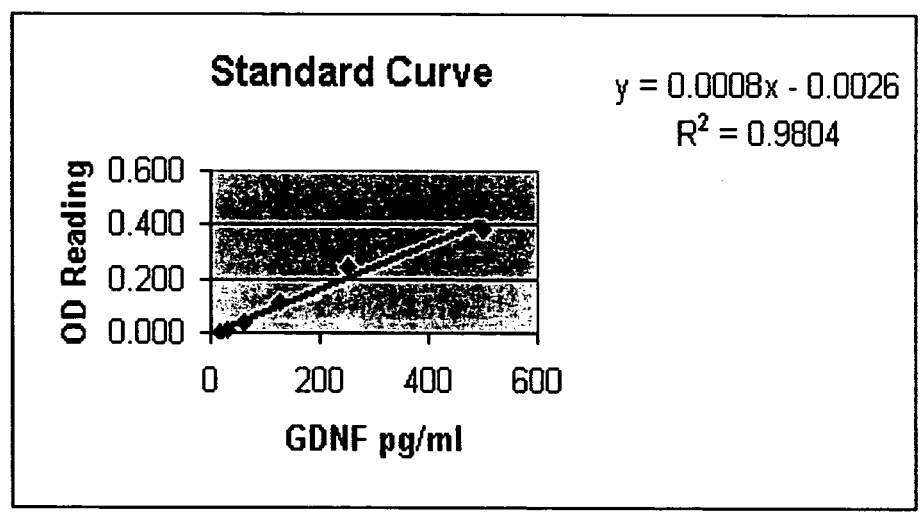
FIG. 30 shows the standard curve using varying concentrations of GDNF.
Figure 31:
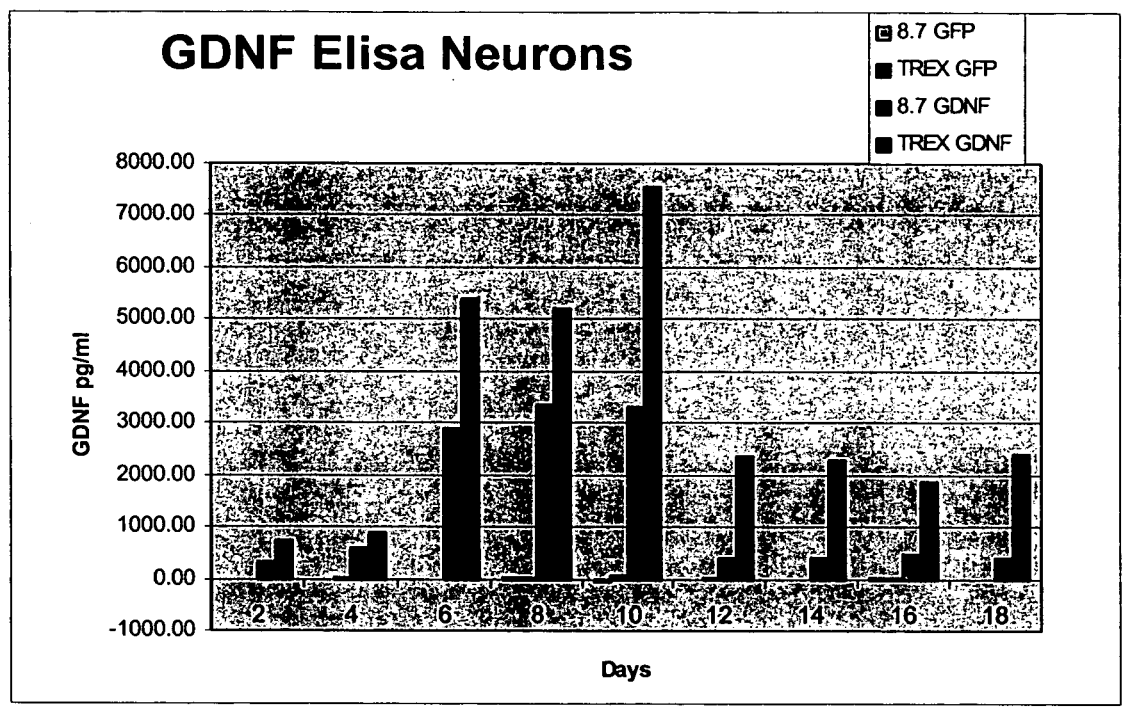
FIG. 31 shows the results of an ELISA measuring GDNF in transduced mouse cortical neurons.
Figure 32:
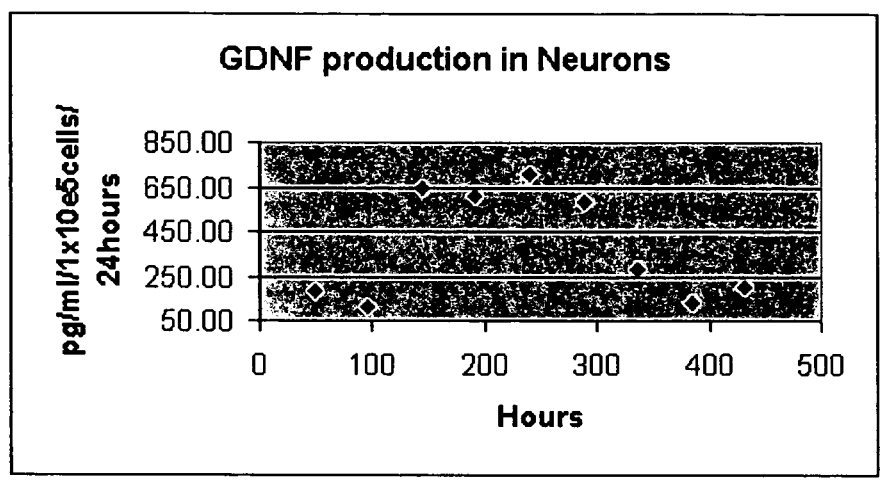
FIG. 32 shows the results of an ELISA measuring GDNF levels per 24 hours in transduced mouse cortical neurons.
Figure 33:
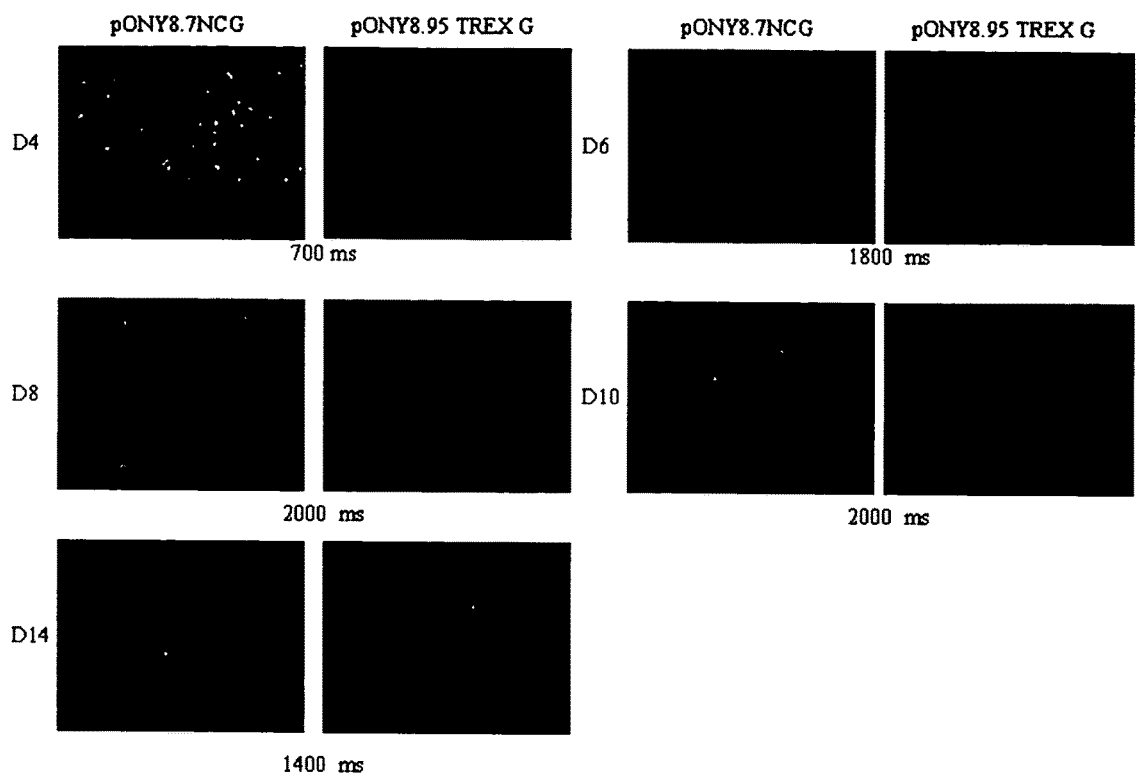
FIG. 33 shows the expression of EGFP in transduced cells.

At the time of transduction, mouse cortical neurons were cultured at a density of 2×105 in a 12-well plate. The viruses were added to the cells at an MOI of 5 for all viruses; the RNA titre was measured to calculate the volume of virus. Transduction occurred on Day 0, with 35% of the cell culture medium removed for ELISA analysis on Days 2, 4, 6, 8, 10, 12, 14, 16, and 18. Doxycycline was added to the culture medium on Day 4 and removed on Day 10. Varying concentrations of GDNF was measured to create a standard curve (FIG. 30). GDNF expressed from pONY8.95TREX-GDNF was present at levels 7-fold higher when cultured in the presence of doxycycline in mouse cortical neurons, compared to untreated cells (FIG. 31). GDNF expressed over an 18 day period is shown as the level of GDNF production per 24 hours in FIG. 32. The expression of EGFP in transduced cells is shown in FIG. 33.

Figure 34:
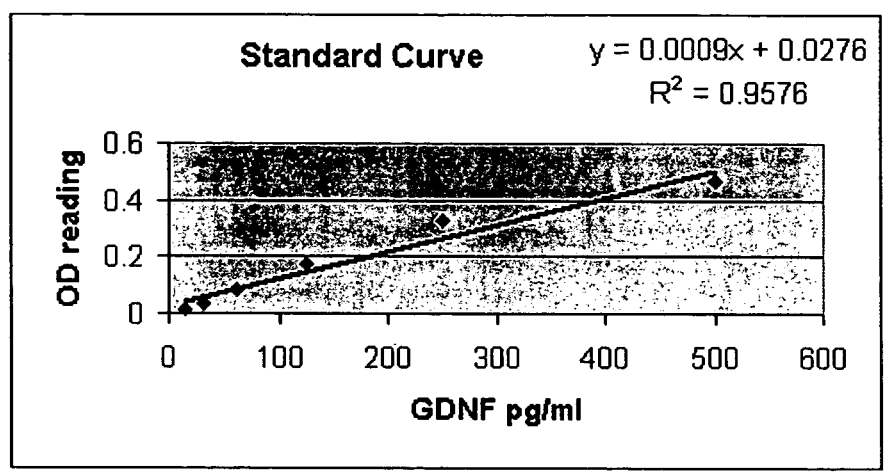
FIG. 34 shows the standard curve using varying concentrations of GDNF.
Figure 35:
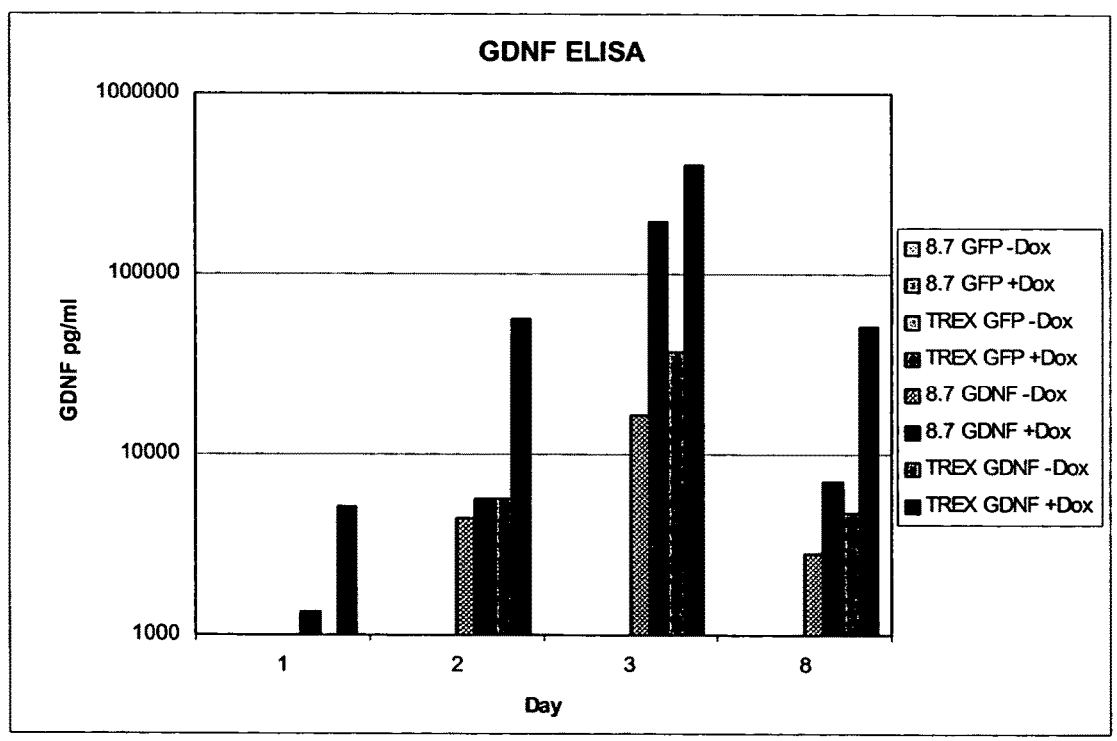
FIG. 35 shows the results of an ELISA measuring GDNF in transduced HEK 293T cells.

In 293T cells cultured at a density of $1.6 \times 10^4$ in 24-well plate, the viruses were added at a MOI of 10. As above, the RNA titre was measured to calculate the volume of virus. Transduction occurred one week prior to splitting the cells, at which time doxycycline was added to the cell culture medium (Day 0). A sample of the culture medium was removed on Days 1, 2, 3, and 8 and used for ELISA. A standard curve was generated using varying concentrations of GDNF (FIG. 34). HEK 293T cells cultured in presence of doxycycline release GDNF at concentrations 10-fold higher than in cells that were not cultured with doxycycline (FIG. 35). The GDNF concentration when expressed from pONY8.95TREX-GDNF was 10-fold higher after 8 days in culture with doxycycline.

Example 25

Figure 36:
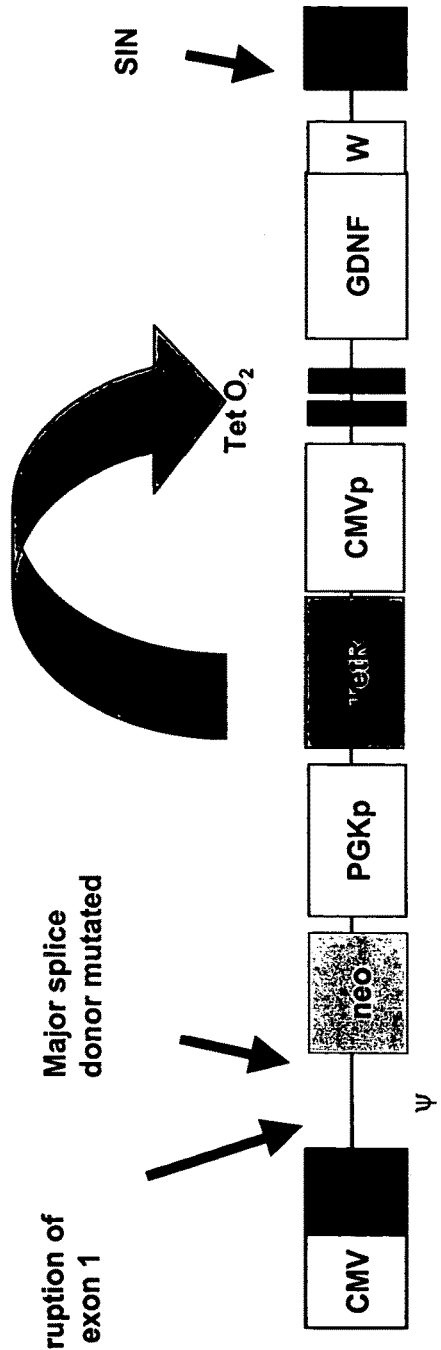
FIG. 36 shows a tetracycline regulated EIAV lentiviral vector expressing GDNF.

An improved version of the tet-ON regulated EIAV vector has been cloned and will be used to validate a regulated EIAV vector system that can be applied stereotaxically in the brain of early PD patients (HY Stage 2-3) to alleviate symptoms and halt disease progression. and this will also be validated in the same model. A GDNF expressing version of this vector is shown in FIG. 36.

The following in vitro experiments will be performed to test the efficacy of the improved vector:
1. A small scale viral prep (VSVG pseudotyped) will be used to demonstrate GDNF expression in a cell line (D117 or HEK293T). GDNF expression will be measured by ELISA.
2. Large scale preps will be produced and titred. Expression levels of GDNF and LacZ will be analyzed.
3. The viral construct will be used to transduce striatal neuronal cultures.
4. The viral construct will be used to demonstrate ON and OFF using doxycycline. The ON and OFF rates will be determined both for protein levels (measured by Western blotting) and RNA levels (measured by Northern blotting).

The following in vivo experiments will be performed to validate rescue of DA neurons using GDNF expressed from the improved vector:
5. Rats will be pre-labeled bilaterally with fluorogold and subjected to unilateral injection of the vectors in the striatum (GDNF n=20 and LacZ n=20). GDNF and lacZ will be expressed for 2 weeks, wherein 10 rats from each group will be administered doxycycline. Water will be administered in control groups. The toxin 6-OHDA will be administered unilaterally in all rats. Subsequently, a group of 5 rats will be preprotected to keep tet ON for 3 weeks. Another group of 5 preprotected rats will have tet OFF first week, ON second week, and OFF for third. Additionally, from a group of 10 non-preprotected rats, 5 will have tet OFF and while the other 5 will have tet ON for 3 weeks. The same groups will be assayed for regulated LacZ. At the end of the three weeks, the animals will be sacrificed, attained with TH and neurons counted.
6. Additionally, neuroprotection experiments will be performed in MPTP treated marmosets. Two experimental groups will be assembled: one group will be pre-protected by vector two weeks before MPTP treatment. A second group will be treated one-week post MPTP treatment. The marmosets will be analysed by behaviour and histology.

The invention will be further described by the following numbered paragraphs:

1. A multicistronic retroviral vector genome comprising a first nucleic acid sequence upstream of an internal regulatory element, such that the level of genomic RNA available for packaging in the absence of rev, or a functional equivalent thereof, is increased.

2. A vector according to paragraph 1 wherein the regulatory element is a promoter or IRES.

3. A vector according to paragraph 1 or 2 in the form of a lentiviral vector genome.

4. A vector according to any preceding paragraph wherein the first nucleic acid sequence is an open reading frame (ORF) or a part thereof.

5. A vector according to any preceding paragraph wherein the first nucleic acid sequence is downstream of a viral LTR.

6. A vector according to paragraph 5 wherein the first nucleic acid sequence is operably linked to the LTR.

7. A vector according to any preceding paragraph wherein a nucleic acid sequence encoding the auxiliary gene rev, or a functional equivalent thereof, is disrupted such that said auxiliary gene is incapable of encoding the functional auxiliary proteins, or removed from the vector genome.

8. The vector of any preceding paragraph wherein the first nucleic acid sequence is a reporter moiety or selectable marker.

9. The vector of any one of paragraphs 1 to 7 wherein the first nucleic acid sequence encodes a modulator gene.

10. The vector of paragraph 9 wherein the modulator gene is selected from tetracycline repressors, such as TetR, and tetracycline-controlled transactivators, such as tTA and rtTA.

11. A vector according to paragraph 10 wherein the tetracycline repressor is codon optimised for expression in a mammalian cell.

12. A vector according to paragraph 10 or 11 wherein the tetracycline repressor is linked to a nuclear localised signal.

13. A vector according to any preceding paragraph further comprises one or more NOIs downstream of the internal promoter or IRES, and optionally operably linked thereto.

14. A vector according to paragraph 13 wherein the NOI gives rise to a therapeutic effect.

15. A vector according to paragraph 13 or 14 wherein one or more of the NOIs are operably linked to a tetracycline operator.

16. A vector according to any one of paragraphs 13 to 15 comprising a further tetracycline repressor downstream of the internal promoter or IRES.

17. A vector according to any preceding paragraph wherein the vector is derived from HIV-1, HIV-2, SIV, FIV, BLV, EIAV, CEV or visna lentivirus.

18. A vector according to any preceding paragraph wherein the vector is derived from a non-primate lentivirus.

19. A vector according to any preceding paragraph wherein the vector genome comprises a cPPT sequence.

20. A vector according to any preceding paragraph wherein the vector genome comprises a post-transcriptional regulatory element or a translational element.

21. A vector according to according to any preceding paragraph wherein the ATG motifs of the gag packaging signal of the wild type lentiviral vector genome are ATTG motifs.

22. A vector according to any preceding paragraph wherein the distance between the R regions of the vector genome is substantially the same as that in the wild type lentiviral vector.

23. A vector of any preceding paragraph wherein the 3' U3 region of the vector genome includes sequence from a viral and/or a eukaryotic promoter.

24. The vector of any preceding paragraph wherein the 3' U3 region of the vector genome includes a wild type viral and/or a eukaryotic promoter.

25. The vector of any preceding paragraph wherein the viral promoter is an EIAV or MLV U3 region.

26. The vector of any preceding paragraph wherein the vector genome is bi- or tricistronic.

27. A retroviral vector production system for producing a retrovirus-derived vector particle, which system comprises a set of nucleic acid sequences encoding the components of the vector including the vector genome of any one of paragraphs, gag and pol proteins, env protein or a functional substitute therefor, wherein the genome of the vector is multicistronic and comprises a first nucleic acid sequence upstream of an internal promoter or an Internal Ribosome Entry Site (IRES), such that the level of genomic RNA available for packaging in the absence of rev, or analogous auxiliary gene from the lentivirus from which said particles are derived, is increased.

28. A production system according to paragraph 27 wherein a nucleic acid sequence encoding the auxiliary gene rev, or analogous auxiliary gene from the lentivirus from which said particles are derived, is disrupted such that said auxiliary gene is incapable of encoding the functional auxiliary proteins, or removed from the system.

29. A production system according to paragraph 27 or 28 wherein the nucleic acid sequences encoding at least one of the auxiliary genes vpr, vif, tat and nef, or analogous auxiliary genes, from the lentivirus from which said particles are derived, are also disrupted such that said auxiliary genes are incapable of encoding the functional auxiliary proteins, or removed from the system.

30. A production system according any one of paragraphs 27 to 29 wherein the vector is derived from HIV-1, HIV-2, SIV, FIV, BLV, EIAV, CEV or visna lentivirus.

31. A production system according to any one of paragraphs 27 to 30 wherein the vector is derived from a non-primate lentivirus.

32. A production system according to any one of paragraphs 27 to 31 wherein the set of nucleic acid sequences encoding the components of the vector includes three DNA constructs which encode the RNA genome of the vector, Gag and Pol proteins, and Env protein, or functional substitutes therefor.

33. A DNA construct for use in the system according to any one of paragraphs 27 to 32 said DNA construct encoding a packagable RNA vector genome as defined in any one of paragraphs.

34. A set of DNA constructs for use in the system of any one of paragraphs 27 to 32 comprising the DNA construct according to paragraph, and a DNA construct encoding Gag and Pol proteins or functional substitute thereof.

35. A set of DNA constructs as according to paragraph 34, further comprising a DNA construct encoding Env protein or a functional substitute thereof.

36. DNA constructs for use in the system according to any one of paragraphs 27 to 32, comprising the DNA constructs according to any one of paragraphs 1 to 26, in one or more expression vectors.

37. A process for preparing a retroviral vector particle comprising introducing a set of nucleic acid sequences or DNA constructs as defined in any one of paragraphs 33 to 36 into a host cell, a obtaining the retroviral vector particle.

38. A retroviral vector particle produced by the system or process according to any one of paragraphs 27 to 32 or 37.

39. A lentivirus-derived vector particle comprising an RNA genome of the vector, Gag and Pol proteins, and Env protein, or functional substitutes therefor, wherein the genome of the vector is as defined in any one of paragraphs 1 to 26.

40. A vector particle according to paragraph 39 wherein a nucleic acid sequence encoding the auxiliary gene rev, or analogous auxiliary gene from the lentivirus from which said particles are derived, is disrupted such that said auxiliary gene is incapable of encoding the functional auxiliary proteins, or removed from the system.

41. A vector particle according to paragraph 39 or 40 wherein the nucleic acid sequences encoding at least one of the auxiliary genes vpr, vif, tat and nef, or analogous auxiliary genes, from the lentivirus from which said particles are derived, are also disrupted such that said auxiliary genes are incapable of encoding the functional auxiliary proteins, or removed from the system.

42. A vector particle according to any one of paragraphs 39 to 41 wherein the vector is derived from HIV-1, HIV-2, SIV, FIV, BLV, EIAV, CEV or visna lentivirus.

43. A cell transduced with the lentiviral vector particle of any one of paragraphs 38 to 42 or DNA construct of any one of paragraphs 33 to 36.

44. A lentiviral vector particle of any one of paragraphs 38 to 42 or DNA construct of any one of paragraphs 32 to 36 or cell of paragraph 43 for use in medicine.

45. A pharmaceutical composition comprising the vector of any one of paragraphs 1 to 26, the system of any one of paragraphs 27 to 32, a particle of any one of paragraphs 38 to 42 or a cell in accordance with paragraph 43, together with a pharmaceutically acceptable carrier or diluent.

46. Use of a lentiviral vector particle of any one of paragraphs 38 to 42 or DNA construct of any one of paragraphs 33 to 36 or cell of paragraph 43 for the preparation of a medicament to deliver an NOI to a target site in need of same.

47. A delivery system in the form of a lentiviral vector particle of any one of paragraphs 38 to 42 or DNA construct of any one of paragraphs 33 to 36 or cell of paragraph 43 for use in medicine.

48. A method for identifying a target moiety and/or an associated modulating moiety wherein the method comprises:
providing a target non-dividing or slowly dividing cell comprising a collection of NOIs encoding more than one modulating moiety;
detecting a phenotypic difference between the target non-dividing or slowly dividing cell encoding or expressing at least one modulating moiety and a control cell lacking the modulating moiety, wherein the phenotypic difference is a consequence of the association of the modulating moiety with the target moiety; and
recovering the target moiety and/or the associated modulating moiety.

49. The method according to paragraph 48 wherein the collection of NOIs is constructed in a viral vector.

50. The method according to paragraph 49 wherein the viral vector is selected from the group consisting of a lentiviral vector, an adenoviral vector, an adeno-associated vector, a herpes vector, a pox viral vector, a parvovirus vector and a baculoviral vector.

51. A method for identifying a target moiety and/or an associated modulating moiety wherein the method comprises:

providing a target cell comprising a collection of NOIs constructed in a lentiviral vector and encoding more than one modulating moiety;

detecting a phenotypic difference between the target cell encoding or expressing at least one modulating moiety and a control cell lacking the modulating moiety, wherein the phenotypic difference is a consequence of the association of the modulating moiety with the target moiety; and recovering the target moiety and/or the associated modulating moiety.

52. The method according to paragraph 51 wherein the target cell is immortalised.

53. A method according to any one of paragraphs 48 to 52 further comprising the step of exposing the cell to a biological response modifier and subsequently detecting a phenotypic change.

54. The method according to any one of paragraphs 48 to 53 wherein the method further comprises isolating and/or sequencing the target moiety and/or the associated modulating moiety.

55. The method according to any one of paragraphs 48 to 54 wherein the phenotypic difference is a difference in transcription or expression of a reporter gene.

56. The method according to paragraph 55 wherein the reporter gene is operably linked to a regulatory moiety.

57. The method of according to any one of paragraphs 48 to 56 wherein the phenotypic difference is a modulation in association of at least one polypeptide with another polypeptide.

58. The method according to any one of paragraphs 48 to 56 wherein the phenotypic difference is the appearance or loss of a detectable phenotype.

59. The method according to any one of paragraphs 48 to 58 wherein the collection of NOIs is selected from the group consisting of a ribozyme library, an antisense library, a cDNA library, an RNAi library and a peptide library.

60. The method according to any one of paragraphs 48 to 59 wherein the NOI is constitutively expressed.

61. The method according to any one of paragraphs 48 to 60 wherein the NOI is under the control of a regulatable promoter.

62. The method according to any one of paragraphs 48 to 61 wherein the target gene is regulatable by the biological response modifier.

63. The method according to any one of paragraphs 48 to 62 wherein the biological response modifier mimics a disease state.

64. The method according to any one of paragraphs 48 to 63 wherein the viral vector is multi-cistronic.

65. The method according to any one of paragraphs 48 to 64 wherein the lentivirus vector is a non-primate lentiviral vector.

66. The method according to paragraph 65 wherein the non-primate lentiviral expression vector is derived from EIAV, FIV, BIV, CAEV or MVV.

67. The method according to any one of paragraphs 48 to 66 wherein the vector comprises a genome as defined in any one of paragraphs 1 to 26.

68. The method of any one of paragraphs 48 to 67 wherein the target cell comprises a reporter moiety operably linked to a regulatable moiety.

69. The method according to paragraph 68 wherein the regulatory moiety is a regulatory element.

70. The method according to paragraph 69 wherein the regulatory element is a promoter.

71. A target moiety and/or an associated modulating moiety identified by the method according to any one of paragraphs 48 to 70.

72. A composition comprising the identified target moiety and/or the associated modulating moiety as defined in paragraph 71 for use in medicine.

73. Use of the identified target moiety and/or the associated modulating moiety as defined in paragraph 71 in the preparation of a medicament for the treatment of a disease associated with the target moiety and/or the associated modulating moiety.

74. A vector comprising:
(i) an optional first nucleotide sequence encoding a selectable marker;
(ii) one or more optional second nucleotide sequences, each independently encoding a marker or modulator gene; and
(iii) a third nucleotide sequence, operably linked to a promoter, encoding a gene product capable of binding to and effecting the cleavage, directly or indirectly, of a nucleotide sequence;
wherein (i), (ii) and (iii) are operably linked to a regulatory sequence capable of directing transcription of (i), (ii) and (iii) as a continuous RNA molecule in a host.

75. A vector comprising:
(a) a first nucleotide sequence encoding a modulator gene;
(b) a second nucleotide sequence encoding a detectable marker gene which is operably linked to a nucleotide sequence upon which said first nucleotide sequence modulates, and a promoter; and
(c) a nucleotide of interest;
wherein (a), (b) and (c) are operably linked to a regulatory sequence capable of directing transcription of (a), (b) and (c) as a continuous RNA molecule in a host.

76. A vector according to paragraph 74 wherein (ii) is out of frame with the regulatory sequence capable of directing its transcription.

77. A vector according to paragraph 75 wherein (c) is out of frame with the regulatory sequence capable of directing transcription of (a).

78. A vector according to any one of paragraphs 74 to 77 wherein the vector is a viral vector.

79. A vector according to paragraph 78 wherein the vector is a lentiviral vector.

80. A vector according to any one of paragraphs 74 to 79 wherein the modulator is an activator or a repressor.

81. A vector according to paragraph 80 wherein the modulator is selected from tetracycline repressors, such as TetR, and tetracycline-controlled transactivators, such as tTA and rtTA, and wherein the detectable marker gene is operably linked to a tetracycline operator.

82. A vector according to paragraph 81 wherein the tetracycline repressor is codon optimised for expression in a mammalian cell.

83. A vector according to any one of paragraphs 74 to 82 wherein the marker gene is selected from an antibiotic resistance gene, a gene encoding a fluorescent protein or a cell surface marker and a suicide gene.

84. A vector according to paragraph 83 wherein the marker gene is selected from GFP, LNGFR and TK.

85. A library vector system comprising a plurality of vectors according to paragraph 74 and any paragraph dependent thereon.

86. A plurality of viral particles, each viral particle comprising a vector according to paragraph 74 and any paragraph dependent thereon.

87. A method for producing a plurality of viral particles which method comprises introducing into producer cells a plurality of vectors according to paragraph 74 and any paragraph dependent thereon.

88. A host cell comprising a vector according to paragraph 74 and any paragraph dependent thereon.

89. A vector system comprising the vector according to paragraph 74 and any paragraph dependent thereon, and the vector according to paragraph 75 and any paragraph dependent thereon, wherein the one or more of the second nucleotide sequences of paragraph 74 is the same as the modulator gene sequence of paragraph 75, and/or one or more of the second nucleotide sequences of paragraph 74 is the same as the marker gene sequence of paragraph 75, and/or the promoter of the third nucleotide sequence of paragraph 74 is the same as the promoter of paragraph 75(b).

90. A method for selecting from a plurality of third nucleotide sequences as defined in paragraph 74, a third nucleotide sequence encoding a gene product capable of binding to and effecting the cleavage, directly or indirectly, of the nucleotide of interest according to paragraph 75; which method comprises:
introducing the vector system according to paragraph 75 into a host cell; and
selecting the host cell in which a detectable marker gene is expressed; and optionally, isolating said third nucleotide sequence and determining its nucleotide sequence.

91. A method according to paragraph 90 that further comprises a selection step to ensure that only cells comprising a vector according to paragraph 74 are present.

92. A third nucleotide sequence as defined in paragraph 74 obtained by the method of paragraph 90 or 91.

REFERENCES

Bieri et al., (1999) Nat. Biotechnol., 17: 1105-1108
Li et al., (2000) Nucleic Acids Research, 28(13): 2605-2612
Beger et al., (2001) PNAS, 98(1): 130-135
Kestler et al., (1999) Human Gene Ther., 10(10): 1619-32
Winter et al., (1994) Annu Rev Immunol., 12: 433-55
Hoogenboom, (1997) Trends Biotechnol., 15: 62-70
Parmley and Smith, (1988) Gene, 73: 305-18
Lowman et al., (1991) Biochemistry, 30: 10832-8
Nissim et al., (1994) Embo J., 13: 692-8
Yelamos et al., (1995) Nature, 376: 225-9
Zaccolo et al., (1996) J. Mol. Biol., 255: 589-603
Leung et al., (I 989) Technique, 1: 11-15
Kowalczykowski et al., (1994) Microbiol. Rev., 58: 401-65
Stemmer, (1994) Nature, 370: 389-91
Stemmer, (1994) Proc. Natl. Acad. Sci. USA, 91: 10747-51
Goodchild, J V K, (1991) Arch. Biochem. Biophys., 284: 386-391
"Molecular Biology and Biotechnology" (Ed. R A Meyers 1995 VCH Publishers Inc p831-8320)
"Retroviruses" (Ed. J M Coffin et al 1997 Cold Spring Harbour Laboratory Press pp 683)
"Retroviruses" 1997 Cold Spring Harbour Laboratory Press Eds: J M Coffin, S M Hughes, H E Varmus pp 758-763
Lewis et al., (1992) EMBO. J., 11: 3053-3058
Lewis et al., (1992) EMBO. J., 11: 3053-3058
Lewis and Emerman (1994) J. Virol., 68: 510-516
Yu et al., (1986) Proc. Natl. Acad. Sci., 83: 3194-3198
Dougherty and Temin (1987) Proc. Natl. Acad. Sci., 84: 1197-1201
Hawley et al., (1987) Proc. Natl. Acad. Sci., 84: 2406-2410
Yee et al., (1987) Proc. Natl. Acad. Sci., 91: 9564-9568
Jolly et al., (1983) Nucleic Acids Res., 11: 1855-1872
Emerman and Temin (1984) Cell, 39: 449-467
Herman and Coffin (1987) Science 236: 845-848
Clabough, et al., (1991) J. Virol., 65: 6242-51
Derse and Newbold (1993) Virology, 194: 530-6
Maury, et al., (1994) Virology, 200: 632-42
Martarano et al., (1994) J. Virol. 68: 3102-11
Senter et al., (1988) Proc. Natl. Acad. Sci., 85: 4842-4846
Mullen et al., (1994) Cancer Res., 54: 1503-1506
Kerr et al., (1990) Cancer Immunol. Immunother., 31: 202-206
Borrelli et al., (1988) Proc. Natl. Acad. Sci., 85: 7572-7576
Friedlos et al., (1997) J. Med. Chem. 40: 1270-1275
Chen et al., (1996) Cancer Res., 56: 1331-1340
Nature Biotechnology (1996) 14: 556
Landau & Littman (1992) J. Virol., 66: 5110
Soneoka et al., (1995) Nucleic Acids Res., 23: 628-633
Tomko et al., (1997) Proc. Natl. Acad. Sci., 94: 3352-2258
Wickham et al., (1993) Cell, 73: 309-319
Wickham et al., (1994) J. Cell Biol., 127: 257-264
Hong et al., (1997) EMBO. 16: 2294-2306
Meyer, et al., (1991) J. Gen. Virol. 72: 1031-1038
Smith and Moss (1983) Gene, 25: 21-28
Upton, et al., (1986) J. Virology, 60: 920
Gershon, et al., (1989) J. Gen. Virol., 70: 525
Weir, et al., (1983) J. Virol., 46: 530
Esposito, et al., (1984) Virology, 135: 561
Hruby, et al., (1983) PNAS, 80: 3411
Kilpatrick, et al., (1985) Virology 143: 399
Binns, et al., (1988) J. Gen. Virol., 69: 1275
Boyle, et al., (1987) Virology, 156: 355
Schnitzlein, et al., (1988) J. Virological Method, 20: 341
Lytvyn, et al., (1992) J. Gen. Virol., 73: 3235-3240
Moss, B. (1991), Science, 252: 1662-7
Merchlinsky, M. et al., (1992) Virology, 190: 522-526
Scheiflinger, F. et al., (1992) Proc. Natl. Acad. Sci., USA. 89: 9977-9981
Merchlinsky, M. et al., (1992) Virology, 190: 522-526
Scheiflinger, F. et al., (1992), Proc. Natl. Acad. Sci. USA, 89: 9977-9981
Pfleiderer et al., (1995) J. General Virology, 76: 2957-2962
Marshall (1998) Nature Biotechnology, 16: 129
Wang and Sememnza (1993) Proc. Natl. Acad. Sci. USA, 90: 4304
Firth et al., (1994) Proc. Natl. Acad. Sci. USA, 91: 6496
Kallio, et al., (1998) Embo J., 17: 6573-86
Semenza, G et al., (1994) J. Biol. Chem., 269: 23757-63
Royds et al., (1998) Mol. Pathol., 51: 55-61
Matsui et al., (1999) Cardiovasc. Res., 42: 104-12
Yan, et al., (1997) J. Biol. Chem., 272: 4287-94
Estes et al., (1995) Exp. Cell Res., 220: 47-54
Gazit et al., (1995) Cancer Res., 55: 1660
Matthias, et al., (1989) NAR, 17: 6418
Carroll, M W, G W Wilkinson & K Lunstrom 2001 Mammalian expression systems and vaccination Genetically Engineered Viruses Ed: C J Ring & E D Blair pp 107-157 BIOS Scientific Oxford UK
Davison & Moss (1989) J. Mol. Biol., 210: 749-769
Attenello and Lee (1984) Science, 226: 187-190
Gazit et al., (1995) Cancer Res., 55: 1660-1663
Wang & Semenza (1993) Proc. Natl. Acad. Sci., 90: 430
Dachs et al., (1997) Nature Med., 5: 515
Firth et al., (1994) Proc. Natl. Acad. Sci., 91: 6496-6500
Madan et al., (1993) Proc. Natl. Acad. Sci., 90: 3928
Semenza and Wang (1992) Mol. Cell Biol., 12: 5447-5454
Takenaka et al., (1989) J. Biol. Chem., 264: 2363-2367
Peshavaria and Day (1991) Biochem. J. 275: 427-433
Inoue et al., (1989) J. Biol. Chem. 264: 14954-14959
O'Hare, M. J. et al., Proc. Natl. Acad. Sci. USA, 98(2): 646-51

Gillett et al., (1994) Cancer Res., 54(7): 1812-7
Yu et al., (2001) Nature, 411(6841): 1017-21
Stirling & Chung (2000) Eur. Respir. J., 16(6): 1158-74
Weltman & Karim (2000) Expert Opin. Investig. Drugs 9(3): 491-6
Cai, H. et al., (2001) Nat. Neurosci., 4(3): 233-4
Vigneri & Wang (2001) Nat. Med., 7(2): 228-34
Gorre et al., (Aug. 3, 2001) Science; 293(5531): 876-80
McCormick (Jul. 19, 2001) Nature; 412(6844): 281-2
Jahagirdar et al., (May 2001) Exp. Hematol.; 29(5): 543-56.
Sillaber et al., (Mar. 15, 2000) Blood.; 95(6): 2118-25
Liu et al., (March 1996) Mol. Cell Biol.; 16(3): 998-1005
Arlinghaus (1998) Crit. Rev. Oncog., 9(1): 1-18
Shah et al., (April 1991) Mol Cell Biol.; 11(4): 1854-60
Zhu et al., (Dec. 11, 1990) Nucleic Acids Res.; 18(23): 7119-7125
Collins et al., (August 1987) Mol. Cell Biol.; 7(8): 2870-2876
Voncken et al., (November 1998) Int. J. Mol. Med.; 2(5): 577-583
Voncken et al., (Mar. 10, 1995) Cell; 80(5): 719-728
Voncken et al., (Apr. 16, 1998) Oncogene; 16(15): 2029-2032
Wetzler et al., (October 1993) J. Clin. Invest; 92(4): 1925-1939
Perkins et al., (Feb. 1, 2000) Blood; 95(3): 1014-22
Porosnicu et al., (May 2001) Leukemia; 15(5): 772-778
Kwong & Todd, (May 1, 1997) Blood; 89(9): 3487-8
Puccetti et al., (Jul. 1, 2000) Cancer Res. 60(13): 3409-3413
Andrews & Collins, (October 1987) Leukemia; 1(10): 718-24
Dalgaard (1957) Acta, Med, Scand., 328: 1-255
Bacolla et al., (May 25, 2001) J. Biol. Chem.; 276(21): 18597-604
Arnaout (2001) Annu. Rev. Med., 52: 93-123
Calvet & Grantham (March 2001) Semin Nephrol. 21(2): 107-23
Boletta et al., (November 2000) Mol. Cell.; 6(5): 1267-73
Grantham (July 2001) Curr Opin Nephrol Hypertens.; 10(4): 533-42
Amould et al., (May 1999) Mol. Cell Biol.; 19(5): 3423-34
Pugh et al., (March 1995) Kidney Int.; 47(3): 774-81
Richard et al., (Mar. 11, 998) J. Clin. Invest.; 101(5): 935-9
Ibraghimov-Beskrovnaya et al., (Jun. 10, 1997) Proc Natl Acad Sci USA., 94(12): 6397-402
Kim (Feb. 15, 2000) Proc. Natl. Acad. Sci. USA. 97(4): 1731-6
Pey et al., (November-December 1999) In Vitro Cell Dev. Biol. Anim. 35(10): 571-9
Miskin et al., (1998 & 2000) Science, 281: 562-565; J. Virol., 74: 9412-9420
Powell et al., J. Virol., 70: 8527-33
Tait et al., J. Biol. Chem., 275: 34656-64
O'Hare, M. J. et al., (2001) Proc. Natl. Acad. Sci. USA., 98(2): 646-51
Cai, H. et al., (2001) Nat. Neurosci., 4(3): 233-4
Emmons S W, Somlo S. (23 Sep. 1999) Nature, 401(6751): 339-40

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

We claim:

1. A lentiviral vector genome for producing a lentiviral vector particle, the lentiviral vector genome comprising: (i) an open reading frame (ORF) upstream of a promoter, wherein the promoter controls the expression of at least one downstream nucleotide sequence of interest (NOI), and (ii) a packaging signal;
   wherein the ORF is a heterologous sequence;
   wherein the ORF is a second NOI, or wherein the ORF encodes a reporter, a selectable marker, or a modulator;
   wherein the ORF is operably linked to an upstream lentiviral long terminal repeat (LTR);
   wherein the lentiviral vector genome is self-inactivating (SIN); and
   wherein nucleic acid sequences encoding functional Rev and functional Rev Response Element (RRE) are absent from the lentiviral vector genome; and
   wherein the lentiviral vector genome lacks a non-lentiviral 5' LTR.

2. The lentiviral vector genome of claim 1, wherein the ORF encodes the reporter or the selectable marker.

3. The lentiviral vector genome of claim 1, wherein the ORF encodes the modulator.

4. The lentiviral vector genome according to claim 3, wherein the modulator is selected from the group consisting of a tetracycline repressor and a tetracycline-controlled transactivator.

5. The lentiviral vector genome according to claim 4, wherein the tetracycline repressor is codon optimised for expression in a mammalian cell.

6. The lentiviral vector genome according to claim 4, wherein the coding sequence for the tetracycline repressor is linked to a nuclear localization signal.

7. The lentiviral vector genome according to claim 1, wherein the at least one downstream NOI is operably linked to a tetracycline operator.

8. The lentiviral vector genome according to claim 1, further comprising a tetracycline repressor coding sequence downstream of the promoter.

9. The lentiviral vector genome according to claim 1, wherein the vector genome is a non-primate lentivirus vector genome.

10. The lentiviral vector genome according to claim 1, wherein the vector genome is selected from the group consisting of HIV-1, HIV-2, SIV, FIV, BIV, EIAV, CEV, CAEV, MVV, and visna lentivirus vector genomes.

11. The lentiviral vector genome according to claim 1, wherein the vector genome comprises a central polypurine tract (cPPT) sequence.

12. The lentiviral vector genome according to claim 1, wherein the vector genome comprises a post-transcriptional regulatory element or a translational element.

13. The lentiviral vector genome according to claim 1, wherein the vector genome comprises a gag packaging signal having ATG motifs, and wherein the ATG motifs are ATTG motifs.

14. The lentiviral vector genome according to claim 1, wherein the vector genome comprises R regions having substantially the same distance between the R regions as that in a wild type lentiviral vector genome.

15. The lentiviral vector genome according to claim 1, wherein the vector genome comprises a 3' U3 region from a viral promoter or a eukaryotic promoter.

16. The lentiviral vector genome according to claim 15, wherein the viral promoter or the eukaryotic promoter is a wild type promoter.

17. The lentiviral vector genome according to claim 15, wherein the viral promoter is an EIAV or an MLV U3 region.

18. The lentiviral vector genome according to claim 1, wherein the vector genome is bi- or tricistronic.

19. A lentiviral vector particle comprising the lentiviral vector genome of claim 1.

20. An isolated cell transduced with the lentiviral vector particle according to claim 19.

21. A pharmaceutical composition comprising the lentiviral vector particle of claim 19, together with a pharmaceutically acceptable carrier or a pharmaceutical diluent.

22. A pharmaceutical composition comprising the lentiviral vector genome of claim 1, together with a pharmaceutically acceptable carrier or a pharmaceutical diluent.

23. The lentiviral vector genome of claim 1, wherein a nucleic acid sequence encoding at least one of auxiliary genes vpr, vif, tat and nef is removed from the genome or disrupted, such that the at least one auxiliary gene is incapable of encoding a functional auxiliary protein.

24. A set of DNA constructs comprising the vector genome according to claim 1, and a DNA construct comprising a nucleic acid sequence encoding Gag and Pol, operably linked to a promoter.

25. The set of DNA constructs according to claim 24, further comprising a DNA construct comprising a nucleic acid sequence encoding Env, operably linked to a promoter.

26. An isolated cell transduced with the set of DNA constructs according to claim 25.

27. A lentiviral vector production system for producing a lentiviral vector particle, which system comprises the lentiviral vector genome of claim 1, a nucleic acid sequence encoding Gag and Pol, and a nucleic acid sequence encoding Env, wherein the nucleic acid sequence encoding Gag and Pol, and the nucleic acid sequence encoding Env are operably linked to one or more internal regulatory elements, wherein a nucleic acid sequence encoding functional Rev is absent from the lentiviral vector production system, and wherein the lentiviral vector production system lacks a non-lentiviral 5' LTR.

28. The lentiviral vector production system according to claim 27, wherein the system comprises three DNA constructs, (i) the vector genome, (ii) the nucleic acid sequence encoding Gag and Pol, and (iii) the nucleic acid sequence encoding Env.

29. The lentiviral vector production system of claim 27, wherein the nucleic acid sequence encoding Gag and Pol is codon optimised.

30. The lentiviral vector production system of claim 27, wherein a nucleic acid sequence encoding at least one of auxiliary genes vpr, vif, tat and nef is removed from the system or disrupted, such that the at least one auxiliary gene is incapable of encoding a functional auxiliary protein.

31. A process for preparing a lentiviral vector particle comprising introducing the lentiviral vector production system according to claim 27 into a host cell and obtaining the lentiviral vector particle.

* * * * *

SEQUENCE LISTING

```
<160> NUMBER OF SEQ ID NOS: 23

<210> SEQ ID NO 1
<211> LENGTH: 6418
<212> TYPE: DNA
<213> ORGANISM: Artificial Sequence
<220> FEATURE:
<223> OTHER INFORMATION: Description of Artificial Sequence: Synthetic
      construct pONY8.1G

<400> SEQUENCE: 1
agatcttgaa taataaaatg tgtgtttgtc cgaaatacgc gttttgagat ttctgtcgcc      60
gactaaattc atgtcgcgcg atagtggtgt ttatcgccga tagagatggc gatattggaa    120
aaattgatat ttgaaaatat ggcatattga aaatgtcgcc gatgtgagtt tctgtgtaac    180
tgatatcgcc atttttccaa aagtgatttt tgggcatacg cgatatctgg cgatagcgct    240
tatatcgttt acggggatg gcgatagacg actttggtga cttgggcgat tctgtgtgtc    300
gcaaatatcg cagtttcgat ataggtgaca gacgatatga ggctatatcg ccgatagagg    360
cgacatcaag ctggcacatg gccaatgcat atcgatctat acattgaatc aatattggcc    420
attagccata ttattcattg gttatatagc ataaatcaat attggctatt ggccattgca    480
tacgttgtat ccatatcgta atatgtacat ttatattggc tcatgtccaa cattaccgcc    540
atgttgacat tgattattga ctagttatta atagtaatca attacggggt cattagttca    600
tagcccatat atggagttcc gcgttacata acttacggta aatggcccgc ctggctgacc    660
```

```
gcccaacgac ccccgcccat tgacgtcaat aatgacgtat gttcccatag taacgccaat    720
agggactttc cattgacgtc aatgggtgga gtatttacgg taaactgccc acttggcagt    780
acatcaagtg tatcatatgc caagtccgcc ccctattgac gtcaatgacg gtaaatggcc    840
cgcctggcat tatgcccagt acatgacctt acgggacttt cctacttggc agtacatcta    900
cgtattagtc atcgctatta ccatggtgat gcggttttgg cagtacacca atgggcgtgg    960
atagcggttt gactcacggg gatttccaag tctccacccc attgacgtca atgggagttt   1020
gttttggcac caaaatcaac gggactttcc aaaatgtcgt aacaactgcg atcgcccgcc   1080
ccgttgacgc aaatgggcgg taggcgtgta cggtgggagg tctatataag cagagctcgt   1140
ttagtgaacc gggcactcag attctgcggt ctgagtccct tctctgctgg gctgaaaagg   1200
cctttgtaat aaatataatt ctctactcag tccctgtctc tagtttgtct gttcgagatc   1260
ctacagttgg cgcccgaaca gggacctgag aggggcgcag accctacctg ttgaacctgg   1320
ctgatcgtag gatccccggg acagcagagg agaacttaca gaagtcttct ggaggtgttc   1380
ctggccagaa cacaggagga caggtaagat tgggagaccc tttgacattg gagcaaggcg   1440
ctcaagaagt tagagaaggt gacggtacaa gggtctcaga aattaactac tggtaactgt   1500
aattgggcgc taagtctagt agacttattt catgatacca actttgtaaa agaaaaggac   1560
tggcagctga gggatgtcat tccattgctg gaagatgtaa ctcagacgct gtcaggacaa   1620
gaaagagagg cctttgaaag aacatggtgg gcaatttctg ctgtaaagat gggcctccag   1680
attaataatg tagtagatgg aaaggcatca ttccagctcc taagagcgaa atatgaaaag   1740
aagactgcta ataaaaagca gtctgagccc tctgaagaat atctctagaa ctagtggatc   1800
ccccgggctg caggagtggg gaggcacgat ggccgctttg gtcgaggcgg atccggccat   1860
tagccatatt attcattggt tatatagcat aaatcaatat tggctattgg ccattgcata   1920
cgttgtatcc atatcataat atgtacattt atattggctc atgtccaaca ttaccgccat   1980
gttgacattg attattgact agttattaat agtaatcaat tacggggtca ttagttcata   2040
gcccatatat ggagttccgc gttacataac ttacggtaaa tggcccgcct ggctgaccgc   2100
ccaacgaccc ccgcccattg acgtcaataa tgacgtatgt tcccatagta acgccaatag   2160
ggactttcca ttgacgtcaa tgggtggagt atttacggta aactgcccac ttggcagtac   2220
atcaagtgta tcatatgcca agtacgcccc ctattgacgt caatgacggt aaatggcccg   2280
cctggcatta tgcccagtac atgaccttat gggactttcc tacttggcag tacatctacg   2340
tattagtcat cgctattacc atggtgatgc ggttttggca gtacatcaat gggcgtggat   2400
agcggtttga ctcacgggga tttccaagtc tccaccccat tgacgtcaat gggagtttgt   2460
tttggcacca aaatcaacgg gactttccaa aatgtcgtaa caactccgcc ccattgacgc   2520
aaatgggcgg taggcatgta cggtgggagg tctatataag cagagctcgt ttagtgaacc   2580
gtcagatcgc ctggagacgc catccacgct gttttgacct ccatagaaga caccgggacc   2640
gatccagcct ccgcggcccc aagcttgttg ggatccaccg tcgccacca tggtgagcaa   2700
gggcgaggag ctgttcaccg gggtggtgcc catcctggtc gagctggacg gcgacgtaaa   2760
cggccacaag ttcagcgtgt ccggcgaggg cgagggcgat gccacctacg gcaagctgac   2820
cctgaagttc atctgcacca ccggcaagct gcccgtgccc tggcccaccc tcgtgaccac   2880
cctgacctac ggcgtgcagt gcttcagccg ctaccccgac cacatgaagc agcacgactt   2940
cttcaagtcc gccatgcccg aaggctacgt ccaggagcgc accatcttct tcaaggacga   3000
cggcaactac aagacccgcg ccgaggtgaa gttcgagggc gacaccctgg tgaaccgcat   3060
```

| | |
|---|---|
| cgagctgaag ggcatcgact tcaaggagga cggcaacatc ctggggcaca agctggagta | 3120 |
| caactacaac agccacaacg tctatatcat ggccgacaag cagaagaacg gcatcaaggt | 3180 |
| gaacttcaag atccgccaca acatcgagga cggcagcgtg cagctcgccg accactacca | 3240 |
| gcagaacacc cccatcggcg acggccccgt gctgctgccc gacaaccact acctgagcac | 3300 |
| ccagtccgcc ctgagcaaag accccaacga aagcgcgat cacatggtcc tgctggagtt | 3360 |
| cgtgaccgcc gccgggatca ctctcggcat ggacgagctg tacaagtaaa gcggccgcga | 3420 |
| ctctagagtc gacctgcagg aattcgatat caagcttatc gataccgtcg aattggaaga | 3480 |
| gctttaaatc ctggcacatc tcatgtatca atgcctcagt atgtttagaa aaacaagggg | 3540 |
| ggaactgtgg ggttttatg aggggtttta taatgatta taagagtaaa aagaaagttg | 3600 |
| ctgatgctct cataaccttg tataacccaa aggactagct catgttgcta ggcaactaaa | 3660 |
| ccgcaataac cgcatttgtg acgcgagttc cccattggtg acgcgttaac ttcctgtttt | 3720 |
| tacagtatat aagtgcttgt attctgacaa ttgggcactc agattctgcg gtctgagtcc | 3780 |
| cttctctgct gggctgaaaa ggcctttgta ataaatataa ttctctactc agtccctgtc | 3840 |
| tctagtttgt ctgttcgaga tcctacagag ctcatgcctt ggcgtaatca tggtcatagc | 3900 |
| tgtttcctgt gtgaaattgt tatccgctca caattccaca caacatacga gccggaagca | 3960 |
| taaagtgtaa agcctggggt gcctaatgag tgagctaact cacattaatt gcgttgcgct | 4020 |
| cactgcccgc tttccagtcg ggaaacctgt cgtgccagct gcattaatga atcggccaac | 4080 |
| gcgcggggag aggcggtttg cgtattgggc gctcttccgc ttcctcgctc actgactcgc | 4140 |
| tgcgctcggt cgttcggctg cggcgagcgg tatcagctca ctcaaaggcg gtaatacggt | 4200 |
| tatccacaga atcaggggat aacgcaggaa agaacatgtg agcaaaaggc cagcaaaagg | 4260 |
| ccaggaaccg taaaaaggcc gcgttgctgg cgtttttcca taggctccgc cccctgacg | 4320 |
| agcatcacaa aaatcgacgc tcaagtcaga ggtggcgaaa cccgacagga ctataaagat | 4380 |
| accaggcgtt ccccctgga agctccctcg tgcgctctcc tgttccgacc ctgccgctta | 4440 |
| ccggatacct gtccgccttt ctcccttcgg aagcgtggc gctttctcat agctcacgct | 4500 |
| gtaggtatct cagttcggtg taggtcgttc gctccaagct gggctgtgtg cacgaacccc | 4560 |
| ccgttcagcc cgaccgctgc gccttatccg gtaactatcg tcttgagtcc aacccggtaa | 4620 |
| gacacgactt atcgccactg gcagcagcca ctggtaacag gattagcaga gcgaggtatg | 4680 |
| taggcggtgc tacagagttc ttgaagtggt ggcctaacta cggctacact agaaggacag | 4740 |
| tatttggtat ctgcgctctg ctgaagccag ttaccttcgg aaaaagagtt ggtagctctt | 4800 |
| gatccggcaa acaaaccacc gctggtagcg gtggtttttt tgtttgcaag cagcagatta | 4860 |
| cgcgcagaaa aaaaggatct caagaagatc ctttgatctt ttctacgggg tctgacgctc | 4920 |
| agtggaacga aaactcacgt taagggattt tggtcatgag attatcaaaa aggatcttca | 4980 |
| cctagatcct tttaaattaa aaatgaagtt ttaaatcaat ctaaagtata tatgagtaaa | 5040 |
| cttggtctga cagttaccaa tgcttaatca gtgaggcacc tatctcagcg atctgtctat | 5100 |
| ttcgttcatc catagttgcc tgactccccg tcgtgtagat aactacgata cgggagggct | 5160 |
| taccatctgg ccccagtgct gcaatgatac cgcgagaccc acgctcaccg gctccagatt | 5220 |
| tatcagcaat aaaccagcca gccggaaggg ccgagcgcag aagtggtcct gcaactttat | 5280 |
| ccgcctccat ccagtctatt aattgttgcc gggaagctag agtaagtagt tcgccagtta | 5340 |
| atagtttgcg caacgttgtt gccattgcta caggcatcgt ggtgtcacgc tcgtcgtttg | 5400 |

-continued

```
gtatggcttc attcagctcc ggttcccaac gatcaaggcg agttacatga tcccccatgt    5460
tgtgcaaaaa agcggttagc tccttcggtc ctccgatcgt tgtcagaagt aagttggccg    5520
cagtgttatc actcatggtt atggcagcac tgcataattc tcttactgtc atgccatccg    5580
taagatgctt ttctgtgact ggtgagtact caaccaagtc attctgagaa tagtgtatgc    5640
ggcgaccgag ttgctcttgc ccggcgtcaa tacgggataa taccgcgcca catagcagaa    5700
ctttaaaagt gctcatcatt ggaaaacgtt cttcggggcg aaaactctca aggatcttac    5760
cgctgttgag atccagttcg atgtaaccca ctcgtgcacc caactgatct tcagcatctt    5820
ttactttcac cagcgtttct gggtgagcaa aaacaggaag gcaaaatgcc gcaaaaaagg    5880
gaataagggc gacacggaaa tgttgaatac tcatactctt cctttttcaa tattattgaa    5940
gcatttatca gggttattgt ctcatgagcg gatacatatt tgaatgtatt tagaaaaata    6000
aacaaatagg ggttccgcgc acatttcccc gaaaagtgcc acctaaattg taagcgttaa    6060
tattttgtta aaattcgcgt taaattttg ttaaatcagc tcattttta accaataggc    6120 cgaaatcggc aaaatccctt ataaatcaaa agaatagacc gagataggt tgagtgttgt    6180 tccagtttgg aacaagagtc cactattaaa gaacgtggac tccaacgtca aagggcgaaa    6240
aaccgtctat cagggcgatg gcccactacg tgaaccatca ccctaatcaa gttttttggg    6300
gtcgaggtgc cgtaaagcac taaatcggaa ccctaaaggg agcccccgat ttagagcttg    6360
acggggaaag ccaacctggc ttatcgaaat taatacgact cactataggg agaccggc    6418
```

<210> SEQ ID NO 2
<211> LENGTH: 9952
<212> TYPE: DNA
<213> ORGANISM: Artificial Sequence
<220> FEATURE:
<223> OTHER INFORMATION: Description of Artificial Sequence: Synthetic construct pONY8.4ZCG

<400> SEQUENCE: 2

```
agatcttgaa taataaaatg tgtgtttgtc cgaaatacgc gttttgagat ttctgtcgcc      60
gactaaattc atgtcgcgcg atagtggtgt ttatcgccga tagagatggc gatattggaa     120
aaattgatat ttgaaaatat ggcatattga aaatgtcgcc gatgtgagtt tctgtgtaac     180
tgatatcgcc attttccaa aagtgatttt tgggcatacg cgatatctgg cgatagcgct     240
tatatcgttt acggggatg gcgatagacg actttggtga cttgggcgat tctgtgtgtc     300
gcaaatatcg cagtttcgat ataggtgaca gacgatatga ggctatatcg ccgatagagg     360
cgacatcaag ctggcacatg gccaatgcat atcgatctat acattgaatc aatattggcc     420
attagccata ttattcattg gttatatagc ataaatcaat attggctatt ggccattgca     480
tacgttgtat ccatatcgta atatgtacat ttatattggc tcatgtccaa cattaccgcc     540
atgttgacat tgattattga ctagttatta atagtaatca attacggggt cattagttca     600
tagcccatat atggagttcc gcgttacata acttacggta aatggcccgc ctggctgacc     660
gcccaacgac ccccgcccat tgacgtcaat aatgacgtat gttcccatag taacgccaat     720
agggactttc cattgacgtc aatgggtgga gtatttacgg taaactgccc acttggcagt     780
acatcaagtg tatcatatgc caagtccgcc ccctattgac gtcaatgacg gtaaatggcc     840
cgcctggcat tatgcccagt acatgacctt acgggacttt cctacttggc agtacatcta     900
cgtattagtc atcgctatta ccatggtgat gcggttttgg cagtacacca atgggcgtgg     960
atagcggttt gactcacggg gatttccaag tctccacccc attgacgtca atgggagttt    1020
```

```
gttttggcac caaaatcaac gggactttcc aaaatgtcgt aacaactgcg atcgcccgcc    1080
ccgttgacgc aaatgggcgg taggcgtgta cggtgggagg tctatataag cagagctcgt    1140
ttagtgaacc gggcactcag attctgcggt ctgagtccct tctctgctgg gctgaaaagg    1200
cctttgtaat aaatataatt ctctactcag tccctgtctc tagtttgtct gttcgagatc    1260
ctacagttgg cgcccgaaca gggacctgag aggggcgcag accctacctg ttgaacctgg    1320
ctgatcgtag gatccccggg acagcagagg agaacttaca gaagtcttct ggaggtgttc    1380
ctggccagaa cacaggagga caggtaagat tgggagaccc tttgacattg gagcaaggcg    1440
ctcaagaagt tagagaaggt gacggtacaa gggtctcaga aattaactac tggtaactgt    1500
aattgggcgc taagtctagt agacttattt cattgatacc aactttgtaa aagaaaagga    1560
ctggcagctg agggattgtc attccattgc tggaagattg taactcagac gctgtcagga    1620
caagaaagag aggcctttga agaacattg gtgggcaatt tctgctgtaa agattgggcc    1680
tccagattaa taattgtagt agattggaaa ggcatcattc cagctcctaa gagcgaaata    1740
ttgaaaagaa gactgctaat aaaaagcagt ctgagccctc tgaagaatat ctctagaact    1800
agtggatccc ccgggctgca ggaattcgat atcaagcttc agctgctcga ggatctgcgg    1860
atccggggaa ttccccagtc tcaggatcca ccatggggga tcccgtcgtt ttacaacgtc    1920
gtgactggga aaaccctggc gttacccaac ttaatcgcct tgcagcacat ccccctttcg    1980
ccagctggcg taatagcgaa gaggcccgca ccgatcgccc ttcccaacag ttgcgcagcc    2040
tgaatggcga atggcgcttt gcctggtttc cggcaccaga agcggtgccg gaaagctggc    2100
tggagtgcga tcttcctgag gccgatactg tcgtcgtccc ctcaaactgg cagatgcacg    2160
gttacgatgc gcccatctac accaacgtaa cctatcccat tacggtcaat ccgccgtttg    2220
ttcccacgga gaatccgacg ggttgttact cgctcacatt taatgttgat gaaagctggc    2280
tacaggaagg ccagacgcga attatttttg atggcgttaa ctcggcgttt catctgtggt    2340
gcaacgggcg ctgggtcggt tacgccagg acagtcgttt gccgtctgaa tttgacctga    2400 gcgcatttt acgcgccgga gaaaaccgcc tcgcggtgat ggtgctgcgt tggagtgacg    2460
gcagttatct ggaagatcag gatatgtggc ggatgagcgg catttccgt gacgtctcgt    2520 tgctgcataa accgactaca caaatcagcg atttccatgt tgccactcgc tttaatgatg    2580
atttcagccg cgctgtactg gaggctgaag ttcagatgtg cggcgagttg cgtgactacc    2640
tacgggtaac agtttctta tggcagggtg aaacgcaggt cgccagcggc accgcgcctt    2700
tcggcggtga aattatcgat gagcgtggtg gttatgccga tcgcgtcaca ctacgtctga    2760
acgtcgaaaa cccgaaactg tggagcgccg aaatcccgaa tctctatcgt gcggtggttg    2820
aactgcacac cgccgacggc acgctgattg aagcagaagc ctgcgatgtc ggtttccgcg    2880
aggtgcggat tgaaaatggt ctgctgctgc tgaacggcaa gccgttgctg attcgaggcg    2940
ttaaccgtca cgagcatcat cctctgcatg gtcaggtcat ggatgagcag acgatggtgc    3000
aggatatcct gctgatgaag cagaacaact ttaacgccgt cgctgttcg cattatccga    3060 accatccgct gtggtacacg ctgtgcgacc gctacggcct gtatgtggtg gatgaagcca    3120
atattgaaac ccacggcatg gtgccaatga atcgtctgac cgatgatccg cgctggctac    3180
cggcgatgag cgaacgcgta acgcgaatgg tgcagcgcga tcgtaatcac ccgagtgtga    3240
tcatctggtc gctggggaat gaatcaggcc acggcgctaa tcacgacgcg ctgtatcgct    3300
ggatcaaatc tgtcgatcct tcccgcccgg tgcagtatga aggcggcgga gccgacacca    3360
cggccaccga tattatttgc ccgatgtacg cgcgcgtgga tgaagaccag cccttcccgg    3420
```

```
ctgtgccgaa atggtccatc aaaaaatggc tttcgctacc tggagagacg cgcccgctga   3480
tcctttgcga atacgcccac gcgatgggta acagtcttgg cggtttcgct aaatactggc   3540
aggcgtttcg tcagtatccc cgtttacagg gcggcttcgt ctgggactgg gtggatcagt   3600
cgctgattaa atatgatgaa aacggcaacc cgtggtcggc ttacggcggt gattttggcg   3660
atacgccgaa cgatcgccag ttctgtatga acggtctggt cttttgccgac cgcacgccgc   3720
atccagcgct gacggaagca aaacaccagc agcagttttt ccagttccgt ttatccgggc   3780
aaaccatcga agtgaccagc gaatacctgt ccgtcatag cgataacgag ctcctgcact   3840
ggatggtggc gctggatggt aagccgctgg caagcggtga agtgcctctg gatgtcgctc   3900
cacaaggtaa acagttgatt gaactgcctg aactaccgca gccggagagc gccgggcaac   3960
tctggctcac agtacgcgta gtgcaaccga acgcgaccgc atggtcagaa gccgggcaca   4020
tcagcgcctg gcagcagtgg cgtctggcgg aaaacctcag tgtgacgctc cccgccgcgt   4080
cccacgccat cccgcatctg accaccagcg aaatggattt ttgcatcgag ctgggtaata   4140
agcgttggca atttaaccgc cagtcaggct ttctttcaca gatgtggatt ggcgataaaa   4200
aacaactgct gacgccgctg cgcgatcagt tcacccgtgc accgctggat aacgacattg   4260
gcgtaagtga agcgacccgc attgacccta acgcctgggt cgaacgctgg aaggcggcgg   4320
gccattacca ggccgaagca gcgttgttgc agtgcacggc agatacactt gctgatgcgg   4380
tgctgattac gaccgctcac gcgtggcagc atcagggaa aaccttattt atcagccgga   4440
aaacctaccg gattgatggt agtggtcaaa tggcgattac cgttgatgtt gaagtggcga   4500
gcgatacacc gcatccggcg cggattggcc tgaactgcca gctggcgcag gtagcagagc   4560
gggtaaactg gctcggatta gggccgcaag aaaactatcc cgaccgcctt actgccgcct   4620
gttttgaccg ctgggatctg ccattgtcag acatgtatac cccgtacgtc ttcccgagcg   4680
aaaacggtct gcgctgcggg acgcgcgaat tgaattatgg cccacaccag tggcgcggcg   4740
acttccagtt caacatcagc cgctacagtc aacagcaact gatggaaacc agccatcgcc   4800
atctgctgca cgcggaagaa ggcacatggc tgaatatcga cggtttccat atggggattg   4860
gtggcgacga ctcctggagc ccgtcagtat cggcggaatt ccagctgagc gccggtcgct   4920
accattacca gttggtctgg tgtcaaaaat aataataacc gggcaggggg gatccgcaga   4980
tccggctgtg aatgtgtgt cagttagggt gtggaaagtc cccaggctcc ccagcaggca   5040
gaagtatgca aagctagaac tagtggatcc cccgggctgc aggagtgggg aggcacgatg   5100
gccgctttgg tcgaggcgga tccggccatt agccatatta ttcattggtt atatagcata   5160
aatcaatatt ggctattggc cattgcatac gttgtatcca tatcataata tgtacattta   5220
tattggctca tgtccaacat taccgccatg ttgacattga ttattgacta gttattaata   5280
gtaatcaatt acgggtcat tagttcatag cccatatatg gagttccgcg ttacataact   5340
tacggtaaat ggcccgcctg gctgaccgcc caacgacccc cgcccattga cgtcaataat   5400
gacgtatgtt cccatagtaa cgccaatagg gactttccat tgacgtcaat gggtggagta   5460
tttacggtaa actgcccact tggcagtaca tcaagtgtat catatgccaa gtacgccccc   5520
tattgacgtc aatgacggta aatggcccgc ctggcattat gcccagtaca tgaccttatg   5580
ggactttcct acttggcagt acatctacgt attagtcatc gctattacca tggtgatgcg   5640
gttttggcag tacatcaatg ggcgtggata gcggtttgac tcacggggat ttccaagtct   5700
ccaccccatt gacgtcaatg ggagtttgtt ttggcaccaa aatcaacggg actttccaaa   5760
```

-continued

```
atgtcgtaac aactccgccc cattgacgca aatgggcggt aggcatgtac ggtgggaggt    5820
ctatataagc agagctcgtt tagtgaaccg tcagatcgcc tggagacgcc atccacgctg    5880
ttttgacctc catagaagac accgggaccg atccagcctc cgcggcccca agcttgttgg    5940
gatccaccgg tcgccaccat ggtgagcaag ggcgaggagc tgttcaccgg ggtggtgccc    6000
atcctggtcg agctggacgg cgacgtaaac ggccacaagt tcagcgtgtc cggcgagggc    6060
gagggcgatg ccacctacgg caagctgacc ctgaagttca tctgcaccac cggcaagctg    6120
cccgtgccct ggcccaccct cgtgaccacc ctgacctacg gcgtgcagtg cttcagccgc    6180
taccccgacc acatgaagca gcacgacttc ttcaagtccg ccatgcccga aggctacgtc    6240
caggagcgca ccatcttctt caaggacgac ggcaactaca agacccgcgc cgaggtgaag    6300
ttcgagggcg acaccctggt gaaccgcatc gagctgaagg gcatcgactt caaggaggac    6360
ggcaacatcc tggggcacaa gctggagtac aactacaaca gccacaacgt ctatatcatg    6420
gccgacaagc agaagaacgg catcaaggtg aacttcaaga tccgccacaa catcgaggac    6480
ggcagcgtgc agctcgccga ccactaccag cagaacaccc ccatcggcga cggccccgtg    6540
ctgctgcccg acaaccacta cctgagcacc cagtccgccc tgagcaaaga ccccaacgag    6600
aagcgcgatc acatggtcct gctggagttc gtgaccgccg ccgggatcac tctcggcatg    6660
gacgagctgt acaagtaaag cggccgcgac tctagcctgc aggaattcga tatcaagctt    6720
atcgataccg tcgaattgga agagctttaa atcctggcac atctcatgta tcaatgcctc    6780
agtatgttta gaaaacaag gggggaactg tggggttttt atgaggggtt ttataaaaat    6840
gaaagacccc acctgtaggt ttggcaagct agcttaagta acgccatttt gcaaggcatg    6900
gaaaaataca taactgagaa tagagaagtt cagatcaagg tcaggaacag atggaacagc    6960
tgaatatggg ccaaacagga tatctgtggt aagcagttcc tgccccggct cagggccaag    7020
aacagatgga acagctgaat atgggccaaa caggatatct gtggtaagca gttcctgccc    7080
cggctcaggg ccaagaacag atggtcccca gatgcggtcc agccctcagc agtttctaga    7140
gaaccatcag atgtttccag ggtgccccaa ggacctgaaa tgaccctgtg ccttatttga    7200
actaaccaat cagttcgctt ctcgcttctg ttcgcgcgct tctgctcccc gagctcaata    7260
aaagagccca accccctca ctcggggggc actcagattc tgcggtctga gtcccttctc    7320
tgctgggctg aaaaggcctt tgtaataaat ataattctct actcagtccc tgtctctagt    7380
ttgtctgttc gagatcctac agagctcatg ccttggcgta atcatggtca tagctgtttc    7440
ctgtgtgaaa ttgttatccg ctcacaattc cacacaacat acgagccgga agcataaagt    7500
gtaaagcctg gggtgcctaa tgagtgagct aactcacatt aattgcgttg cgctcactgc    7560
ccgctttcca gtcgggaaac ctgtcgtgcc agctgcatta atgaatcggc caacgcgcgg    7620
ggagaggcgg tttgcgtatt gggcgctctt ccgcttcctc gctcactgac tcgctgcgct    7680
cggtcgttcg gctgcggcga gcggtatcag ctcactcaaa ggcggtaata cggttatcca    7740
cagaatcagg ggataacgca ggaaagaaca tgtgagcaaa aggccagcaa aaggccagga    7800
accgtaaaaa ggccgcgttg ctggcgtttt tccataggct ccgcccccct gacgagcatc    7860
acaaaaatcg acgctcaagt cagaggtggc gaaacccgac aggactataa agataccagg    7920
cgtttccccc tggaagctcc ctcgtgcgct ctcctgttcc gaccctgccg cttaccggat    7980
acctgtccgc ctttctccct tcgggaagcg tggcgcttc tcatagctca cgctgtaggt    8040
atctcagttc ggtgtaggtc gttcgctcca agctgggctg tgtgcacgaa ccccccgttc    8100
agcccgaccg ctgcgcctta tccggtaact atcgtcttga gtccaacccg gtaagacacg    8160
```

```
acttatcgcc actggcagca gccactggta acaggattag cagagcgagg tatgtaggcg    8220
gtgctacaga gttcttgaag tggtggccta actacggcta cactagaagg acagtatttg    8280
gtatctgcgc tctgctgaag ccagttacct tcggaaaaag agttggtagc tcttgatccg    8340
gcaaacaaac caccgctggt agcggtggtt ttttgtttg  caagcagcag attacgcgca    8400
gaaaaaagg  atctcaagaa gatcctttga tcttttctac ggggtctgac gctcagtgga    8460
acgaaaactc acgttaaggg attttggtca tgagattatc aaaaaggatc ttcacctaga    8520
tccttttaaa ttaaaaatga agttttaaat caatctaaag tatatatgag taaacttggt    8580
ctgacagtta ccaatgctta atcagtgagg cacctatctc agcgatctgt ctatttcgtt    8640
catccatagt tgcctgactc cccgtcgtgt agataactac gatacgggag ggcttaccat    8700
ctggccccag tgctgcaatg ataccgcgag acccacgctc accggctcca gatttatcag    8760
caataaacca gccagccgga agggccgagc gcagaagtgg tcctgcaact ttatccgcct    8820
ccatccagtc tattaattgt tgccgggaag ctagagtaag tagttcgcca gttaatagtt    8880
tgcgcaacgt tgttgccatt gctacaggca tcgtggtgtc acgctcgtcg tttggtatgg    8940
cttcattcag ctccggttcc caacgatcaa ggcgagttac atgatccccc atgttgtgca    9000
aaaaagcggt tagctccttc ggtcctccga tcgttgtcag aagtaagttg gccgcagtgt    9060
tatcactcat ggttatggca gcactgcata attctcttac tgtcatgcca tccgtaagat    9120
gcttttctgt gactggtgag tactcaacca agtcattctg agaatagtgt atgcggcgac    9180
cgagttgctc ttgcccggcg tcaatacggg ataataccgc gccacatagc agaactttaa    9240
aagtgctcat cattggaaaa cgttcttcgg ggcgaaaact ctcaaggatc ttaccgctgt    9300
tgagatccag ttcgatgtaa cccactcgtg cacccaactg atcttcagca tcttttactt    9360
tcaccagcgt ttctgggtga gcaaaaacag gaaggcaaaa tgccgcaaaa aagggaataa    9420
gggcgacacg gaaatgttga atactcatac tcttcctttt tcaatattat tgaagcattt    9480
atcagggtta ttgtctcatg agcggataca tatttgaatg tatttagaaa aataaacaaa    9540
taggggttcc gcgcacattt ccccgaaaag tgccacctaa attgtaagcg ttaatatttt    9600
gttaaaattc gcgttaaatt tttgttaaat cagctcattt tttaaccaat aggccgaaat    9660
cggcaaaatc ccttataaat caaaagaata gaccgagata gggttgagtg ttgttccagt    9720
ttggaacaag agtccactat taaagaacgt ggactccaac gtcaaagggc gaaaaaccgt    9780
ctatcagggc gatggcccac tacgtgaacc atcaccctaa tcaagttttt tggggtcgag    9840
gtgccgtaaa gcactaaatc ggaaccctaa agggagcccc cgatttagag cttgacgggg    9900
aaagccaacc tggcttatcg aaattaatac gactcactat agggagaccg gc            9952
```

<210> SEQ ID NO 3  
<211> LENGTH: 9924  
<212> TYPE: DNA  
<213> ORGANISM: Artificial Sequence  
<220> FEATURE:  
<223> OTHER INFORMATION: Description of Artificial Sequence: Synthetic construct pONY8.4GCZ

<400> SEQUENCE: 3

```
agatcttgaa taataaaatg tgtgtttgtc cgaaatacgc gttttgagat ttctgtcgcc     60
gactaaattc atgtcgcgcg atagtggtgt ttatcgccga tagagatggc gatattggaa    120
aaattgatat ttgaaaatat ggcatattga aaatgtcgcc gatgtgagtt tctgtgtaac    180
tgatatcgcc atttttccaa aagtgatttt tgggcatacg cgatatctgg cgatagcgct    240
```

-continued

```
tatatcgttt acggggatg gcgatagacg actttggtga cttgggcgat tctgtgtgtc    300
gcaaatatcg cagtttcgat ataggtgaca gacgatatga ggctatatcg ccgatagagg    360
cgacatcaag ctggcacatg gccaatgcat atcgatctat acattgaatc aatattggcc    420
attagccata ttattcattg gttatatagc ataaatcaat attggctatt ggccattgca    480
tacgttgtat ccatatcgta atatgtacat ttatattggc tcatgtccaa cattaccgcc    540
atgttgacat tgattattga ctagttatta atagtaatca attacggggt cattagttca    600
tagcccatat atggagttcc gcgttacata acttacggta aatggcccgc ctggctgacc    660
gcccaacgac ccccgcccat tgacgtcaat aatgacgtat gttcccatag taacgccaat    720
agggactttc cattgacgtc aatgggtgga gtatttacgg taaactgccc acttggcagt    780
acatcaagtg tatcatatgc caagtccgcc ccctattgac gtcaatgacg gtaaatggcc    840
cgcctggcat tatgcccagt acatgacctt acgggacttt cctacttggc agtacatcta    900
cgtattagtc atcgctatta ccatggtgat gcggttttgg cagtacacca atgggcgtgg    960
atagcggttt gactcacggg gatttccaag tctccacccc attgacgtca atgggagttt   1020
gttttggcac caaaatcaac gggactttcc aaaatgtcgt aacaactgcg atcgcccgcc   1080
ccgttgacgc aaatgggcgg taggcgtgta cggtgggagg tctatataag cagagctcgt   1140
ttagtgaacc gggcactcag attctgcggt ctgagtccct tctctgctgg gctgaaaagg   1200
cctttgtaat aaatataatt ctctactcag tccctgtctc tagtttgtct gttcgagatc   1260
ctacagttgg cgcccgaaca gggacctgag aggggcgcag accctacctg ttgaacctgg   1320
ctgatcgtag gatccccggg acagcagagg agaacttaca gaagtcttct ggaggtgttc   1380
ctggccagaa cacaggagga caggtaagat tgggagaccc tttgacattg gagcaaggcg   1440
ctcaagaagt tagagaaggt gacggtacaa gggtctcaga aattaactac tggtaactgt   1500
aattgggcgc taagtctagt agacttattt cattgatacc aactttgtaa aagaaaagga   1560
ctggcagctg agggattgtc attccattgc tggaagattg taactcagac gctgtcagga   1620
caagaaagag aggcctttga agaacattg gtgggcaatt tctgctgtaa agattgggcc   1680
tccagattaa taattgtagt agattggaaa ggcatcattc cagctcctaa gagcgaaata   1740
ttgaaaagaa gactgctaat aaaaagcagt ctgagccctc tgaagaatat ctctagagtc   1800
gacggtaccg cgggcccggg atccaccggt cgccaccatg gtgagcaagg gcgaggagct   1860
gttcaccggg gtggtgccca tcctggtcga gctggacggc gacgtaaacg gccacaagtt   1920
cagcgtgtcc ggcgagggcg agggcgatgc cacctacggc aagctgaccc tgaagttcat   1980
ctgcaccacc ggcaagctgc ccgtgccctg gcccaccctc gtgaccaccc tgacctacgg   2040
cgtgcagtgc ttcagccgct accccgacca catgaagcag cacgacttct tcaagtccgc   2100
catgcccgaa ggctacgtcc aggagcgcac catcttcttc aaggacgacg gcaactacaa   2160
gacccgcgcc gaggtgaagt tcgagggcga caccctggtg aaccgcatcg agctgaaggg   2220
catcgacttc aaggaggacg gcaacatcct ggggcacaag ctggagtaca actacaacag   2280
ccacaacgtc tatatcatgg ccgacaagca gaagaacggc atcaaggtga acttcaagat   2340
ccgccacaac atcgaggacg gcagcgtgca gctcgccgac cactaccagc agaacacccc   2400
catcggcgac ggccccgtgc tgctgcccga caaccactac ctgagcaccc agtccgccct   2460
gagcaaagac cccaacgaga agcgcgatca catggtcctg ctggagttcg tgaccgccgc   2520
cgggatcact ctcggcatgg acgagctgta caagtaaagc ggccgctcta gaactagtgg   2580
```

```
atccccaggg ctgcaggagt ggggaggcac gatggccgct ttggtcgagg cggatccggc    2640
cattagccat attattcatt ggttatatag cataaatcaa tattggctat tggccattgc    2700
atacgttgta tccatatcat aatatgtaca tttatattgg ctcatgtcca acattaccgc    2760
catgttgaca ttgattattg actagttatt aatagtaatc aattacgggg tcattagttc    2820
atagcccata tatggagttc cgcgttacat aacttacggt aaatggcccg cctggctgac    2880
cgcccaacga cccccgccca ttgacgtcaa taatgacgta tgttcccata gtaacgccaa    2940
tagggacttt ccattgacgt caatgggtgg agtatttacg gtaaactgcc cacttggcag    3000
tacatcaagt gtatcatatg ccaagtacgc cccctattga cgtcaatgac ggtaaatggc    3060
ccgcctggca ttatgcccag tacatgacct tatgggactt tcctacttgg cagtacatct    3120
acgtattagt catcgctatt accatggtga tgcggttttg gcagtacatc aatgggcgtg    3180
gatagcggtt tgactcacgg ggatttccaa gtctccaccc cattgacgtc aatgggagtt    3240
tgttttggca ccaaaatcaa cgggactttc caaaatgtcg taacaactcc gccccattga    3300
cgcaaatggg cggtaggcat gtacggtggg aggtctatat aagcagagct cgtttagtga    3360
accgtcagat cgcctggaga cgccatccac gctgttttga cctccataga agacaccggg    3420
accgatccag cctccgcggc cccaagcttc agctgctcga ggatctgcgg atccgggaa    3480 ttccccagtc tcaggatcca ccatggggga tcccgtcgtt ttacaacgtc gtgactggga    3540
aaaccctggc gttacccaac ttaatcgcct tgcagcacat ccccctttcg ccagctggcg    3600
taatagcgaa gaggcccgca ccgatcgccc ttcccaacag ttgcgcagcc tgaatggcga    3660
atggcgcttt gcctggtttc cggcaccaga agcggtgccg gaaagctggc tggagtgcga    3720
tcttcctgag gccgatactg tcgtcgtccc ctcaaactgg cagatgcacg gttacgatgc    3780
gcccatctac accaacgtaa cctatcccat tacggtcaat ccgccgtttg ttcccacgga    3840
gaatccgacg ggttgttact cgctcacatt taatgttgat gaaagctggc tacaggaagg    3900
ccagacgcga attattttg atggcgttaa ctcggcgttt catctgtggt gcaacgggcg    3960
ctgggtcggt tacggccagg acagtcgttt gccgtctgaa tttgacctga gcgcattttt    4020
acgcgccgga gaaaaccgcc tcgcggtgat ggtgctgcgt tggagtgacg gcagttatct    4080
ggaagatcag gatatgtggc ggatgagcgg cattttccgt gacgtctcgt tgctgcataa    4140
accgactaca caaatcagcg atttccatgt tgccactcgc tttaatgatg atttcagccg    4200
cgctgtactg gaggctgaag ttcagatgtg cggcgagttg cgtgactacc tacgggtaac    4260
agtttcttta tggcagggtg aaacgcaggt cgccagcggc accgcgcctt cggcggtga    4320 aattatcgat gagcgtggtg gttatgccga tcgcgtcaca ctacgtctga acgtcgaaaa    4380
cccgaaactg tggagcgccg aaatcccgaa tctctatcgt gcggtggttg aactgcacac    4440
cgccgacggc acgctgattg aagcagaagc ctgcgatgtc ggtttccgcg aggtgcggat    4500
tgaaaatggt ctgctgctgc tgaacggcaa gccgttgctg attcgaggcg ttaaccgtca    4560
cgagcatcat cctctgcatg gtcaggtcat ggatgagcag acgatggtgc aggatatcct    4620
gctgatgaag cagaacaact taacgccgt gcgctgttcg cattatccga accatccgct    4680
gtggtacacg ctgtgcgacc gctacggcct gtatgtggtg gatgaagcca atattgaaac    4740
ccacggcatg gtgccaatga atcgtctgac cgatgatccg cgctggctac cggcgatgag    4800
cgaacgcgta acgcgaatgg tgcagcgcga tcgtaatcac ccgagtgtga tcatctggtc    4860
gctggggaat gaatcaggcc acggcgctaa tcacgacgcg ctgtatcgct ggatcaaatc    4920
tgtcgatcct tcccgcccgg tgcagtatga aggcggcgga gccgacacca cggccaccga    4980
```

```
tattatttgc cgatgtacg cgcgcgtgga tgaagaccag cccttccggg ctgtgccgaa    5040
atggtccatc aaaaaatggc tttcgctacc tggagagacg cgcccgctga tcctttgcga    5100
atacgcccac gcgatgggta acagtcttgg cggtttcgct aaatactggc aggcgtttcg    5160
tcagtatccc cgtttacagg gcggcttcgt ctgggactgg gtggatcagt cgctgattaa    5220
atatgatgaa aacggcaacc cgtggtcggc ttacggcggt gattttggcg atacgccgaa    5280
cgatcgccag ttctgtatga acggtctggt ctttgccgac cgcacgccgc atccagcgct    5340
gacggaagca aaacaccagc agcagttttt ccagttccgt ttatccgggc aaaccatcga    5400
agtgaccagc gaataccgtgt tccgtcatag cgataacgag ctcctgcact ggatggtggc    5460
gctggatggt aagccgctgg caagcggtga agtgcctctg gatgtcgctc cacaaggtaa    5520
acagttgatt gaactgcctg aactaccgca gccggagagc gccgggcaac tctggctcac    5580
agtacgcgta gtgcaaccga acgcgaccgc atggtcagaa gccgggcaca tcagcgcctg    5640
gcagcagtgg cgtctggcgg aaaacctcag tgtgacgctc cccgccgcgt cccacgccat    5700
cccgcatctg accaccagcg aaatggattt ttgcatcgag ctgggtaata agcgttggca    5760
atttaaccgc cagtcaggct ttcttttcaca gatgtggatt ggcgataaaa acaactgct    5820 gacgccgctg cgcgatcagt tcacccgtgc accgctggat aacgacattg gcgtaagtga    5880
agcgacccgc attgacccta acgcctgggt cgaacgctgg aaggcggcgg ccattacca    5940 ggccgaagca gcgttgttgc agtgcacggc agatacactt gctgatgcgg tgctgattac    6000
gaccgctcac gcgtggcagc atcaggggaa aaccttattt atcagccgga aaacctaccg    6060
gattgatggt agtggtcaaa tggcgattac cgttgatgtt gaagtggcga gcgatacacc    6120
gcatccggcg cggattggcc tgaactgcca gctggcgcag gtagcagagc gggtaaactg    6180
gctcggatta gggccgcaag aaaactatcc cgaccgcctt actgccgcct gttttgaccg    6240
ctgggatctg ccattgtcag acatgtatac ccgtacgtc ttcccgagcg aaaacggtct    6300
gcgctgcggg acgcgcgaat tgaattatgg cccacaccag tggcgcggcg acttccagtt    6360
caacatcagc cgctacagtc aacagcaact gatggaaacc agccatcgcc atctgctgca    6420
cgcggaagaa ggcacatggc tgaatatcga cggtttccat atggggattg gtggcgacga    6480
ctcctggagc ccgtcagtat cggcggaatt ccagctgagc gccggtcgct accattacca    6540
gttggtctgg tgtcaaaaat aataataacc gggcaggggg gatccgcaga tccggctgtg    6600
gaatgtgtgt cagttagggt gtggaaagtc cccaggctcc ccagcaggca gaagtatgca    6660
aagcatgcct gcaggaattc gatatcaagc ttatcgatac cgtcgaattg gaagagcttt    6720
aaatcctggc acatctcatg tatcaatgcc tcagtatgtt tagaaaaaca aggggggaac    6780
tgtgggtttt ttatgagggg ttttataaaa atgaaagacc ccacctgtag gtttggcaag    6840
ctagcttaag taacgccatt ttgcaaggca tggaaaaata cataactgag aatagagaag    6900
ttcagatcaa ggtcaggaac agatggaaca gctgaatatg ggccaaacag gatatctgtg    6960
gtaagcagtt cctgccccgg ctcagggcca agaacagatg aacagctga atatgggcca    7020 aacaggatat ctgtggtaag cagttcctgc cccggctcag ggccaagaac agatggtccc    7080
cagatgcggt ccagccctca gcagtttcta gagaaccatc agatgtttcc agggtgcccc    7140
aaggacctga aatgaccctg tgccttattt gaactaacca atcagttcgc ttctcgcttc    7200
tgttcgcgcg cttctgctcc ccgagctcaa taaaagagcc cacaccccct cactcggggg    7260
gcactcagat tctgcggtct gagtcccttc tctgctgggc tgaaaaggcc tttgtaataa    7320
```

```
atataattct ctactcagtc cctgtctcta gtttgtctgt tcgagatcct acagagctca   7380
tgccttggcg taatcatggt catagctgtt tcctgtgtga aattgttatc cgctcacaat   7440
tccacacaac atacgagccg gaagcataaa gtgtaaagcc tggggtgcct aatgagtgag   7500
ctaactcaca ttaattgcgt tgcgctcact gcccgctttc cagtcgggaa acctgtcgtg   7560
ccagctgcat taatgaatcg gccaacgcgc ggggagaggc ggtttgcgta ttgggcgctc   7620
ttccgcttcc tcgctcactg actcgctgcg ctcggtcgtt cggctgcggc gagcggtatc   7680
agctcactca aaggcggtaa tacggttatc cacagaatca ggggataacg caggaaagaa   7740
catgtgagca aaaggccagc aaaaggccag gaaccgtaaa aaggccgcgt tgctggcgtt   7800
tttccatagg ctccgccccc ctgacgagca tcacaaaaat cgacgctcaa gtcagaggtg   7860
gcgaaacccg acaggactat aaagatacca ggcgtttccc cctggaagct ccctcgtgcg   7920
ctctcctgtt ccgaccctgc cgcttaccgg atacctgtcc gcctttctcc cttcgggaag   7980
cgtggcgctt tctcatagct cacgctgtag gtatctcagt tcggtgtagg tcgttcgctc   8040
caagctgggc tgtgtgcacg aacccccgt tcagcccgac cgctgcgcct tatccggtaa   8100
ctatcgtctt gagtccaacc cggtaagaca cgacttatcg ccactggcag cagccactgg   8160
taacaggatt agcagagcga ggtatgtagg cggtgctaca gagttcttga agtggtggcc   8220
taactacggc tacactagaa ggacagtatt tggtatctgc gctctgctga agccagttac   8280
cttcggaaaa agagttggta gctcttgatc cggcaaacaa accaccgctg gtagcggtgg   8340
tttttttgtt tgcaagcagc agattacgcg cagaaaaaaa ggatctcaag aagatccttt   8400
gatcttttct acggggtctg acgctcagtg gaacgaaaac tcacgttaag ggattttggt   8460
catgagatta tcaaaaagga tcttcaccta gatccttta aattaaaaat gaagttttaa   8520
atcaatctaa agtatatatg agtaaacttg gtctgacagt taccaatgct taatcagtga   8580
ggcacctatc tcagcgatct gtctatttcg ttcatccata gttgcctgac tccccgtcgt   8640
gtagataact acgatacggg agggcttacc atctggcccc agtgctgcaa tgataccgcg   8700
agacccacgc tcaccggctc cagatttatc agcaataaac cagccagccg aagggccga   8760
gcgcagaagt ggtcctgcaa ctttatccgc ctccatccag tctattaatt gttgccggga   8820
agctagagta agtagttcgc cagttaatag tttgcgcaac gttgttgcca ttgctacagg   8880
catcgtggtg tcacgctcgt cgtttggtat ggcttcattc agctccggtt cccaacgatc   8940
aaggcgagtt acatgatccc ccatgttgtg caaaaaagcg gttagctcct tcggtcctcc   9000
gatcgttgtc agaagtaagt tggccgcagt gttatcactc atggttatgg cagcactgca   9060
taattctctt actgtcatgc catccgtaag atgcttttct gtgactggtg agtactcaac   9120
caagtcattc tgagaatagt gtatgcggcg accgagttgc tcttgcccgg cgtcaatacg   9180
ggataatacc gcgccacata gcagaacttt aaaagtgctc atcattggaa aacgttcttc   9240
ggggcgaaaa ctctcaagga tcttaccgct gttgagatcc agttcgatgt aacccactcg   9300
tgcacccaac tgatcttcag catctttac tttcaccagc gtttctgggt gagcaaaaac   9360
aggaaggcaa aatgccgcaa aaaagggaat aagggcgaca cggaaatgtt gaatactcat   9420
actcttcctt tttcaatatt attgaagcat ttatcagggt tattgtctca tgagcggata   9480
catatttgaa tgtatttaga aaaataaaca ataggggtt ccgcgcacat ttccccgaaa   9540
agtgccacct aaattgtaag cgttaatatt ttgttaaaat tcgcgttaaa ttttgttaa   9600
atcagctcat ttttaacca ataggccgaa atcggcaaaa tcccttataa atcaaaagaa   9660
tagaccgaga tagggttgag tgttgttcca gtttggaaca agagtccact attaaagaac   9720
```

```
gtggactcca acgtcaaagg gcgaaaaacc gtctatcagg gcgatggccc actacgtgaa    9780
ccatcaccct aatcaagttt tttggggtcg aggtgccgta aagcactaaa tcggaaccct    9840
aaagggagcc cccgatttag agcttgacgg ggaaagccaa cctggcttat cgaaattaat    9900
acgactcact atagggagac cggc                                           9924

<210> SEQ ID NO 4
<211> LENGTH: 9138
<212> TYPE: DNA
<213> ORGANISM: Artificial Sequence
<220> FEATURE:
<223> OTHER INFORMATION: Description of Artificial Sequence: Synthetic
      construct pONY8.1Zhyb

<400> SEQUENCE: 4
agatcttgaa taataaaatg tgtgtttgtc cgaaatacgc gttttgagat ttctgtcgcc      60
gactaaattc atgtcgcgcg atagtggtgt ttatcgccga tagagatggc gatattggaa    120
aaattgatat ttgaaaatat ggcatattga aaatgtcgcc gatgtgagtt tctgtgtaac    180
tgatatcgcc atttttccaa aagtgatttt tgggcatacg cgatatctgg cgatagcgct    240
tatatcgttt acggggatg gcgatagacg actttggtga cttgggcgat tctgtgtgtc     300
gcaaatatcg cagtttcgat ataggtgaca gacgatatga ggctatatcg ccgatagagg    360
cgacatcaag ctggcacatg gccaatgcat atcgatctat acattgaatc aatattggcc    420 attagcccata ttattcattg gttatatagc ataaatcaat attggctatt ggccattgca    480
tacgttgtat ccatatcgta atatgtacat ttatattggc tcatgtccaa cattaccgcc    540
atgttgacat tgattattga ctagttatta atagtaatca attacggggt cattagttca    600
tagcccatat atggagttcc gcgttacata acttacggta aatggcccgc ctggctgacc    660
gcccaacgac ccccgcccat tgacgtcaat aatgacgtat gttcccatag taacgccaat    720
agggactttc cattgacgtc aatgggtgga gtatttacgg taaactgccc acttggcagt    780
acatcaagtg tatcatatgc caagtccgcc ccctattgac gtcaatgacg gtaaatggcc    840
cgcctggcat tatgcccagt acatgacctt acgggacttt cctacttggc agtacatcta    900
cgtattagtc atcgctatta ccatggtgat gcggttttgg cagtacacca atgggcgtgg    960
atagcggttt gactcacggg gatttccaag tctccacccc attgacgtca atgggagttt   1020
gttttggcac caaaatcaac gggactttcc aaaatgtcgt aacaactgcg atcgcccgcc   1080
ccgttgacgc aaatgggcgg taggcgtgta cggtgggagg tctatataag cagagctcgt   1140
ttagtgaacc gggcactcag attctgcggt ctgagtccct tctctgctgg gctgaaaagg   1200
cctttgtaat aaatataatt ctctactcag tccctgtctc tagtttgtct gttcgagatc   1260
ctacagttgg cgcccgaaca gggacctgag aggggcgcag accctacctg ttgaacctgg   1320
ctgatcgtag gatccccggg acagcagagg agaacttaca gaagtcttct ggaggtgttc   1380
ctggccagaa cacaggagga caggtaagat tgggagaccc tttgacattg gagcaaggcg   1440
ctcaagaagt tagagaaggt gacggtacaa gggtctcaga aattaactac tggtaactgt   1500
aattgggcgc taagtctagt agacttattt catgatacca actttgtaaa agaaaaggac   1560
tggcagctga gggatgtcat tccattgctg gaagatgtaa ctcagacgct gtcaggacaa   1620
gaaagagagg cctttgaaag aacatggtgg gcaatttctg ctgtaaagat gggcctccag   1680
attaataatg tagtagatgg aaaggcatca ttccagctcc taagagcgaa atatgaaaag   1740
aagactgcta ataaaagca gtctgagccc tctgaagaat atctctagaa ctagtggatc   1800
```

```
ccccgggctg caggagtggg gaggcacgat ggccgctttg gtcgaggcgg atccggccat   1860
tagccatatt attcattggt tatatagcat aaatcaatat tggctattgg ccattgcata   1920
cgttgtatcc atatcataat atgtacattt atattggctc atgtccaaca ttaccgccat   1980
gttgacattg attattgact agttattaat agtaatcaat tacggggtca ttagttcata   2040
gcccatatat ggagttccgc gttacataac ttacggtaaa tggcccgcct ggctgaccgc   2100
ccaacgaccc ccgcccattg acgtcaataa tgacgtatgt tcccatagta acgccaatag   2160
ggactttcca ttgacgtcaa tgggtggagt atttacggta aactgcccac ttggcagtac   2220
atcaagtgta tcatatgcca gtacgcccc ctattgacgt caatgacggt aaatggcccg   2280
cctggcatta tgcccagtac atgaccttat gggactttcc tacttggcag tacatctacg   2340
tattagtcat cgctattacc atggtgatgc ggttttggca gtacatcaat gggcgtggat   2400
agcggtttga ctcacgggga tttccaagtc tccaccccat tgacgtcaat gggagtttgt   2460
tttggcacca aaatcaacgg gactttccaa aatgtcgtaa caactccgcc ccattgacgc   2520
aaatgggcgg taggcatgta cggtgggagg tctatataag cagagctcgt ttagtgaacc   2580
gtcagatcgc ctggagacgc catccacgct gttttgacct ccatagaaga caccgggacc   2640
gatccagcct ccgcggcccc aagcttcagc tgctcgagga tctgcggatc cggggaattc   2700
cccagtctca ggatccacca tgggggatcc cgtcgtttta caacgtcgtg actgggaaaa   2760
ccctggcgtt acccaactta atcgccttgc agcacatccc cctttcgcca gctggcgtaa   2820
tagcgaagag gcccgcaccg atcgcccttc ccaacagttg cgcagcctga atggcgaatg   2880
gcgctttgcc tggtttccgg caccagaagc ggtgccggaa agctggctgg agtgcgatct   2940
tcctgaggcc gatactgtcg tcgtcccctc aaactggcag atgcacggtt acgatgcgcc   3000
catctacacc aacgtaacct atcccattac ggtcaatccg ccgtttgttc ccacggagaa   3060
tccgacgggt tgttactcgc tcacatttaa tgttgatgaa agctggctac aggaaggcca   3120
gacgcgaatt attttgatg gcgttaactc ggcgtttcat ctgtggtgca acgggcgctg   3180
ggtcggttac ggccaggaca gtcgtttgcc gtctgaattt gacctgagcg cattttacg   3240 cgccggagaa aaccgcctcg cggtgatggt gctgcgttgg agtgacggca gttatctgga   3300
agatcaggat atgtggcgga tgagcggcat tttccgtgac gtctcgttgc tgcataaacc   3360
gactacacaa atcagcgatt tccatgttgc cactcgcttt aatgatgatt tcagccgcgc   3420
tgtactggag gctgaagttc agatgtgcgg cgagttgcgt gactacctac gggtaacagt   3480
ttctttatgg cagggtgaaa cgcaggtcgc cagcggcacc gcgccttcg gcggtgaaat   3540 tatcgatgag cgtggtggtt atgccgatcg cgtcacacta cgtctgaacg tcgaaaaccc   3600
gaaactgtga agccgaaaa tcccgaatct ctatcgtgcg gtggttgaac tgcacaccgc   3660
cgacggcacg ctgattgaag cagaagcctg cgatgtcggt ttccgcgagg tgcggattga   3720
aaatggtctg ctgctgctga acggcaagcc gttgctgatt cgaggcgtta ccgtcacga   3780 gcatcatcct ctgcatggtc aggtcatgga tgagcagacg atggtgcagg atatcctgct   3840
gatgaagcag aacaacttta acgccgtgcg ctgttcgcat tatccgaacc atccgctgtg   3900
gtacacgctg tgcgaccgct acggcctgta tgtggtggat gaagccaata ttgaaaccca   3960
cggcatggtg ccaatgaatc gtctgaccga tgatccgcgc tggctaccgg cgatgagcga   4020
acgcgtaacg cgaatggtgc agcgcgatcg taatcacccg agtgtgatca tctggtcgct   4080
ggggaatgaa tcaggccacg gcgctaatca cgacgcgctg tatcgctgga tcaaatctgt   4140
```

```
cgatccttcc cgcccggtgc agtatgaagg cggcggagcc gacaccacgg ccaccgatat    4200
tatttgcccg atgtacgcgc gcgtggatga agaccagccc ttcccggctg tgccgaaatg    4260
gtccatcaaa aaatggcttt cgctacctgg agagacgcgc ccgctgatcc tttgcgaata    4320
cgcccacgcg atgggtaaca gtcttggcgg tttcgctaaa tactggcagg cgtttcgtca    4380
gtatccccgt ttacagggcg gcttcgtctg ggactgggtg gatcagtcgc tgattaaata    4440
tgatgaaaac ggcaacccgt ggtcggctta cggcggtgat tttggcgata cgccgaacga    4500
tcgccagttc tgtatgaacg gtctggtctt tgccgaccgc acgccgcatc cagcgctgac    4560
ggaagcaaaa caccagcagc agtttttcca gttccgttta ccgggcaaa ccatcgaagt    4620 gaccagcgaa tacctgttcc gtcatagcga taacgagctc ctgcactgga tggtggcgct    4680
ggatggtaag ccgctggcaa gcggtgaagt gcctctggat gtcgctccac aaggtaaaca    4740
gttgattgaa ctgcctgaac taccgcagcc ggagagcgcc gggcaactct ggctcacagt    4800
acgcgtagtg caaccgaacg cgaccgcatg gtcagaagcc gggcacatca gcgcctggca    4860
gcagtggcgt ctggcggaaa acctcagtgt gacgctcccc gccgcgtccc acgccatccc    4920
gcatctgacc accagcgaaa tggatttttg catcgagctg ggtaataagc gttggcaatt    4980
taaccgccag tcaggctttc tttcacagat gtggattggc gataaaaaac aactgctgac    5040
gccgctgcgc gatcagttca cccgtgcacc gctggataac gacattggcg taagtgaagc    5100
gacccgcatt gaccctaacg cctgggtcga acgctggaag gcggcgggcc attaccaggc    5160
cgaagcagcg ttgttgcagt gcacggcaga tacacttgct gatgcggtgc tgattacgac    5220
cgctcacgcg tggcagcatc aggggaaaac cttatttatc agccggaaaa cctaccggat    5280
tgatggtagt ggtcaaatgg cgattaccgt tgatgttgaa gtggcgagcg atacaccgca    5340
tccggcgcgc attggcctga actgccagct ggcgcaggta gcagagcggg taaactggct    5400
cggattaggg ccgcaagaaa actatcccga ccgccttact gccgcctgtt ttgaccgctg    5460
ggatctgcca ttgtcagaca tgtataccc gtacgtcttc ccgagcgaaa acggtctgcg    5520
ctgcgggacg cgcgaattga attatggccc acaccagtgg cgcggcgact tccagttcaa    5580
catcagccgc tacagtcaac agcaactgat ggaaaccagc catcgccatc tgctgcacgc    5640
ggaagaaggc acatggctga atatcgacgg tttccatatg gggattggtg gcgacgactc    5700
ctggagcccg tcagtatcgg cggaattcca gctgagcgcc ggtcgctacc attaccagtt    5760
ggtctggtgt caaaaataat aataaccggg caggggggat ccgcagatcc ggctgtggaa    5820
tgtgtgtcag ttagggtgtg aaagtcccc aggctcccca gcaggcagaa gtatgcaaag    5880
catgcctgca ggaattcgat atcaagctta tcgataccgt cgaattggaa gagctttaaa    5940
tcctggcaca tctcatgtat caatgcctca gtatgtttag aaaacaagg ggggaactgt    6000 ggggttttta tgaggggttt tataatgaaa gaccccacct gtaggtttgg caagctagct    6060
taagtaacgc cattttgcaa ggcatggaaa aatacataac tgagaataga gaagttcaga    6120
tcaaggtcag gaacagatgg aacagctgaa tatgggccaa acaggatatc tgtggtaagc    6180
agttcctgcc ccggctcagg gccaagaaca gatggaacag ctgaatatgg ccaaacagg    6240 atatctgtgg taagcagttc ctgccccggc tcagggccaa gaacagatgg tcccagatg    6300 cggtccagcc ctcagcagtt tctagagaac catcagatgt ttccagggtg ccccaaggac    6360
ctgaaatgac cctgtgcctt atttgaacta accaatcagt tcgcttctcg cttctgttcg    6420
cgcgcttctg ctccccgagc tcaataaaag agccacaac ccctcactcg ggggggcactc    6480 agattctgcg gtctgagtcc cttctctgct gggctgaaaa ggcctttgta ataaatataa    6540
```

```
ttctctactc agtccctgtc tctagtttgt ctgttcgaga tcctacagag ctcatgcctt    6600
ggcgtaatca tggtcatagc tgtttcctgt gtgaaattgt tatccgctca caattccaca    6660
caacatacga gccggaagca taaagtgtaa agcctggggt gcctaatgag tgagctaact    6720
cacattaatt gcgttgcgct cactgcccgc tttccagtcg ggaaacctgt cgtgccagct    6780
gcattaatga atcggccaac gcgcggggag aggcggtttg cgtattgggc gctcttccgc    6840
ttcctcgctc actgactcgc tgcgctcggt cgttcggctg cggcgagcgg tatcagctca    6900
ctcaaaggcg gtaatacggt tatccacaga atcaggggat aacgcaggaa agaacatgtg    6960
agcaaaaggc cagcaaaagg ccaggaaccg taaaaaggcc gcgttgctgg cgttttccca    7020
taggctccgc cccccctgacg agcatcacaa aaatcgacgc tcaagtcaga ggtggcgaaa    7080
cccgacagga ctataaagat accaggcgtt tccccctgga agctccctcg tgcgctctcc    7140
tgttccgacc ctgccgctta ccggatacct gtccgccttt ctcccttcgg aagcgtggc    7200
gctttctcat agctcacgct gtaggtatct cagttcggtg taggtcgttc gctccaagct    7260
gggctgtgtg cacgaacccc ccgttcagcc cgaccgctgc gccttatccg gtaactatcg    7320
tcttgagtcc aacccggtaa gacacgactt atcgccactg gcagcagcca ctggtaacag    7380
gattagcaga gcgaggtatg taggcggtgc tacagagttc ttgaagtggt ggcctaacta    7440
cggctacact agaaggacag tatttggtat ctgcgctctg ctgaagccag ttaccttcgg    7500
aaaaagagtt ggtagctctt gatccggcaa acaaaccacc gctggtagcg tggtttttt    7560
tgtttgcaag cagcagatta cgcgcagaaa aaaaggatct caagaagatc ctttgatctt    7620
ttctacgggg tctgacgctc agtggaacga aaactcacgt taagggattt tggtcatgag    7680
attatcaaaa aggatcttca cctagatcct tttaaattaa aaatgaagtt ttaaatcaat    7740
ctaaagtata tatgagtaaa cttggtctga cagttaccaa tgcttaatca gtgaggcacc    7800
tatctcagcg atctgtctat ttcgttcatc catagttgcc tgactccccg tcgtgtagat    7860
aactacgata cgggagggct taccatctgg ccccagtgct gcaatgatac cgcgagaccc    7920
acgctcaccg gctccagatt tatcagcaat aaaccagcca gccggaaggg ccgagcgcag    7980
aagtggtcct gcaactttat ccgcctccat ccagtctatt aattgttgcc gggaagctag    8040
agtaagtagt tcgccagtta atagtttgcg caacgttgtt gccattgcta caggcatcgt    8100
ggtgtcacgc tcgtcgtttg gtatggcttc attcagctcc ggttcccaac gatcaaggcg    8160
agttacatga tcccccatgt tgtgcaaaaa agcggttagc tccttcggtc ctccgatcgt    8220
tgtcagaagt aagttggccg cagtgttatc actcatggtt atggcagcac tgcataattc    8280
tcttactgtc atgccatccg taagatgctt ttctgtgact ggtgagtact caaccaagtc    8340
attctgagaa tagtgtatgc ggcgaccgag ttgctcttgc ccggcgtcaa tacgggataa    8400
taccgcgcca catagcagaa ctttaaaagt gctcatcatt ggaaaacgtt cttcggggcg    8460
aaaactctca aggatcttac cgctgttgag atccagttcg atgtaaccca ctcgtgcacc    8520
caactgatct tcagcatctt ttactttcac cagcgtttct gggtgagcaa aaacaggaag    8580
gcaaaatgcc gcaaaaaagg gaataagggc gacacggaaa tgttgaatac tcatactctt    8640
cctttttcaa tattattgaa gcattatcag ggttattgt ctcatgagcg gatacatatt    8700
tgaatgtatt tagaaaaata aacaaatagg ggttccgcgc acatttcccc gaaaagtgcc    8760
acctaaattg taagcgttaa tattttgtta aaattcgcgt taaattttg ttaaatcagc    8820
tcatttttta accaataggc cgaaatcggc aaaatccctt ataaatcaaa agaatagacc    8880
```

```
gagatagggt tgagtgttgt tccagtttgg aacaagagtc cactattaaa gaacgtggac    8940
tccaacgtca aagggcgaaa aaccgtctat cagggcgatg gcccactacg tgaaccatca    9000
ccctaatcaa gttttttggg gtcgaggtgc cgtaaagcac taaatcggaa ccctaaaggg    9060
agcccccgat ttagagcttg acggggaaag ccaacctggc ttatcgaaat taatacgact    9120
cactataggg agaccggc                                                  9138
```

<210> SEQ ID NO 5
<211> LENGTH: 7327
<212> TYPE: DNA
<213> ORGANISM: Artificial Sequence
<220> FEATURE:
<223> OTHER INFORMATION: Description of Artificial Sequence: Synthetic
      construct pONY8.4TCOG

<400> SEQUENCE: 5

```
agatcttgaa taataaaatg tgtgtttgtc cgaaatacgc gttttgagat ttctgtcgcc     60
gactaaattc atgtcgcgcg atagtggtgt ttatcgccga tagagatggc gatattggaa    120
aaattgatat ttgaaaatat ggcatattga aaatgtcgcc gatgtgagtt tctgtgtaac    180
tgatatcgcc atttttccaa aagtgatttt tgggcatacg cgatatctgg cgatagcgct    240
tatatcgttt acggggatg gcgatagacg actttggtga cttgggcgat tctgtgtgtc    300
gcaaatatcg cagtttcgat ataggtgaca gacgatatga ggctatatcg ccgatagagg    360
cgacatcaag ctggcacatg gccaatgcat atcgatctat acattgaatc aatattggcc    420
attagccata ttattcattg gttatatagc ataaatcaat attggctatt ggccattgca    480
tacgttgtat ccatatcgta atatgtacat ttatattggc tcatgtccaa cattaccgcc    540
atgttgacat tgattattga ctagttatta atagtaatca attacggggt cattagttca    600
tagcccatat atggagttcc gcgttacata acttacggta aatggcccgc ctggctgacc    660
gcccaacgac ccccgcccat tgacgtcaat aatgacgtat gttcccatag taacgccaat    720
agggactttc cattgacgtc aatgggtgga gtatttacgg taaactgccc acttggcagt    780
acatcaagtg tatcatatgc caagtccgcc ccctattgac gtcaatgacg gtaaatggcc    840
cgcctggcat tatgcccagt acatgacctt acgggacttt cctacttggc agtacatcta    900
cgtattagtc atcgctatta ccatggtgat gcggttttgg cagtacacca atgggcgtgg    960
atagcggttt gactcacggg gatttccaag tctccacccc attgacgtca atgggagttt   1020
gttttggcac caaaatcaac gggactttcc aaaatgtcgt aacaactgcg atcgcccgcc   1080
ccgttgacgc aaatgggcgg taggcgtgta cggtgggagg tctatataag cagagctcgt   1140
ttagtgaacc gggcactcag attctgcggt ctgagtccct tctctgctgg gctgaaaagg   1200
cctttgtaat aaatataatt ctctactcag tccctgtctc tagtttgtct gttcgagatc   1260
ctacagttgg cgcccgaaca gggacctgag aggggcgcag accctacctg ttgaacctgg   1320
ctgatcgtag gatccccggg acagcagagg agaacttaca gaagtcttct ggaggtgttc   1380
ctggccagaa cacaggagga caggtaagat tgggagaccc tttgacattg gagcaaggcg   1440
ctcaagaagt tagagaaggt gacggtacaa gggtctcaga aattaactac tggtaactgt   1500
aattgggcgc taagtctagt agacttattt cattgatacc aactttgtaa agaaaagga    1560 ctggcagctg agggattgtc attccattgc tggaagattg taactcagac gctgtcagga   1620
caagaaagag aggcctttga agaacattg tgggcaatt tctgctgtaa agattgggcc      1680
tccagattaa taattgtagt agattggaaa ggcatcattc cagctcctaa gagcgaaata   1740
```

```
ttgaaaagaa gactgctaat aaaaagcagt ctgagccctc tgaagaatat ctctagcgtc    1800
gaccaattga tgtctagatt agataaaagt aaagtgatta acagcgcatt agagctgctt    1860
aatgaggtcg gaatcgaagg tttaacaacc cgtaaactcg cccagaagct aggtgtagag    1920
cagcctacat tgtattggca tgtaaaaaat aagcgggctt tgctcgacgc cttagccatt    1980
gagatgttag ataggcacca tactcacttt tgcccttag aaggggaaag ctggcaagat    2040
tttttacgta ataacgctaa aagttttaga tgtgctttac taagtcatcg cgatggagca    2100
aaagtacatt taggtacacg gcctacagaa aaacagtatg aaactctcga aaatcaatta    2160
gcctttttat gccaacaagg ttttcacta gagaatgcat tatatgcact cagcgctgtg    2220
gggcatttta ctttaggttg cgtattggaa gatcaagagc atcaagtcgc taaagaagaa    2280
agggaaacac ctactactga tagtatgccg ccattattac gacaagctat cgaattattt    2340
gatcaccaag gtgcagagcc agccttctta ttcggccttg aattgatcat atgcggatta    2400
gaaaaacaac ttaaatgtga aagtgggtcc gcgtacagcg gatcccggga attcagatct    2460
tattaaggta cctaacggac cgcggttaac cagctgagca ctggccggcc taggtggccg    2520
gttcgaatta ggtaccgatg tacgggccag atatacgcgt tgacattgat tattgactag    2580
ttattaatag taatcaatta cggggtcatt agttcatagc ccatatatgg agttccgcgt    2640
tacataactt acggtaaatg gcccgcctgg ctgaccgccc aacgacccc gcccattgac    2700 gtcaataatg acgtatgttc ccatagtaac gccaataggg actttccatt gacgtcaatg    2760
ggtggagtat ttacggtaaa ctgcccactt ggcagtacat caagtgtatc atatgccaag    2820
tacgccccct attgacgtca atgacggtaa atggcccgcc tggcattatg cccagtacat    2880
gaccttatgg gactttccta cttggcagta catctacgta ttagtcatcg ctattaccat    2940
ggtgatgcgg ttttggcagt acatcaatgg gcgtggatag cggtttgact cacggggatt    3000
tccaagtctc cacccccattg acgtcaatgg gagtttgttt tggaaccaaa atcaacggga    3060
ctttccaaaa tgtcgtaaca actccgcccc attgacgcaa atgggcggta ggcgtgtacg    3120
gtgggaggtc tatataagca gagctctccc tatcagtgat agagatctcc ctatcagtga    3180
tagagatcgt cgacgagctc gtttagtgaa ccgtcagatc gcctggagac gccatccacg    3240
ctgttttgac ctccatagaa gacaccggga ccgatccagc ctccggactc tagcgtttaa    3300
acttaagctt gttgggatcc accggtcgcc accatggtga gcaagggcga ggagctgttc    3360
accggggtgg tgcccatcct ggtcgagctg gacggcgacg taaacggcca caagttcagc    3420
gtgtccggcg agggcgaggg cgatgccacc tacggcaagc tgaccctgaa gttcatctgc    3480
accaccggca agctgcccgt gccctggccc accctcgtga ccaccctgac ctacggcgtg    3540
cagtgcttca gccgctaccc cgaccacatg aagcagcacg acttcttcaa gtccgccatg    3600
cccgaaggct acgtccagga gcgcaccatc ttcttcaagg acgacggcaa ctacaagacc    3660
cgcgccgagg tgaagttcga gggcgacacc ctggtgaacc gcatcgagct gaagggcatc    3720
gacttcaagg aggacggcaa catcctgggg cacaagctgg agtacaacta caacagccac    3780
aacgtctata tcatggccga caagcagaag aacggcatca aggtgaactt caagatccgc    3840
cacaacatcg aggacggcag cgtgcagctc gccgaccact accagcagaa cacccccatc    3900
ggcgacggcc ccgtgctgct gcccgacaac cactacctga gcacccagtc cgccctgagc    3960
aaagacccca acgagaagcg cgatcacatg gtcctgctgg agttcgtgac cgccgccggg    4020
atcactctcg gcatggacga gctgtacaag taaagcggcc gcgactctag cctgcaggaa    4080
ttcgatatca agcttatcga taccgtcgaa ttggaagagc tttaaatcct ggcacatctc    4140
```

```
atgtatcaat gcctcagtat gtttagaaaa acaagggggg aactgtgggg ttttatgag      4200
gggttttata aaaatgaaag accccacctg taggtttggc aagctagctt aagtaacgcc      4260
attttgcaag gcatggaaaa atacataact gagaatagag aagttcagat caaggtcagg      4320
aacagatgga acagctgaat atgggccaaa caggatatct gtggtaagca gttcctgccc      4380
cggctcaggg ccaagaacag atggaacagc tgaatatggg ccaaacagga tatctgtggt      4440
aagcagttcc tgcccggct cagggccaag aacagatggt cccagatgc ggtccagccc        4500
tcagcagttt ctagagaacc atcagatgtt ccagggtgc cccaaggacc tgaaatgacc       4560
ctgtgcctta tttgaactaa ccaatcagtt cgcttctcgc ttctgttcgc gcgcttctgc      4620
tccccgagct caataaaaga gcccacaacc cctcactcgg ggggcactca gattctgcgg      4680
tctgagtccc ttctctgctg ggctgaaaag gcctttgtaa taaatataat tctctactca      4740
gtccctgtct ctagtttgtc tgttcgagat cctacagagc tcatgccttg gcgtaatcat      4800
ggtcatagct gtttcctgtg tgaaattgtt atccgctcac aattccacac aacatacgag      4860
ccggaagcat aaagtgtaaa gcctggggtg cctaatgagt gagctaactc acattaattg      4920
cgttgcgctc actgcccgct ttccagtcgg gaaacctgtc gtgccagctg cattaatgaa      4980
tcggccaacg cgcggggaga ggcggtttgc gtattgggcg ctcttccgct tcctcgctca      5040
ctgactcgct gcgctcggtc gttcggctgc ggcgagcggt atcagctcac tcaaaggcgg      5100
taatacggtt atccacagaa tcaggggata acgcaggaaa gaacatgtga gcaaaaggcc      5160
agcaaaaggc caggaaccgt aaaaaggccg cgttgctggc gtttttccat aggctccgcc      5220
ccctgacga gcatcacaaa atcgacgct caagtcagag gtggcgaaac ccgacaggac        5280
tataaagata ccaggcgttt ccccctggaa gctccctcgt gcgctctcct gttccgaccc      5340
tgccgcttac cggatacctg tccgcctttc tcccttcggg aagcgtggcg ctttctcata      5400
gctcacgctg taggtatctc agttcggtgt aggtcgttcg ctccaagctg ggctgtgtgc      5460
acgaacccc cgttcagccc gaccgctgcg ccttatccgg taactatcgt cttgagtcca       5520
acccggtaag acacgactta tcgccactgg cagcagccac tggtaacagg attagcagag      5580
cgaggtatgt aggcggtgct acagagttct tgaagtggtg cctaactac ggctacacta       5640
gaaggacagt atttggtatc tgcgctctgc tgaagccagt taccttcgga aaaagagttg      5700
gtagctcttg atccggcaaa caaaccaccg ctggtagcgg tggttttttt gtttgcaagc      5760
agcagattac gcgcagaaaa aaaggatctc aagaagatcc tttgatcttt tctacggggt      5820
ctgacgctca gtggaacgaa aactcacgtt aagggatttt ggtcatgaga ttatcaaaaa      5880
ggatcttcac ctagatcctt ttaaattaaa aatgaagttt taaatcaatc taaagtatat      5940
atgagtaaac ttggtctgac agttaccaat gcttaatcag tgaggcacct atctcagcga      6000
tctgtctatt tcgttcatcc atagttgcct gactccccgt cgtgtagata actacgatac      6060
gggagggctt accatctggc cccagtgctg caatgatacc gcgagaccca cgctcaccgg      6120
ctccagattt atcagcaata aaccagccag ccggaagggc cgagcgcaga agtggtcctg      6180
caactttatc cgcctccatc cagtctatta attgttgccg gaagctaga gtaagtagtt       6240
cgccagttaa tagtttgcgc aacgttgttg ccattgctac aggcatcgtg gtgtcacgct      6300
cgtcgtttgg tatggcttca ttcagctccg gttcccaacg atcaaggcga gttacatgat      6360
cccccatgtt gtgcaaaaaa gcggttagct ccttcggtcc tccgatcgtt gtcagaagta      6420
agttggccgc agtgttatca ctcatggtta tggcagcact gcataattct cttactgtca      6480
```

```
tgccatccgt aagatgcttt tctgtgactg gtgagtactc aaccaagtca ttctgagaat    6540
agtgtatgcg gcgaccgagt tgctcttgcc cggcgtcaat acgggataat accgcgccac    6600
atagcagaac tttaaaagtg ctcatcattg gaaaacgttc ttcggggcga aaactctcaa    6660
ggatcttacc gctgttgaga tccagttcga tgtaacccac tcgtgcaccc aactgatctt    6720
cagcatcttt tactttcacc agcgtttctg ggtgagcaaa aacaggaagg caaaatgccg    6780
caaaaaaggg aataagggcg acacggaaat gttgaatact catactcttc ctttttcaat    6840
attattgaag catttatcag ggttattgtc tcatgagcgg atacatattt gaatgtattt    6900
agaaaaataa acaaataggg gttccgcgca catttccccg aaaagtgcca cctaaattgt    6960
aagcgttaat attttgttaa aattcgcgtt aaattttttgt taaatcagct catttttta    7020 ccataggcc gaaatcggca aaatccctta taaatcaaaa gaatagaccg atagggtt     7080 gagtgttgtt ccagtttgga acaagagtcc actattaaag aacgtggact ccaacgtcaa    7140
agggcgaaaa accgtctatc agggcgatgg cccactacgt gaaccatcac cctaatcaag    7200
ttttttgggg tcgaggtgcc gtaaagcact aaatcggaac cctaaaggga gcccccgatt    7260
tagagcttga cggggaaagc caacctggct tatcgaaatt aatacgactc actataggga    7320
gaccggc                                                              7327
```

<210> SEQ ID NO 6
<211> LENGTH: 7326
<212> TYPE: DNA
<213> ORGANISM: Artificial Sequence
<220> FEATURE:
<223> OTHER INFORMATION: Description of Artificial Sequence: Synthetic
      construct pONY8.4TsynCOG/pONY8.4TsynCOG1

<400> SEQUENCE: 6

```
agatcttgaa taataaaatg tgtgtttgtc cgaaatacgc gttttgagat ttctgtcgcc      60
gactaaattc atgtcgcgcg atagtggtgt ttatcgccga tagagatggc gatattggaa    120
aaattgatat ttgaaaatat ggcatattga aaatgtcgcc gatgtgagtt tctgtgtaac    180
tgatatcgcc atttttccaa aagtgatttt tgggcatacg cgatatctgg cgatagcgct    240
tatatcgttt acggggatg gcgatagacg actttggtga cttgggcgat tctgtgtgtc    300
gcaaatatcg cagtttcgat ataggtgaca gacgatatga ggctatatcg ccgatagagg    360
cgacatcaag ctggcacatg gccaatgcat atcgatctat acattgaatc aatattggcc    420
attagccata ttattcattg gttatatagc ataaatcaat attggctatt ggccattgca    480
tacgttgtat ccatatcgta atatgtacat ttatattggc tcatgtccaa cattaccgcc    540
atgttgacat tgattattga ctagttatta atagtaatca attacggggt cattagttca    600
tagcccatat atggagttcc gcgttacata acttacggta atggcccgc ctggctgacc    660 gcccaacgac ccccgcccat tgacgtcaat aatgacgtat gttcccatag taacgccaat    720
agggactttc cattgacgtc aatgggtgga gtatttacgg taaactgccc acttggcagt    780
acatcaagtg tatcatatgc caagtccgcc cctattgac gtcaatgacg gtaaatggcc    840
cgcctggcat tatgcccagt acatgacctt acgggacttt cctacttggc agtacatcta    900
cgtattagtc atcgctatta ccatggtgat gcggttttgg cagtacacca atgggcgtgg    960
atagcggttt gactcacggg gatttccaag tctccacccc attgacgtca tgggagttt    1020 gttttggcac caaaatcaac gggactttcc aaaatgtcgt aacaactgcg atcgcccgcc    1080
ccgttgacgc aaatgggcgg taggcgtgta cggtgggagg tctatataag cagagctcgt    1140
```

```
ttagtgaacc gggcactcag attctgcggt ctgagtccct tctctgctgg gctgaaaagg      1200
cctttgtaat aaatataatt ctctactcag tccctgtctc tagtttgtct gttcgagatc      1260
ctacagttgg cgcccgaaca gggacctgag aggggcgcag accctacctg ttgaacctgg      1320
ctgatcgtag gatccccggg acagcagagg agaacttaca gaagtcttct ggaggtgttc      1380
ctggccagaa cacaggagga caggtaagat tgggagaccc tttgacattg gagcaaggcg      1440
ctcaagaagt tagagaaggt gacggtacaa gggtctcaga aattaactac tggtaactgt      1500
aattgggcgc taagtctagt agacttattt cattgatacc aactttgtaa aagaaaagga      1560
ctggcagctg agggattgtc attccattgc tggaagattg taactcagac gctgtcagga      1620
caagaaagag aggcctttga agaacattg gtgggcaatt tctgctgtaa agattgggcc       1680
tccagattaa taattgtagt agattggaaa ggcatcattc cagctcctaa gagcgaaata      1740
ttgaaaagaa gactgctaat aaaaagcagt ctgagccctc tgaagaatat ctctagcgtc      1800
gaccaattgc cgccaccatg agccgcctgg acaagagcaa agtgatcaac tccgccctgg      1860
agctgctgaa tgaggtcggc atcgaggac tgaccacgcg caagctggcc caaaagctgg       1920
gcgtcgagca gccgaccctg tattggcatg tgaagaacaa gagggccctc ctggacgcgc      1980
tcgccatcga aatgctggat cggcaccaca cccacttctg tccctcgaa ggcgagagct       2040 ggcaggactt tctgagaaac aacgccaagt ccttccgctg cgccctcctg agccatcgcg      2100
atggggccaa ggtgcacctg ggacgcggc ccactgagaa acagtacgaa accctggaga       2160
atcagctggc gttcctctgc cagcaggggt tctccctgga gaacgccctc tacgcactct      2220
ccgccgtggg ccactttaca ctcggttgcg tgctggagga ccaggagcac caagtcgcta      2280
aggaggagcg ggagaccccc accaccgact ccatgccccc actgctgagg caggcgattg      2340
agctgttcga ccaccaggga gcagagcctg cgttcctctt cgggctggaa ctcatcatct      2400
gcggcctgga gaagcagctg aagtgcgaga gcggctccgc ctacagcggc agcagggagt      2460
tccgctctta ctaacggacc gcggttaacc agctgagcac tggccggcct aggtggccgg      2520
ttcgaattag gtaccgatgt acgggccaga tatacgcgtt gacattgatt attgactagt      2580
tattaatagt aatcaattac ggggtcatta gttcatagcc catatatgga gttccgcgtt      2640
acataactta cggtaaatgg cccgcctggc tgaccgccca acgacccccg cccattgacg      2700
tcaataatga cgtatgttcc catagtaacg ccaatagga ctttccattg acgtcaatgg       2760
gtggagtatt tacggtaaac tgcccacttg gcagtacatc aagtgtatca tatgccaagt      2820 acgccccta ttgacgtcaa tgacggtaaa tggcccgcct ggcattatgc ccagtacatg       2880
accttatggg actttcctac ttggcagtac atctacgtat tagtcatcgc tattaccatg      2940
gtgatgcggt tttggcagta catcaatggg cgtggatagc ggtttgactc acggggattt      3000
ccaagtctcc accccattga cgtcaatggg agtttgtttt ggaaccaaaa tcaacgggac      3060
tttccaaaat gtcgtaacaa ctccgcccca ttgacgcaaa tgggcggtag gcgtgtacgg      3120
tgggaggtct atataagcag agctctccct atcagtgata gagatctccc tatcagtgat      3180
agagatcgtc gacgagctcg tttagtgaac cgtcagatcg cctggagacg ccatccacgc      3240
tgttttgacc tccatagaag acaccgggac cgatccagcc tccggactct agcgtttaaa      3300
cttaagcttg ttgggatcca ccggtcgcca ccatggtgag caagggcgag gagctgttca      3360
ccggggtggt gcccatcctg gtcgagctgg acggcgacgt aaacggccac aagttcagcg      3420
tgtccggcga gggcgagggc gatgccacct acggcaagct gaccctgaag ttcatctgca      3480
ccaccggcaa gctgcccgtg ccctggccca ccctcgtgac caccctgacc tacggcgtgc      3540
```

```
agtgcttcag ccgctacccc gaccacatga agcagcacga cttcttcaag tccgccatgc    3600
ccgaaggcta cgtccaggag cgcaccatct tcttcaagga cgacggcaac tacaagaccc    3660
gcgccgaggt gaagttcgag ggcgacaccc tggtgaaccg catcgagctg aagggcatcg    3720
acttcaagga ggacggcaac atcctggggc acaagctgga gtacaactac aacagccaca    3780
acgtctatat catggccgac aagcagaaga acggcatcaa ggtgaacttc aagatccgcc    3840
acaacatcga ggacggcagc gtgcagctcg ccgaccacta ccagcagaac cccccatcg     3900
gcgacggccc cgtgctgctg cccgacaacc actacctgag cacccagtcc gccctgagca    3960
aagaccccaa cgaaagcgc gatcacatgg tcctgctgga gttcgtgacc gccgccggga     4020
tcactctcgg catggacgag ctgtacaagt aaagcggccg cgactctagc ctgcaggaat    4080
tcgatatcaa gcttatcgat accgtcgaat tggaagagct ttaaatcctg gcacatctca    4140
tgtatcaatg cctcagtatg tttagaaaaa caagggggga actgtggggt ttttatgagg    4200
ggttttataa aaatgaaaga ccccacctgt aggtttggca agctagctta agtaacgcca    4260
ttttgcaagg catggaaaaa tacataactg agaatagaga agttcagatc aaggtcagga    4320
acagatggaa cagctgaata tgggccaaac aggatatctg tggtaagcag ttcctgcccc    4380
ggctcagggc caagaacaga tggaacagct gaatatgggc caaacaggat atctgtggta    4440
agcagttcct gccccggctc agggccaaga acagatggtc cccagatgcg gtccagccct    4500
cagcagtttc tagagaacca tcagatgttt ccagggtgcc ccaaggacct gaaatgaccc    4560
tgtgccttat ttgaactaac caatcagttc gcttctcgct tctgttcgcg cgcttctgct    4620
ccccgagctc aataaaagag cccacaaccc ctcactcggg gggcactcag attctgcggt    4680
ctgagtccct tctctgctgg gctgaaaagg ccttttgtaat aaatataatt ctctactcag    4740
tccctgtctc tagtttgtct gttcgagatc ctacagagct catgccttgg cgtaatcatg    4800
gtcatagctg tttcctgtgt gaaattgtta tccgctcaca attccacaca acatacgagc    4860
cggaagcata aagtgtaaag cctggggtgc ctaatgagtg agctaactca cattaattgc    4920
gttgcgctca ctgcccgctt tccagtcggg aaacctgtcg tgccagctgc attaatgaat    4980
cggccaacgc gcggggagag gcggtttgcg tattgggcgc tcttccgctt cctcgctcac    5040
tgactcgctg cgctcggtcg ttcggctgcg gcgagcggta tcagctcact caaaggcggt    5100
aatacggtta tccacagaat caggggataa cgcaggaaag aacatgtgag caaaaggcca    5160
gcaaaaggcc aggaaccgta aaaaggccgc gttgctggcg ttttccata ggctccgccc     5220
ccctgacgag catcacaaaa atcgacgctc aagtcagagg tggcgaaacc cgacaggact    5280
ataaagatac caggcgtttc ccctggaag ctccctcgtg cgctctcctg ttccgaccct     5340
gccgcttacc ggatacctgt ccgcctttct cccttcggga agcgtggcgc tttctcatag    5400
ctcacgctgt aggtatctca gttcggtgta ggtcgttcgc tccaagctgg gctgtgtgca    5460
cgaaccccc gttcagcccg accgctgcgc cttatccggt aactatcgtc ttgagtccaa     5520
cccggtaaga cacgacttat cgccactggc agcagccact ggtaacagga ttagcagagc    5580
gaggtatgta ggcggtgcta cagagttctt gaagtggtgg cctaactacg gctacactag    5640
aaggacagta tttggtatct gcgctctgct gaagccagtt accttcggaa aaagagttgg    5700
tagctcttga tccggcaaac aaaccaccgc tggtagcggt ggttttttg tttgcaagca     5760
gcagattacg cgcagaaaaa aaggatctca agaagatcct ttgatctttt ctacgggtc     5820
tgacgctcag tggaacgaaa actcacgtta agggattttg gtcatgagat tatcaaaaag    5880
```

| | |
|---|---|
| gatcttcacc tagatccttt taaattaaaa atgaagtttt aaatcaatct aaagtatata | 5940 |
| tgagtaaact tggtctgaca gttaccaatg cttaatcagt gaggcaccta tctcagcgat | 6000 |
| ctgtctattt cgttcatcca tagttgcctg actcccgtc gtgtagataa ctacgatacg | 6060 |
| ggagggctta ccatctggcc ccagtgctgc aatgataccg cgagacccac gctcaccggc | 6120 |
| tccagattta tcagcaataa accagccagc cggaagggcc gagcgcagaa gtggtcctgc | 6180 |
| aactttatcc gcctccatcc agtctattaa ttgttgccgg gaagctagag taagtagttc | 6240 |
| gccagttaat agtttgcgca acgttgttgc cattgctaca ggcatcgtgg tgtcacgctc | 6300 |
| gtcgtttggt atggcttcat tcagctccgg ttcccaacga tcaaggcgag ttacatgatc | 6360 |
| ccccatgttg tgcaaaaaag cggttagctc cttcggtcct ccgatcgttg tcagaagtaa | 6420 |
| gttggccgca gtgttatcac tcatggttat ggcagcactg cataattctc ttactgtcat | 6480 |
| gccatccgta agatgctttt ctgtgactgg tgagtactca accaagtcat tctgagaata | 6540 |
| gtgtatgcgg cgaccgagtt gctcttgccc ggcgtcaata cgggataata ccgcgccaca | 6600 |
| tagcagaact ttaaaagtgc tcatcattgg aaaacgttct cggggcgaaa actctcaag | 6660 |
| gatcttaccg ctgttgagat ccagttcgat gtaacccact cgtgcaccca actgatcttc | 6720 |
| agcatctttt actttcacca gcgtttctgg gtgagcaaaa acaggaaggc aaaatgccgc | 6780 |
| aaaaaaggga ataagggcga cacggaaatg ttgaatactc atactcttcc ttttcaata | 6840 |
| ttattgaagc atttatcagg gttattgtct catgagcgga tacatatttg aatgtattta | 6900 |
| gaaaaataaa caaataggg ttccgcgcac atttccccga aagtgccac ctaaattgta | 6960 |
| agcgttaata ttttgttaaa attcgcgtta aattttgtt aaatcagctc attttttaac | 7020 |
| caataggccg aaatcggcaa aatcccttat aaatcaaaag aatagaccga gatagggttg | 7080 |
| agtgttgttc cagtttggaa caagagtcca ctattaaaga acgtggactc caacgtcaaa | 7140 |
| gggcgaaaaa ccgtctatca gggcgatggc ccactacgtg aaccatcacc ctaatcaagt | 7200 |
| tttttggggt cgaggtgccg taaagcacta atcggaacc ctaaagggag cccccgattt | 7260 |
| agagcttgac ggggaaagcc aacctggctt atcgaaatta atacgactca ctatagggag | 7320 |
| accggc | 7326 |

<210> SEQ ID NO 7
<211> LENGTH: 657
<212> TYPE: DNA
<213> ORGANISM: Unknown Organism
<220> FEATURE:
<223> OTHER INFORMATION: Description of Unknown Organism: wild-type Tet
      repressor sequence

<400> SEQUENCE: 7

| | |
|---|---|
| atgagccgcc tggacaagag caaagtgatc aactccgccc tggagctgct gaatgaggtc | 60 |
| ggcatcgagg gactgaccac gcgcaagctg gcccaaaagc tgggcgtcga gcagccgacc | 120 |
| ctgtattggc atgtgaagaa caagagggcc ctcctggacg cgctcgccat cgaaatgctg | 180 |
| gatcggcacc acacccactt ctgtcccctc gaaggcgaga gctggcagga ctttctgaga | 240 |
| aacaacgcca gtccttccg ctgcgccctc aacaacgcca gtccttccg ctgcgccctc | 300 |
| ctggggacgc ggcccactga gaaacagtac gaaaccctgg agaatcagct ggcgttcctc | 360 |
| tgccagcagg ggttctcct ggagaacgcc ctctacgcac tctccgccgt gggccacttt | 420 |
| acactcggtt gcgtgctgga ggaccaggag acactcggtt gcgtgctgga ggaccaggag | 480 |
| cccaccaccg actccatgcc cccactgctg aggcaggcga ttgagctgtt cgaccaccag | 540 |

```
ggagcagagc ctgcgttcct cttcgggctg gaactcatca tctgcggcct ggagaagcag    600
ctgaagtgcg agagcggctc cgcctacagc ggcagcaggg agttccgctc ttactaa      657
```

<210> SEQ ID NO 8
<211> LENGTH: 657
<212> TYPE: DNA
<213> ORGANISM: Artificial Sequence
<220> FEATURE:
<223> OTHER INFORMATION: Description of Artificial Sequence:
      codon-optimised Tet repressor sequence

<400> SEQUENCE: 8

```
atgtctagat tagataaaag taaagtgatt aacagcgcat tagagctgct taatgaggtc    60
ggaatcgaag gtttaacaac ccgtaaactc gcccagaagc taggtgtaga gcagcctaca   120
ttgtattggc atgtaaaaaa taagcgggct ttgctcgacg ccttagccat tgagatgtta   180
gataggcacc atactcactt ttgccccttta gaagggggaaa gctggcaaga tttttacgt   240 aataacgcta aagttttag atgtgcttta ctaagtcatc gcgatggagc aaaagtacat    300
ttaggtacac ggcctacaga aaaacagtat gaaactctcg aaaatcaatt agccttttta   360
tgccaacaag ttttttcact agagaatgca ttatatgcac tcagcgctgt ggggcatttt   420
actttaggtt gcgtattgga agatcaagag catcaagtcg ctaaagaaga aagggaaaca   480
cctactactg atagtatgcc gccattatta cgacaagcta tcgaattatt tgatcaccaa   540
ggtgcagagc cagccttctt attcggcctt gaattgatca tatgcggatt agaaaaacaa   600
cttaaatgtg aaagtgggtc cgcgtacagc ggatcccggg aattcagatc ttattaa     657
```

<210> SEQ ID NO 9
<211> LENGTH: 636
<212> TYPE: DNA
<213> ORGANISM: Artificial Sequence
<220> FEATURE:
<223> OTHER INFORMATION: Description of Artificial Sequence:
      codon-optimised GDNE

<400> SEQUENCE: 9

```
atgaagctgt gggacgtggt ggccgtgtgc ctggtgctgc tgcacaccgc ctccgccttc    60
cccctgcccg ccggcaagcg ccccccctgag gccccgccg aggaccgctc cctgggccgc   120
cgcagggccc ccttcgccct gagcagcgac agcaacatgc ccgaggacta ccccgaccag   180
ttcgacgacg tgatggactt catccaggcc accatcaagc gcctgaagcg cagccccgac   240
aagcagatgg ccgtgctgcc ccgccgcgag cgcaaccgcc aggccgccgc tgccaacccc   300
gagaactccc gcggcaaggg ccgccgcggc cagcgcggca gaaccgcgg ctgcgtgctg   360 accgccatcc acctgaacgt gaccgacctg ggcctgggct acgagaccaa ggaggagctg   420
atcttccgct actgcagcgg cagctgcgac gccgccgaga ccacctacga caagatcctg   480
aagaacctgt cccgcaaccg ccgcctggtg agcgacaaag tgggccaggc ctgctgccgc   540
cccatcgcct tcgacgacga cctgagcttc ctggacgaca acctggtgta ccacatcctg   600
cgcaagcact ccgccaagcg ctgcggctgc atctga                             636
```

<210> SEQ ID NO 10
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 10
gccgccacca ugg                                                        13

<210> SEQ ID NO 11
<211> LENGTH: 7
<212> TYPE: PRT
<213> ORGANISM: Unknown Organism
<220> FEATURE:
<223> OTHER INFORMATION: Description of Unknown Sequence: IXIT
      CaN-binding motif

<400> SEQUENCE: 11

Ser Pro Arg Ile Glu Ile Thr
 1               5

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 12
caaagcatgc ctgcaggaat tcg                                             23

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 13
gagcgcagcg agtcagtgag cgag                                            24

<210> SEQ ID NO 14
<211> LENGTH: 55
<212> TYPE: DNA
<213> ORGANISM: Artificial Sequence
<220> FEATURE:
<223> OTHER INFORMATION: Description of Artificial Sequence: Primer

<400> SEQUENCE: 14
gccaaaccta caggtggggt ctttcattat aaaaccctc ataaaaaccc cacag           55

<210> SEQ ID NO 15
<211> LENGTH: 55
<212> TYPE: DNA
<213> ORGANISM: Artificial Sequence
<220> FEATURE:
<223> OTHER INFORMATION: Description of Artificial Sequence: Primer

<400> SEQUENCE: 15
ctgtggggtt tttatgaggg gttttataat gaaagacccc acctgtaggt ttggc          55

<210> SEQ ID NO 16
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 16
gaagggactc agaccgcaga atctgagtgc cccccgagtg aggggttgtg ggctct         56
```

<210> SEQ ID NO 17
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 17
agagcccaca acccctcact cgggggcac tcagattctg cggtctgagt cccttc         56

<210> SEQ ID NO 18
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide construct EIAV PPT/U3

<400> SEQUENCE: 18
caaagcatgc ctgcaggaat tcgatatcaa gcttatcgat accgtcgaat tggaagagct    60
ttaaatcctg gcacatctca tgtatcaatg cctcagtatg tttagaaaaa caaggggga    120 actgtggggt ttttatgagg ggttttataa                                    150

<210> SEQ ID NO 19
<211> LENGTH: 447
<212> TYPE: DNA
<213> ORGANISM: Artificial Sequence
<220> FEATURE:
<223> OTHER INFORMATION: Description of Artificial Sequence: Synthetic
      polynucleotide construct MLV U3

<400> SEQUENCE: 19
tgaaagaccc cacctgtagg tttggcaagc tagcttaagt aacgccattt tgcaaggcat    60
ggaaaaatac ataactgaga atagagaagt tcagatcaag gtcaggaaca gatggaacag   120
ctgaatatgg gccaaacagg atatctgtgg taagcagttc ctgccccggc tcagggccaa   180
gaacagatgg aacagctgaa tatgggccaa acaggatatc tgtggtaagc agttcctgcc   240
ccggctcagg gccaagaaca gatggtcccc agatgcggtc cagccctcag cagtttctag   300
agaaccatca gatgtttcca gggtgcccca aggacctgaa atgaccctgt gccttatttg   360
aactaaccaa tcagttcgct tctcgcttct gttcgcgcgc ttctgctccc cgagctcaat   420
aaaagagccc acaaccctc actcggg                                        447

<210> SEQ ID NO 20
<211> LENGTH: 395
<212> TYPE: DNA
<213> ORGANISM: Artificial Sequence
<220> FEATURE:
<223> OTHER INFORMATION: Description of Artificial Sequence: Synthetic
      polynucleotide construct MLV U3/EIAV R/U5

<400> SEQUENCE: 20
gggcactcag attctgcggt ctgagtccct tctctgctgg gctgaaaagg cctttgtaat    60
aaatataatt ctctactcag tccctgtctc tagtttgtct gttcgagatc ctacagagct   120
catgccttgg cgtaatcatg gtcatagctg tttcctgtgt gaaattgtta tccgctcaca   180
attccacaca acatacgagc cggaagcata agtgtaaag cctggggtgc ctaatgagtg    240
agctaactca cattaattgc gttgcgctca ctgcccgctt tccagtcggg aaacctgtcg   300
tgccagctgc attaatgaat cggccaacgc gcggggagag gcggtttgcg tattgggcgc   360
tcttccgctt cctcgctcac tgactcgctg cgctc                              395

```
<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      nuclear localisation signal
<220> FEATURE:
<221> NAME/KEY: CDS
<222> LOCATION: (1)..(24)

<400> SEQUENCE: 21 gac ccc aag aag aag cgc aag gtg taa                               27
Asp Pro Lys Lys Lys Arg Lys Val
 1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      nuclear localisation signal

<400> SEQUENCE: 22

Asp Pro Lys Lys Lys Arg Lys Val
 1               5

<210> SEQ ID NO 23
<211> LENGTH: 539
<212> TYPE: DNA
<213> ORGANISM: Artificial Sequence
<220> FEATURE:
<223> OTHER INFORMATION: Description of Artificial Sequence: Synthetic
      hybrid long terminal repeat region

<400> SEQUENCE: 23
tgtggggttt ttatgagggg ttttataatg aaagacccca cctgtaggtt tggcaagcta      60
gcttaagtaa cgccattttg caaggcatgg aaaaatacat aactgagaat agagaagttc     120
agatcaaggt caggaacaga tggaacagct gaatatgggc caaacaggat atctgtggta     180
agcagttcct gccccggctc agggccaaga acagatggaa cagctgaata tgggccaaac     240
aggatatctg tggtaagcag ttcctgcccc ggctcagggc caagaacaga tggtccccag     300
atgcggtcca gccctcagca gtttctagag aaccatcaga tgtttccagg gtgccccaag     360
gacctgaaat gaccctgtgc cttatttgaa ctaaccaatc agttcgcttc tcgcttctgt     420
tcgcgcgctt ctgctccccg agctcaataa aagagcccac aacccctcac tcggggggca     480
ctcagattct gcggtctgag tcccttctct gctgggctga aaaggccttt gtaataaat      539
```